(12) United States Patent
Hoyt et al.

(10) Patent No.: US 9,073,929 B2
(45) Date of Patent: Jul. 7, 2015

(54) ALDOSTERONE SYNTHASE INHIBITORS

(75) Inventors: Scott B. Hoyt, Hoboken, NJ (US);
Whitney Lane Petrilli, Jersey City, NJ (US); Clare London, Chatham, NJ (US);
Yusheng Xiong, Plainsboro, NJ (US);
Jerry Andrew Taylor, Trenton, NJ (US);
Amjad Ali, Freehold, NJ (US); Michael Man-Chu Lo, Edison, NJ (US);
Timothy J. Henderson, Edison, NJ (US); Qingzhong Hu, Saarbrücken (DE); Rolf Hartmann, Saarbrücken (DE); Lina Yin, Saarbrücken (DE); Ralf Heim, Wiesbaden (DE); Emmanuel Bey, Forbach (DE); Rohit Saxena, Uttar Pradesh (IN); Swapan Kumar Samanta, Bangalore (IN);
Bheemashankar A. Kulkarni, Bangalore (IN)

(73) Assignees: ElexoPharm GmbH, Saarbrucken (DE); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/112,945

(22) PCT Filed: Apr. 20, 2012

(86) PCT No.: PCT/US2012/034417
§ 371 (c)(1),
(2), (4) Date: Oct. 21, 2013

(87) PCT Pub. No.: WO2012/148808
PCT Pub. Date: Nov. 1, 2012

(65) Prior Publication Data
US 2014/0045819 A1    Feb. 13, 2014

Related U.S. Application Data

(60) Provisional application No. 61/479,209, filed on Apr. 26, 2011.

(51) Int. Cl.
C07D 471/04    (2006.01)
C07D 487/04    (2006.01)
C07D 519/00    (2006.01)
A61K 31/41     (2006.01)
A61K 45/06     (2006.01)

(52) U.S. Cl.
CPC .............. *C07D 487/04* (2013.01); *A61K 31/41* (2013.01); *A61K 45/06* (2013.01); *C07D 471/04* (2013.01); *C07D 519/00* (2013.01)

(58) Field of Classification Search
USPC .......................................... 546/119; 514/293
See application file for complete search history.

(56) References Cited

U.S. PATENT DOCUMENTS

| | | |
|---|---|---|
| 4,374,773 A | 2/1983 | Branca et al. |
| 4,845,079 A | 7/1989 | Luly et al. |
| 4,885,292 A | 12/1989 | Ryono et al. |
| 4,894,437 A | 1/1990 | TenBrink et al. |
| 4,980,283 A | 12/1990 | Huang et al. |
| 5,034,512 A | 7/1991 | Hudspeth et al. |
| 5,036,053 A | 7/1991 | Himmelsbach et al. |
| 5,036,054 A | 7/1991 | Kaltenbronn et al. |
| 5,055,466 A | 10/1991 | Weller, III et al. |
| 5,063,207 A | 11/1991 | Doherty et al. |
| 5,063,208 A | 11/1991 | Rosenberg et al. |
| 5,064,965 A | 11/1991 | Ocain et al. |
| 5,066,643 A | 11/1991 | Abeles et al. |
| 5,071,837 A | 12/1991 | Doherty et al. |
| 5,075,451 A | 12/1991 | Ocain et al. |

(Continued)

FOREIGN PATENT DOCUMENTS

| | | |
|---|---|---|
| WO | 9940094 | 8/1999 |
| WO | 2009135651 | 11/2009 |
| WO | 2012012478 | 1/2012 |

OTHER PUBLICATIONS

Azizi; Nephrology Dialysis Transplantation, 2012, 0, 1-8.*

(Continued)

*Primary Examiner* — John Mabry
*Assistant Examiner* — Daniel Carcanague
(74) *Attorney, Agent, or Firm* — Kenrick L. Vidale; Catherine D. Fitch

(57) ABSTRACT

This invention relates to tricyclic triazole analogs of the formula I or their pharmaceutically acceptable salts, wherein the variable are defined herein. The inventive compounds selectively inhibit aldosterone synthetase. This invention also provides for pharmaceutical compositions comprising the compounds of Formula I or their salts as well as to methods for the treatment, amelioration or prevention of conditions that could be treated by inhibiting aldosterone synthetase.

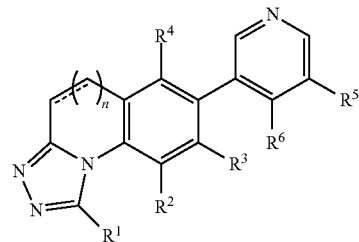

20 Claims, No Drawings

(56) References Cited

U.S. PATENT DOCUMENTS

| 5,089,471 | A | 2/1992 | Hanson et al. |
| 5,095,119 | A | 3/1992 | Ocain et al. |
| 5,098,924 | A | 3/1992 | Poss |
| 5,104,869 | A | 4/1992 | Albright et al. |
| 5,106,835 | A | 4/1992 | Albright et al. |
| 5,114,937 | A | 5/1992 | Hamby et al. |
| 5,116,835 | A | 5/1992 | Ruger et al. |

OTHER PUBLICATIONS

Hu; Inhibition of Steroidogenic Cytochrome P450 Enzymes as Treatments for the Related Hormone Dependent Diseases—Doctoral Dissertation, Saarland University (Dec. 29, 2010) pp. 1-145.*
Lucas, et al., Tackling Aldosterone-mediated disorders: Lead optimization providing a series of 3-pyridine-based aldosterone synthase inhibitors with improved pharmacological properties—Doctoral Dissertation, Saarland University (2008) pp. 1-139.
Gilbert et al., Curr. Opin. Endocrinol. Diabetes Obes., vol. 17 (2010) pp. 199-204.
Pitt et al., New Engl. J. Med. vol. 341 (1999) pp. 709-717.
Pitt et al., New Engl. J. Med. vol. 348 (2003) pp. 1382-1390.
MacFayden et al., Cardiovasc. Res. vol. 35 (1997) pp. 30-34.
Soberman et al., Curr. Hypertens. Rep. vol. 2 (2000) pp. 451-456.
Kawamoto et al., Proc. Natl. Acad. Sci. USA, vol. 89 (1992) pp. 1458-1462.
Taymans et al., J. Clin. Endocrinol. Metab. vol. 83 (1998) pp. 1033-1036.
Lucas et al., J. Med. Chem (2008) vol. 51 pp. 8077-8087.
Lucas et al., J. Med. Chem., vol. 54 (2011) pp. 2307-2309.
Still et al., J. Org. Chem, vol. 43 (1978) p. 2923-2925.
Ehmer et al., J. Steroid Biochem. Mol. Biol. vol. 81 (2002) pp. 173-179.
International Search Report for PCT/US12/34417 (Jul. 18, 2012).
Written Opinion of the International Searching Authority for PCT/US12/34417 (Jul. 4, 2012).
Abstract of dissertation of Qingzhong Hu: Inhibition of steroidogenic cytochrome P450 enzymes as treatments for the related hormone dependent diseases, 2010.

* cited by examiner

ALDOSTERONE SYNTHASE INHIBITORS

CROSS REFERENCE TO RELATED APPLICATIONS

This application is the National Stage of International Application No. PCT/US2012/034417 filed on Apr. 20, 2012, which claims the benefit under 35 U.S.C. 119(e) of U.S. Provisional Application No. 61/479,209, filed Apr. 26, 2011.

FIELD OF THE INVENTION

The present invention relates to tricyclic triazole analogues, which selectively inhibit aldosterone synthetase (CYP11B2) with diminished inhibition or affect on steroid-11-β-hydroxylase (CYP11B1) inhibitors. The inventive compounds have utility in treating cardiovascular diseases such as hypertension or heart failure. The present invention also relates to pharmaceutical compositions comprising the inventive compounds as well as processes for their preparation.

BACKGROUND OF THE INVENTION

Aldosterone is a steroid hormone secreted in the adrenal cortex. In primary cells of the distal tubules and collecting ducts of the kidney, aldosterone binding to the mineralocorticoid receptor (MR) results in the retention of sodium and water and excretion of potassium, which in turn leads to increased blood pressure. Aldosterone also causes inflammation that leads to fibrosis and remodeling in the heart, vasculature and kidney. This inflammation may proceed by MR-dependent as well as MR-independent mechanisms (Gilbert, K. C. et al., Curr. Opin. Endocrinol. Diabetes Obes., vol. 17, 2010, pp. 199-204).

Mineralocorticoid receptor antagonists (MRAs), such as spironolactone and eplerenone, have been used previously to block the effects of aldosterone binding to MR. When given in addition to standard therapies such as angiotensin-converting enzyme (ACE) inhibitors and loop diuretics, the nonselective MRA spironolactone and the selective MRA eplerenone significantly reduced morbidity and mortality in patients with heart failure or myocardial infarction (Pitt, B. et al., New Engl. J. Med., vol. 341, 1999, pp. 709-717; Pitt, B. et al., New Engl. J. Med., vol. 348, 2003, pp. 1382-1390). However, the nonselective MRA spironolactone can also bind to and act at other steroid receptors, and as a consequence its use is associated with sexual side effects such as gynecomastia, dysmenorrhea and impotence (Pitt, B. et al., New Engl. J. Med., vol. 341, 1999, pp. 709 717; MacFadyen, R. J. et al., Cardiovasc. Res., vol. 35, 1997, pp 30-34: Soberman, J. E. et al., Curr. Hypertens. Rep., vol. 2, 2000, pp 451-456). Additionally, both spironolactone and eplerenone are known to cause elevated plasma potassium levels (hyperkalemia) and elevated aldosterone levels.

An alternative method of blocking the effects of aldosterone is to inhibit its biosynthesis. CYP11B2 is a mitochondrial cytochrome P450 enzyme that catalyzes the final oxidative steps in the conversion of 11-deoxycorticosterone, a steroidal precursor, to aldosterone (Kawamoto, T. et al., Proc. Natl. Acad. Sci. USA, vol. 89, 1992, pp. 1458-1462). Compounds that inhibit CYP11B2 should thus inhibit the formation of aldosterone. Such compounds, particularly those of nonsteroidal structure, should provide the beneficial effects of MRAs, without the adverse effects derived from steroid receptor binding or MR-independent inflammatory pathways.

CYP11B1 is a related enzyme that catalyzes the formation of glucocorticoids, such as cortisol, an important regulator of glucose metabolism. Because human CYP11B2 and CYP11B1 are greater than 93% homologous, it is possible for nonselective compounds to inhibit both enzymes (Kawamoto, T. et al., Proc. Natl. Acad. Sci. USA, vol. 89, 1992, pp 1458-1462; Taymans, S. E. et al., J. Clin. Endocrinol. Metab., vol. 83, 1998, pp 1033-1036). It would be preferable, however, for therapeutic agents to selectively inhibit CYP11B2 and the formation of aldosterone with diminished inhibition of, or affect on, CYP11B1 and the production of cortisol.

WO 2009/135651 to Elexopharm describes 6-pyridin-3yl-3,4,-dihydro-1H-quinolin-2-one derivatives as being CYP11B2 inhibitors. Two compounds described therein are lactam derivatives of the formula:

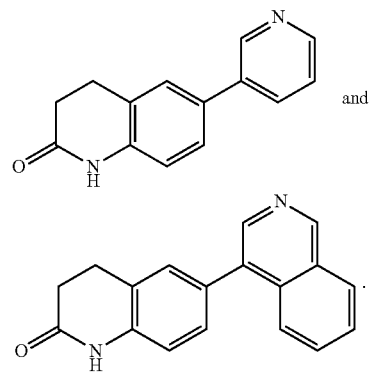

and

Structurally similar lactam and thiolactam compounds are disclosed by Lucas et al., J. Med. Chem. 2008, 51, 8077-8087; those compounds are said to be potential inhibitors of CYP11B2. Lucas et al. in J. Med. Chem. 2011, 54, 2307-2309 describes certain pyridine substituted 3,4-dihydro-1H-quinolin-2-ones as being highly potent as selective inhibitors of CYP11B2 and WO 2012/012478 to Merck describes benzimidazole analogues as having the ability to CYP11B2. An abstract of a dissertation reports that a series of novel heterocyclic-substituted 4,5-dihydro-[1,2,4]triazolo[4,3a]quinolones was evaluated for its aldosterone synthase activity; one of the compounds is reported as exhibiting excellent selectivity of CYP11B2 over CYP11B1.

WO 1999/40094 to Bayer AG describes oxazolidinone derivatives with azol-containing tricycles as possessing antimicrobial activity. An example of one of the compounds disclosed therein is:

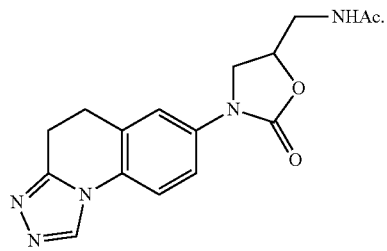 [SMILES: CC(=O)NCC1CN(c2ccc3c(c2)CCc2nncn2-3)C(=O)O1]

The compounds of the invention provide an alternative to previous treatments for elevated aldosterone levels and inhibit CYP11B2.

SUMMARY OF THE INVENTION

In it many embodiments, the present invention provides for a novel class of tricyclic triazole analogues, which are inhibitors of CYP11B2, or metabolites, stereoisomers, salts, solvates or polymorphs thereof, processes of preparing such compounds, pharmaceutical compositions comprising one or more such compounds, processes of preparing pharmaceutical compositions comprising one or more such compounds and methods of treatment, prevention, inhibition or amelioration of one or more disease states associated with inhibiting CYP11B2 by administering an effective amount at least one of the inventive tricyclic triazole analogues to a patient in need thereof.

In one aspect, the present application discloses a compound or a pharmaceutically acceptable salt, metabolite, solvate, prodrug or polymorph of said compound, said compound having the general structure shown in Formula 1

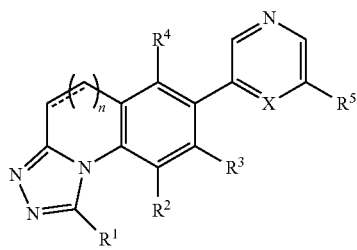

I or a pharmaceutically acceptable salt thereof
wherein:
X is N or C($R^6$);
$R^1$ is H; alkyl optionally independently substituted one or more times (e.g., 1 to 4 times) by halogen, —$OR^7$, $NR^8R^9$, —CN, —$N(R^{11})C(O)R^7$, —$C(O)N(R^8)(R^9)$, —$C(O)OR^7$, or —$S(O)_m$—$R^7$; cycloalkyl optionally independently substituted one or more times (e.g., 1 to 4 times) by halogen, alkyl, haloalkyl, —$OR^7$, —$NR^8R^9$, —CN, —$N(R^{11})C(O)R^7$, —$C(O)N(R^8)(R^9)$, —$C(O)OR^7$ or —$S(O)_m$—$R^7$; aryl optionally independently substituted one or more times (e.g., 1 to 4 times) by halogen, alkyl, haloalkyl, cycloalkyl, —CN, —$NR^8R^9$ —$N(R^{11})C(O)R^7$,—$C(O)N(R^8)(R^9)$,—$C(O)OR^7$, or —$S(O)_m$—$R^7$; or heteroaryl optionally independently substituted one or more times (e.g., 1 to 4 times) by halogen, alkyl, haloalkyl, cycloalkyl, —$OR^7$, —CN, —$NR^8R^9$, —$N(R^{11})C(O)R^7$, —$C(O)N(R^8)(R^9)$, —$C(O)OR^7$ or —$S(O)_m$—$R^7$;

$R^2$ is H; halogen; —CN; alkyl optionally independently substituted one or more times (e.g., 1 to 4 times) by halogen; or cycloalkyl optionally independently substituted once or twice by alkyl or halogen;

$R^3$ is H; halogen; —CN; alkyl optionally independently substituted one or more times (e.g., 1 to 4 times) by halogen; or cycloalkyl optionally independently substituted once or twice by alkyl or halogen;

$R^4$ is H; halogen; —CN; alkyl optionally independently substituted one or more times (e.g., 1 to 4 times) by halogen; or cycloalkyl optionally independently substituted once or twice by alkyl or halogen;

$R^5$ is H; halogen; —CN; —$OR^7$; —$NR^8R^9$; —$N(R^{11})C(O)R^7$; —$C(O)OR^7$; —$C(O)N(R^8)(R^9)$; —$C(O)OR^7$; —$N(R^{11})S(O)_{2R}^7$; —$S(O)_2N(R^8)(R^9)$; —$S(O)_m$—$R^7$; alkyl optionally independently substituted one or more times (e.g., 1 to 5 times) by halogen, —$OR^7$, —$NR^8R^9$, —CN, —$N(R^{11})C(O)$ $R^7$, —$C(O)N(R^8)(R^9)$, —$C(O)OR^7$ or —$S(O)_m$—$R^7$; cycloalkyl optionally independently substituted one or more times (e.g., 1 to 4 times) by halogen, alkyl, haloalkyl, aryl (optionally substituted once or twice by halogen, alkyl, haloalkyl, cycloalkyl or aryl), heteroaryl (optionally substituted once or twice by halogen, alkyl, haloalkyl, cycloalkyl or aryl), —$OR^7$, —$NR^8R^9$, —CN, —$N(R^{11})C(O)R^7$, —$C(O)N(R^8)(R^9)$, —$C(O)OR^7$ or —$S(O)_m$—$R^7$; aryl optionally independently substituted one or more times (e.g., 1 to 4 times) by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$ $N(R^{11})C(O)R^7$, —$C(O)N(R^8)(R^9)$, —$C(O)OR^7$ or —$S(O)_m$—$R^7$; aralkyl wherein the aryl ring is optionally independently substituted one or more times (e.g., 1 to 4 times) by halogen, alkyl, haloalkyl, cycloalkyl, aryl (optionally substituted once or twice by halogen, alkyl, or haloalkyl), heteroaryl (optionally substituted one or twice by halogen, alkyl, or haloalkyl), —$OR^7$, —CN, —$NR^8R^9$ —$N(R^{11})C(O)R^7$, —$C(O)N(R^8)$ $(R^9)$, —$C(O)OR^7$ or —$S(O)_m$—$R^7$ and the alkyl chain is straight or branched an optionally substituted one or more times (e.g., 1 to 6 times) by halogen or —$OR^7$; heterocycloalkyl optionally independently substituted one or more times (e.g., 1 to 4 times) by halogen, alkyl, haloalkyl, —$OR^7$, —CN, —$NR^8R^9$ —$N(R^{11})C(O)R^7$, —$C(O)N(R^8)(R^9)$, —$C(O)OR^7$ or —$S(O)$, $R^7$; heteroaryl optionally independently substituted one or more times (e.g., 1 to 4 times) by halogen, alkyl, haloalkyl, cycloalkyl, aryl (optionally substituted one or twice by halogen, alkyl, or haloalkyl), heteroaryl (optionally substituted one or twice by halogen, alkyl, or haloalkyl), —$OR^7$, —CN, —$NR^8R^9$, —$N(R^{11})C(O)R^7$, —$C(O)N(R^8)(R^9)$, —$C(O)OR^7$ or —$S(O)_m$—$R^7$; or heteroaralkyl wherein the heteroaryl ring is optionally independently substituted one or more times (e.g., 1 to 4 times) by halogen, alkyl, haloalkyl, cycloalkyl, aryl (optionally substituted one or twice by halogen, alkyl, or haloalkyl), heteroaryl (optionally substituted one or twice by halogen, alkyl, or haloalkyl), —$OR^7$, —CN, —$NR^8R^9N(R^{11})C(O)R^7$, —$C(O)$ $N(R^8)(R^9)$, —$C(O)OR^7$ or —$S(O)_m$—$R^7$ and the alkyl chain is straight or branched an optionally substituted one or more times (e.g., 1 to 6 times) by halogen or $OR^7$;

$R^6$ is H; halogen; —CN; —$OR^7$; —$NR^8R^9$; —$N(R^{11})C(O)$ $R^7$; —$C(O)N(R^8)(R^9)$; —$C(O)R^7$; —$C(O)OR^7$; —$N(R^{11})S$ $(O)_2R^7$; —$S(O)_2N(R^8)(R^9)$; —$S(O)_m$—$R^7$; alkyl optionally independently substituted one or more times (e.g., 1 to 5 times) by halogen, —$OR^7$, —$NR^8R^9$, —CN, —$N(R^{11})C(O)$ $R^7$, —$C(O)N(R^8)(R^9)$, —$C(O)OR^7$ or —$S(O)_m$—$R^7$; cycloalkyl optionally independently substituted one or more times (e.g., 1 to 4 times) by halogen, alkyl, haloalkyl, aryl (optionally substituted once or twice by halogen, alkyl, haloalkyl, cycloalkyl or aryl), heteroaryl (optionally substituted once or twice by halogen, alkyl, haloalkyl, cycloalkyl or aryl), —$OR^7$, —$NR^8R^9$, —CN, —$N(R^{11})C(O)R^7$, —$C(O)N$ $(R^8)(R^9)$, —$C(O)OR^8$ or —$S(O)_m$—$R^8$; aryl optionally independently substituted one or more times (e.g., 1 to 4 times) by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$ —$N(R^{11})C(O)$ $(R^7)$, —$C(O)N(R^8)(R^9)$, —$C(O)OR^7$ or —$S(O)_m$—$R^7$; aralkyl wherein the aryl ring is optionally independently substituted one or more times (e.g., 1 to 4 times) by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$ —$N(R^{11})C(O)R^7$, —$C(O)N(R^8$ ($R^9$), —C(O)O$R^7$ or —S(O)$_m$—$R^7$ and the alkyl chain is straight or branched an optionally substituted one or more times (e.g., 1 to 6 times) by halogen or —O$R^7$; heterocycloalkyl optionally substituted one or more times (e.g., 1 to 4 times) by halogen, alkyl, haloalkyl, cycloalkyl, aryl (optionally substituted one or twice by halogen, alkyl, or haloalkyl), heteroaryl (optionally substituted once or twice by halogen, alkyl, or haloalkyl), —CN, —CN, —N$R^8R^9$N($R^{11}$)C(O)$R^7$, —C(O)N($R^8$)($R^9$), —C(O)O$R^7$ or —S(O)$_m$—$R^7$; heteroaryl optionally substituted one or more times (e.g., 1 to 4 times) by halogen, alkyl, haloalkyl, cycloalkyl, aryl (optionally substituted one or twice by halogen, alkyl, or haloalkyl), heteroaryl (optionally substituted once or twice by halogen, alkyl, or haloalkyl), —O$R^7$, —CN, —N$R^8R^9$, N($R^{11}$)C(O)$R^7$, —C(O)N($R^8$)($R^9$), —C(O)O$R^7$ or —S(O)$_m$—$R^7$; or heteroaralkyl wherein the heteroaryl ring is optionally independently substituted one or more times (e.g., 1 to 4 times) by halogen, alkyl, haloalkyl, cycloalkyl, aryl (optionally substituted one or twice by halogen, alkyl, or haloalkyl), heteroaryl (optionally substituted once or twice by halogen, alkyl, or haloalkyl), —O$R^7$, —CN, —N$R^8R^9$ —N($R^{11}$)C(O)$R^7$, —C(O)N($R^8$)($R^9$), —C(O)O$R^7$ or —S(O)$_m$—$R^7$ and the alkyl chain is straight or branched an optionally substituted one or more times (e.g., 1 to 6 times) by halogen or —O$R^7$;

or $R^5$ and $R^6$ are joined together to form a 5-7 membered carbocyclic or heterocyclic ring that is fused to the pyridyl ring to which $R^5$ and $R^6$ are attached, wherein the ring formed by $R^5$ and $R^6$ is optionally independently substituted by 1 to 3 $R^{10}$;

$R^7$ is independently selected from the group consisting of H; alkyl optionally independently substituted one or more times (e.g., 1 to 4 times) by halogen, —O$R^{11}$, —N$R^8R^9$, —CN, —N($R^{11}$)C(O)$R^{11}$, —C(O)N($R^8$)($R^9$), —C(O)O$R^{11}$ or —S(O)$_m$—$R^{11}$, aryl (optionally substituted once or twice by halogen, alkyl, or haloalkyl), heteroaryl (optionally substituted once or twice by halogen, alkyl, or haloalkyl); cycloalkyl optionally independently substituted one or more times (e.g., 1 to 4 times) by halogen, alkyl, haloalkyl, —O$R^{11}$, —N$R^8R^9$, —CN, —N($R^{11}$)C(O)$R^{11}$, —C(O)N($R^8$)($R^9$), —C(O)O$R^{11}$ or —S(O)$_m$—$R^{11}$; aryl optionally independently substituted one or more times (e.g., 1 to 4 times) by halogen, alkyl, haloalkyl, cycloalkyl, —OH, —O$R^{11}$, —N$R^8R^9$, —CN, —N($R^{11}$)C(O)$R^{11}$, —C(O)N($R^8$)($R^9$), —C(O)O$R^{11}$ or —S(O)$_m$—$R^{11}$; or heteroaryl optionally independently substituted one or more times (e.g., 1 to 4 times) by halogen, alkyl, haloalkyl, cycloalkyl, —O$R^{11}$, —N$R^8R^9$, —CN, —N($R^9$)C(O)$R^{11}$, —C(O)N($R^8$)($R^9$), —C(O)O$R^{11}$ or —S(O)$_m$—$R^{11}$;

$R^5$ is independently H or alkyl;

$R^9$ is independently H or alkyl;

$R^{10}$ is independently H; halogen; —CN; —O$R^7$; —N$R^8R^9$; —N($R^{11}$)C(O)$R^7$; —C(O)N($R^7$)($R^8$); —C(O)N($R^8$)($R^9$); —C(O)O$R^7$; —S(O)$_m$—$R^7$; alkyl optionally independently substituted one or more times (e.g., 1 to 4 times) by halogen, —O$R^7$, —N$R^8R^9$, —CN, —N($R^{11}$)C(O)$R^7$, —C(O)N($R^8$)($R^9$), —C(O)O$R^7$ or —S(O)$_m$—$R^7$; cycloalkyl optionally independently substituted one or more times (e.g., 1 to 4 times) by halogen, alkyl, haloalkyl, —O$R^7$, —N$R^8R^9$, —CN, —N($R^{11}$)C(O)$R^7$, —C(O)N($R^8$)($R^9$), —C(O)O$R^8$ or —S(O)$_m$—$R^8$; aryl optionally independently substituted one or more times (e.g., 1 to 3 times) by halogen, alkyl, haloalkyl, cycloalkyl, —O$R^7$, —CN, —N$R^8R^9$ —N($R^{11}$)C(O)($R^7$), —C(O)N($R^7$)($R^8$), —C(O)O$R^7$ or —S(O)$_m$—$R^7$; heterocycloalkyl optionally independently substituted one or more times (e.g., 1 to 4 times) by halogen, alkyl, haloalkyl, —O$R^7$, —CN, —N$R^8R^9$ —N($R^{11}$)C(O)$R^7$, —C(O)N($R^8$)($R^9$), —C(O)O$R^7$ or —S(O)$_m$—$R^7$; or heteroaryl optionally independently substituted one or more times (e.g., 1 to 4 times) by halogen, alkyl, haloalkyl, cycloalkyl, —O$R^7$, —CN, —N$R^8R^9$)C(O)$R^7$, —C(O)N($R^8$)($R^9$), —C(O)O$R^7$ or —S(O)$_m$—$R^7$;

$R^{11}$ is independently H or alkyl;

---- is an optional double bond;

n is 1 or 2; and m is 0, 1 or 2.

Another aspect of the present invention is pharmaceutical compositions comprising a therapeutically effective amount of at least one compound of Formula 1 or a pharmaceutically acceptable salt thereof and a pharmaceutically acceptable carrier.

Another aspect of the present invention is pharmaceutical compositions comprising a therapeutically effective amount of at least one compound of Formula I or a pharmaceutically acceptable salt thereof, a therapeutically effective amount of at least one additional therapeutic agent and a pharmaceutically acceptable carrier.

It is further contemplated that the combination of the invention could be provided as a kit comprising in a single package at least one compound of Formula I or a pharmaceutically acceptable salt thereof in a pharmaceutical composition, and at least one separate pharmaceutical composition, such as, for example a separate pharmaceutical composition comprising a therapeutic agent.

The compounds of the present invention could be useful in the treatment, amelioration or prevention of one or more conditions associated with inhibiting CYP11B2 by administering a therapeutically effective amount of at least one compound of Formula 1 or a pharmaceutically acceptable salt thereof to a mammal in need of such treatment. Conditions that could be treated or prevented by inhibiting CYP11B2 include hypertension, heart failure such as congestive heart failure, diastolic dysfunction, left ventricular diastolic dysfunction, diastolic heart failure, systolic dysfunction, hypokalemia, renal failure, in particular chronic renal failure, restenosis, metabolic syndrome, nephropathy, post-myocardial infarction, coronary heart diseases, increased formation of collagen, fibrosis and remodeling following hypertension and endothelial dysfunction, cardiovascular diseases, renal dysfunction, liver diseases, vascular diseases, cerebrovascular diseases, retinopathy, neuropathy, insulinopathy, endothelial dysfunction, ischemia, myocardial and vascular fibrosis, myocardial necrotic lesions, vascular damage, myocardial infarction, left ventricular hypertrophy, cardiac lesions, vascular wall hypertrophy, endothelial thickening or fibrinoid necrosis of coronary arteries.

Another embodiment of the present invention is the use of a compound of Formula I or a pharmaceutically acceptable salt thereof for the manufacture of a medicament for the treatment, amelioration or prevention of one or more conditions associated with inhibiting CYP11B2 in a patient.

DETAILED DESCRIPTION

In an embodiment, the present invention provides compounds represented by structural Formula I, or pharmaceutically acceptable salt thereof, wherein the various moieties are as described as above.

Another embodiment of the present invention are compounds or their pharmaceutically acceptable salts of Formula I represented by structural Formula II

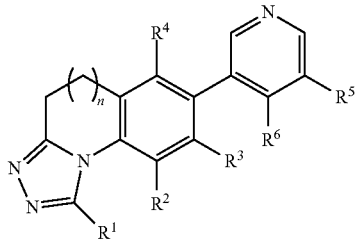

or a pharmaceutically acceptable salt thereof
wherein:

$R^1$ is H; alkyl optionally independently substituted one or more times (e.g., 1 to 3 times) by halogen. —$OR^7$, $NR^8R^9$, —CN, —N($R^{11}$)C(O)$R^7$, —C(O)N($R^8$)($R^9$), —C(O)$OR^7$, or —S(O)$_m$—$R^7$; cycloalkyl optionally independently substituted one or more times (e.g., 1 to 3 times) by halogen, alkyl, haloalkyl, —$OR^7$, —CN, —N($R^{11}$)C(O)$R^7$, —C(O)N($R^8$)($R^9$), —C(O)$OR^7$ or —S(O)$_m$—$R^7$; aryl optionally independently substituted one or more times (e.g., 1 to 3 times) by halogen, alkyl, haloalkyl, cycloalkyl, —$OR^7$, —CN, —$NR^8R^9$ —N($R^{11}$)C(O)$R^7$, —C(O)N($R^8$)($R^9$), —C(O)$OR^7$, or —S(O)$_m$—$R^7$; or heteroaryl optionally independently substituted one or more times (e.g., 1 to 3 times) by halogen, alkyl, haloalkyl, cycloalkyl, —$OR^7$, —CN, —$NR^8R^9$, N($R^{11}$)C(O)$R^7$, —C(O)N($R^8$)($R^9$), —C(O)$OR^7$ or —S(O)$_m$—$R^7$;

$R^2$ is H; halogen; —CN; alkyl optionally independently substituted one or more times (e.g., 1 to 3 times) by halogen; or cyclopropyl optionally independently substituted once or twice by alkyl or halogen;

$R^3$ is H; halogen; —CN; alkyl optionally independently substituted one or more times (e.g., 1 to 3 times) by halogen; or cyclopropyl optionally independently substituted once or twice by alkyl or halogen;

$R^4$ is H; halogen; —CN; alkyl optionally independently substituted one or more times (e.g., 1 to 3 times) by halogen; or cycloalkyl optionally independently substituted once or twice by alkyl or halogen;

$R^5$ is H; halogen; —CN; —$OR^7$; —$NR^8R^9$; —N($R^{11}$)C(O)$R^7$; —C(O)$R^7$; —C(O)N($R^8$)($R^9$); —C(O)$OR^7$; —S(O)$_m$—$R^7$; alkyl optionally independently substituted one or more times (e.g., 1 to 3 times) by halogen, —$OR^7$, —$NR^8R^9$, —CN, —N($R^{11}$)C(O)$R^7$, —C(O)N($R^8$)($R^9$), —C(O)$OR^7$ or —S(O)$_m$—$R^7$; cycloalkyl optionally independently substituted one or more times (e.g., 1 to 3 times) by halogen, alkyl, haloalkyl, aryl (optionally substituted once or twice by halogen, alkyl, haloalkyl, cycloalkyl or aryl), heteroaryl (optionally substituted once or twice by halogen, alkyl, haloalkyl, cycloalkyl or aryl), —$OR^7$, —$NR^8R^9$, —CN, —N($R^{11}$)C(O)$R^7$, —C(O)N($R^8$)($R^9$), —C(O)$OR^7$ or —S(O)$_m$—$R^7$; aryl optionally independently substituted one or more times (e.g., 1 to 3 times) by halogen, alkyl, haloalkyl, cycloalkyl, aryl (optionally substituted one or twice by halogen, alkyl, or haloalkyl), heteroaryl (optionally substituted one or twice by halogen, alkyl, or haloalkyl), —$OR^7$, —CN, —$NR^8R^9$ —N($R^{11}$)C(O)$R^7$, —C(O)N($R^8$)($R^9$), —C(O)$OR^7$ or —S(O)$_m$—$R^7$; aralkyl wherein the aryl ring is optionally independently substituted one or more times (e.g., 1 to 3 times) by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$ —N($R^{11}$)C(O)$R^7$, —C(O)N($R^8$)($R^9$), —C(O)$OR^7$ or —S(O)$_m$—$R^7$ and the alkyl chain is straight or branched an optionally substituted one or more times (e.g., 1 to 6 times) by halogen or —$OR^7$; heterocycloalkyl optionally independently substituted one or more times (e.g., 1 to 3 times) by halogen, alkyl, haloalkyl, —$OR^7$, —CN, —$NR^8R^9$ —N($R^{11}$)C(O)$R^7$, —C(O)N($R^8$)($R^9$), —C(O)$OR^7$ or —S(O)$_m$—$R^7$; heteroaryl optionally independently substituted one or more times (e.g., 1 to 3 times) by halogen, alkyl, haloalkyl, cycloalkyl, aryl (optionally substituted one or twice by halogen, alkyl, or haloalkyl), heteroaryl (optionally substituted one or twice by halogen, alkyl, or haloalkyl), —$OR^7$, —CN, —$NR^8R^9$, N($R^{11}$)C(O) $R^7$, —C(O)N($R^8$)($R^9$), —C(O)$OR^7$ or —S(O)$_m$—$R^7$; or heteroaralkyl wherein the heteroaryl ring is optionally independently substituted one or more times (e.g., 1 to 3 times) by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), $OR^7$; —CN, —$NR^8R^9$ —N($R^{11}$)C(O)$R^7$, —C(O)N($R^8$)($R^9$), —C(O)$OR^7$ or —S(O)$_m$—$R^7$ and the alkyl chain is straight or branched an optionally substituted one or more times (e.g., 1 to 6 times) by halogen or —$OR^7$;

$R^6$ is H; halogen; —CN; —$OR^7$; —$NR^8R^9$; —N($R^{11}$)C(O)$R^7$; —C(O)N($R^8$)($R^9$); —C(O)$R^7$, —C(O)$OR^7$; —S(O)$_m$—$R^7$; alkyl optionally independently substituted one or more times (e.g., 1 to 5 times) by halogen, —$OR^7$, —$NR^8R^9$, —CN, —N($R^{11}$)C(O)$R^7$, —C(O)N($R^8$)($R^9$), —C(O)$OR^7$ or —S(O)$_m$—$R^7$; cycloalkyl optionally independently substituted one or more times (e.g., 1 to 3 times) by halogen, alkyl, haloalkyl, aryl (optionally substituted once or twice by halogen, alkyl, haloalkyl, cycloalkyl or aryl), heteroaryl (optionally substituted one or twice by halogen, alkyl, haloalkyl, cycloalkyl or aryl), —$OR^7$, —$NR^8R^9$, —CN, —N($R^{11}$)C(O) $R^7$, —C(O)N($R^8$)($R^9$), —C(O)$OR^8$ or —S(O)$_m$—$R^8$; aryl optionally independently substituted one or more times (e.g., 1 to 3 times) by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$ —N($R^{11}$)C(O)($R^7$), —C(O)N($R^8$)($R^9$), —C(O)$OR^7$ or —S(O)$_m$—$R^7$; aralkyl wherein the aryl ring is optionally independently substituted one or more times (e.g., 1 to 3 times) by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$ —N($R^{11}$)C(O)$R^7$, —C(O)N($R^8$)($R^9$), —C(O)$OR^7$ or —S(O)$_m$—$R^7$ and the alkyl chain is straight or branched an optionally substituted one or more times (e.g., 1 to 6 times) by halogen or —$OR^7$; heterocycloalkyl optionally independently substituted one or more times (e.g., 1 to 3 times) by halogen, alkyl, haloalkyl, cycloalkyl, —$OR^7$, —CN, —$NR^8R^9$ —N($R^{11}$)C(O)$R^7$, —C(O)N($R^8$)($R^9$), —C(O)$OR^7$ or —S(O)$_m$—$R^7$; heteroaryl optionally independently substituted one or more times (e.g., 1 to 3 times) by halogen, alkyl, haloalkyl, cycloalkyl, aryl (optionally substituted one or twice by halogen, alkyl, or haloalkyl), heteroaryl (optionally substituted one or twice by halogen, alkyl, or haloalkyl), —$OR^7$, —CN, —$NR^8R^9$, —N($R^{11}$)C(O)$R^7$, —C(O)N($R^8$)($R^9$), —C(O) $OR^7$ or —S(O)$_m$—$R^7$; or heteroaralkyl wherein the heteroaryl ring is optionally independently substituted one or more times (e.g., 1 to 3 times) by halogen, alkyl, haloalkyl, cycloalkyl, aryl (optionally substituted once or twice by halogen, alkyl, or haloalkyl), heteroaryl (optionally substituted one or twice by halogen, alkyl, or haloalkyl), —CN, —$NR^8R^9$ —N($R^{11}$)C(O)$R^7$, —C(O)N($R^8$)($R^9$), —C(O)$OR^7$ or —S(O)$_m$—$R^7$ and the alkyl chain is straight or branched an optionally substituted one or more times (e.g., 1 to 6 times) by halogen or —$OR^7$;

or R⁵ and R⁶ are joined together to form a 5-7 membered carbocyclic or heterocyclic ring that is fused to the pyridyl ring to which R⁵ and R⁶ are attached, wherein the ring formed by R⁵ and R⁶ is optionally independently substituted by 1 to 3 R¹⁰;

R⁷ is independently selected from the group consisting of H; alkyl optionally independently substituted one or more times (e.g., 1 to 3 times) by halogen, —OR¹¹, —NR⁸R⁹, —N(R¹¹)C(O)R¹¹, —C(O)N(R⁸)(R⁹), —C(O)OR¹¹ or —S(O)ₘ—R⁷, aryl (optionally substituted once or twice by halogen, alkyl, or haloalkyl), heteroaryl (optionally substituted once or twice by halogen, alkyl, or haloalkyl); cycloalkyl optionally independently substituted one or more times (e.g., 1 to 3 times) by halogen, alkyl, haloalkyl, —OR¹¹, —NR⁸R⁹, —CN, —N(R¹¹)C(O)R¹¹, —C(O)N(R⁸)(R⁹), —C(O)OR¹¹ or —S(O)ₘ—R¹¹; aryl optionally independently substituted one or more times (e.g., 1 to 3 times) by halogen, alkyl, haloalkyl, cycloalkyl, —OH, —OR¹¹, —NR⁸R⁹, —CN, —N(R¹¹)C(O)R¹¹, —C(O)N(R⁸)(R⁹), —C(O)OR¹¹ or —S(O)ₘ—R¹¹; or heteroaryl optionally independently substituted one or more times (e.g., 1 to 3 times) by halogen, alkyl, haloalkyl, cycloalkyl, —OR¹¹, —NR⁸R⁹, —CN, —N(R⁹)C(O)R¹¹, —C(O)N(R⁸)(R⁹), —C(O)OR¹¹ or —S(O)ₘ—R¹¹;

R⁸ is independently H or alkyl;

R⁹ is independently H or alkyl;

R¹⁰ is independently H; halogen; —CN; —OR⁷; —NR⁸R⁹; —N(R¹¹)C(O)R⁷; —C(O)N(R⁷)(R⁸); —C(O)N(R⁸)(R⁹); —C(O)OR⁷; —S(O)ₘ—R⁷; alkyl optionally independently substituted one or more times (e.g., 1 to 3 times) by halogen, —OR⁷, —NR⁸R⁹, —CN, N(R¹¹)C(O)R⁷, —C(O)N(R⁸)(R⁹), —C(O)OR⁷ or —S(O)ₘ—R⁷; cycloalkyl optionally independently substituted one or more times (e.g., 1 to 3 times) by halogen, alkyl, haloalkyl, —OR⁷, —NR⁸R⁹, —CN, —N(R¹¹)C(O)R⁷, —C(O)N(R⁸)(R⁹), —C(O)OR⁸ or —S(O)ₘ—R⁸; aryl optionally independently substituted one or more times (e.g., 1 to 3 times) by halogen, alkyl, haloalkyl, cycloalkyl, —OR⁷, —CN, —NR⁸R⁹ —N(R¹¹)C(O)(R⁷), —C(O)N(R⁷)(R⁸), —C(O)OR⁷ or —S(O)ₘ—R⁷; heterocycloalkyl optionally independently substituted one or more times (e.g., 1 to 3 times) by halogen, alkyl, haloalkyl, —OR⁷, —CN, —NR⁸R⁹ —N(R¹¹)C(O)R⁷, —C(O)N(R⁸)(R⁹), —C(O)OR⁷ or —S(O)ₘ—R⁷; or heteroaryl optionally independently substituted one or more times (e.g., 1 to 3 times) by halogen, alkyl, haloalkyl, cycloalkyl, —OR⁷, —CN, —NR⁸R⁹, —N(R¹¹)C(O)R⁷, —C(O)N(R⁸)(R⁹), —C(O)OR⁷ or —S(O)ₘ—R⁷;

R¹¹ is independently H or alkyl;

n is 1 or 2; and m is 0, 1 or 2.

Another embodiment of the present invention is compounds or their pharmaceutically acceptable salts of Formula I represented by structural Formula III

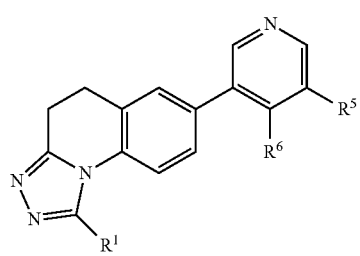

III wherein R¹, R⁵ and R⁶ are as defined in Formula I or Formula II.

Another embodiment of the present invention is compounds or their pharmaceutically acceptable salts of Formula I represented by structural Formula IV

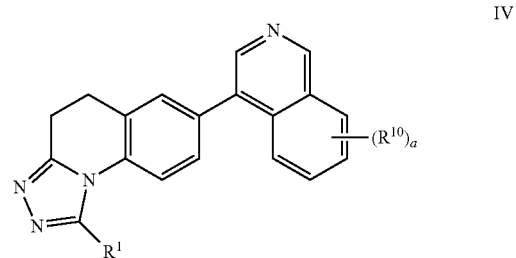

IV wherein R¹ and R¹⁰ are as defined in Formula I or Formula II and a is 0, 1 or 2 (e.g, where a is 0 or where a is 1 and R¹⁰ is alkyl or halo).

Another embodiment of the present invention is compounds or their pharmaceutically acceptable salts of Formula I represented by structural Formula V:

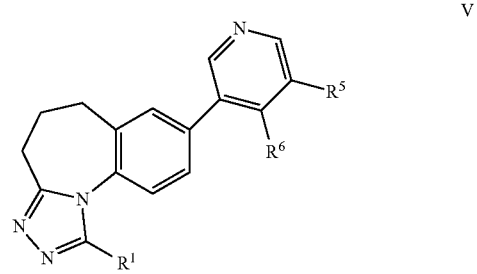

V wherein R¹, R⁵ and R⁶ are as defined in Formula I or Formula II.

Another embodiment of the present invention is compounds or their pharmaceutically acceptable salts of Formula I represented by structural formula VI

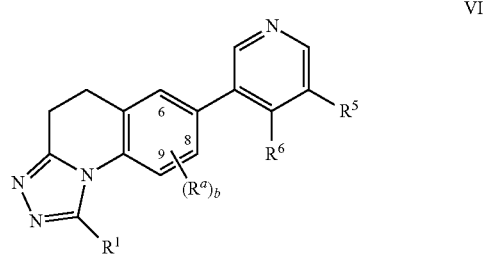

VI wherein R¹, R⁵ and R⁶ are as defined in Formula I, Rᵃ is at the 6-, 8-, and/or 9-positions and is independently halogen (e.g., —F or —Cl), —CN, alkyl (e.g., methyl or ethyl) or cycloalkyl (e.g., cyclopropyl) and b is 1, 2 or 3 (e.g., 1 or 2).

Another embodiment of the present invention is compounds or their pharmaceutically acceptable salts of Formula I represented by structural formula VII

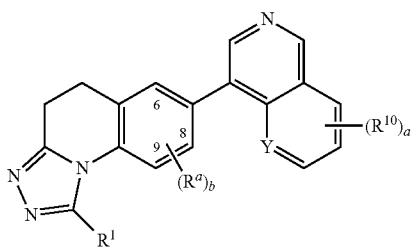

VII wherein $R^1$ is as defined in Formula I, $R^a$ is at the 6-, 8-, and/or 9-positions and is independently halogen (e.g., —F or —Cl), —CN, alkyl (e.g., methyl or ethyl) or cycloalkyl (e.g., cyclopropyl), $R^{10}$ is alkyl or halo, Y is N or CH; a is 0 or 1 and b is 1, 2 or 3 (e.g., 1 or 2).

Another embodiment of the present invention is compounds or their pharmaceutically acceptable salts of Formula I represented by structural formula VI

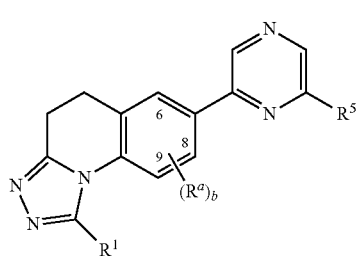

VIII wherein $R^1$ and $R^5$ are as defined in Formula I, $R^a$ is at the 6-, 8-, and/or 9-positions and is independently halogen (e.g., —F or —Cl), —CN, alkyl (e.g., methyl or ethyl) or cycloalkyl (e.g., cyclopropyl) and h is 1, 2 or 3 (e.g., 1 or 2).

Another embodiment of the present invention is compounds or their pharmaceutically acceptable salts of Formula I represented by structural formula IX

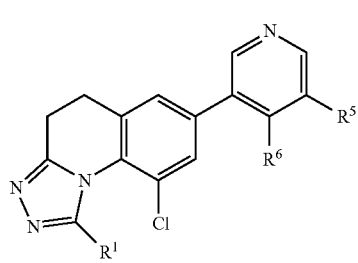

IX wherein $R^1$, $R^5$ and $R^6$ are as defined in Formula I.

Another embodiment of the present invention is compounds or their pharmaceutically acceptable salts of Formula I represented by structural formula X

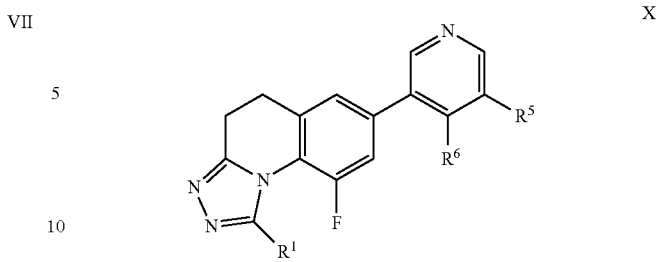

X wherein $R^1$, $R^5$ and $R^6$ are as defined in Formula I.

Another embodiment of the present invention are compounds or their pharmaceutically acceptable salts of Formulae I, II, III, IV, V, VI, VII, VIII, IX or X wherein $R^1$ is H, alkyl (e.g., methyl, ethyl, n-propyl, i-propyl, n-butyl, iso-butyl, see-butyl, tert-butyl), haloalkyl (e.g., —CF$_3$), cycloalkyl (e.g., cyclopropyl or cyclohexyl), phenyl, halo-substituted phenyl, alkyl-substituted (e.g., methyl or ethyl)-substituted phenyl, heteroaryl, alkyl-substituted or cyclopropyl-substituted heteroaryl (where heteroaryl is. e.g., pyridyl, pyrazinyl, furanyl, thienyl, pyrimidinyl, pyridone, isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl, and 7-azaindolyl (with isoxazolyl, isothiazolyl, oxazolyl, thiazolyl, triazole, pyrazolyl, oxadiazolyl, tetrazolyl more preferred) or heterocycloalkyl (e.g., piperidyl, pyrrolidinyl, piperazinyl, morpholinyl, thiomorpholinyl, thiazolidinyl, 1,3-dioxanyl, 1,4-dioxanyl, tetrahydrofuranyl, tetrahydrothiopyranyl, oxetanyl, azetidinyl and tetrahydrothiophenyl.

Another embodiment of the present invention is any of the embodiments of Formulae I, II, III, IV, V, VI, VII, VIII, IX or X described above wherein $R^1$ is H or alkyl (e.g., methyl).

Another embodiment of the present invention is any of the embodiments of Formulae I, II, III, V, VI, VIII, IX or X described above or their pharmaceutically acceptable salts thereof wherein $R^6$ is H and $R^5$ is H, —C(O)O$R^7$ (e.g., $R^7$ is $C_1$-$C_4$-alkyl or phenyl), —S(O)$_2R^7$ (e.g., $R^7$ is $C_1$-$C_4$-alkyl or phenyl), or oxetanyl.

Another embodiment of the present invention is any of the embodiments of Formulae 1, II, III, V, VI, VIII, IX or X wherein $R^5$ is H, halogen, alkyl, haloalkyl, N($R^{11}$)SO$_2R^7$ or —C(O)$R^7$ (e.g., $R^7$ is in each case $C_1$-$C_4$-alkyl or phenyl) and $R^6$ is H, alkyl or cycloalkyl.

Another embodiment of the present inventions are any of the embodiments of Formula I, II, III, V, VI, VIII, IX or X described above or their pharmaceutically acceptable salts thereof wherein
$R^5$ is a group of the formulae:

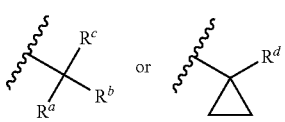

where:
$R^a$ is —$C_1$-$C_4$-alkyl optionally substituted with 1 to 3 —F (e.g. —CF$_3$);
$R^b$ is halogen, —OH, or —$C_1$-$C_4$-alkyl optionally substituted with 1 to 3 —F (e.g. —CF$_3$);

$R^c$ is halogen, —OH, —$C_1$-$C_4$-alkyl substituted with 1 to 3 —F (e.g. —$CF_3$) or —O—$C_1$-$C_4$-alkyl substituted with 1 to 3 —F (e.g. —$OCF_3$), —O—$C_1$-$C_4$-alkyl optionally substituted with 1 to 3 —F (e.g. —$OCF_3$), —C(O)O—$C_1$-$C_4$-alkyl, —S(O)$_2$—$C_1$-$C_4$-alkyl, —C(O)N($C_1$-$C_4$-alkyl)(cyclopropyl or heteroaryl, which is optionally substituted by $C_1$-$C_4$alkyl, phenyl, $C_1$-$C_4$-alkyl substituted with 1 to 3 —F (e.g. —$CF_3$) or cyclopropyl, and the heteroaryl ring is triazole or oxadiazole; and $R^d$ is —$C_1$-$C_4$-alkyl, —C(O)O—$C_1$-$C_3$-alkyl, —S(O)$_2$—$C_1$-$C_3$-alkyl, or heteroaryl, which is optionally substituted by $C_1$-$C_4$alkyl, phenyl, $C_1$-$C_4$-alkyl substituted with 1 to 3 —F (e.g. —$CF_3$) or cyclopropyl, and the heteroaryl ring is triazole or oxadiazole; and $R^6$ is H or alkyl.

Another embodiment of the present inventions are any of the embodiments of Formula I, II, III, V or IV described above or their pharmaceutically acceptable salts thereof wherein $R^6$ is H and $R^5$ is a group of the formulae:

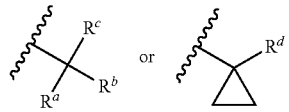

where:
$R^a$ is —$C_1$-$C_3$-alkyl optionally substituted with 1 to 3 —F (e.g. —$CF_3$);

$R^b$ is —OH, or —$C_1$-$C_3$-alkyl optionally substituted with 1 to 3 —F (e.g. —$CF_3$);

$R^c$ is —OH, —$C_1$-$C_3$-alkyl substituted with 1 to 3 —F (e.g. —$CF_3$) or —O—$C_1$-$C_3$-alkyl substituted with 1 to 3 —F (e.g. —$OCF_3$), —O—$C_1$-$C_3$-alkyl optionally substituted with 1 to 3 —F (e.g. —$OCF_3$), —C(O)O—$C_1$-$C_3$-alkyl, —S(O)$_2$—$C_1$-$C_3$-alkyl, —C(O)N($C_1$-$C_3$-alkyl)($C_1$-$C_3$-alkyl) or heteroaryl, which is optionally substituted by $C_1$-$C_3$alkyl, phenyl, $C_1$-$C_3$-alkyl substituted with 1 to 3 —F (e.g. —$CF_3$) or cyclopropyl, and the heteroaryl ring is triazole or oxadiazole; and $R^d$ is —$C_1$-$C_3$-alkyl, —C(O)O—$C_1$-$C_3$-alkyl, —S(O)$_2$—$C_1$-$C_3$-alkyl, or heteroaryl, which is optionally substituted by $C_1$-$C_3$alkyl, phenyl, $C_1$-$C_3$-alkyl substituted with 1 to 3 —F (e.g. —$CF_3$) or cyclopropyl, and the heteroaryl ring is triazole or oxadiazole.

Another embodiment of this invention is a compound of Formulae VI, VII or VIII or a pharmaceutically acceptable salt thereof in any of the embodiments above wherein b is 1 and $R^a$ is substituted on the 6-position.

Another embodiment of this invention is a compound of Formulae VI, VII or VIII or a pharmaceutically acceptable salt thereof in any of the embodiments above wherein b is 1 and $R^a$ is substituted on the 8-position.

Another embodiment of this invention is a compound of Formulae VI, VII or VIII or a pharmaceutically acceptable salt thereof in any of the embodiments above wherein b is 1 $R^a$ is substituted on the 9-position.

Another embodiment of this invention is a compound of Formulae VI, VII or VIII or a pharmaceutically acceptable salt thereof in any of the embodiments above wherein b is 2 and $R^a$ is substituted on the 6- and 8-positions.

Another embodiment of this invention is a compound of Formulae VI, VII or VIII or a pharmaceutically acceptable salt thereof in any of the embodiments above wherein b is 2 and $R^a$ is substituted on the 6- and 9-positions.

Another embodiment of this invention is a compound of Formulae VI, VII or VIII or a pharmaceutically acceptable salt thereof in any of the embodiments above wherein b is 2 and $R^a$ is substituted on the 8- and 9-positions.

Another embodiment of this invention is a compound of Formulae VI, VIII, IX or X or a pharmaceutically acceptable salt thereof in any of the embodiment above wherein and $R^5$ is hydrogen, halogen, —CN, alkyl, haloalkyl, cycloalkyl, hydroxy-substituted alkyl, hydroxy substituted-haloalkyl, alkoxy, haloalkoxy, phenyl, —C(O)$R^7$ or —N(H)SO$_2$$R^7$, where $R^7$ is alkyl or phenyl, and $R^6$ is hydrogen, —CN, alkyl, haloalkyl, cycloalkyl, cyano, hydroxy-substituted alkyl, alkoxy, haloalkoxy or —C(O)$R^7$, where $R^7$ is alkyl or phenyl.

Another embodiment of this invention are the compounds of Formulae VI or VII or their pharmaceutically acceptable salts wherein the following compounds are excluded: 9-fluoro-7-(5-fluoro-pyridin-3-yl)-1-methyl-4,5-dihydro-[1,2,4]triazolo[4,3-a]quinoline; 9-fluoro-7-(5-methoxy-pyridin-3-yl)-1-methyl-4,5-dihydro-[1,2,4]triazolo[4,3-a]quinoline; 1-[5-(9-fluoro-1-methyl-4,5-dihydro-[1,2,4]triazolo[4,3-a]quinolin-7-yl)-pyridin-3-yl]-ethanol; 1-[5-(9-fluoro-1-methyl-4,5-dihydro-[1,2,4]triazolo[4,3-a]quinolin-7-yl)-pyridin-3-yl]-ethanone; 9-fluoro-1-methyl-7-(5-trifluoromethyl-pyridin-3-yl)-4,5-dihydro-[1,2,4]triazolo[4,3-a]quinoline; 9-fluoro-1-methyl-7-(5-phenyl-pyridin-3-yl)-4,5-dihydro-[1,2,4]triazolo[4,3-a]quinoline; 9-fluoro-1-methyl-7-(4-methyl-pyridin-3-yl)-4,5-dihydro-[1,2,4]triazolo[4,3-a]quinoline 9-fluoro-7-isoquinolin-4-yl-1-methyl-4,5-dihydro-[1,2,4]triazolo[4,3-a]quinoline; and 9-fluoro-1-methyl-7-pyridin-3-yl-4,5-dihydro-[1,2,4]triazolo[4,3-a]quinoline; 9-fluoro-7-pyridin-3-yl-4,5-dihydro-[1,2,4]triazolo[4,3-a]quinoline; 8-fluoro-1-methyl-7-pyridin-3-yl-4,5-dihydro-[1,2,4]triazolo[4,3-a]quinoline; or 8-fluoro-7-pyridin-3-yl-4,5-dihydro-[1,2,4]triazolo[4,3-a]quinoline.

As used above, and throughout this disclosure, the following terms, unless otherwise indicated, shall be understood to have the following meanings:

"Patient" includes both human and animals.

"Mammal" means humans and other mammalian animals.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched.

"Halo" refers to fluorine, chlorine, bromine or iodine radicals. Preferred are fluoro, chloro or bromo, and more preferred are fluoro and chloro.

"Halogen" means fluorine, chlorine, bromine, or iodine. Preferred are fluorine, chlorine and bromine.

"Haloalkyl" means a halo-alkyl-group in which the alkyl group is as previously described. The bond to the parent moiety is through the alkyl. Non-limiting examples of suitable haloalkyl groups include fluoromethyl, difluoromethyl, —$CH_2CF_3$, —$CH_2CHF_2$—$CH_2CH_2F$, or an alkyl group with one or more terminal carbons tri-substituted with a halogen (e.g., —F) such as, for example —C$_1$-C$_3$alkyl-CF3, —CH(CH$_3$)(CF$_3$), —CH(CF$_3$)$_2$ and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Aryl" means an aromatic monocyclic or multicyclic ring system comprising about 6 to about 14 carbon atoms, preferably about 6 to about 10 carbon atoms. Non-limiting examples of suitable aryl groups include phenyl, naphthyl, indenyl, tetrahydronaphthyl and indanyl.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocycloalkyl root name means that at least a nitrogen, oxygen or sulfur atom respectively is present as a ring atom. Any —NH in a heterocycloalkyl ring may exist protected such as, for example, as an —N(Boc), —N(CBz), —N(Tos) group and the like; such protections are also considered part of this invention. The nitrogen or sulfur atom of the heterocycloalkyl ring can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,3-dioxanyl, 1,4-dioxanyl, tetrahydrofuranyl, tetrahydrothiopyranyl, oxetanyl, tetrahydrothiophenyl, lactam, lactone, and the like, "Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination, provided that the rings do not include adjacent oxygen and/or sulfur atoms. N-oxides of the ring nitrogens are also included, as well as compounds wherein a ring nitrogen is substituted by an alkyl group to form a quaternary amine. Preferred heteroaryls contain about 5 to about 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, quinoxalinyl, phthalazinyl, oxindolyl, naphthyridyl (e.g., 1, 5 or 1,7), pyrido[2,3]imidazolyl, imidazo[1,2-a]pyridinyl, imidazo[2,1-b]thiazolyl, benzofuranyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl, 7-azaindolyl and the like. The term "heteroaryl" also refers to partially saturated heteroaryl moieties such as, for example, tetrahydroisoquinolyl, tetrahydroquinolyl and the like. All positional isomers are contemplated, e.g., 2-pyridyl, 3-pyridyl and 4-pyridyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

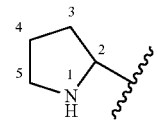

there is no —OH attached directly to carbons marked 2 and 5.

It should also be noted that tautomeric forms such as, for example, the moieties:

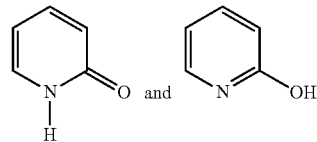 [SMILES: O=c1cccc[nH]1 ; "and" ; Oc1ccccn1]

are considered equivalent in certain embodiments of this invention.

When R$^5$ and R$^6$ are joined together to form a 5-7 membered carbocyclic ring that is fused to the pyridyl ring to which R$^5$ and R$^6$ are attached, "carbocyclic" means a cycloalkyl, aryl or partially unsaturated ring composed of 5-7 carbon atoms wherein two of the carbons are shared between the fused rings. When R$^5$ and R$^6$ are joined together to form a 5-7 membered heterocyclic ring that is fused to the pyridyl ring to which R$^5$ and R$^6$ are attached, "heterocyclic" means a fully statutated, partially saturated or aromatic ring composed of carbon atoms and one, two or three heteroatoms selected form N, S, or O, wherein two of the carbons are shared between the fused rings. Representative ring include:

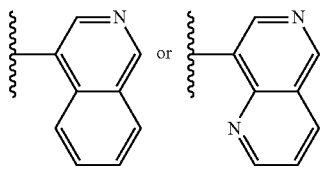

When a moiety can be optionally substituted, it means that each carbon and heteroatom (when present) available for substitution in the given moiety may be independently unsubstituted or substituted with specified number of substituents that are the same or different at each occurrence and which result in the creation of a stable structure as is understood to be reasonable by one skilled in the art.

Unless expressly depicted or described otherwise, variables depicted in a structural formula with a "floating" bond, such as $R^{10}$ in structural Formula IV or VII, are permitted on any available carbon atom in the ring to which each is attached.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of this invention as those of a specific formula or embodiment, e.g., Formula I (which includes the compounds of Formulae II-X all embodiments herein) or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding physiologically or toxicologically acceptable salts, in particular the pharmaceutically utilizable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamidic acid, phenylpropionic acid, gluconic acid, ascorbic acid, isonicotinic acid, citric acid, adipic acid, etc. If the compounds of Formula I simultaneously contain acidic and basic groups in the molecule, the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Compounds of the present invention are effective at inhibiting the synthesis of aldosterone by inhibiting CYP11B2 (aldosterone synthase) and they are therefore useful agents for the therapy and prophylaxis of disorders that are associated with elevated aldosterone levels. Accordingly, an object of the instant invention is to provide a method for inhibiting aldosterone synthase, and more particularly selectively inhibiting CYP11B2, in a patient in need thereof, comprising administering a compound of Formula I to the patient in an amount effective to inhibit aldosterone synthesis, or more particularly to selectively inhibit CYP11B2, in the patient. A selective inhibitor of CYP11B2 is intended to mean a compound that preferentially inhibits CYP11B2 as compared to CYP11B1. The inhibition of CYP11B2, as well inhibition of CYP11B1, by the compounds of Formula I can be examined, for example, in the inhibition assays described below.

In general, compounds that have activity as aldosterone synthase inhibitors can be identified as those compounds which have an $IC_{50}$ of less than or equal to about 10 µM; preferably less than or equal to about 250 nM; and most preferably less than or equal to about 100 nM, in the V79-Human-CYP11B2 Assay described below. In general, aldosterone synthase inhibitors that are selective for inhibition of CYP11B2 as compared to CYP11B1 are those that show at least 3-fold greater inhibition for CYP11B2 compared to CYP11B1; preferably at least 20-fold inhibition for CYP11B2 compared to CYP11B1; and more preferably at least 100-fold greater inhibition for CYP11B2 compared to CYP11B1, in the V79-Human-CYP11B2 Assay as compared to the V79-Human-CYP11B1 Assay.

Due to their ability to inhibit CYP11B2, the compounds of the present invention are useful to treat and/or ameliorate the risk for hypertension, hypokalemia, renal failure (e.g., chronic renal failure), restenosis, Syndrome X, nephropathy, post-myocardial infarction, coronary heart diseases, increased formation of collagen, fibrosis and remodeling following hypertension and endothelial dysfunction, cardiovascular diseases, renal dysfunction, liver diseases, vascular diseases, cerebrovascular diseases, retinopathy, neuropathy, insulinopathy, endothelial dysfunction, heart failure (e.g., congestive heart failure), diastolic heart failure, left ventricle diastolic dysfunction, diastolic heart failure, systolic dysfunction, ischemia, myocardial and vascular fibrosis, myocardial necrotic lesions, vascular damage, myocardial infarction, left ventricular hypertrophy, cardiac lesions, vascular wall hypertrophy, endothelial thickening or necrosis of coronary arteries.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 30 mg/kg, preferably 0.001 to 20 mg/kg, in particular 0.01 to 10 mg/kg (in each case mg per kg of bodyweight) is appropriate for administration to an adult weighing approximately 75 kg in order to obtain the desired results. The daily dose is preferably administered in a single dose or, in particular when larger amounts are administered, can be divided into several, for example two, three or four individual doses, and may be, for example but not limited to, 0.1 mg, 0.25 mg, 0.5 mg, 0.75 mg, 1 mg, 1.25 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose.

The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

In the methods of treatment of this invention, the compound may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of Formula I and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients. Furthermore, a therapeutically effective amount of a compound of this invention can be used for the preparation of a medicament useful for inhibiting aldosterone synthase, inhibiting CYP11B2, for normalizing a disturbed aldosterone balance, or for treating or preventing any of the medical conditions described herein, in dosage amounts described herein.

The amount of active compound of Formula I and its pharmaceutically acceptable salts in the pharmaceutical composition may be, for example but not limited to, from 0.1 to 200 mg, preferably from 0.1 to 50 mg, per dose on a Free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

Since the compounds of Formula I inhibit aldosterone synthase, apart from use as pharmaceutically active compounds in human medicine and veterinary medicine, they can also be employed as a scientific tool or as aid for biochemical investigations in which such an effect on aldosterone synthase and aldosterone levels is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents (or therapeutic agents) may be administered in combination with a compound of Formula I. An additional active agent (or agents) is intended to mean a pharmaceutically active agent (or agents) different from the compound of Formula I. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme (ACE) inhibitors (e.g, alacepril, benazepril, captopril, ceronapril, cilazapril, delapril, enalapril, enalaprilat, fosinopril, imidapril, lisinopril, moexepril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists (e.g., candesartan, eprosartan, irbesartan, losartan, olmesartan, telmisartan, valsartan) neutral endopeptidase inhibitors (e.g., thiorphan and phosphoramidon), aldosterone antagonists, renin inhibitors (e.g. urea derivatives of di- and tri-peptides (See U.S. Pat. No. 5,116, 835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No.

4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4 (S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, bepridil, diltiazem, felodipine, gallopamil, nicardipine, nifedipine, nilu- dipine, nimodipine, nisoldipine veraparmil), potassium channel activators (e.g., nicorandil, pinacidil, cromakalim, minoxidil, aprilkalim, loprazolam), diuretics (e.g., hydrochlorothiazide) including loop diuretics such as ethacrynic acid, furosemide, bumetanide and torsemide, sympatholitics, beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, pravastatin, atorvastatin rosuvastatin, ezetimibe); niacin in immediate-release or controlled release forms, and particularly in niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, stigliptin, metformin, rosiglitazone); or with other drugs beneficial for the prevention or the treatment of the above-mentioned diseases including nitroprusside and diazoxide.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods and one skilled in the art would have resources such as *Chemical Abstracts* or *Beilstein* at his or her disposal to assist in devising an alternative method of preparing a specific compound.

The compounds of the present invention can be prepared according to the procedures of the following Schemes using appropriate materials and are further exemplified by the specific Examples which follow. Moreover, by utilizing the procedures described herein, one of ordinary skill in the art can readily prepare additional compounds of the present invention claimed herein.

Throughout the synthetic schemes, abbreviations are used with the following meanings unless otherwise indicated:
AIBN=2,2'-azabisisobutyronitrile; Ac=acetate; aq, Ar=aryl; BOC, Boc t-butyloxycarbonyl; BSA=bovine serum albumin; Bu=butyl, t-Bu=tert-butyl; BuLi, n-BuLi=n-butyllithium; CBZ, Cbz=Benzyloxycarbonyl; conc, conc.=concentrated; c-Pr=cyclopropyl; Cy=cyclohexyl; dba=dibenzylideneacetone; DCM=dichloromethane; Dess Martin Periodinane, DMP=1,1,1-tris(acetyloxy)-1,1-dihydro-1,2-benziodoxol-3-(1H)-one; DIBAL, DIBAL-H=diisobutylaluminum hydride; DIPEA=N,N-Diisopropylethylamine; DMEM=Dulbecco's modified eagle medium; DMF=N,N-dimethylformamide; DMSO=dimethylsulfoxide; eq.=equivalent(s); EDC=N-[3-(dimethylamino)propyl]-N-ethylcarbodiimide; EDTA=ethylenediaminetetraacetic acid; Et=ethyl; EtOAc=ethyl acetate; EtOH=ethanol; FBS=Fetal Bovine Serum; h, hr=hour; HATU=N-[(dimethylamino)-1H-1,2,3-triazolo[4,5-b]pyridin-1-ylmethylene]-N-methylmethanaminium hexafluorophosphate N-oxide; HPLC=High pressure liquid chromatography; HTRF=homogenous time resolved fluorescence; IPA, i-PrOH=isopropanol; i-Pr=isopropyl; LAH=Lithium aluminum hydride; Lawesson's Reagent=2,4-bis(4-methoxyphenyl)-1,3,2,4-dithiadiphosphetane 2,4-disulfide; LCMS=liquid chromatography–mass spectroscopy; Me=methyl; MeOH=methanol; min, min.=minute; μW=microwave; Ms=methanesulfonyl; NaHMDS=sodium hexamethyldisilazide; NBS=N-bromosuccinimide; NMR=nuclear magnetic resonance; OMs, mesyl=methanesulfonyl; Oxone, OXONE®=potassium peroxymonosulfate; PBS=phosphate buffered saline; PdCl$_2$(dppf)=dichloro[1,1'-bis(diphenylphosphino) ferrocene]palladium(II); Pd$_2$(dba)$_3$=tris(dibenzylidineacetone) dipalladium; Pd/C=palladium on activated carbon; Ph=phenyl; PPA=polyphosphoric acid; Pr=propyl; Py=pyridyl; PyBOP=(benzotriazol-1-yloxy)tripyrrolidinophosphonium hexafluorophosphate; RT, rt=room temperature; sat.=saturated; TBAF=tetrabutylammonium fluoride; TEA=triethylamine; THF=tetrahydrofuran; triflate, OTf=trifluoromethanseulfonate; and TMS=trimethylsilane.

Fused triazoles are known in the literature, and may be prepared by a variety of methods by those skilled in the art. One such method, shown in Scheme 1, involves initial Suzuki coupling of a benzolactam halide such as 1 with a pyridyl boronic acid or ester such as 2. Such couplings may be effected in a variety of ways, for instance by heating 1 and 2 in the presence of a base such as potassium carbonate and a catalyst such as bis(di-tert-butyl(4-dimethylaminophenyl) phosphine)dichloropalladium(II) 3 ("catalyst 3") in a mixed solvent system such as 2-methylpropan-2-ol and water to provide coupled product 4. Heating of 4 in the presence of 2,4-bis(4-methoxyphenyl)-1,3,2,4-dithiadiphosphetane 2,4-dioxide (Lawesson's reagent) in a solvent such as toluene may then effect conversion of lactam 4 to thiolactam 5. Reaction of 5 with a hydrazide at elevated temperature in a solvent such as cyclohexanol may then provide fused triazole product 6.

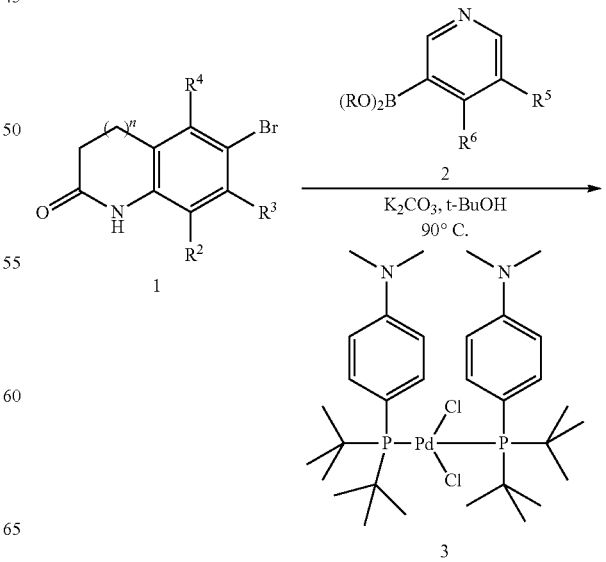

Scheme 1

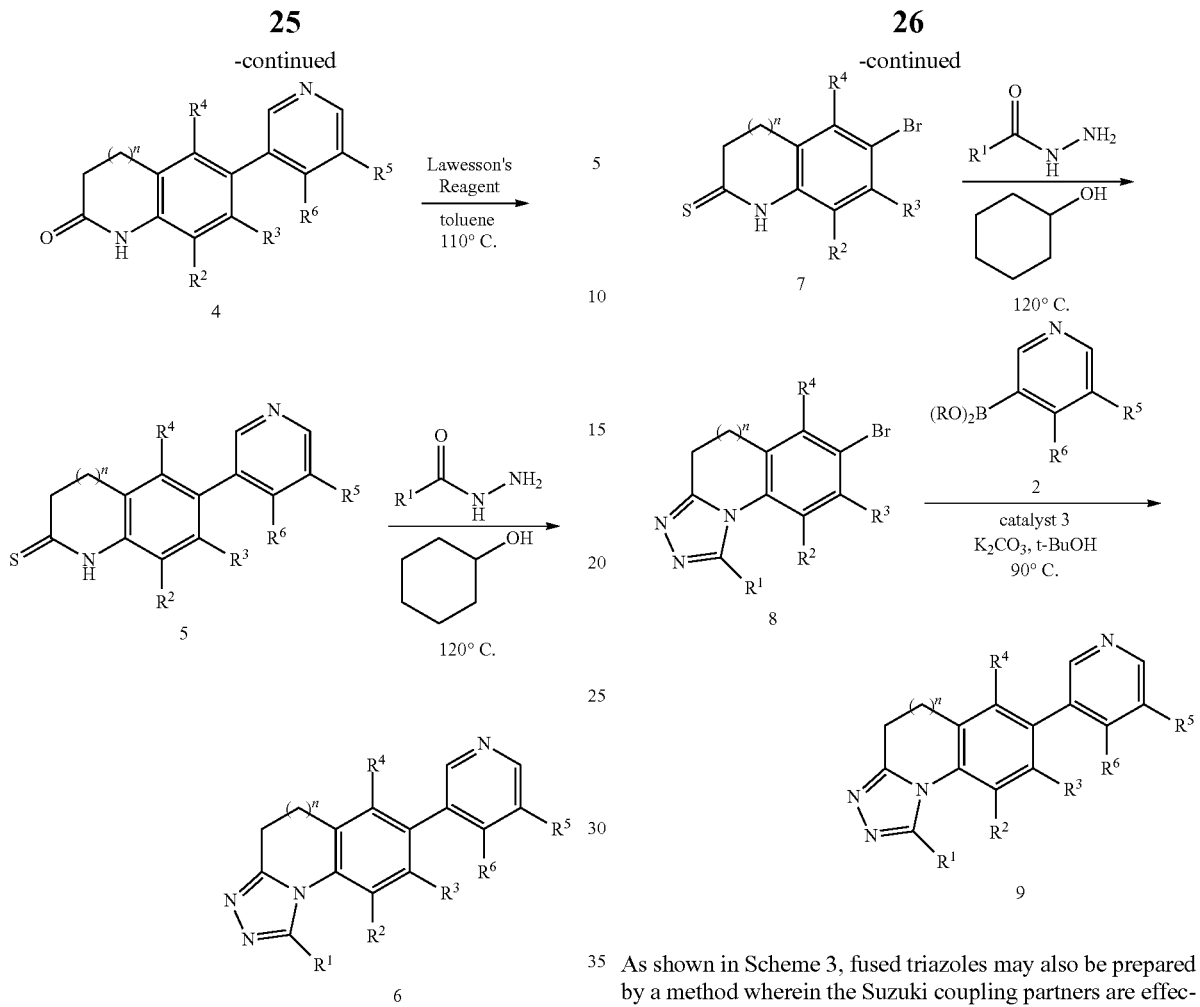

An alternative method for the preparation of fused triazoles is outlined in Scheme 2. In this approach, benzolactam 1 is initially treated with 2,4-bis(4-methoxyphenyl)-1,3,2,4-dithiadiphosphetane 2,4-dioxide (Lawesson's reagent) in a solvent such as toluene to yield thiolactam 7. Heating of 7 and a hydrazide in a solvent such as cyclohexanol then effects conversion of the thiolactam to triazole 8. Suzuki coupling of 8 with a pyridyl boronic acid or ester such as 2 under the same conditions used for the conversion of 1 to 4 above may then provide fused triazole 6. The pyridyl boronic acids and esters employed in these couplings may be obtained commercially, or may be synthesized according to procedures outlined in Schemes 8, 11-15, and 19-21.

As shown in Scheme 3, fused triazoles may also be prepared by a method wherein the Suzuki coupling partners are effectively 'reversed'. Thus, heating of bromide 8 and 4,4,4',4',5,5,5',5'-octamethyl-2,2'-bi-1,3,2-dioxaborolane in the presence of a catalyst such as tris(dibenzylideneacetone)dipalladium (0), a ligand such as tricyclohexylphosphine, and a base such as potassium acetate in a solvent such as 1,4-dioxane can provide boronate ester 9. Ester 9 may then be coupled with pyridyl bromide 10 by heating in the presence of a catalyst such as tetrakis(triphenylphosphine)palladium (0) and a base such as $K_3PO_4$ in a mixed solvent system such as acetonitrile and water to afford fused triazole 6. Alternatively, compounds 9 and 10 may be coupled by heating in the presence of catalyst 3 and a base such as potassium carbonate in a mixed solvent system such as 2-methylpropan-2-ol and water. The pyridyl bromides 10 employed in these reactions may be obtained commercially, or may be synthesized according to procedures outlined in Schemes 4 and 5.

Scheme 2

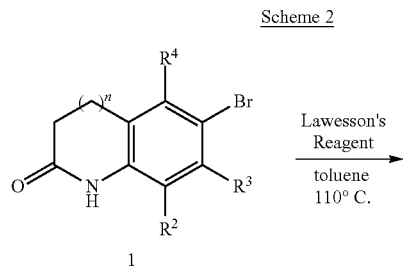

Scheme 3

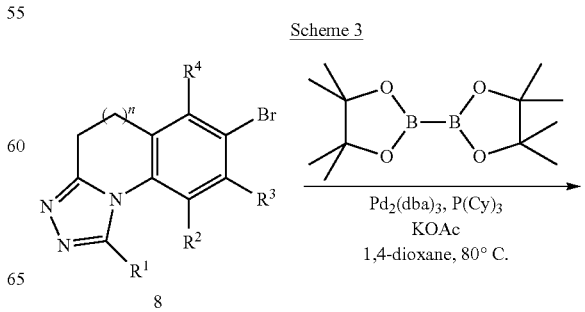

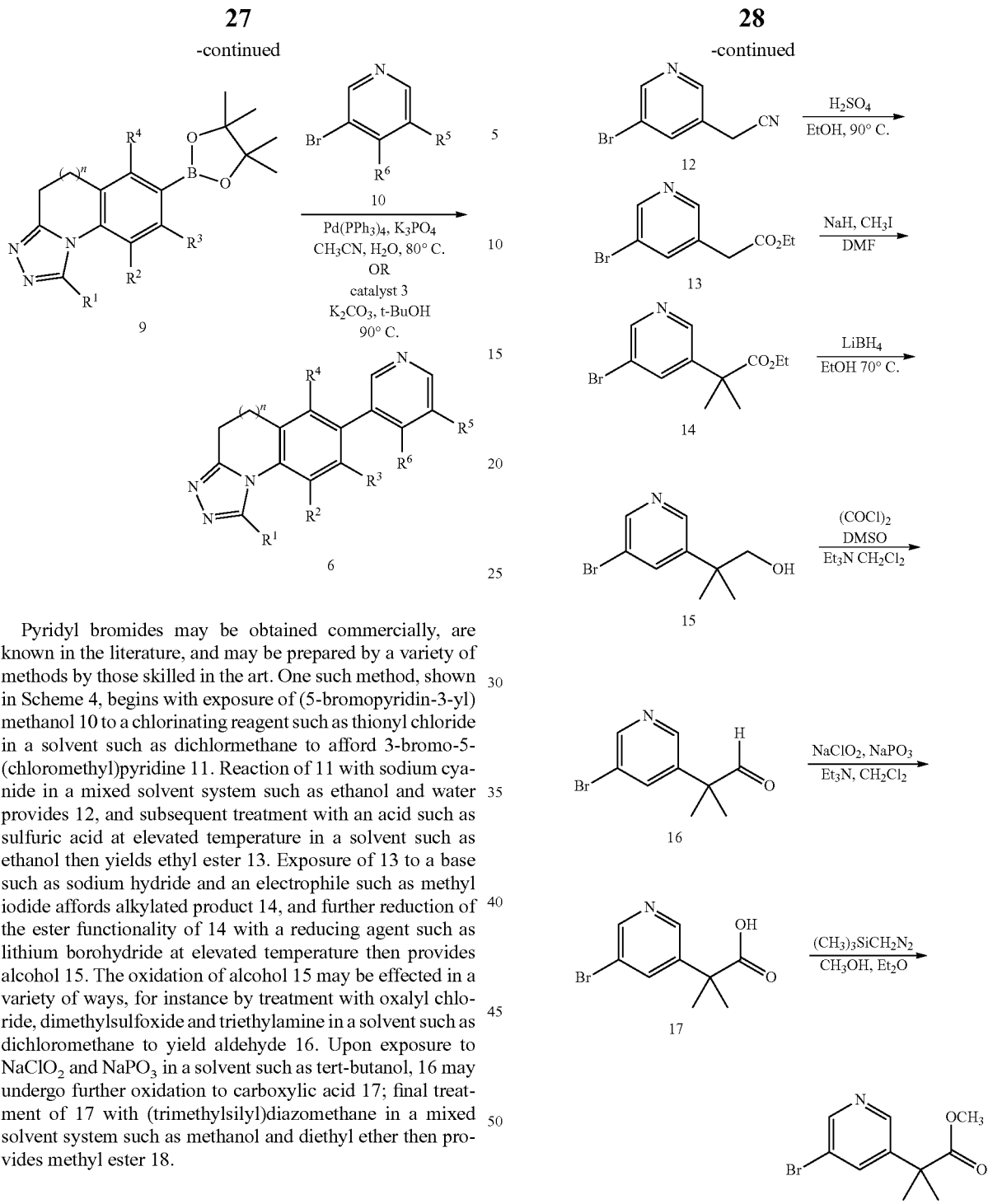

Pyridyl bromides may be obtained commercially, are known in the literature, and may be prepared by a variety of methods by those skilled in the art. One such method, shown in Scheme 4, begins with exposure of (5-bromopyridin-3-yl) methanol 10 to a chlorinating reagent such as thionyl chloride in a solvent such as dichlormethane to afford 3-bromo-5-(chloromethyl)pyridine 11. Reaction of 11 with sodium cyanide in a mixed solvent system such as ethanol and water provides 12, and subsequent treatment with an acid such as sulfuric acid at elevated temperature in a solvent such as ethanol then yields ethyl ester 13. Exposure of 13 to a base such as sodium hydride and an electrophile such as methyl iodide affords alkylated product 14, and further reduction of the ester functionality of 14 with a reducing agent such as lithium borohydride at elevated temperature then provides alcohol 15. The oxidation of alcohol 15 may be effected in a variety of ways, for instance by treatment with oxalyl chloride, dimethylsulfoxide and triethylamine in a solvent such as dichloromethane to yield aldehyde 16. Upon exposure to NaClO$_2$ and NaPO$_3$ in a solvent such as tert-butanol, 16 may undergo further oxidation to carboxylic acid 17; final treatment of 17 with (trimethylsilyl)diazomethane in a mixed solvent system such as methanol and diethyl ether then provides methyl ester 18.

Scheme 4

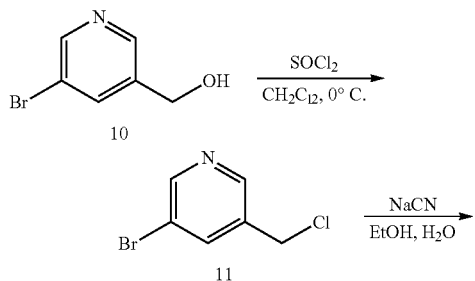

Fused triazoles bearing amide sidechains may be prepared as shown in Scheme 5. Boronate ester 9 and pyridyl bromide 17 may be coupled in a variety of ways, for instance by heating in the presence of a catalyst such as tetrakis(triphenylphosphine)-palladium (0) and a base such as K$_3$PO$_4$ in a mixed solvent system such as acetonitrile and water to afford 19. Upon exposure to O-(7-azabenzotriazol-1-yl)-N,N,N'N'-tetramethyluronium hexafluorophosphate (HATU) and diisopropylethylamine, carboxylic acid 19 may undergo coupling with a primary or secondary amine to afford amide 20.

Scheme 5

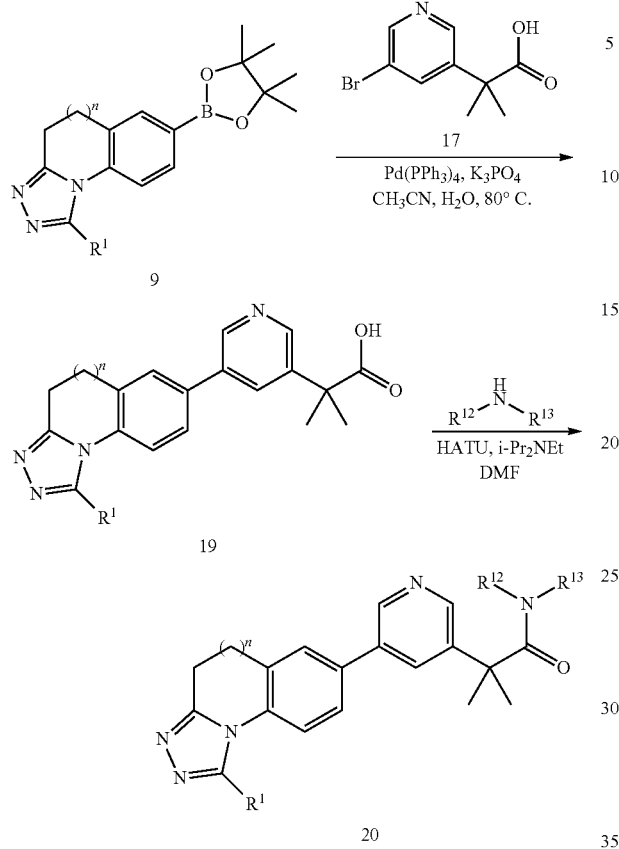

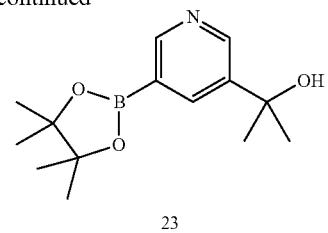

Pyridyl boronate esters may be obtained commercially, are known in the literature, and may be prepared by a variety of methods by those skilled in the art. One such method, shown in Scheme 6, begins with treatment of 3,5-dibromopyridine 21 with n-butyllithium and acetone in a solvent such as toluene at low temperature to provide 22. Heating of bromide 22 and 4,4,4',4',5,5,5',5'-octamethyl-2,2'-bi-1,3,2-dioxaborolane in the presence of a catalyst such as dichloro[1,1'-bis(diphenylphosphino)ferrocene]palladium (II) and a base such as potassium acetate in a solvent such as 1,4-dioxane then affords boronate ester 23.

Scheme 6

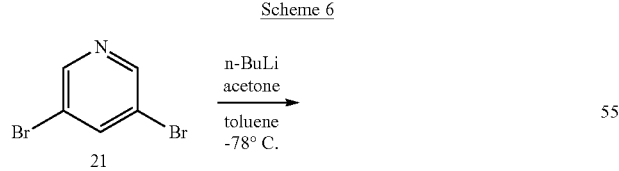

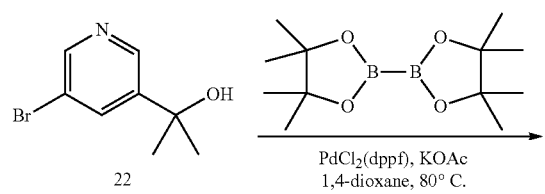

Triazoles bearing alcohol or ether sidechains may be prepared as shown in Scheme 7. Triazole bromide 8 and boronate ester 23 may be coupled in a variety of ways, for instance by heating in the presence of a catalyst such as 3 and a base such as potassium carbonate in a mixed solvent system such as 2-methylpropan-2-ol and water to afford 24. Treatment of alcohol 24 with a base such as sodium hydride and an alkyl iodide in a solvent such as tetrahydrofuran or N,N-dimethylformamide then affords ether 25.

Scheme 7

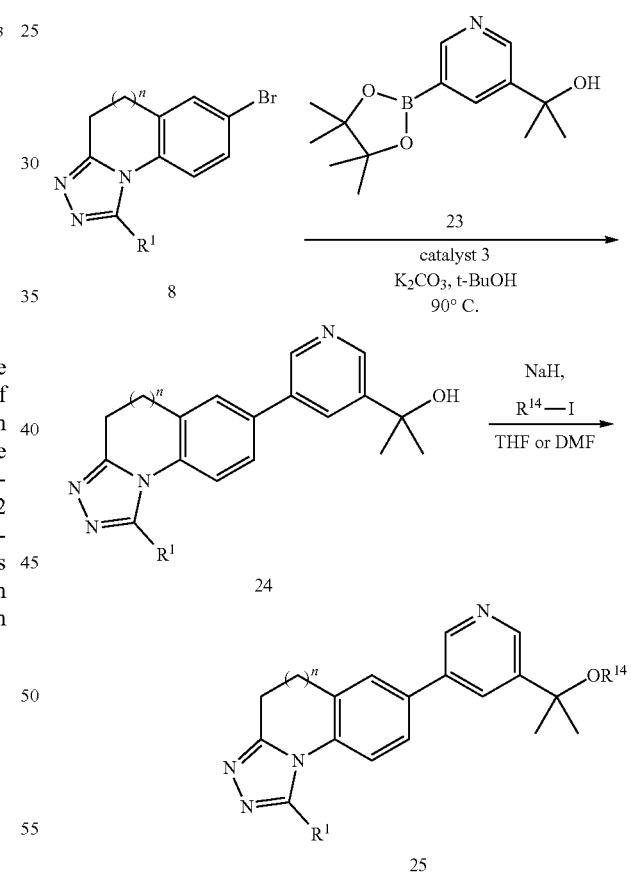

Pyridyl boronic acids may be obtained commercially, are known in the literature, and may be prepared by a variety of methods by those skilled in the art. One such method, shown in Scheme 8, begins with treatment of 1-(5-bromopyridin-3-yl)ethanone 26 with (trifluoromethyl)trimethylsilane and tetrabutylammonium fluoride in a solvent such as tetrahydrofuran to provide 27. Heating of bromide 27 and 4,4,4',4',5,5,5',5'-octamethyl-2,2'-bi-1,3,2-dioxaborolane in the presence of a catalyst such as tris(dibenzylideneacetone)dipalladium (0), a ligand such as tricyclohexylphosphine, and a base such as potassium acetate in a solvent such as 1,4-dioxane then affords boronic acid 28.

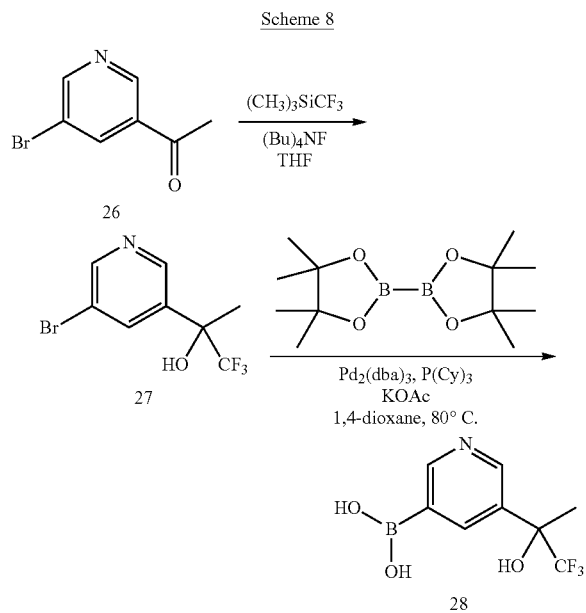

An alternative method for the preparation of pyridyl boronic acids is outlined in Scheme 9. In this approach, treatment of methyl 5-bromopyridine-3-carboxylate 29 with (trifluoromethyl)trimethylsilane and tetrabutylammonium fluoride in a solvent such as tetrahydrofuran provides 30. Heating of bromide 30 and 4,4,4',4',5,5,5',5'-octamethyl-2,2'-bi-1,3,2-dioxaborolane in the presence of a catalyst such as tris(dibenzylideneacetone)dipalladium (0), a ligand such as tricyclohexylphosphine, and a base such as potassium acetate in a solvent such as 1,4-dioxane then affords boronic acid 31.

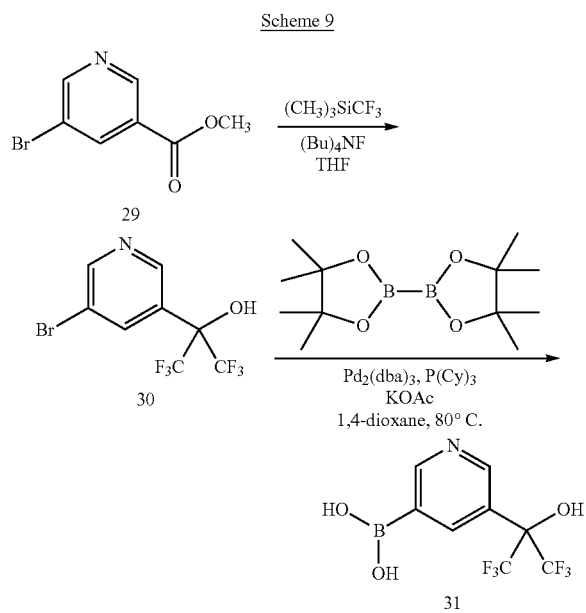

A method for the preparation of pyridyl boronic acids bearing trifluoromethoxy sidechains is outlined in Scheme 10. Initial treatment of alcohol 15 with a base such as sodium hydride, carbon disulfide, and an alkyl halide such as iodomethane in a solvent such as dimethylformamide provides adduct 32. Exposure of 32 to 1,3-dibromo-5,5-dimethylimidazolidine-2,4-dione 33 and HF-pyridine in a solvent such as dichloromethane at low temperature then affords trifluoromethoxy derivative 34. Heating of 34 and 4,4,4',4',5,5,5',5'-octamethyl-2,2'-bi-1,3,2-dioxaborolane in the presence of a catalyst such as tris(dibenzylideneacetone)dipalladium (0), a ligand such as tricyclohexylphosphine, and a base such as potassium acetate in a solvent such as 1,4-dioxane yields boronic acid 35.

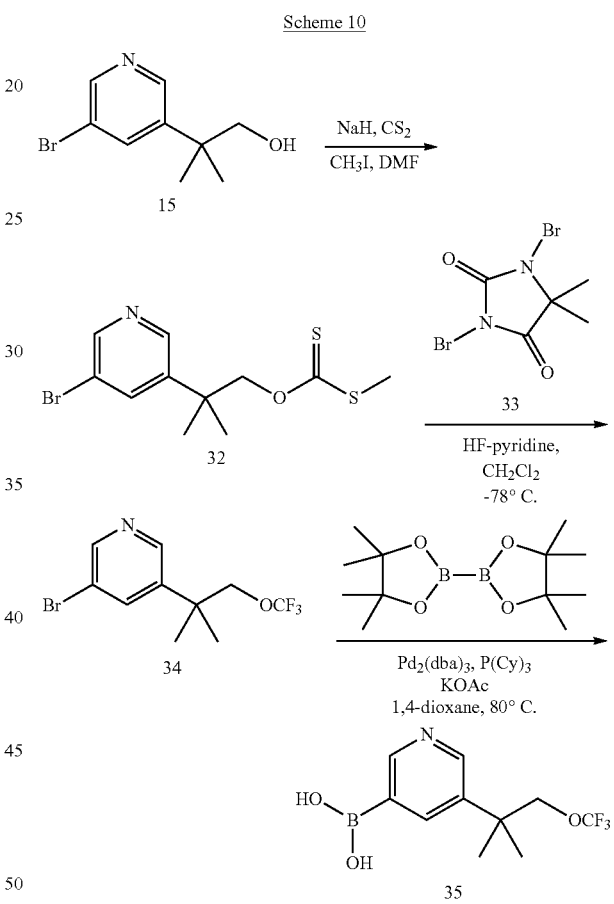

Pyridyl boronic acids bearing cyclopropyl substituents may be synthesized in a variety of ways. One such method, shown in Scheme 11, involves treatment of (5-bromopyridin-3-yl)acetic acid 36 with (trimethylsilyl)diazomethane in a mixed solvent system such as methanol and diethyl ether to yield methyl ester 37. Exposure of 37 to a base such as sodium hydride and 1,2-dibromoethane in a mixed solvent system such as N,N-dimethylformamide and tetrahydrofuran then affords cyclopropyl derivative 38. Heating of 38 and 4,4,4',4',5,5,5',5'-octamethyl-2,2'-bi-1,3,2-dioxaborolane in the presence of a catalyst such as tris(dibenzylideneacetone)dipalladium (0), a ligand such as tricyclohexylphosphine, and a base such as potassium acetate in a solvent such as 1,4-dioxane yields boronic acid 39.

Scheme 11

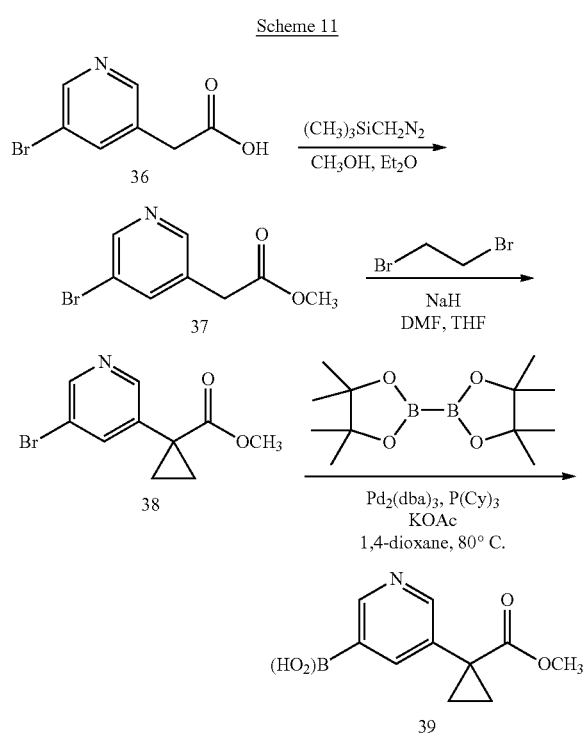

Pyridyl boronic acids bearing oxadiazole substituents may be synthesized as outlined in Scheme 12. In this approach, methyl ester 38 is treated with a base such as aqueous sodium hydroxide in a solvent such as tetrahydrofuran to give carboxylic acid 40. In the presence of an activating agent such as (benzotriazol-1-yloxy)tripyrrolidino phosphonium hexafluorophosphate (PyBOP) and a base such as triethylamine, acid 40 may undergo condensation with a carboximidamide to give an intermediate which, upon heating in a solvent such as toluene, cyclizes to afford oxadiazole 41. Heating of 41 and 4,4,4',4',5,5,5',5'-octamethyl-2,2'-bi-1,3,2-dioxaborolane in the presence of a catalyst such as tris(dibenzylideneacetone)dipalladium (0), a ligand such as tricyclohexylphosphine, and a base such as potassium acetate in a solvent such as 1,4-dioxane then yields boronic acid 42.

Scheme 12

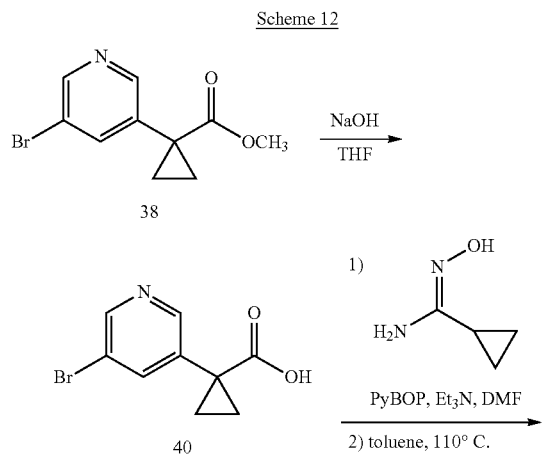

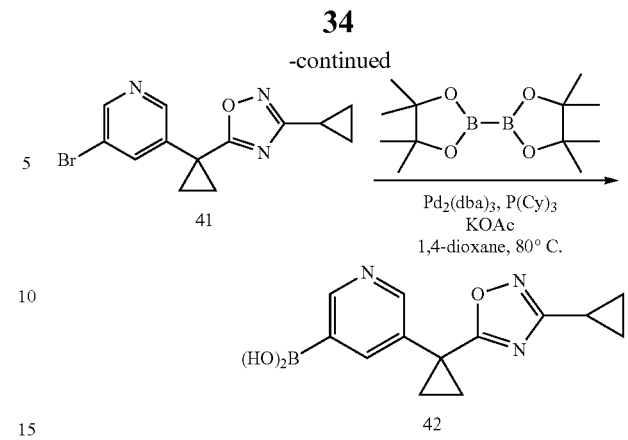

Fused triazoles bearing oxadiazole sidechains may be synthesized by a variety of methods. One such method, outlined in Scheme 13, begins with the heating of aryl bromide 8 and boronic acid 39 in the presence of a catalyst such as 3 and a base such as potassium carbonate to afford coupled product 43. Heating of ester 43, amide oxime 44 (where $R^{14}$ could be a substituent for heteroaryl) and a base such as sodium ethoxide in a solvent such as ethanol then provides oxadiazole 45.

Scheme 13

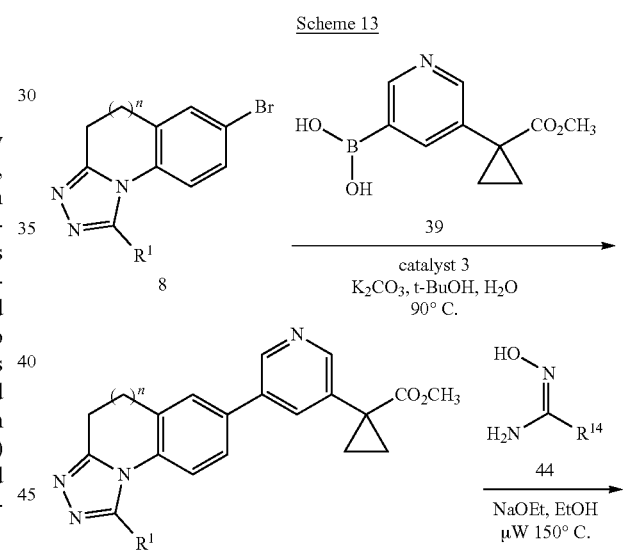

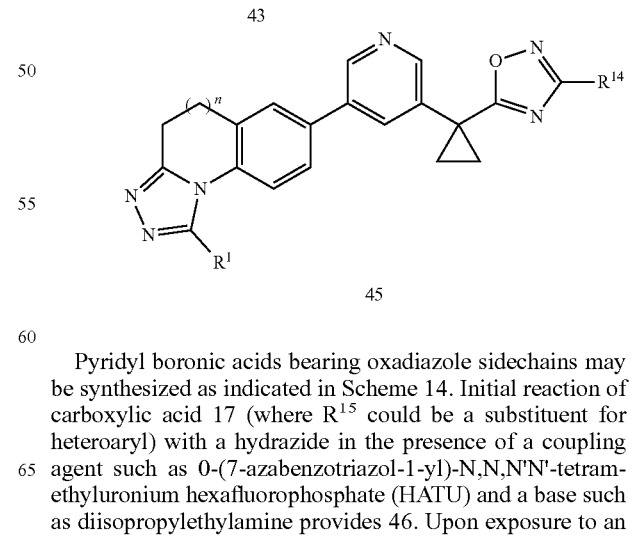

Pyridyl boronic acids bearing oxadiazole sidechains may be synthesized as indicated in Scheme 14. Initial reaction of carboxylic acid 17 (where $R^{15}$ could be a substituent for heteroaryl) with a hydrazide in the presence of a coupling agent such as 0-(7-azabenzotriazol-1-yl)-N,N,N'N'-tetramethyluronium hexafluorophosphate (HATU) and a base such as diisopropylethylamine provides 46. Upon exposure to an activating agent such as POCl₃, 46 may then undergo dehydrative cyclization to afford oxadiazole 47. Heating of 47 and boronic ester 9 in the presence of a catalyst such as 3 and a base such as potassium carbonate in a mixed solvent system such as tert-butanol and water then yields triazole 48.

Scheme 14

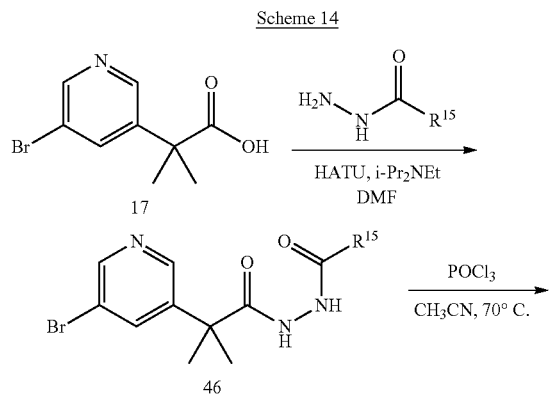

Scheme 15

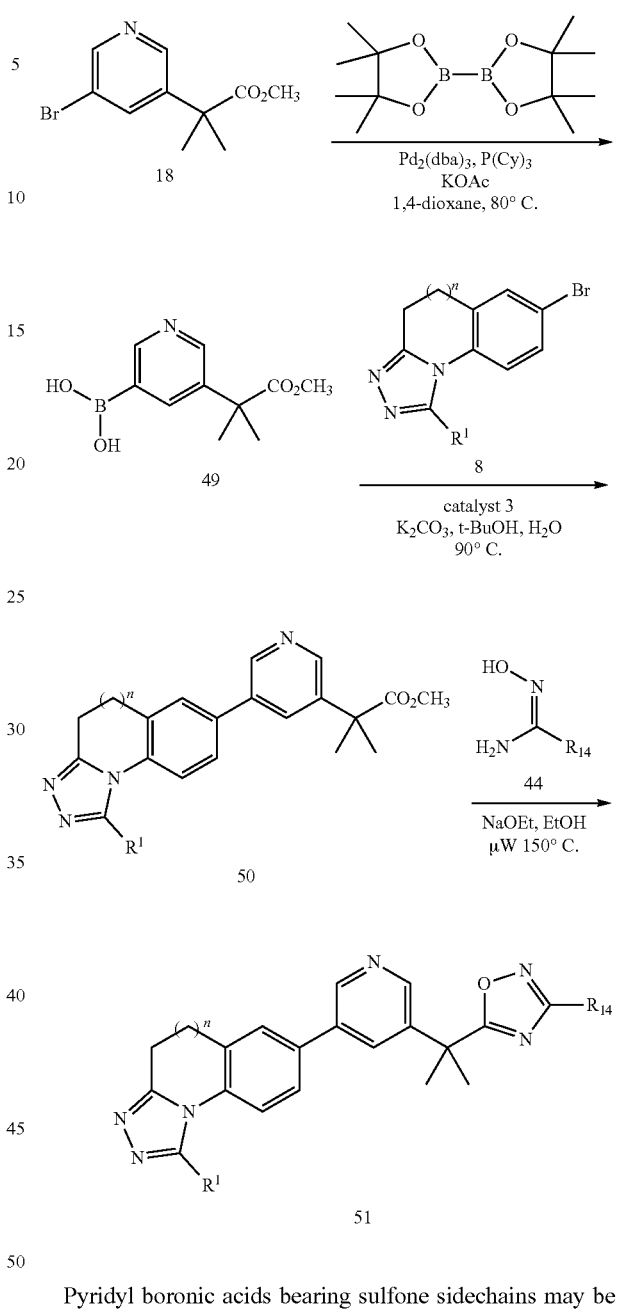

Fused triazoles bearing oxadiazole sidechains may be synthesized by a variety of methods. One such method, outlined in Scheme 15, begins with the heating of aryl bromide 18 and 4,4,4',4',5,5,5',5'-octamethyl-2,2'-bi-1,3,2-dioxaborolane in the presence of a catalyst such as tris(dibenzylideneacetone) dipalladium (0), a ligand such as tricyclohexylphosphine, and a base such as potassium acetate to yield 49. Boronic acid 49 may be coupled to aryl bromide 8 by numerous methods, for instance by heating in the presence of a catalyst such as 3 and a base such as potassium carbonate to afford coupled product 50. Heating of 50, amide oxime 44 and a base such as sodium ethoxide in a solvent such as ethanol then provides oxadiazole 51.

Pyridyl boronic acids bearing sulfone sidechains may be prepared by a variety of methods. As shown in Scheme 16, one such method involves initial treatment of alcohol 10 with a base such as sodium hydride and an activating agent such as methanesulfonyl chloride in a solvent such as tetrahydrofuran to provide mesylate 52. Exposure of 52 to ethanethiol and a base such as sodium hydride yields adduct 53, which upon treatment with an oxidizing agent such as OXONE® is converted to sulfone 54. Exposure of 54 to a base such as potassium tert-butoxide and an alkyl halide such as iodomethane results in alkylation to afford 55. Heating of 55 and 4,4,4',4', 5,5,5',5'-octamethyl-2,2'-bi-1,3,2-dioxaborolane in the presence of a catalyst such as tris(dibenzylideneacetone)dipalladium (0), a ligand such as tricyclohexylphosphine, and a base such as potassium acetate in a solvent such as 1,4-dioxane then yields boronic acid 56.

Scheme 16

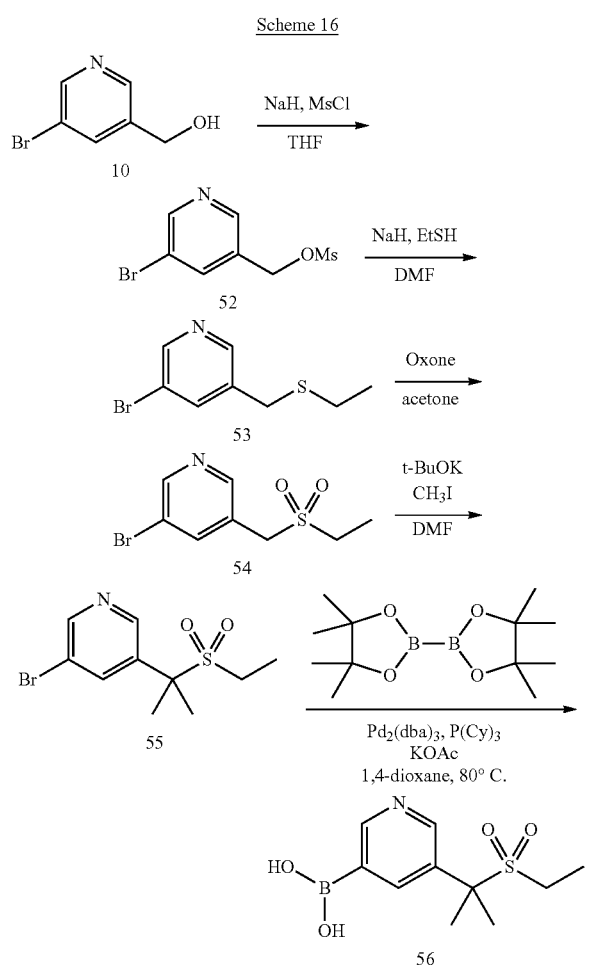

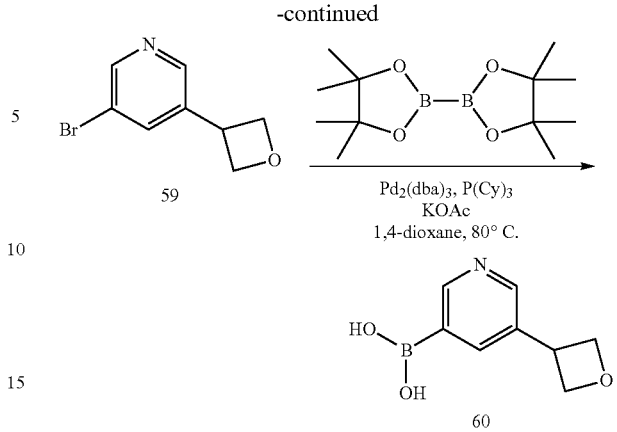

Pyridyl boronic acids substituted with oxetanes may be prepared as shown in Scheme 17. Heating of (5-bromopyridin-3-yl)boronic acid 57 in the presence of a catalyst such as nickel iodide, a base such as sodium bis(trimethylsilyl)amide (NaHMDS), a ligand such as trans-2-aminocyclohexanol 58 and 3-iodooxetane provides coupled product 59. Heating of 59 and 4,4,4',4',5,5,5',5'-octamethyl-2,2'-bi-1,3,2-dioxaborolane in the presence of a catalyst such as tris(dibenzylideneacetone)dipalladium (0), a ligand such as tricyclohexylphosphine, and a base such as potassium acetate in a solvent such as 1,4-dioxane then yields boronic acid 60.

Scheme 17

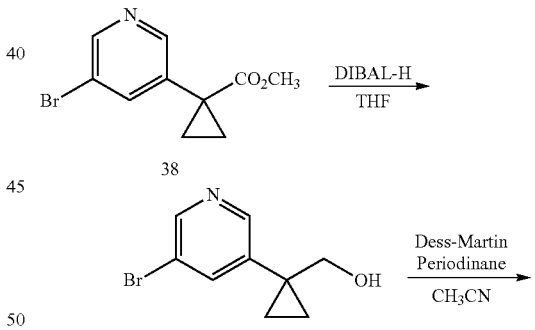

Pyridyl boronic acids substituted with vinylcyclopropanes may be prepared as shown in Scheme 18. Initial treatment of ester 38 with a reducing agent such as lithium aluminum hydride in a solvent such as tetrahydrofuran yields alcohol 61. Alcohol 61 may be subsequently oxidized in a variety of ways, for instance by treatment with Doss-Martin periodinane, to afford aldehyde 62. Exposure of aldehyde 62 to methyltriphenylphosphonium bromide and a base such as sodium amide then effects Wittig olefination to provide vinylcyclopropane 63. Upon heating in the presence of 4,4,4',4',5,5',5'-octamethyl-2,2'-bi-1,3,2-dioxaborolane, a catalyst such as tris(dibenzylideneacetone)dipalladium (0), a ligand such as tricyclohexylphosphine, and a base such as potassium acetate, 63 may then be converted to its boronic acid derivative 64.

Scheme 18

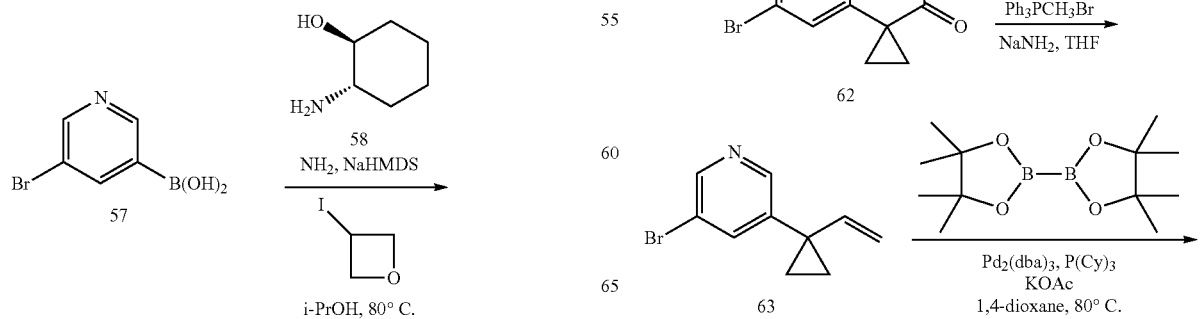

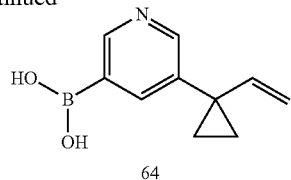

Fused triazoles bearing substituted cyclopropyl sidechains may be prepared by a variety of methods. One such method, outlined in Scheme 19, begins with the heating of aryl bromide 8 and boronic acid 64 in the presence of a catalyst such as 3 and a base such as potassium carbonate to afford coupled product 65. Hydrogenation of 65 in the presence of a catalyst such as rhodium on alumina in a solvent such as ethyl acetate then yields ethylcyclopropyl derivative 66.

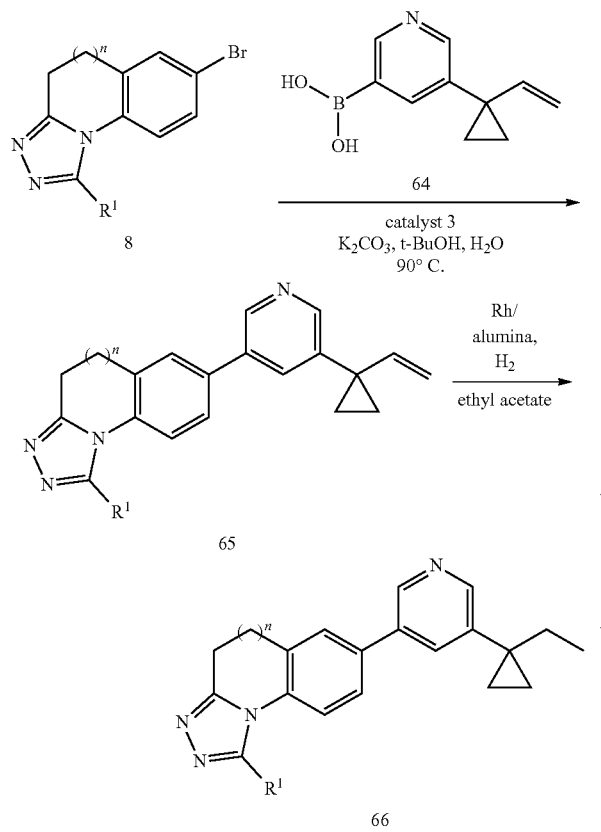

As will be known to those skilled in the art, in all schemes, the products of Formula I and all synthetic intermediates may be purified from unwanted side products, reagents and solvents by recrystallization, trituration, preparative thin layer chomatography, flash chomatography on silica gel as described by W. C. Still et al, J. Org. Chem. 1978, 43, 2923, or reverse-phase HPLC. Compounds purified by HPLC may be isolated as the corresponding salt.

Additionally, in some instances the final compounds of Formula I and synthetic intermediates may be comprised of a mixture of cis and trans isomers, enantiomers or diastereomers. As will be known to those skilled in the art, such cis and trans isomers, enantiomers and diastereomers may be separated by various methods including crystallization, chomatography using a homochiral stationary phase and, in the case of cis/trans isomers and diastereomers, normal-phase and reverse-phase chomatography.

Chemical reactions were monitored by LCMS, and the purity and identity of the reaction products were assayed by LCMS (electrospray ionization) and NMR. Data for $^1$H NMR are reported with chemical shift (δ ppm), multiplicity (s=singlet, d=doublet, t=triplet, q=quartet, m=multiplet, br s=broad singlet, br m=broad multiplet), coupling constant (Hz), and integration. Unless otherwise noted, all LCMS ions listed are [M+H]. All temperatures are degrees Celsius unless otherwise noted In the Examples, some intermediates and final compounds having a chiral carbon were prepared as racemates, and some chiral intermediates were resolved and the enantiomers were used separately to synthesize enantiomeric downstream intermediates and final products. In some cases racemic final products may have been resolved. In the instances where chiral compounds were separated by chiral HPLC purification, the term "enantiomer A" or "ent A" refers to the first eluting enantiomer and the downstream compounds derived from this enantiomer. The term "enantiomer B" or "ent B" refers to the second eluting enantiomer and the downstream compounds derived from this enantiomer. The term "rac" refers to a racemic mixture. As a result, the chemical nomenclature may indicate that an S and/or an R enantiomer were obtained, but the absolute stereochemistry of the separate enantiomers A and/or B was not determined.

The following examples are provided so that the invention might be more fully understood. They should not be construed as forming the only genus that is considered as the invention or limiting the invention in any way.

The following is illustrative of the processes used for making some the intermediates employed in the examples below.

INTERMEDIATE A

Synthesis of 3-bromo-4,5-dimethylpyridine (A)

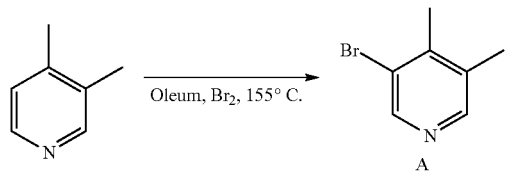

3,4-Dimethylpyridine (20 g, 0.186 mol) was added slowly to ice cold oleum (400 mL) with vigorous stirring. The solution was heated to 155° C. and bromine (12.2 mL, 0.223 mol) was added drop wise very slowly. The reaction mass was heated at 155° C. for 24 h. After cooling to room temperature, the mixture was carefully poured into ice water and basified using 10% aqueous sodium hydroxide solution. The compound was then extracted with ethyl acetate (2×500 mL). The organic solution was dried over sodium sulphate and evaporated to yield oil which was purified by column chromatography (20% ethyl acetate/hexane) to obtain the title compound. $^1$H NMR (400 MHz, CDCl$_3$) δ 8.49 (s, 1H), 8.22 (s, 1H), 2.36 (s, 3H), 2.30 (s, 3H).

INTERMEDIATE B

Synthesis of 3-bromo-5-methoxy-4-methylpyridine (B)

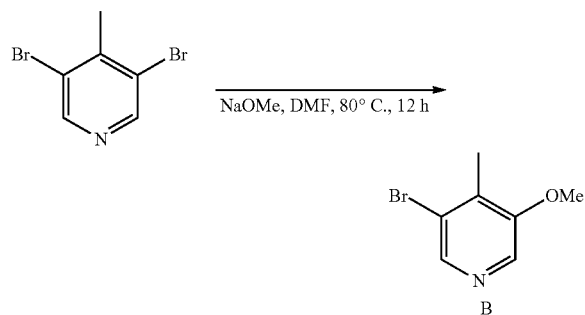

To a freshly prepared sodium methoxide from sodium metal (0.165 g, 0.0072 mol) and methanol (2.5 mL), 3,5-dibromo-4-methyl-pyridine (1.0 g, 0.0040 mol) dissolved in N,N-dimethylformamide (10 mL) was added and heated at 80° C. overnight. Reaction was diluted with ethyl acetate and quenched with ice water, and layers were separated. The aqueous layer was extracted with ethyl acetate (3×20 mL). The combined organic extracts were washed with saturated aqueous sodium chloride solution, dried over sodium sulphate and concentrated to provide the title compound. $^1$H NMR (400 MHz, CDCl$_3$) δ 8.33 (s, 1H), 8.09 (s, 1H), 3.05 (s, 3H), 2.32 (s, 3H).

INTERMEDIATE D

Synthesis of 2-(5-bromopyridin-3-yl)propan-2-ol (D)

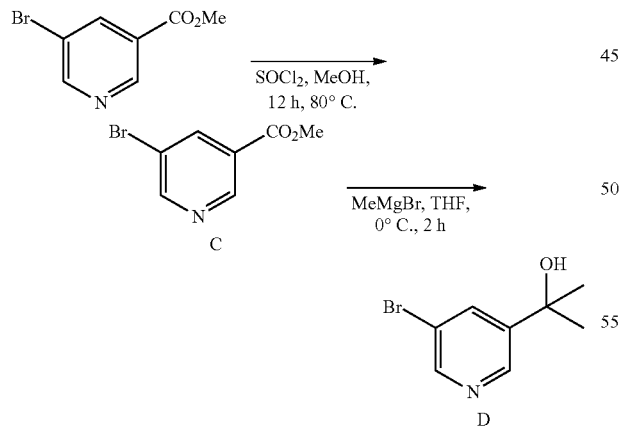

Step A: methyl 5-bromonicotinate (C)

(1.0 g, 0.005 mol) in methanol (40 mL) was added thionyl chloride (0.7 mL, 0.01 mol) at 0-5° C. The mixture was heated under reflux overnight, thionyl chloride was evaporated. Residue was dissolved in ethyl acetate and washed with saturated aqueous sodium bicarbonate solution, water and saturated aqueous sodium chloride solution subsequently. The combined organic solvent was evaporated to provide the title compound. $^1$H NMR (400 MHz, CDCl$_3$) δ 9.13 (s, 1H), 8.84 (s, 1H), 8.43 (s, 1H), 3.97 (s, 3H).

Step B: 2-(5-bromopyridin-3-yl)propan-2-ol (D)

Compound methyl 5-bromonicotinate (0.9 g, 0.0042 mol) was taken in tetrahydrofuran (25 mL) and cooled to −30° C. Methyl magnesium bromide (4.2 mL, 0.0126 mol, 3M in tetrahydrofuran) was added and stirred for 3 h at the same temperature. Reaction mixture was quenched with sat ammonium chloride solution and layers were separated. The aqueous layer was extracted with ethyl acetate (3×30 mL). The combined organic extracts were washed with saturated aqueous sodium chloride solution, dried over sodium sulphate and concentrated to provide the title compound. $^1$H NMR (400 MHz, CDCl$_3$) δ 8.63 (s, 1H), 8.56 (s, 1H), 8.00 (s, 1H), 1.60 (s, 6H).

INTERMEDIATE E

Synthesis of 3-bromo-5-fluoro-4-methylpyridine (E)

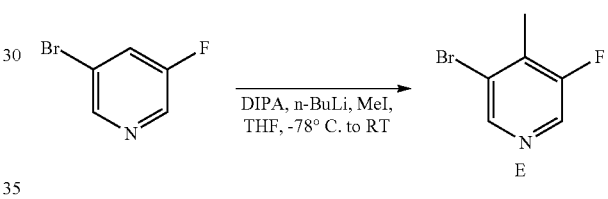

To the solution of diisopropylamine (10.08 mL, 0.0738 mol) in tetrahydrofuran (80 mL), n-butyl lithium (46 mL, 0.0738 mol, 1.6M), was added at −78° C. and then it was warmed to 0° C. and stirred for 30 min, then it was cooled to −78° C. and the solution of 3-bromo-5-fluoro-pyridine (10.0 g, 0.056 mol) in tetrahydrofuran (10 mL) was added and stirred for 30 min. Methyl iodide (4 mL, 0.062 mol) was added to reaction mixture and allowed to room temperature for 2 h. Reaction mass was quenched with saturated ammonium chloride (100 mL) solution. The aqueous layer was extracted with ethyl acetate (3×100 mL). The combined organic extracts were washed with saturated aqueous sodium chloride solution, dried over sodium sulphate and concentrated to provide the title compound. $^1$H NMR (400 MHz, CDCl$_3$) δ 8.49 (s, 1H), 8.31 (s, 1H), 2.38 (s, 3H). LCMS (M+3): 192.2.

Intermediate F in Table IN-1 was prepared using chemistry described for Intermediate E.

TABLE IN-1

| INTERMEDIATE | Structure | IUPAC Name | LCMS |
|---|---|---|---|
| F | ![structure] | 3-bromo-4-ethyl-5-fluoropyridine | 203.8 |

INTERMEDIATE H

Synthesis of 3-bromo-4-cyclopropyl-5-methylpyridine (G)

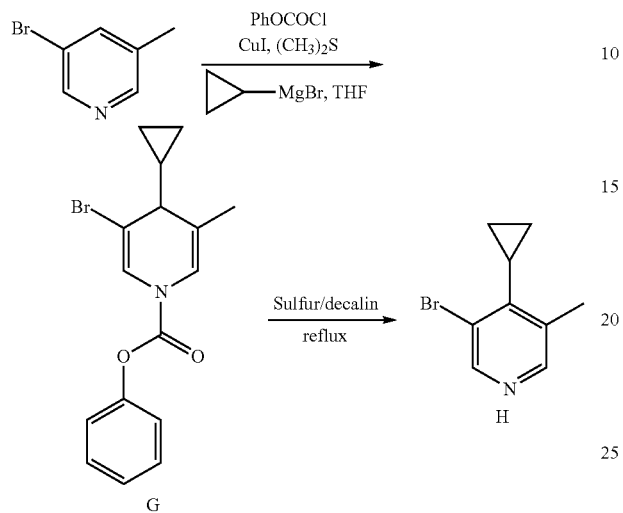

Step A: Intermediate G

To a mixture of copper iodide (1.082 g, 0.0056 mol), dimethyl sulphide (2.78 mL, 0.0380 mol) and 3-bromo-5-methylpyridine (1.0 g, 0.0056 mol) in anhydrous tetrahydrofuran (25 mL) at room temperature was added phenyl chloroformate (0.764 mL, 0.0060 mol) and the mixture was stirred for 40-50 min. To this suspension at −25 to −20° C. was added cyclopropyl magnesium bromide (12.13 mL, 0.0060 mol, 0.5M solution in tetrahydrofuran) over 30-40 min. The mixture was stirred at this temperature for 30 min. and then warmed slowly to room temperature over 1.0-1.5 h. The reaction mixture was quenched with 20% ammonium chloride (25 mL), followed by extraction of the aqueous layer with ethyl acetate (50 mL). The organic layer was washed with 20% ammonium chloride (25 mL), then saturated aqueous sodium chloride solution (25 mL), and dried over anhydrous sodium sulphate. Silica gel chromatography using 0-5% ethyl acetate-hexane gradient yielded crude title compound.

Step B: 3-bromo-4-cyclopropyl-5-methylpyridine (H)

A mixture of the crude dihydropyridine (1.4 g, 0.0041 mol) and sulphur (0.132 g, 0.0041 mol) were heated at reflux in decalin (10 mL) for a period of 3 h, then cooled to room temperature. Purification by silica gel chromatography, eluting first with hexanes, then with a 2-5% ethyl acetate-hexane gradient, gave the title compound. $^1$H NMR (400 MHz, DMSO-$d_6$): δ 8.46 (s, 1H), 8.28 (s, 1H), 2.52 (s, 3H), 1.81-1.75 (m, 1H), 1.12-1.08 (m, 2H), 0.65-0.61 (m, 2H), MS (M+1) 214.0.

The following intermediates in Table IN-2 was prepared using chemistry described for Intermediate H

TABLE IN-2

| INTERMEDIATE | Structure | IUPAC Name | LCMS |
|---|---|---|---|
| I | Br⟶⟨pyridine with cyclopropyl, F⟩ | 3-bromo-4-cyclopropyl-5-fluoropyridine | 218.1 |
| J | Br⟶⟨pyridine with methyl, Cl⟩ | 3-bromo-5-chloro-4-methylpyridine | 208.2 |

INTERMEDIATE M

Synthesis of 3-bromo-4-(difluoromethoxy)pyridine (M)

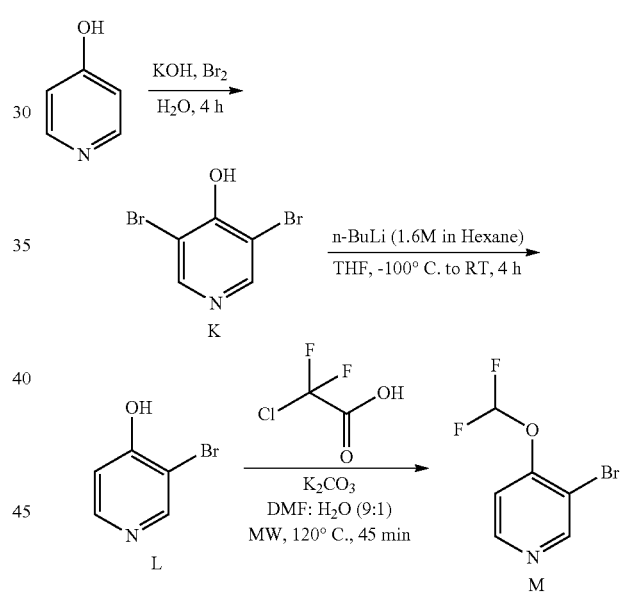

Step A: 3,5-Dibromopyridin-4-ol (K)

To a stirred solution of potassium hydroxide (2.35 g, 0.042 mol) in water (40 mL) was added pyridin-4-ol (2.0 g, 0.021 mol) and mixture was cooled to 0° C. To the above solution bromine was added slowly at 0° C. and stirred for 3 h. The reaction mixture was filtered and washed the solid with cold water, hexane and dried under vacuum to obtain the title compound. MS (M+1): 251.8.

Step B: 3,5-Dibromopyridin-4-ol (L)

To a stirred solution of 3,5-dibromopyridin-4-ol (IN-11; 2.5 g, 0.00988 mol) in dry tetrahydrofuran (100 mL) at −100° C. was added 1.6 M t-butyl lithium in hexane (15.6 mL, 0.0247 mol) drop wise under nitrogen atmosphere and stirred for 2 h at −100° C. The reaction mixture was quenched with water (1.77 g, 0.0988 mol) at −100° C. and allows the reaction mixture to RT slowly. The reaction mixture was evaporated. The obtained crude was purified with silica gel chromatography by 0-12% methanol in dichloromethane to afford the title compound. $^1$H NMR (400 MHz, DMSO-$d_6$) δ: 11.71 (s, 1H), 8.15 (s, 1H), 7.66-7.65 (d, J=5.6 Hz, 1H), 6.20-6.18 (d, J=6.4 Hz, 1H). MS (M+1): 173.8.

Step C: 3-Bromo-4-(difluoromethoxy)pyridine (M)

To a stirred solution of 3-bromopyridin-4-ol (L); 0.5 g, 0.00287 mol) in mixture of N,N-dimethylformamide (10.0 mL), water (1 mL), was added 2-chloro-2,2-difluoroacetic acid (0.74 g, 0.00574 mol) and potassium carbonate (0.47 g, 0.00344 mol). The resulting mixture was heated under microwave irradiation at 120° C. for 45 min. The reaction mixture was cooled to room temperature and poured into water (10.0 mL) and extracted with ethyl acetate (2×50.0 mL). Combined organic phase was washed with saturated sodium bicarbonate solution, water, saturated aqueous sodium chloride solution, dried over sodium sulphate, filtered and concentrated under vacuum to afford crude product. The crude was purified by silica gel (60-120) column chromatography using 0-8% methanol in dichloromethane to afford the title compound (IN-13). $^1$H NMR (400 MHz, DMSO-$d_6$) δ: 8.606-8.60 (d, J=2.4 Hz, 1H), 8.08-8.05 (dd, J=5.2 Hz, 1H), 7.67-7.37 (t, J=58.8 Hz, 1H), 6.38-6.36 (dd, J=7.2 Hz, 1H). MS (M+1): 223.8.

INTERMEDIATE N

Synthesis of
3-bromo-5-cyclopropyl-4-methylpyridine (N)

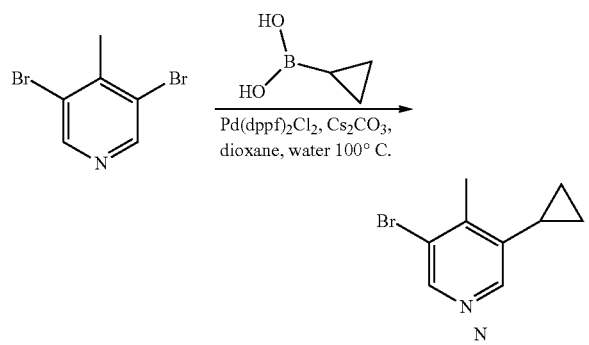

To a stirred solution of 3,5-dibromo-4-methylpyridine (1.0 g, 0.0039 mol) and cyclopropylboronic acid (0.34 g, 0.0039 mol) in the mixture of 1,4-dioxan (35 mL) and water (15 mL) was added cesium carbonate (2.59 g, 0.00797 mol). Reaction mass was purging with argon for the 20 min. After 20 min, Pd(dppf)$_2$Cl$_2$ (0.14 g, 0.000199 mol) was added. The reaction mixture was heated to 100° C. and stirred for 6 h. The reaction mixture was cooled to room temperature, filtered the reaction mixture through CELITE bed and the CELITE bed was thoroughly washed with ethyl acetate. The filtrate was concentrated under vacuum. The residue was dissolved with dichloromethane and washed with water, saturated aqueous sodium chloride solution, dried over sodium sulphate, concentrated under vacuum, which was purified with silica gel (60-120) column chromatography by 0-2.5% ethyl acetate in hexane to afford the title compound (IN-14). $^1$H NMR (400 MHz, CdCl$_3$) δ 8.51 (s, 1H), 8.17 (s, 1H), 2.52 (s, 3H), 1.87-1.82 (m, 1H), 1.03-0.99 (m 2H), 0.71-0.68 (m, 2H). MS (M+1): 211.8.

INTERMEDIATE P 3-bromo-5-cyclopropylisonicotinonitrile (O)

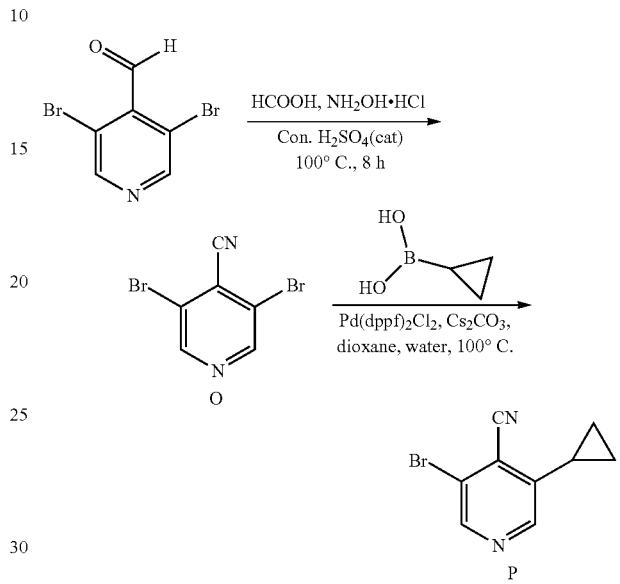

Step A: 3,5-dibromoisonicotinonitrile (IN-15)

To a solution of 3,5-dibromoisonicotinaldehyde (2.0 g, 0.0075 mol) in formic acid was added hydroxyl amine hydrochloride (14 mL) and concentrated sulfuric acid (5 drops) under argon atmosphere. The reaction mixture was heated to reflux for 8 h. After 8 h, the mixture was cooled to room temperature and concentrated. The residue was dissolved in diethyl ether, washed diethyl ether with saturated solution of sodium bicarbonate, water, saturated aqueous sodium chloride solution, dried over sodium sulphate and concentrated to afford the title compound. $^1$H NMR (400 MHz, CdCl$_3$) δ 8.81 (s, 2H).

Step B: 3-bromo-5-cyclopropylisonicotinonitrile (P)

To a stirred solution of 3,5-dibromoisonicotinonitrile (O); 2.25 g, 0.00859 mol) and cyclopropylboronic acid (0.73 g, 0.00859 mol) in the mixture of 1,4-dioxan (70 mL) and water (30 mL) was added cesium carbonate (5.59 g, 0.0171 mol). Reaction mass was purged with argon for the 20 min. After 20 min, Pd(dppf)$_2$Cl$_2$ (0.31 g, 0.000429 mol) was added. The reaction mixture was heated to 100° C. and stirred for 6 h. The reaction mixture was cooled to room temperature, filtered the reaction mixture through CELITE bed and the CELITE bed was thoroughly washed with ethyl acetate. The filtrate was concentrated under vacuum. The residue was dissolved with dichloromethane and organic layer was washed with water, saturated aqueous sodium chloride solution, dried over sodium sulphate, concentrated under vacuum, which was purified with silica gel (60-120) column chromatography by 0-12% ethyl acetate in hexane to afford the title compound.

¹H NMR (400 MHz, DMSO-d₆) δ 8.79 (s, 1H), 8.43 (s, 1H), 2.16-2.10 (m, 1H), 1.22-1.13 (m, 2H), 1.04-0.98 (m, 2H). MS (M+1): 222.9.

INTERMEDIATE Q

Synthesis of 3-bromo-4-chloro-5-fluoropyridine (Q)

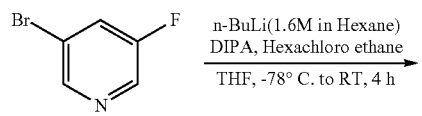

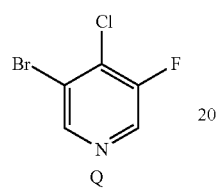

To a stirred solution of diisopropylamine (0.48 mL, 0.0034 mol) in dry tetrahydrofuran (10 mL) was added 1.6 M n-butyl lithium in hexane (2.39 mL, 0.00369 mol) drop wise under nitrogen atmosphere at −78° C. and stirred for 30 min at −78° C. To the above stirred mixture was added a solution of 3-bromo-5-fluoropyridine (0.5 g, 0.00284 mol) in dry tetrahydrofuran at −78° C. and stirred for 45 min. After 45 min, a solution of hexachloroethane in dry tetrahydrofuran was added to the above reaction mixture at −78° C. and stirred for 30 min at −78° C. The reaction mixture was slowly warmed to RT and stirred for 1 h. The reaction was quenched with saturated solution of ammonium chloride (10 mL) and extracted with diethyl ether (25 mL x 3). The combined organic layer was washed with water, saturated aqueous sodium chloride solution, dried over anhydrous sodium sulphate and evaporated. The obtained crude was purified with silica gel chromatography by hexane to afford the title compound. ¹H NMR (400 MHz, CDCl₃) δ: 8.58 (s, 1H), 8.43 (s, 1H). MS (M+1): 209.9.

INTERMEDIATE R & S

Synthesis of (S)-1-(5-bromopyridin-3-yl)ethanol and (R)-1-(5-bromopyridin-3-yl)ethanol (IN-18 & IN-19)

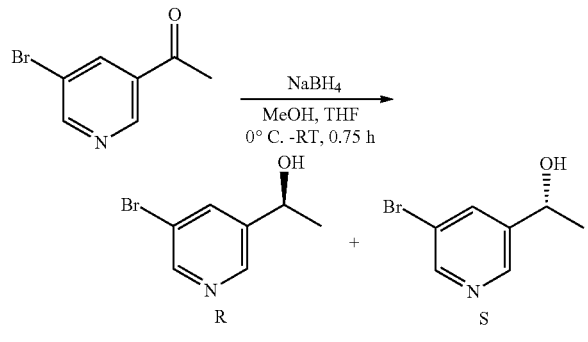

To a stirred solution of 1-(5-bromopyridin-3-yl)ethanone (4.8 g, 0.024 mol) in methanol (110.0 mL) and tetrahydrofuran (22.0 mL) cooled to 0° C., added sodium borhydride (1.7 g, 0.048 mol) and the resulting mixture was allowed to stir at room temperature for 0.75 h. The reaction mixture was concentrated and diluted with water (75 mL) and extracted with ethyl acetate (2×75 mL). The combined organics were dried over sodium sulphate and concentrated under vacuum to obtain racemic mixture. The racemic mixture was separated by chiral HPLC (analytical conditions: column: CHIRALPAK IA (250 mm×4.6 mm×5 µm), mobile phase: n-heptane: 0.1% diethylamine in ethanol, flow rate: 1.0 mL/min) to get two isomers. MS (M+2): 204.1.

INTERMEDIATE T

Synthesis of N-(5-bromopyridin-3-yl)benzenesulfonamide (T)

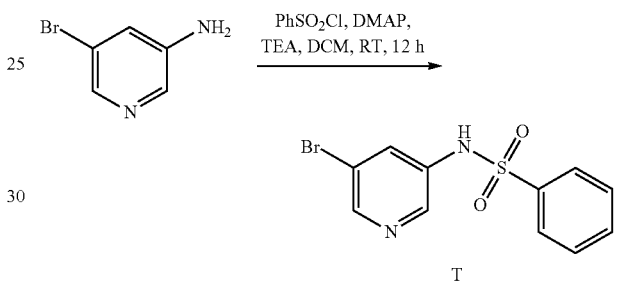

To a stirred solution of 5-bromo-3-pyridinamine (2 g, 11.56 mmol), triethylamine (6.6 mL, 47.39 mmol) in dichloromethane (40 mL) at 0° C. under nitrogen atmosphere. The reaction mixture was stirred for 15 min and then benzenesulfonyl chloride (3.21 mL, 23.69 mmol) was added slowly to give a brown solution. The reaction mixture was stirred for 2 h at room temperature. Diluted with dichloromethane and then washed with saturated aqueous sodium chloride solution, separated the organic layer, dried over sodium sulphate, concentrated under high vacuum, light yellow solid obtained. The solid was dissolved in methanol (20 mL), cooled to 0° C., added 10N aqueous sodium hydroxide (20 mL) solution. The reaction mixture was stirred for 1 h and then distilled out methanol completely, extracted with ethyl acetate. The combined organic layer was washed with saturated aqueous sodium chloride solution, dried over sodium sulphate and concentrated under vacuum to obtain the title compound MS (M+1): 315.2.

INTERMEDIATE U

Synthesis of N-(5-bromopyridin-3-yl)ethanesulfonamide (IN-21)

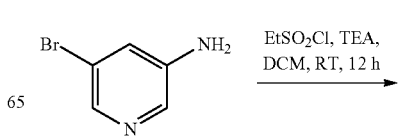

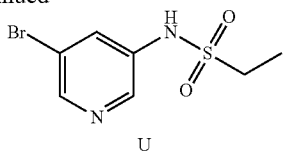

To a stirred solution of 5-bromo-3-pyridinamine (0.8 g, 4.62 mmol), triethylamine (2.6 mL, 18.48 mmol) in dichloromethane (20 mL) at 0° C. under inert atmosphere. The reaction mixture was stirred for 15 min and then ethyl sulfonyl chloride (0.88 mL, 9.24 mmol) was added slowly. The reaction mixture was stirred for 2 h at room temperature. Diluted with dichloromethane and then washed with saturated aqueous sodium chloride solution, separated the organic layer, dried over sodium sulphate, concentrated under high vacuum, light yellow solid obtained. The solid was dissolved in methanol (10 mL), cooled to 0° C., added 10N aqueous sodium hydroxide (10 mL) solution. The reaction mixture was stirred for 1 h and then methanol was evaporated completely and extracted with ethyl acetate. The combined organic layer was washed with saturated aqueous sodium chloride solution, dried over sodium sulphate and concentrated under vacuum to obtain the title compound. MS (M+1): 266.9.

INTERMEDIATE V 5-bromo-4-methylnicotinonitrile (V)

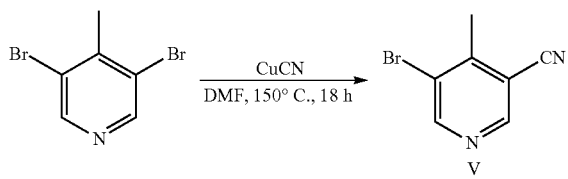

To a stirred solution of 3,5-dibromo-4-methylpyridine (2.0 g, 7.97 mmol) in dry N,N-dimethylformamide (10 mL) was added copper cyanide (1.07 g, 11.95 mmol) at room temperature. The reaction mixture was heated at 150° C. for 6 h, cooled it, quenched with water (5 mL) and extracted with 50% ethyl acetate/hexane (2×100 mL). The combined organic layer was washed with saturated aqueous sodium chloride solution, dried over sodium sulphate and concentrated under vacuum to obtain the title compound. MS (M+1): 199.1.

INTERMEDIATE Y

Synthetic of 3-bromo-4-chloro-5-cyclopropylpyridine

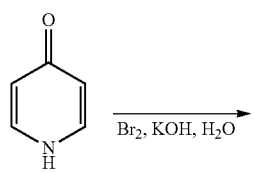

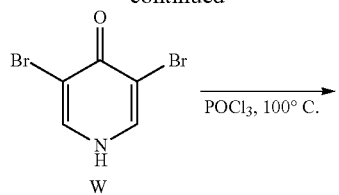

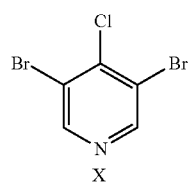

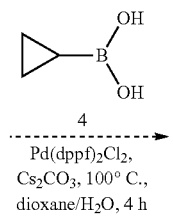

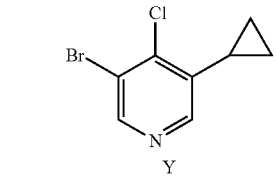

Step A: 3,5-dibromo-4-(1H)-pyridone (W)

To an ice-cooled solution of pyridine-4-one 9 (2 g, 21.03 mmol) and potassium hydroxide (2.35 g, 42 mmol) in water (40 mL) was added bromine (7.58 mL, 147.5 mmol) drop wise. The reaction mixture was stirred for 2 h at 0-5° C. The precipitate was filtered off, washed with a copious amount of water and then hexane, dried in vacuum to obtain the title compound. MS (M+1): 253.8.

Step B: 3,5-dibromo-4-chloropyridine (X)

To 3,5-dibromo-4-(1H)-pyridone (W, 1.0 g, 3.97 mmol) was added phosphorous oxychloride (5 mL) and the mixture was heated at 100° C. for 2 h. The mixture was poured into ice/water (25 g) and basified by the addition of a saturated solution of sodium hydrogen carbonate. The mixture was extracted with dichloromethane (2×20 mL), the combined organic extracts were washed with saturated aqueous sodium chloride solution (25 mL), dried over sodium sulphate and concentrated under vacuum to obtain the title compound. MS (M+1): 271.8.

Step B: 3-bromo-4-chloro-5-cyclopropylpyridine (Y)

To a stirred solution of 3,5-dibromo-4-chloropyridine (X, 0.5 g, 1.84 mmol) and cyclopropylboronic acid (0.17 g, 2.02 mmol), cesium carbonate (1.19 g, 3.68 mmol) in the mixture of 1,4-dioxan (10 mL) and water (2 mL). The reaction mass was purged with nitrogen for 15 min. Then catalyst Pd(dppf)$_2$Cl$_2$ (0.075 g, 0.09 mmol) was added and allowed to stir at 100° C. for 4 h. The reaction mixture was filtered through Mite bed and filter bed was thoroughly washed with ethyl acetate. The collected organic parts were concentrated under vacuum to afford the crude compound, which was purified by column chromatography using 10-40% ethyl acetate/hexane as an eluent to obtain title compound. MS (M+1): 233.0.

INTERMEDIATE AA

Synthesis of 3-bromo-4-cyclopropylpyridine (AA)

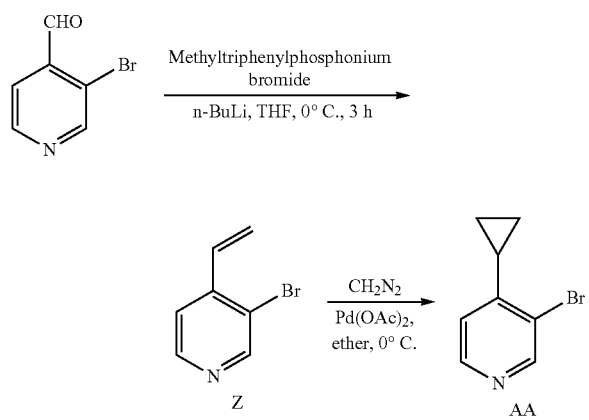

Step A: 3-bromo-4-vinylpyridine (Z)

To a stirred suspension of methyltriphenylphosphonium bromide in dry tetrahydrofuran (15 mL) at 0° C. was added n-butyl lithium (3.87 mL, 3.87 mmol) with constant stirring, yellow colour was observed. The yellow colour suspension was allowed to stir at room temperature for 40 min. After 40 min, the reaction mixture was cooled to 0° C. and 3-bromoisonicotinaldehyde (0.6 g, 3.23 mmol) in tetrahydrofuran (5 mL) was added drop wise, the yellow colour was disappeared. Reaction mass was allowed to stir at 0° C. to room temperature for 3 h. The reaction mixture was diluted with water (30 mL) and extracted with ether (3×25 mL). The combined organic layers were washed with saturated aqueous sodium chloride solution, dried over sodium sulphate and concentrated under vacuum to afford the crude compound which was purified by column chromatography to obtain the title compound. $^1$H NMR (400 MHz, CDCl$_3$) δ: 8.69 (s, 1H), 8.45 (d, J=4.8 Hz, 1H), 7.41 (d, J=4.8 Hz, 1H), 7.02-6.95 (m, 1H), 5.95-5.91 (d, J=17.6 Hz, 1H), 5.60-5.57 (d, J=10.8 Hz, 1H). MS (M+2): 185.8.

Step B: 3-bromo-4-cyclopropylpyridine (AA)

To a stirred solution of 3-bromo-4-vinylpyridine (Z, 0.4 g, 2.2 mmol) in ether (20 mL) was added palladium acetate (catalytic) and diazomethane (required for preparation, N-nitroso-N-methylurea-1.03 g, 10.0 mmol; 40% potassium hydroxide, 10 mL; ether, 20 mL) portion wise at 0° C. for 10 min. The reaction mixture was stirred at 0° C. for 0.5 h. The reaction mixture was filter through CELITE bed and concentrated under vacuum to afford the crude compound to obtain the title compound. $^1$H NMR (400 MHz, CDCl$_3$) δ: 8.62 (s, 1H), 8.34-8.33 (d, J=5.2 Hz, 1H), 6.72-6.71 (d, J=4.8 Hz, 1H), 2.25-2.18 (m, 1H), 1.17-1.12 (m, 2H), 0.80-0.76 (m, 2H). MS (M+2): 200.2.

INTERMEDIATE EE

Synthesis of 4-bromo-8-fluoroisoquinoline (EE)

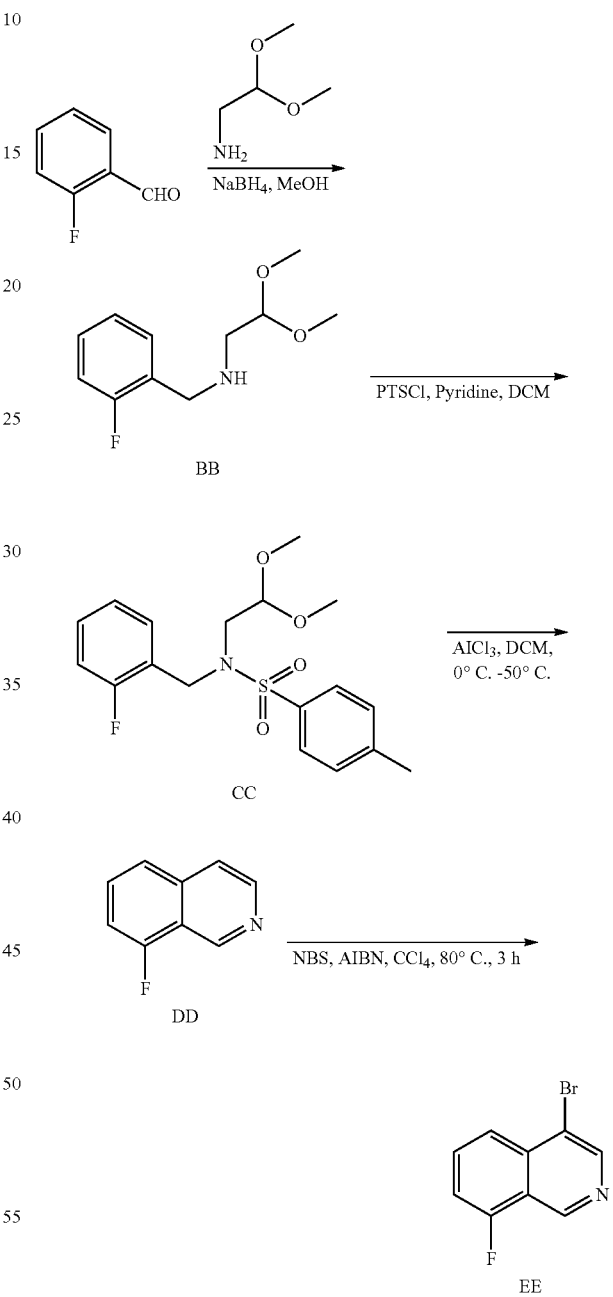

Step A: N-(2-fluorobenzyl)-2,2-dimethoxyethanamine (BB)

A mixture of 2-fluorobenzaldehyde (20.0 g, 0.161 mol) and dimethoxy-ethylamine (16.9 g, 0.161 mol) in methanol (250 mL) was heated at 65° C. for 1.5 h. The solution was allowed to cool to room temperature overnight and treated with sodium borohydride (6.1 g, 0.161 mol) in portions over a period of 40 min. The resultant mixture was stirred at room temperature for 3 h and quenched with water (500 mL). The product mixture was concentrated to about 500 mL and extracted with diethyl ether (3×300 mL). The ethereal extracts were combined, washed with saturated aqueous sodium chloride solution, dried over anhydrous sodium sulfate, filtered, and concentrated under vacuum to provide the title compound. $^1$H NMR (400 MHz, CDCl$_3$) δ 7.34-7.30 (t, 1H, J=7.6 Hz), 7.26-7.19 (m, 1H), 7.11-7.07 (t, 1H, J=7.6 Hz), 7.04-6.99 (t, 1H, J=9.2 Hz).

Step B: N-(2,2-dimethoxyethyl)-N-(2-fluorobenzyl)-4-methylbenzenesulfonamide (CC)

N-(2-fluorobenzyl)-2,2-dimethoxyethanamine (BB; 33.0 g, 0.154 mol) were dissolved in 200 mL of dichloromethane and pyridine (50.2 g, 0.417 mol) was added. At 0° C. a solution of p-toluene sulphonyl chloride (58.0 g, 0.201 mol) in dichloromethane (500 mL) was added drop wise. The reaction was allowed to warm to room temperature and stirring is continued until conversion was completed. For workup, the reaction mixture was extracted twice with 2M aqueous hydrochloric acid, twice with saturated aqueous sodium bicarbonate and once with saturated aqueous sodium chloride solution. The organic layer was dried over sodium sulphate, evaporated to dryness and the obtained crude product was purified by silica gel chromatography to yield the title compound. $^1$H NMR (400 MHz, CDCl$_3$) δ 7.69-7.67 (2H, m), 7.43-7.39 (m, 1H), 7.29-7.21 (m, 3H), 7.12-7.08 (m, 1H), 6.99-6.95 (m, 1H), 4.52 (s, 2H), 4.39-4.37 (t, 1H, J=5.2 Hz), 3.26-3.24 (m, 8H), 2.42 (s, 3H).

Step C: N-(2,2-dimethoxyethyl)-N-(2-fluorobenzyl)-4-methylbenzenesulfonamide (IN-DD)

Aluminum chloride (6.34 g, 0.047 mol) was suspended in 150 mL of dichloromethane. At 0° C., a solution of N-(2,2-dimethoxyethyl)-N-(2-fluorobenzyl)-4-methylbenzenesulfonamide (CC; 5.0 g, 0.013 mol) in 150 mL, of dichloromethane was added and heated to 50° C. for 2 h. Then solution was poured into ice water, the layers were separated, the aqueous phase was extracted twice with dichloromethane and the combined organic layers were then washed twice with sodium bicarbonate solution. The organic layer was dried over sodium sulphate, evaporated to dryness and the obtained crude product was purified by silica gel chromatography to obtain the title compound (IN-30). $^1$H NMR (400 MHz, CDCl$_3$) δ 9.54 (s, 1H), 8.61-8.59 (d, J=1H, J=6 Hz), 7.67-7.60 (m, 3H), 7.26-7.21 (m, 1H).

Step D: 4-bromo-8-fluoroisoquinoline (EE)

To a solution of N-(2,2-dimethoxyethyl)-N-(2-fluorobenzyl)-4-methylbenzenesulfonamide (DD; 0.6 g, 0.0041 mol) in carbon tetrachloride (15 mL) was added N-bromosuccinimide (1.08 g, 0.00603 mol) followed by AIBN (0.06 g, 0.00041 mol) and heated for 3 h at 80° C. Then carbon tetrachloride was evaporated and the crude was purified by column chromatography to get the title compound. $^1$H NMR (400 MHz, CDCl$_3$) δ 9.46 (1H, s), 8.80 (s, 1H), 7.97-7.95 (d, J=8.4 Hz, 1H), 7.79-7.74 (m, 1H), 7.35-7.31 (dd, J=8.0, 9.6 Hz, 1H).

Example 1

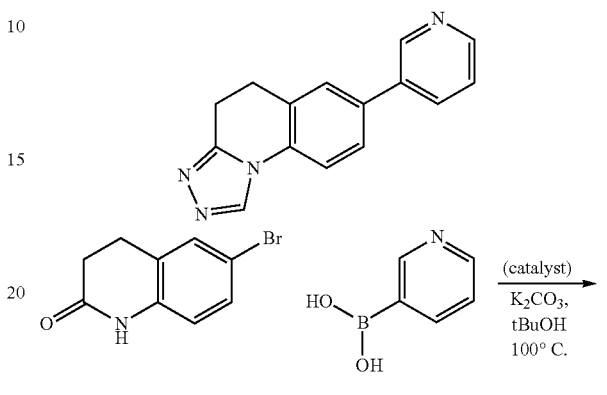

Step A. 6-(pyridin-3-yl)-3,4-dihydroquinolin-2(1H)-one

A sealable tube containing 6-bromo-3,4-dihydroquinolin-2(1H)-one (0.10 g, 0.44 mmol), 3-pyridylboronic acid (0.56 g, 4.6 mmol), bis(di-tert-butyl(4-dimethylamino phenyl)phosphine)dichloropalladium(II) (6.3 mg, 8.9 μmol), and potassium carbonate (0.18 g, 1.3 mmol) was flushed with nitrogen before tert-butanol (4.9 mL) and water (0.6 mL) were added. The tube was flushed again with nitrogen, sealed tightly and heated to 100° C. overnight. The reaction was then cooled to room temperature, poured into saturated aqueous sodium chloride solution and extracted with ethyl acetate. The organic extracts were combined, washed with water, dried over sodium sulfate, filtered and concentrated. Purification by flash chromatography on silica gel (0-15% methanol in ethyl acetate) provided the title compound: LCMS m/z 225.27 [M+H]$^+$; $^1$H NMR (500 MHz, CD$_3$OD) δ 8.77 (s, 1H), 8.47 (d, J=4.8 Hz, 1H), 8.06 (ddd, J=1.7, 2.0, 8.1 Hz, 1H), 7.52 (s, 1H), 7.50-7.47 (m, 2H), 6.99 (d, J=8.1 Hz, 1H), 3.05 (t, J=7.5, 7.7 Hz, 2H), 2.61 (t, J=7.5, 7.7 Hz, 2H).

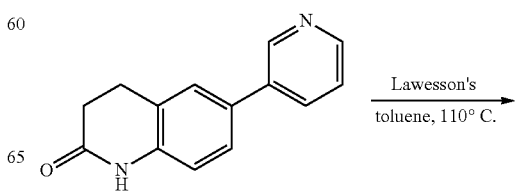

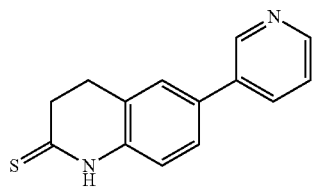

Step B. 6-(pyridin-3-yl)-3,4-dihydroquinoline-2(1H)-thione

To the title compound from Example 1 Step A (200 mg, 0.892 mmol) and 2,4-bis(4-methoxyphenyl)-1,3,2,4-dithiadiphosphetane-2,4-disulfide (180 mg, 0.446 mmol) was added toluene (1.8 mL). The suspension was heated to reflux for 45 minutes. The reaction was then cooled to room temperature and concentrated under reduced pressure. Purification by flash chromatography on silica gel (0-15% methanol in ethyl acetate) provided the title compound: LCMS m/z 241.22 [M+H]+; 1H NMR (500 MHz, CD3OD) δ 8.86 (d, J=2.0 Hz, 1H), 8.55 (dd, J=1.5, 4.8 Hz, 1H), 8.11 (ddd, J=1.9, 2.2, 8.2 Hz, 1H), 7.61-7.58 (m, 2H), 7.53 (dd, J=4.9, 8.0 Hz, 1H), 7.20 (d, J=8.1 Hz, 1H), 3.09-3.06 (m, 2H), 2.99-2.96 (m, 2H).

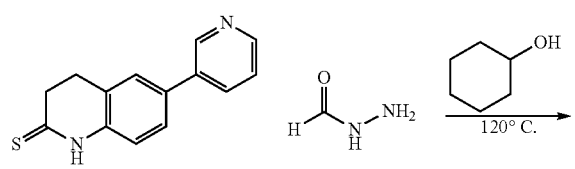

Step C. 7-(pyridin-3-yl)-4,5-dihydro[1,2,4]triazolo[4,3-a]quinoline

A flask containing the title compound from Example 1 Step B (20 mg, 0.08 mmol), formic hydrazide (6.0 mg, 0.10 mmol) and cyclohexanol (0.50 ml, 0.08 mmol) was heated to reflux for 6 hours. The reaction was cooled to room temperature, diluted with dimethylsulfoxide, acidified with trifluoroacetic acid and passed through a syringe filter. Purification by reverse phase HPLC (C18 column, 10 to 100% acetonitrile/water, both 0.1% v/v trifluoroacetic acid) provided the title compound: LCMS m/z 249.16 [M+H]+; 1H NMR (500 MHz, CD3OD) δ 9.90 (s, 1H), 9.30 (d, J=2.0 Hz, 1H), 9.01 (ddd, J=1.5, 1.9, 8.2 Hz, 1H), 8.93 (d, J=5.6 Hz, 1H), 8.23 (dd, J=5.8, 8.2 Hz, 1H), 8.10-8.07 (m, 2H), 8.02 (dd, J=1.9, 8.4 Hz, 1H), 3.46-3.43 (m, 2H), 3.38-3.35 (m, 2H).

Example 2

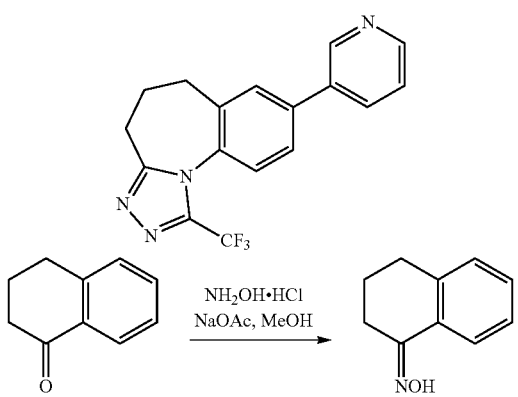

Step A. (1E)-N-hydroxy-3,4-dihydro-1(2H)-naphthalenimine

A mixture of 3,4-dihydro-1-(2H)-naphthalenone (72.4 g, 0.495 mol), hydroxylamine hydrochloride (139 g, 1.98 mol), sodium acetate (162 g, 1.98 mol), methanol (500 mL) and water (100 mL) was refluxed for 6 hours. The reaction mixture was diluted with water (2 L), and extracted with ether (800 mL). The organic layer was washed with water, dried and concentrated. The residue was crystallized from ether/hexane to give the title compound: LCMS m/z=162.0 [M+H]+.

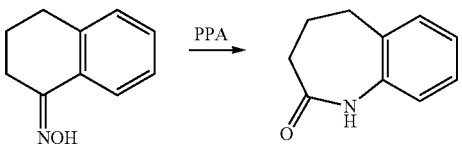

Step B. 1,3,4,5-tetrahydro-2H-1-benzazepin-2-one

A mixture of polyphosphoric acid (600 g, preheated to 120° C.) and the title compound from Example 2 Step A (70 g, 0.434 mol) was stirred for 20 minutes. After the reaction was complete, the reaction mixture was poured onto ice and the resulting solid was collected. It was recrystallized from chloroform and diethylether to give the title compound: LCMS m/z 162.0 [M+H]+.

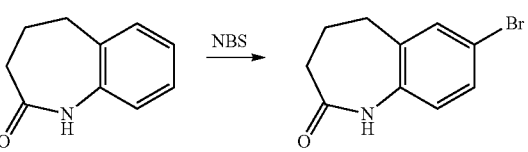

Step C. 7-bromo-1,3,4,5-tetrahydro-2H-1-benzazepin-2-one

To a solution of the title compound from Example 2 Step B (17.0 g, 106 mmol) in N,N-dimethylformamide (500 mL)

was added N-bromosuccinimide (25.2 g, 141 mmol) at room temperature, and then the mixture was refluxed for 16 hours. The reaction mixture was diluted with ethyl acetate (1 L), and the separated organic layer was washed with 0.1 M aqueous sodium hydroxide solution and saturated aqueous sodium chloride solution, dried over Na$_2$SO$_4$, filtered and concentrated. Purification by flash chromatography on silica gel (petroleum ether:ethyl acetate=12:1 to 3:1) provided a crude product that was recrystallized from ethyl acetate and petroleum ether (v:v=1:10) to give the title compound: LCMS m/z=241 [M+2+H]$^+$. $^1$H NMR (400 MHz, d6-DMSO): δ 9.56 (s, 1H), 7.46 (s, 1H), 7.37 (d, J=8.4 Hz, 1H), 6.87 (d, J=8.4 Hz, 1H), 2.65 (m, 2H), 2.12-2.07 (m, 4H).

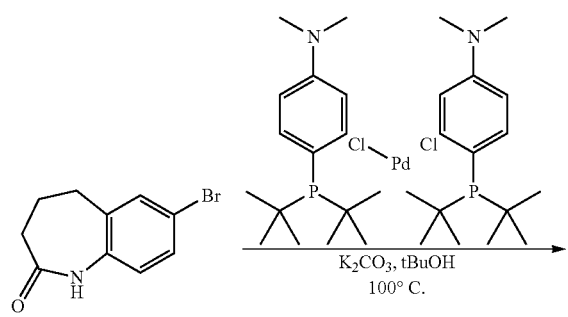

Step D. 7-(3-pyridinyl)-1,3,4,5-tetrahydro-2H-1-benzazepin-2-one

A sealable tube containing the title compound from Example 2 Step C (0.300 g, 1.25 mmol), 3-pyridylboronic acid (0.200 g, 1.62 mmol), bis(di-tert-butyl(4-dimethylaminophenyl)phosphine)dichloropalladium(II) (0.018 g, 0.025 mmol) and potassium carbonate (0.368 g, 3.75 mmol) was flushed with nitrogen before tort-butanol (14.0 mL) and water (1.6 mL) were added. It was flushed again with nitrogen, sealed tightly and heated to 100° C. overnight. The reaction was then cooled to room temperature, poured into saturated aqueous sodium chloride solution and extracted with ethyl acetate. The organic extracts were combined, washed with water, dried over sodium sulfate, filtered and concentrated. Purification by flash chromatography on silica gel (0-12% methanol in ethyl acetate) provided the title compound: LCMS m/z 239.09 [M+H]$^+$; $^1$H NMR (500 MHz, CD$_3$OD) δ 8.72 (s, 1H), 8.46 (d, J=4.2 Hz, 1H), 7.86 (ddd, J=1.8, 1.9, 8.0 Hz, 1H), 7.41-7.39 (m, 2H), 7.35 (dd, J=4.8, 7.9 Hz, 1H), 7.04 (d, J=7.9 Hz, 1H), 2.81 (t, J=7.2 Hz, 2H), 2.35-2.31 (m, 2H), 2.26-2.20 (m, 2H).

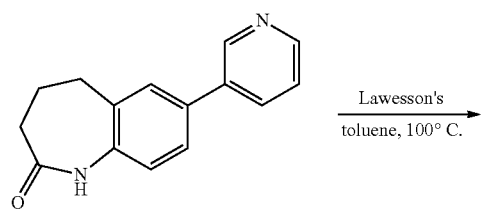

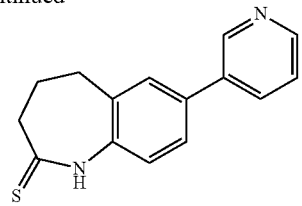

Step E. 7-(3-pyridinyl)-1,3,4,5-tetrahydro-2H-1-benzazepine-2-thione

The title compound from Example 2 Step D (0.200 g, 0.839 mmol) and 2,4-bis(4-methoxyphenyl)-1,3,2,4-dithiadiphosphetane2,4-disulfide (0.255 g, 0.629 mmol) were suspended in toluene (1.7 mL) and then heated to reflux for several hours. The reaction solution was then cooled to room temperature and concentrated. Purification by flash chromatography on silica gel (0-10% methanol in ethyl acetate) provided the title compound: LCMS m/z 255.03 [M+H]$^+$; $^1$H NMR (500 MHz, d6-DMSO) δ 8.81 (s, 1H), 8.48-8.47 (m, 1H), 8.02 (d, J=7.9 Hz, 1H), 7.58-7.56 (m, 2H), 7.42 (dd, J=4.8, 7.9 Hz, 1H), 7.13 (d, J=8.1 Hz, 1H), 2.74-2.71 (m, 2H), 2.68-2.65 (m, 2H), 2.26-2.20 (m, 2H).

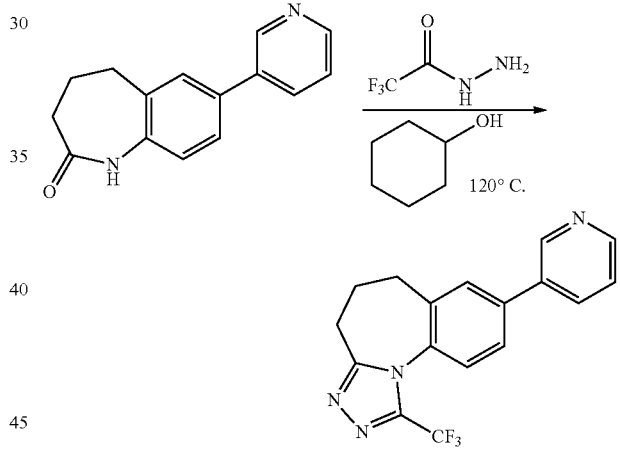

Step F. 8-(3-pyridinyl)-1-(trifluoromethyl)-5,6-dihydro-4H-[1,2,4]triazolo[4,3-a][1]benzazepine A flask containing the title compound from Example 2 Step E (9.0 mg, 0.04 mmol), 2,2,2-trifluoroacetohydrazide (3.2 mg, 0.04 mmol) and cyclohexanol (0.50 mL) was heated at 120° C. overnight. The reaction was then concentrated to give a residue that was diluted with dimethylsulfoxide, acidified with trifluoroacetic acid, and passed through a syringe filter before being purified by reverse phase HPLC (C18 column, 10 to 100% acetonitrile/water, both 0.1% v/v trifluoroacetic acid). Fractions containing product were combined, 1 M hydrochloric acid was added, and the solution concentrated to provide the title compound: LCMS m/z 330.99 [M+H]$^+$; $^1$H NMR (500 MHz, CDCl$_3$) δ 9.09 (br s, 1H), 8.76 (br s, 1H), 8.26 (d, J=Hz, 1H), 7.75-7.59 (m, 4H), 3.34 (br s, 1H), 2.90-2.85 (m, 1H), 2.52-2.40 (m, 3H), 2.27 (br s, 1H).

The compounds in Table 1 were all prepared using chemistry described in Examples 1 or 2.

TABLE 1

| Example | Structure | IUPAC Name | LCMS |
|---|---|---|---|
| 3 | 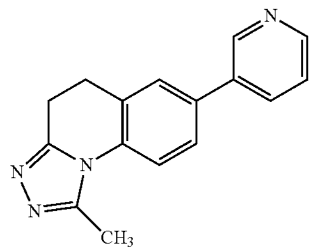 [SMILES: Cc1nnc2n1-c1ccc(-c3cccnc3)cc1CC2] | 1-methyl-7-(pyridin-3-yl)-4,5-dihydro[1,2,4]triazolo[4,3-a]quinoline | 263.15 |
| 4 | 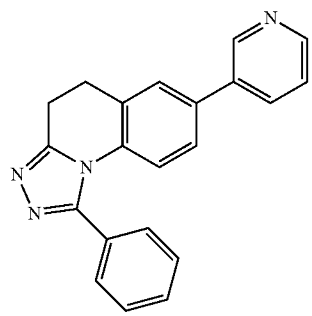 [SMILES: c1ccc(-c2nnc3n2-c2ccc(-c4cccnc4)cc2CC3)cc1] | 1-phenyl-7-(pyridin-3-yl)-4,5-dihydro[1,2,4]triazolo[4,3-a]quinoline | 325.08 |
| 5 | 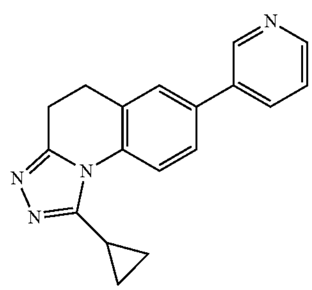 [SMILES: c1cncc(-c2ccc3c(c2)CCc2nnc(C4CC4)n2-3)c1] | 1-cyclopropyl-7-(pyridin-3-yl)-4,5-dihydro[1,2,4]triazolo[4,3-a]quinoline | 289.08 |
| 6 | 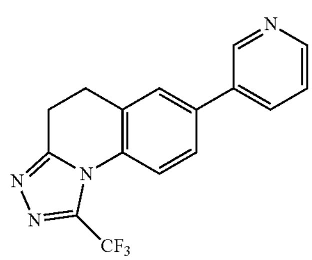 [SMILES: FC(F)(F)c1nnc2n1-c1ccc(-c3cccnc3)cc1CC2] | 7-(pyridin-3-yl)-1-(trifluoromethyl)-4,5-dihydro[1,2,4]triazolo[4,3-a]quinoline | 317.03 |
| 7 | 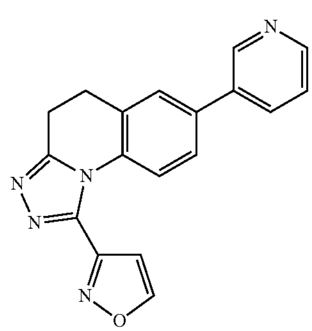 [SMILES: c1cncc(-c2ccc3c(c2)CCc2nnc(-c4ccon4)n2-3)c1] | 1-(isoxazol-3-yl)-7-(pyridin-3-yl)-4,5-dihydro[1,2,4]triazolo[4,3-a]quinoline | 316.05 |

TABLE 1-continued

| Example | Structure | IUPAC Name | LCMS |
|---|---|---|---|
| 8 | 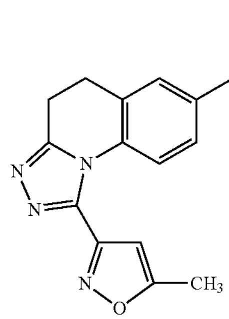 | 1-(5-methylisoxazol-3-yl)-7-(pyridin-3-yl)-4,5-dihydro[1,2,4]triazolo[4,3-a]quinoline | 330.02 |
| 9 | 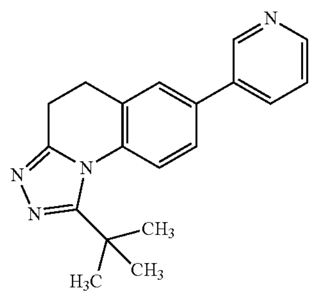 [SMILES: CC(C)(C)c1nnc2n1-c1ccc(-c3cccnc3)cc1CC2] | 1-tert-butyl-7-(pyridin-3-yl)-4,5-dihydro[1,2,4]triazolo[4,3-a]quinoline | 305.09 |
| 10 | 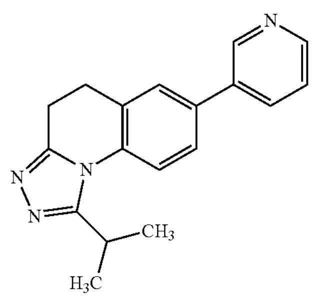 [SMILES: CC(C)c1nnc2n1-c1ccc(-c3cccnc3)cc1CC2] | 1-(propan-2-yl)-7-(pyridin-3-yl)-4,5-dihydro[1,2,4]triazolo[4,3-a]quinoline | 291.09 |
| 11 | 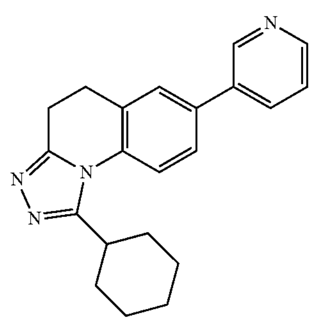 [SMILES: c1cncc(-c2ccc3c(c2)CCc2nnc(C4CCCCC4)n2-3)c1] | 1-cyclohexyl-7-(pyridin-3-yl)-4,5-dihydro[1,2,4]triazolo[4,3-a]quinoline | 331.08 |
| 12 | 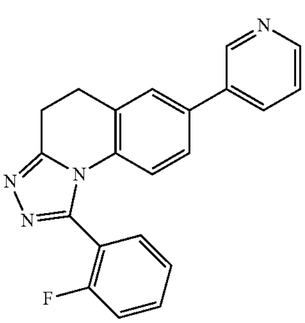 [SMILES: Fc1ccccc1-c1nnc2n1-c1ccc(-c3cccnc3)cc1CC2] | 1-(2-fluorophenyl)-7-(pyridin-3-yl)-4,5-dihydro[1,2,4]triazolo[4,3-a]quinoline | 342.98 |

TABLE 1-continued

| Example | Structure | IUPAC Name | LCMS |
|---|---|---|---|
| 13 | 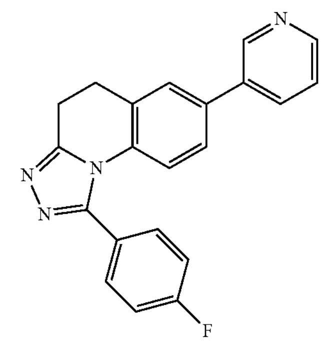 [SMILES: Fc1ccc(-c2nnc3n2-c2ccc(-c4cccnc4)cc2CC3)cc1] | 1-(4-fluorophenyl)-7-(pyridin-3-yl)-4,5-dihydro[1,2,4]triazolo[4,3-a]quinoline | 342.97 |
| 14 | 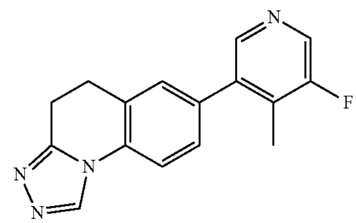 [SMILES: Cc1c(F)cncc1-c1ccc2c(c1)CCc1nncn1-2] | 7-(5-fluoro-4-methylpyridin-3-yl)-4,5-dihydro-[1,2,4]triazolo[4,3-a]quinoline | 281.2 |
| 15 | 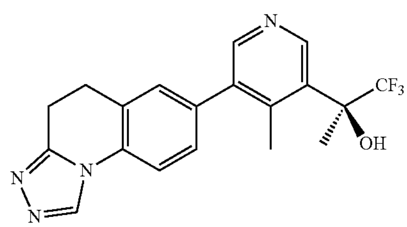 [SMILES: Cc1c(-c2ccc3c(c2)CCc2nncn2-3)cncc1[C@](C)(O)C(F)(F)F] | (S)-2-(5-(4,5-dihydro-[1,2,4]triazolo[4,3-a]quinolin-7-yl)-4-methylpyridin-3-yl)-1,1,1-trifluoropropan-2-ol | 361.1 |
| 16 | 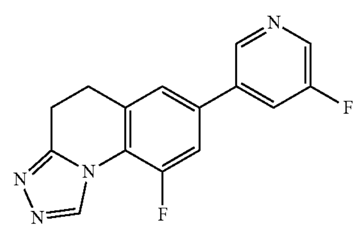 [SMILES: Fc1cncc(-c2cc(F)c3c(c2)CCc2nncn2-3)c1] | 9-fluoro-7-(5-fluoropyridin-3-yl)-4,5-dihydro-[1,2,4]triazolo[4,3-a]quinoline | 285.1 |
| 17 | 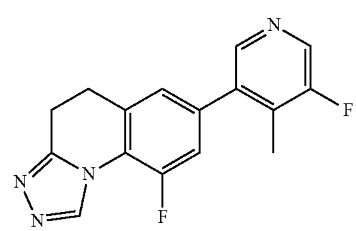 [SMILES: Cc1c(F)cncc1-c1cc(F)c2c(c1)CCc1nncn1-2] | 9-fluoro-7-(5-fluoro-4-methyl pyridin-3-yl)-4,5-dihydro-[1,2,4]triazolo[4,3a] quinoline | 299.1 |
| 18 | 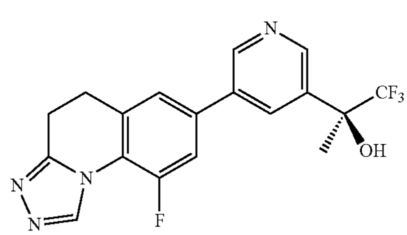 [SMILES: C[C@](O)(c1cncc(-c2cc(F)c3c(c2)CCc2nncn2-3)c1)C(F)(F)F] | (S)-1,1,1-trifluror-2-(5-(9-fluoro-4,5-dihydro-[1,2,4]triazolo[4,3a]quinolin-7-yl)pyridin-3-yl)propan-2-ol | 379.1 |

TABLE 1-continued

| Example | Structure | IUPAC Name | LCMS |
|---|---|---|---|
| 19 | 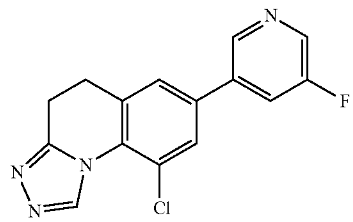 [SMILES: Fc1cncc(-c2cc(Cl)c3c(c2)CCc2nncn2-3)c1] | 9-chloro-7-(5-fluoropyridin-3-yl)-4,5-dihydro-[1,2,4]triazolo[4,3-a]quinoline | 301.1 |
| 20 | 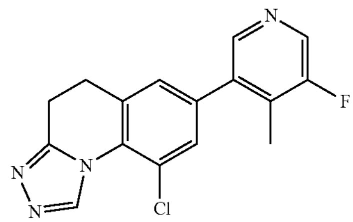 [SMILES: Cc1c(F)cncc1-c1cc(Cl)c2c(c1)CCc1nncn1-2] | 9-chloro-7-(5-fluoro-4-methylpyridin-3-yl)-4,5-dihydro-[1,2,4]triazolo[4,3-a]quinoline | 315.1 |
| 21 | 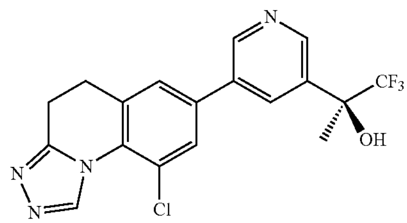 [SMILES: C[C@](O)(c1cncc(-c2cc(Cl)c3c(c2)CCc2nncn2-3)c1)C(F)(F)F] | (S)-2-(5-(9-chloro-4,5-dihydro-[1,2,4]triazolo[4,3-a]quinolin-7-yl)pyridin-3-yl)-1,1,1-trifluoropropan-2-ol | 395.1 |

Example 22

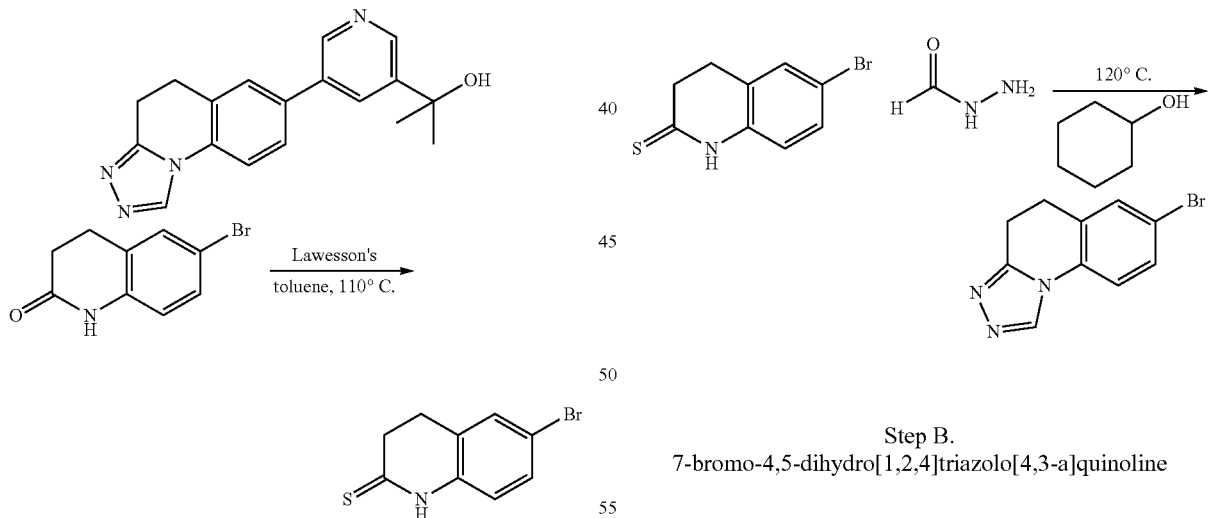

Step A. 6-bromo-3,4-dihydroquinoline-2(1H)-thione 6-bromo-3,4-dihydroquinolin-2-(1H)-one (1.00 g, 4.42 mmol) and 2,4-bis(4-methoxyphenyl)-1,3,2,4-dithiadiphosphetane2,4-disulfide (0.895 g, 2.21 mmol) were suspended in toluene (110 mL) and then heated to 110° C. overnight. The reaction was then cooled to room temperature and concentrated under reduced pressure. Dichloromethane was added, giving a mixture that was filtered to provide the title compound: LCMS m/z 243.95 [M+2+H]$^+$; $^1$H NMR (500 MHz, DMSO) δ 7.44 (s, 1H), 7.39 (d, J=8.4 Hz, 1H), 7.01 (d, J=8.4 Hz, 1H), 2.92-2.89 (m, 2H), 2.81-2.78 (m, 2H).

Step B.
7-bromo-4,5-dihydro[1,2,4]triazolo[4,3-a]quinoline

A flask containing the title compound from Example 22, Step A (0.200 g, 0.826 mmol), formic hydrazide (0.099 g, 1.65 mmol) and cyclohexanol (6.00 ml, 0.826 mmol) was heated to 120° C. for 16 hours. The reaction was then cooled to room temperature, poured into water and extracted with ethyl acetate. The organic extracts were combined, washed with brine, dried over sodium sulfate, filtered and concentrated. Purification by flash chromatography on silica gel (0-15% methanol in ethyl acetate) provided the title compound: LCMS m/z 251.90 [M+2+H]$^+$; $^1$H NMR (500 MHz, CD$_3$OD) δ 9.12 (s, 1H), 7.63-7.54 (m, 3H), 3.19-3.16 (m, 2H), 3.11-3.08 (m, 2H).

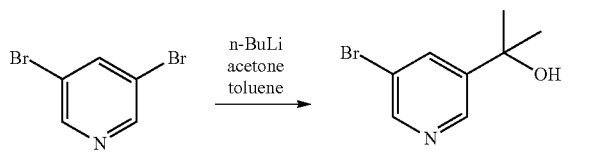 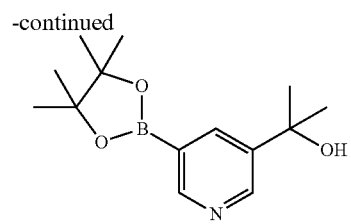

Step C. 2-(5-bromo-3-pyridinyl)-2-propanol

To a 5000-mL 4-necked round-bottom flask purged and maintained with an inert atmosphere of nitrogen was added a solution of 3,5-dibromopyridine (264 g, 1.12 mol) in toluene (3000 mL). The solution was cooled to −78° C., and a solution of n-butyllithium in hexanes (2.6 M, 475 mL, 1.24 mol) was then added, giving a solution that was stirred for 2 hours at −78° C. Acetone (108 g, 1.86 mol) was then added. After 1 hour, the reaction mixture was quenched by addition of 350 mL saturated aqueous ammonium chloride solution. The resulting solution was extracted with ethyl acetate. The organic extracts were combined, dried over anhydrous sodium sulfate and concentrated under reduced pressure. Purification by flash chromatography on silica gel (ethyl acetate/petroleum ether 1:10-1:5) provided the title compound: $^1$H NMR (400 MHz, CDCl$_3$): δ 8.63 (s, 1H), 8.56 (s, 1H), 8.01 (s, 1H), 1.61 (s, 6H).

Step D. 2-[5-(4,4,5,5-tetramethyl-1,3,2-dioxaborolan-2-yl)-3-pyridinyl]-2-propanol To a 5000-mL 4-necked round-bottom flask purged and maintained with an inert atmosphere of nitrogen were added a solution of the title compound from Example 22 Step C (160 g, 395 mmol) in 1,4-dioxane (2000 mL), 4,4,5,5-tetramethyl-2-(4,4,5,5-tetramethyl-1,3,2-dioxaborolan-2-yl)-1,3,2-dioxaborolane (240 g, 498 mmol), potassium acetate (240 g, 1.63 mol), and PdCl$_2$(dppf) (30 g, 23 mmol). The resulting solution was stirred for 4 hours at 80° C. The reaction was then cooled to room temperature, filtered and concentrated under reduced pressure. The residual solution was diluted with hexanes and filtered. HCl gas was bubbled through the filtrate. The resulting mixture was filtered, and the solids diluted with dichloromethane, then concentrated under reduced pressure. The residue was diluted with H$_2$O, and washed sequentially with diethyl ether, dichloromethane, and hexanes. The aqueous layer was adjusted to pH 7-8 with saturated aqueous sodium carbonate solution, then extracted with dichloromethane. The organic extracts were combined, dried and concentrated under vacuum to afford the title compound: $^1$H NMR (400 MHz, CDCl$_3$): δ 8.83 (s, 1H), 8.19 (s, 1H), 1.62 (s, 6H), 1.36 (s, 12H).

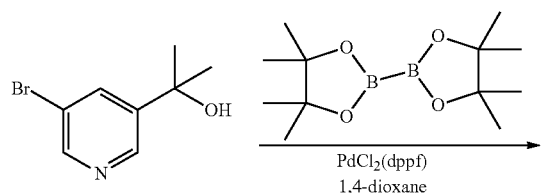

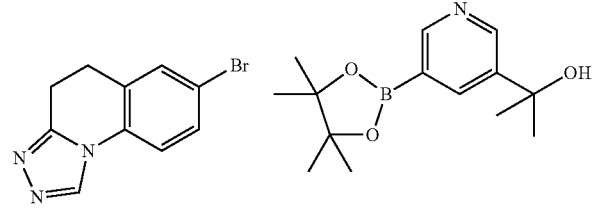 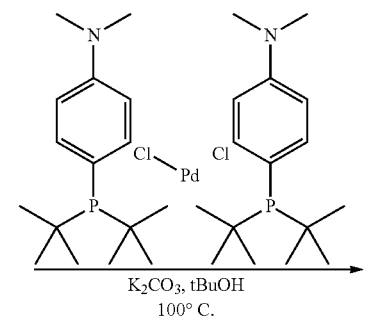

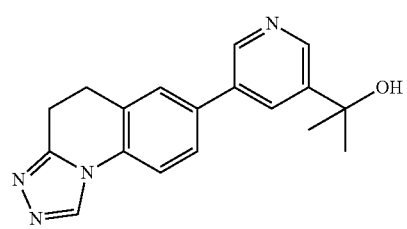

Step E. 2-[5-(4,5-dihydro[1,2,4]triazolo[4,3-a]quinolin-7-yl)pyridin-3-yl]propan-2-ol To a sealable tube containing the title compound from Example 22 Step B (0.075 g, 0.300 mmol), the title compound from Example 22 Step D (0.103 g, 0.390 mmol) and bis(di-tert-butyl(4-dimethylaminophenyl)phosphine)dichloropalladium(II) (10.6 mg, 0.015 mmol) was added tert-butanol (3.3 mL). The tube was flushed with nitrogen before the addition of potassium carbonate (0.12 g, 0.90 mmol) and water (0.42 mL). It was flushed again with nitrogen, sealed and heated to 100° C. overnight. The reaction was then cooled to room temperature, poured into saturated aqueous sodium chloride solution and extracted with ethyl acetate. The organic extracts were combined, washed with water, dried over sodium sulfate, filtered and concentrated. The resulting residue was diluted with dimethylsulfoxide, passed through a syringe filter and purified by HPLC (C18 column, 10 to 100% acetonitrile/water, both 0.1% v/v trifluoroacetic acid) to provide the title compound: LCMS m/z 307.03 [M+H]$^+$; $^1$H NMR (500 MHz, DMSO) δ 9.38 (s, 1H), 8.98 (s, 1H), 8.80 (s, 1H), 8.51 (s, 1H), 7.95-7.87 (m, 3H), 3.15 (s, 4H), 1.55 (s, 6H).

The compounds in Table 2 were all prepared using chemistry described in Example 22. Pyridyl boronic acids were either prepared as described in Example 22 Steps C and D, or were obtained commercially.

TABLE 2

| Example | Structure | IUPAC Name | LCMS |
|---|---|---|---|
| 23 | 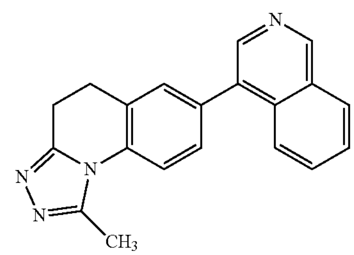 | 7-(isoquinolin-4-yl)-1-methyl-4,5-dihydro[1,2,4]triazolo[4,3-a]quinoline | 313.08 |
| 24 | 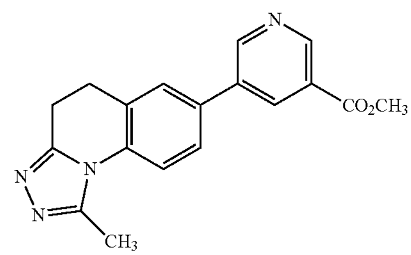 | methyl 5-(1-methyl-4,5-dihydro[1,2,4]triazolo[4,3-a]quinolin-7-yl)pyridine-3-carboxylate | 321.04 |
| 25 | 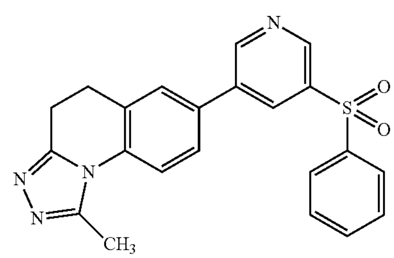 [SMILES: Cc1nnc2n1-c1ccc(-c3cncc(S(=O)(=O)c4ccccc4)c3)cc1CC2] | 1-methyl-7-[5-(phenylsulfonyl)pyridin-3-yl]-4,5-dihydro[1,2,4]triazolo[4,3-a]quinoline | 402.94 |
| 26 | 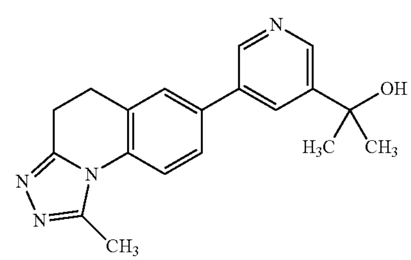 [SMILES: Cc1nnc2n1-c1ccc(-c3cncc(C(C)(C)O)c3)cc1CC2] | 2-[5-(1-methyl-4,5-dihydro[1,2,4]triazolo[4,3-a]quinolin-7-yl)pyridin-3-yl]propan-2-ol | 321.04 |

TABLE 2-continued

| Example | Structure | IUPAC Name | LCMS |
|---|---|---|---|
| 27 | 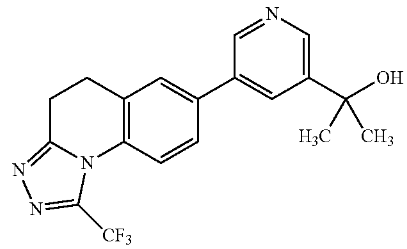 | 2-{5-[1-(trifluoromethyl)-4,5-dihydro[1,2,4]triazolo[4,3-a]quinolin-7-yl]pyridin-3-yl}propan-2-ol | 375.02 |
| 28 | 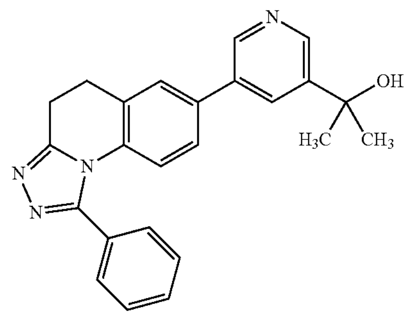 [SMILES: CC(C)(O)c1cncc(-c2ccc3c(c2)CCc2nnc(-c4ccccc4)n2-3)c1] | 2-[5-(1-phenyl-4,5-dihydro[1,2,4]triazolo[4,3-a]quinolin-7-yl)pyridin-3-yl]propan-2-ol | 383.04 |
| 29 | 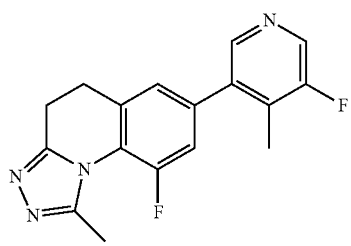 [SMILES: Cc1c(F)cncc1-c1cc(F)c2c(c1)CCc1nnc(C)n1-2] | 9-fluoro-7-(5-fluoro-4-methyl pyridin-3-yl)-1-methyl-4,5-dihydro-[1,2,4]triazolo[4,3-a] quinoline | 313.15 |
| 30 | 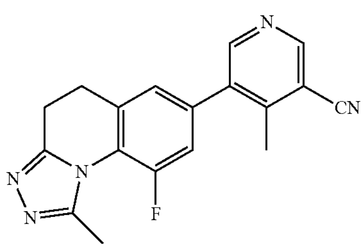 [SMILES: Cc1c(C#N)cncc1-c1cc(F)c2c(c1)CCc1nnc(C)n1-2] | 5-(9-fluoro-1-methyl-4,5-dihydro-[1,2,4]triazolo[4,3a] quinolin-7-yl)-4-methylnicotinonitrile | 320.1 |
| 31 | 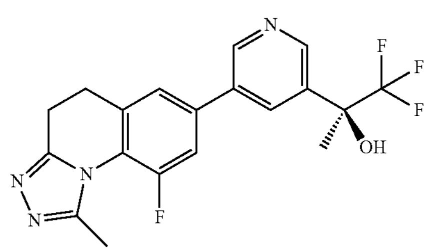 [SMILES: Cc1nnc2n1-c1c(F)cc(-c3cncc([C@](C)(O)C(F)(F)F)c3)cc1CC2] | (S)-1,1,1-trifluoro-2-(5-(9-fluoro-1-methyl-4,5-dihydro-[1,2,4] triazolo[4,3-a]quinolin-7-yl)pyridin-3-yl)propan-2-ol | 393.1 |
| 32 | 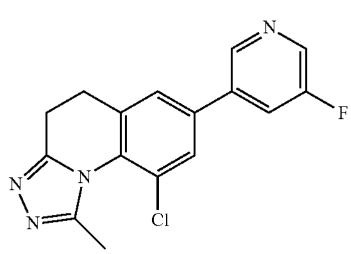 [SMILES: Cc1nnc2n1-c1c(Cl)cc(-c3cncc(F)c3)cc1CC2] | 9-chloro-7-(5-fluoropyridin-3-yl)-1-methyl-4,5-dihydro-[1,2,4]triazolo[4,3-a]quinoline | 315.1 |

TABLE 2-continued

| Example | Structure | IUPAC Name | LCMS |
|---|---|---|---|
| 33 | 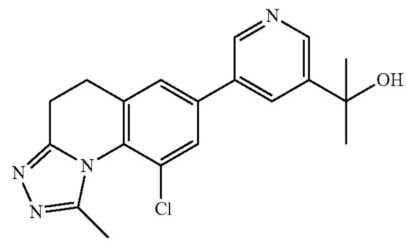 [SMILES: Cc1nnc2n1-c1c(Cl)cc(-c3cncc(C(C)(C)O)c3)cc1CC2] | 2-(5-(9-chloro-1-methyl-4,5,-dihydro-[1,2,4]triazolo[4,3-a]quinolin-7-yl)pyridin-3-yl)propan-2-ol | 355.1 |
| 34 | 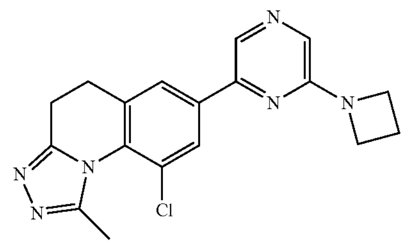 [SMILES: Cc1nnc2n1-c1c(Cl)cc(-c3cncc(N4CCC4)n3)cc1CC2] | 7-(6-(azetidin-1-yl)pyrazin-2-yl)-9-chloro-1-methyl-4,5-dihydro-[1,2,4]triazolo[4,3-a]quinoline | 353.1 |
| 35 | Enantiomer A | 1-(5-(9-chloro-1-methyl-4,5-dihydro-[1,2,4]triazolo[4,3-a]quinolin-7-yl)pyridin-3-yl)-2,2,2-trifluoroethanol | 395.1 |
| 36 | Enantiomer B | 1-(5-(9-chloro-1-methyl-4,5-dihydro-[1,2,4]triazolo[4,3-a]quinolin-7-yl)pyridin-3-yl)-2,2,2-trifluoroethanol | 395.1 |
| 37 | Enantiomer A | 1-(5-(9-chloro-1-methyl-4,5-dihydro-[1,2,4]triazolo[4,3-a]quinolin-7-yl)-4-methylpyridin-3-yl)-1,1,1-trifluoropropan-2-ol | 423.1 |
| 38 | Enantiomer B | 1-(5-(9-chloro-1-methyl-4,5-dihydro-[1,2,4]triazolo[4,3-a]quinolin-7-yl)-4-methylpyridin-3-yl)-1,1,1-trifluoropropan-2-ol | 423.1 |

TABLE 2-continued

| Example | Structure | IUPAC Name | LCMS |
|---|---|---|---|
| 39 | 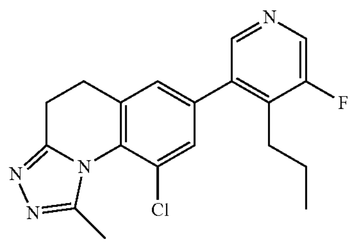 [SMILES: CCCc1c(F)cncc1-c1cc(Cl)c2c(c1)CCc1nnc(C)n1-2] | 9-chloro-7-(5-fluoro-4-propylpyridin-3-yl)-1-methyl-4,5-dihydro-[1,2,4]triazolo[4,3-a]quinoline | 357.1 |
| 40 | 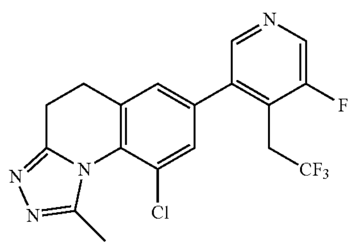 [SMILES: Cc1nnc2n1-c1c(Cl)cc(-c3cncc(F)c3CC(F)(F)F)cc1CC2] | 9-chloro-7-(5-fluoro-4-(2,2,2-trifluoroethyl)pyridin-3-yl)-1-methyl-4,5-dihydro-[1,2,4]triazolo[4,3-a]quinoline | 369.9 |
| 41 | 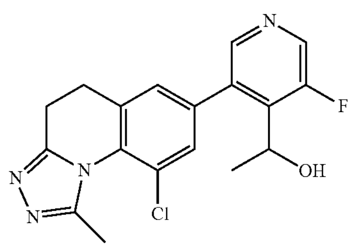 [SMILES: Cc1nnc2n1-c1c(Cl)cc(-c3cncc(F)c3C(C)O)cc1CC2] | 1-(3-(9-chloro-1-methyl-4,5-dihydro-[1,2,4]triazolo[4,3-a]quinolin-7-yl)-5-fluoropyridin-4-yl)ethanol | 359.1 |
| 42 | 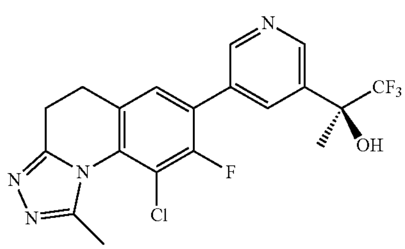 [SMILES: Cc1nnc2n1-c1c(cc(-c3cncc([C@](C)(O)C(F)(F)F)c3)c(F)c1Cl)CC2] | (S)-2-(5-(9-chloro-8-fluoro-1-methyl-4,5-dihydro-[1,2,4]trifluoro[4,3-a]quinolin-7-yl)pyridin-3-yl)-1,1,1-trifluoropropan-2-ol | 427.0 |
| 43 | 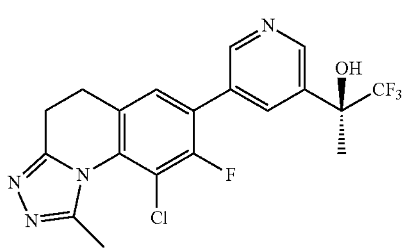 | (R)-2-(5-(9-chloro-8-fluoro-1-methyl-4,5-dihydro-[1,2,4]trifluoro[4,3-a]quinolin-7-yl)pyridin-3-yl)-1,1,1-trifluoropropan-2-ol | 427.0 |
| 44 | 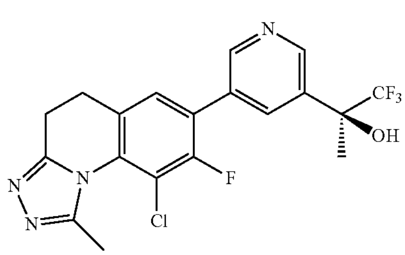 [SMILES: Cc1nnc2n1-c1c(cc(-c3cncc([C@](C)(O)C(F)(F)F)c3)c(F)c1Cl)CC2] | (S)-2-(5-(9-chloro-8-fluoro-1-methyl-4,5-dihydro-[1,2,4]trifluoro[4,3-a]quinolin-7-yl)pyridin-3-yl)-1,1,1-trifluoropropan-2-ol | 425.0 |

TABLE 2-continued

| Example | Structure | IUPAC Name | LCMS |
|---|---|---|---|
| 45 | 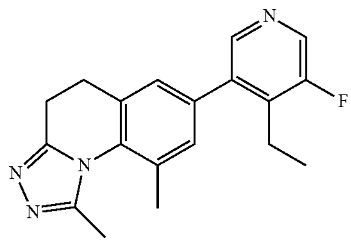 [SMILES: CCc1c(F)cncc1-c1cc(C)c2c(c1)CCc1nnc(C)n1-2] | 7-(4-ethyl-5-fluoropyridin-3-yl)-1,9-dimethyl-4,5-dihydro-[1,2,4]triazolo[4,3-a]quinoline | 323.2 |
| 46 | 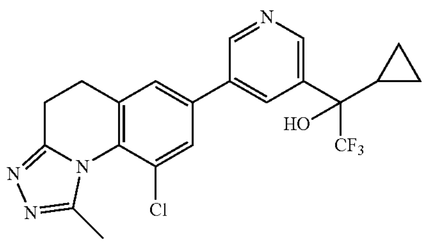 [SMILES: Cc1nnc2n1-c1c(Cl)cc(-c3cncc(C(O)(C4CC4)C(F)(F)F)c3)cc1CC2] | 1-(5-(9-chloro-1-methyl-4,5-dihydro-[1,2,4]triazolo[4,3-a]quinolin-7-yl)pyridin-3-yl)-1-cyclopropyl-2,2,2-trifluoroethanol | 435.0 |
| 47 | 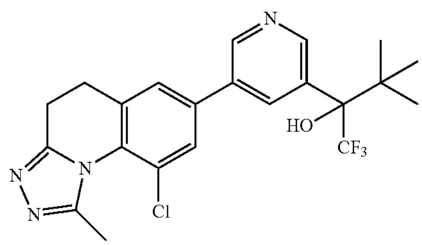 [SMILES: Cc1nnc2n1-c1c(Cl)cc(-c3cncc(C(O)(C(C)(C)C)C(F)(F)F)c3)cc1CC2] | 2-(5-(9-chloro-1-methyl-4,5-dihydro-[1,2,4]triazolo[4,3-a]quinolin-7-yl)pyridin-3-yl)-1,1,1-trifluoro-3,3-dimethylbutan-2-ol | 451.0 |

Example 48

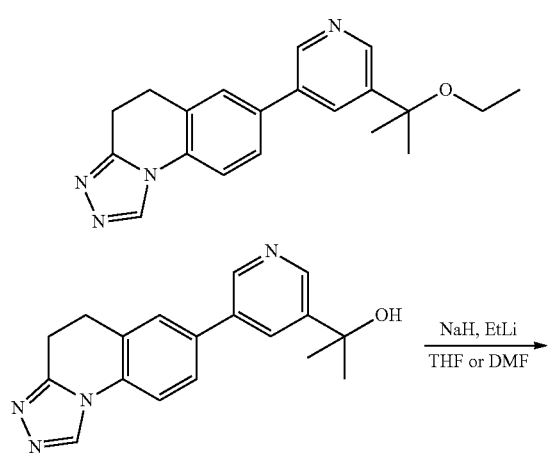

Step A. 7-[5-(2-ethoxypropan-2-yl)pyridin-3-yl]-4,5-dihydro[1,2,4]triazolo[4,3-a]quinoline To a cooled (0° C.) solution of the title compound from Example 22 Step E (80 mg, 0.26 mmol) in N,N-dimethylformamide (2.5 mL) was added sodium hydride (60% dispersion in mineral oil, 26 mg, 0.65 mmol). The resulting suspension was stirred at 0° C. for 30 minutes, and iodoethane (0.025 mL, 0.313 mmol) was then added. The reaction was stirred for 1 hour and was then quenched with aqueous 0.1% trifluoroacetic acid solution. It was then diluted with water and acetonitrile, passed through a syringe filter and purified by HPLC (C18 column, 10 to 100% acetonitrile/water, both 0.1% v/v trifluoroacetic acid) to provide the title compound: LCMS m/z 335.07 [M+H]$^+$; $^1$H NMR (500 MHz, CD$_3$OD) δ 10.16 (s, 1H), 9.21 (s, 1H), 8.95 (s, 1H), 8.93 (s, 1H), 8.15 (d, J=8.5 Hz, 1H), 8.04 (d, J=8.4 Hz, 1H), 3.53-3.40 (m, 6H), 1.70 (s, 6H), 1.24 (t, J=7.0 Hz, 3H).

Example 49

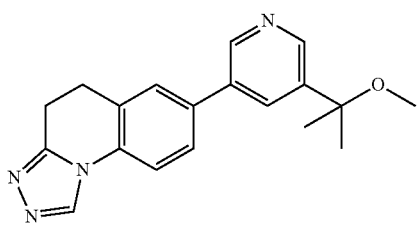

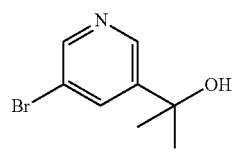

NaH, MeI, DMF

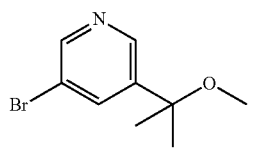

Step A. 3-bromo-5-(2-methoxypropan-2-yl)pyridine

To a solution of sodium hydride (60% dispersion in mineral oil, 46 mg, 1.2 mmol) in N,N-dimethylformamide (4.6 mL) at 0° C. was added a solution of the title compound from Example 22 Step C (100 mg, 0.463 mmol) in N,N-dimethylformamide (4.6 mL). After warming to room temperature and stirring for 1 hour, the solution was cooled back to 0° C. and iodomethane (35 µl, 0.56 mmol) was added. After stirring overnight, the reaction was poured into water and extracted with ethyl acetate. The organic extracts were combined, washed with saturated aqueous sodium chloride solution, dried over sodium sulfate and concentrated under reduced pressure to afford the title compound: LCMS m/z 232.97 [M+H]+.

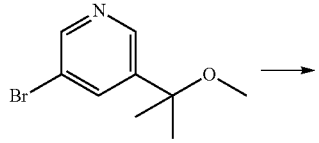

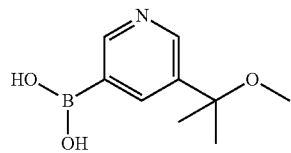

Step B.
[5-(2-methoxypropan-2-yl)pyridin-3-yl]boronic acid

To a vial containing the title compound from Example 49 Step A (0.07 g, 0.30 mmol), bis(pinacolato)diboron (0.093 g, 0.37 mmol), potassium acetate (0.090 g, 0.91 mmol), tris(dibenzylideneacetone)dipalladium (0) (0.028 g, 0.030 mmol) and tricyclohexylphosphine (0.017 g, 0.061 mmol) was added 1,4-dioxane (3.0 mL). The vial was flushed with nitrogen, sealed tightly and heated to 80° C. overnight. The reaction was then concentrated under reduced pressure to provide the title compound which was used without further purification.

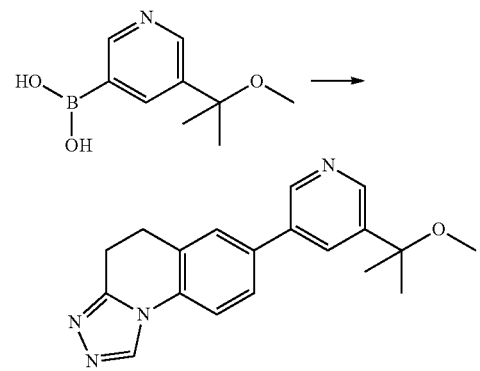

Step C. 7-[5-(2-methoxypropan-2-yl)pyridin-3-yl]-4,5-dihydro[1,2,4]triazolo[4,3-a]quinoline To a vial containing the title compound from Example 22 Step B (30 mg, 0.12 mmol), the title compound from Example 49 Step B (28 mg, 0.14 mmol), bis(di-tert-butyl(4-dimethylaminophenyl)phosphine)dichloropalladium(II) (4.3 mg, 6.0 µmol) and potassium carbonate (50 mg, 0.36 mmol) was added tert-butanol (1.3 mL) and water (167 µL). The reaction was heated to 90° C. overnight. The reaction was then concentrated under reduced pressure, diluted with acetonitrile and purified by HPLC (C18 column, 10 to 100% acetonitrile/water, both 0.1% v/v trifluoroacetic acid) to provide the title compound: LCMS m/z 320.99 [M+H]+; $^1$H NMR (500 MHz, d6-DMSO) δ 9.38 (s, 1H), 8.94 (s, 1H), 8.68 (s, 1H), 8.24 (s, 1H), 7.93-7.86 (m, 3H) 3.15 (s, 4H), 3.08 (s, 3H), 1.56 (s, 6H).

The compounds in Table 3 were all prepared using chemistry described in Examples 48 or 49.

TABLE 3

| Example | Structure | IUPAC Name | LCMS |
|---|---|---|---|
| 50 | 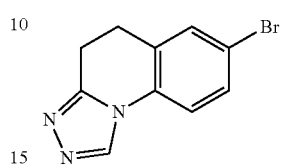 | 7-[5-(2-methoxypropan-2-yl)pyridin-3-yl]-1-methyl-4,5-dihydro[1,2,4]triazolo[4,3-a]quinoline | 335.11 |

TABLE 3-continued

| Example | Structure | IUPAC Name | LCMS |
|---|---|---|---|
| 51 | 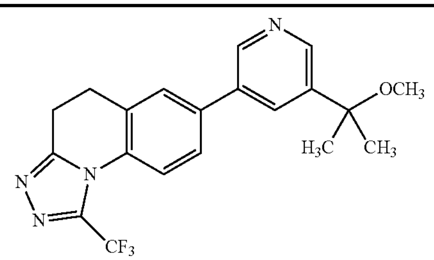 | 7-[5-(2-methoxypropan-2-yl)pyridin-3-yl]-1-(trifluoromethyl)-4,5-dihydro[1,2,4]triazolo[4,3-a]quinoline | 388.95 |
| 52 | 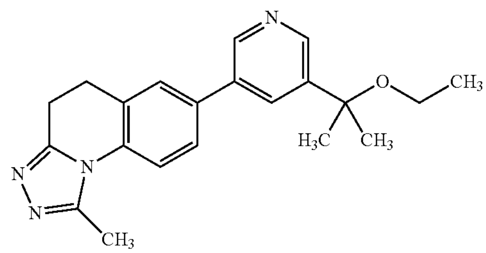 [SMILES: CCOC(C)(C)c1cncc(-c2ccc3c(c2)CCc2nnc(C)n2-3)c1] | 7-[5-(2-ethoxypropan-2-yl)pyridin-3-yl]-1-methyl-4,5-dihydro[1,2,4]triazolo[4,3-a]quinoline | 349.10 |

Example 53

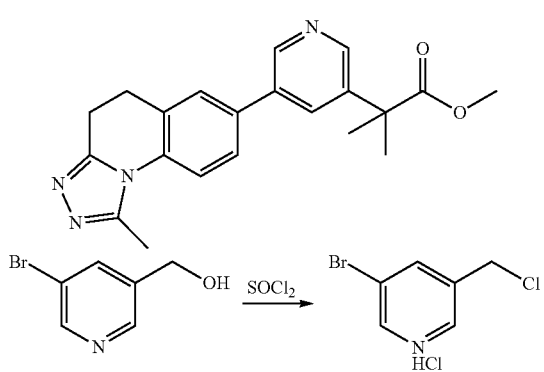

Step A. 3-bromo-5-(chloromethyl)pyridine

To a cooled (0° C.) solution of (5-bromopyridin-3-yl)methanol (38.8 g, 0.206 mol) in dichloromethane (0.6 L) was added a solution of thionyl chloride (149 mL, 2.05 mol) in dichloromethane (200 mL). The resulting mixture was stirred at reflux overnight. The reaction was then concentrated under reduced pressure, and the resulting residue was recrystallized from diethyl ether to provide the title compound: LCMS m/z 206 [M+H]$^+$; $^1$H NMR (300 MHz, d6-DMSO) δ 12.66 (s, 1H), 8.69-8.74 (m, 2H), 8.25 (s, 1H), 4.83 (s, 2H).

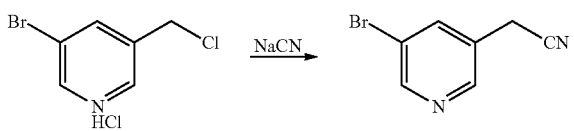

Step B. (5-bromo-3-pyridinyl)acetonitrile

A solution of the title compound from Example 53 Step A dissolved in 500 mL of ethyl acetate was made basic with saturated aqueous sodium bicarbonate solution. The organic layer was washed with saturated aqueous sodium chloride solution and concentrated. The residue was dissolved in 400 mL of ethanol at room temperature and was added to a solution of sodium cyanide in 90 mL of water. Then the mixture was stirred at reflux overnight. The mixture was cooled to room temperature and poured into water. It was extracted with dichloromethane, the organic layer was dried and concentrated to give the crude product which was purified by flash chromatograph on silica gel (petroleum ether:ethyl acetate=20:1-5:1) to give the title compound: LCMS m/z 197 [M+H]$^+$; $^1$H NMR (300 MHz, CDCl$_3$) δ 8.67 (s, 1H), 8.51 (s, 1H), 7.89 (s, 1H), 3.78 (s, 2H).

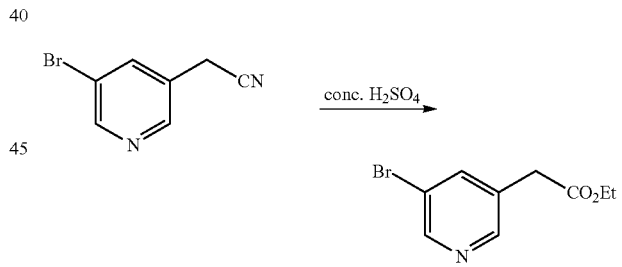

Step C. ethyl(5-bromo-3-pyridinyl)acetate

To a mixture of ethanol (10 mL) and conc. H$_2$SO$_4$ (4 mL) was added the title compound from Example 53 Step B (0.50 g, 2.5 mmol) in 3 mL of ethanol at room temperature. The mixture was stirred at 90° C. overnight. The reaction was poured into ice and made basic with saturated aqueous sodium bicarbonate solution. It was then extracted with ethyl acetate (2×30 mL), the organic layer was dried, concentrated and purified by flash chromatography on silica gel (petroleum ether:ethyl acetate=10:1) to give the title compound: LCMS m/z 244 [M+H]$^+$; $^1$H NMR (300 MHz, CDCl$_3$) δ 8.60 (s, 1H), 8.44 (s, 1H), 7.82 (s, 1H), 4.17-4.20 (m, 2H), 3.61 (s, 2H), 1.27-1.30 (m, 3H).

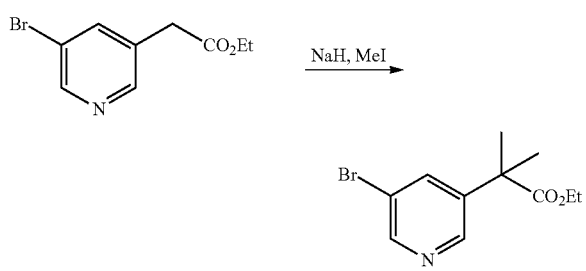

Step D. ethyl 2-(5-bromo-3-pyridinyl)-2-methylpropanoate

To a suspension of sodium hydride (251 mg, 5.33 mmol) in 10 mL of N,N-dimethylformamide at 0° C. was added a solution of the title compound from Example 53 Step C (520 mg, 2.13 mmol) in N,N-dimethylformamide (2 mL). After 1 hour, iodomethane (0.29 mL, 4.67 mmol) in 2 mL of N,N-dimethylformamide was added. The resulting mixture was then allowed to warm to room temperature over 2 hours. The reaction was then quenched by addition of water, extracted and purified by flash chromatograph on silica gel (petroleum ether:ethyl acetate 40:1-20:1) to give the title compound: LCMS m/z 272 [M+H]$^+$; $^1$H NMR (300 MHz, CDCl$_3$) δ 8.53-8.56 (m, 2H), 7.80 (s, 1H), 4.10-4.18 (m, 2H), 1.60 (s, 2H), 1.18-1.22 (m, 3H).

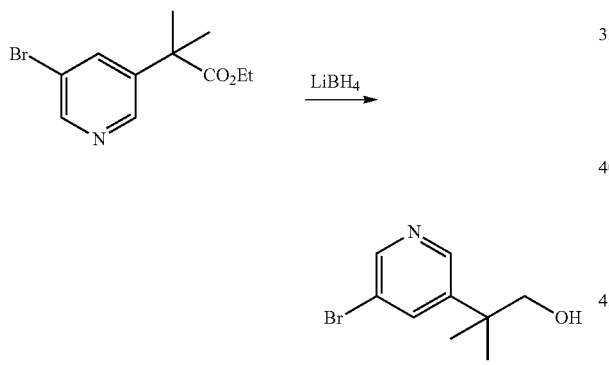

Step E. 2-(5-bromo-3-pyridinyl)-2-methyl-1-propanol

To a solution of the title compound from Example 53 Step D (93 g, 0.34 mol) in ethanol (1.2 L) was added lithium borohydride (16.6 g, 0.75 mol). The resulting mixture was heated to reflux and stirred overnight. The reaction was then cooled to room temperature and poured onto ice. The mixture was extracted with ethyl acetate, and the organic layer washed with saturated aqueous sodium chloride solution, dried over magnesium sulfate, filtered and concentrated under reduced pressure. Purification by flash chromatograph on silica gel (petroleum ether/ethyl acetate=40/1-8/1) provided the title compound: LCMS m/z 230 [M+H]$^+$; $^1$H NMR (300 MHz, CDCl$_3$) δ 8.58 (s, 1H), 8.52 (s, 1H), 7.97 (s, 1H), 4.82-4.86 (m, 1H), 3.44-3.46 (m, 2H), 1.24 (s, 6H).

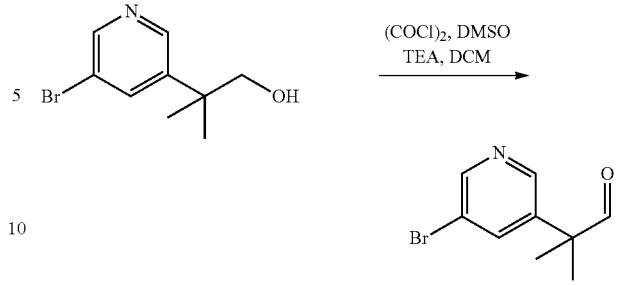

Step F. 2-(5-bromopyridin-3-yl)-2-methylpropanal

A solution of oxalyl chloride in dichloromethane (2.0 M, 0.869 mL, 1.74 mmol) was diluted with dichloromethane (2 mL) and then a solution of dimethylsulfoxide (0.250 mL, 3.50 mmol) in dichloromethane (1 mL) was added at −78° C. After stirring for 15 minutes, a solution of the title compound from Example 53 Step E (0.200 g, 0.869 mmol) in dichloromethane (3 mL) was added. The resulting reaction stirred for 30 minutes before triethylamine (0.600 mL, 4.35 mmol) was added. The reaction warmed to room temperature slowly and stirred overnight. It was quenched with the addition of water and then extracted with dichloromethane. The combined organics were washed with saturated aqueous sodium chloride solution, dried over sodium sulfate, filtered and concentrated under reduced pressure. Purification by flash chromatography on silica gel (25-100% ethyl acetate in hexanes) provided the title compound: LCMS m/z 229.87 [M+2H]$^+$; $^1$H NMR (500 MHz, CDCl$_3$) δ 9.53 (s, 1H), 8.61 (s, 1H), 8.47 (s, 1H), 7.73 (s, 1H), 1.51 (s, 6H).

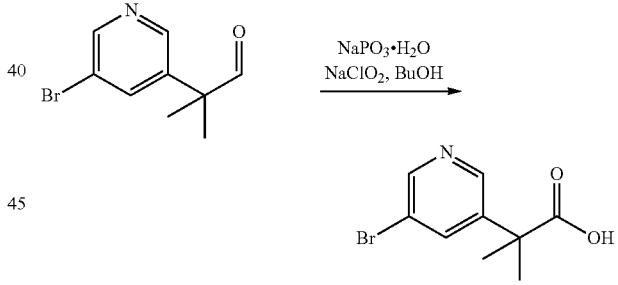

Step C. 2-(5-bromopyridin-3-yl)-2-methylpropanoic acid

To a cooled (0° C.) solution of the title compound from Example 53 Step F (0.100 g, 0.438 mmol) in tert-butanol (2.2 mL) was added an aqueous solution of sodium-m-phosphate monohydrate (2.0 M, 0.658 mL, 1.32 mmol). After several minutes, an aqueous solution of sodium chlorite (2.0M, 0.77 ml, 1.54 mmol) was added. The resulting reaction was allowed to warm to room temperature where it stirred until complete. The reaction was concentrated under reduced pressure, then diluted with aqueous 0.1% trifluoroacetic acid solution and passed through a syringe filter. Purification by HPLC (C18 column, 10 to 100% acetonitrile/water, both 0.1% v/v trifluoroacetic acid) provided the title compound: LCMS m/z 245.97 [M+2+H]$^+$; $^1$H NMR (500 MHz, CD$_3$OD) δ 8.64 (s, 1H), 8.62 (s, 1H), 8.19 (s, 1H), 1.62 (s, 6H).

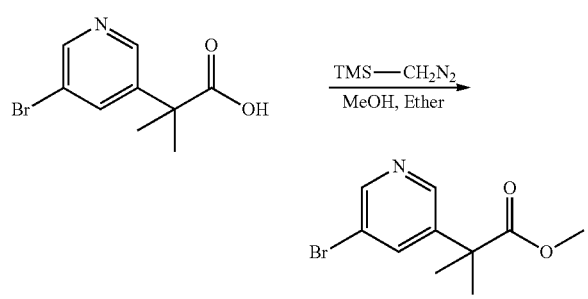

Step H. methyl 2-(5-bromopyridin-3-yl)-2-methylpropanoate

To a solution of the title compound from Example 53 Step G (0.350 g, 1.43 mmol) in diethyl ether (8.6 mL) and methanol (5.7 mL) was added a solution of (trimethylsilyl)diazomethane in diethyl ether (2.0 M, 1.08 mL, 2.16 mmol). The reaction stirred for 1 hour before being quenched with acetic acid. The reaction solution was then concentrated under reduced pressure and purified by flash chromatography on silica gel (0-80% ethyl acetate in hexanes) to provide the title compound: LCMS m/z 259.83 [M+2+H]+; 1H NMR (500 MHz, DMSO) δ 8.54 (s, 1H), 8.50 (s, 1H), 7.99 (s, 1H), 3.68 (s, 3H), 1.60 (s, 6H).

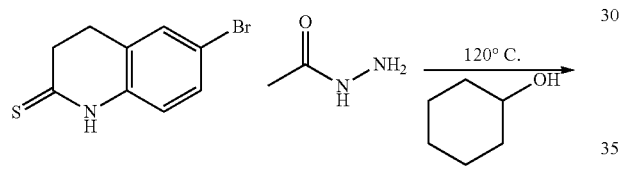

Step I. 7-bromo-1-methyl-4,5-dihydro[1,2,4]triazolo[4,3-a]quinoline

A flask containing the title compound from Example 22 Step A (100 mg, 0.413 mmol), acetic hydrazide (40.8 mg, 0.496 mmol) and cyclohexanol (2.00 ml, 0.413 mmol) was heated at reflux for 2 days. The reaction was then poured into water and extracted with ethyl acetate. The organic extracts were combined, washed with brine, dried over sodium sulfate, filtered and concentrated under reduced pressure. Purification by flash chromatography on silica gel (0-15% methanol in ethyl acetate) provided the title compound: LCMS m/z 265.99 [M+2+H]+; 1H NMR (500 MHz, CDCl3) δ 7.53 (br s, 1H), 7.50 (d, J=8.57 Hz, 1H), 7.35 (d, J=8.57 Hz, 1H), 3.13-3.11 (m, 2H), 3.00-2.98 (m, 2H), 2.74 (s, 3H).

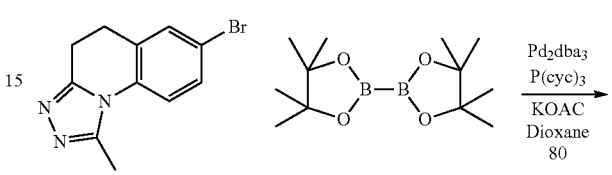

Step J. 1-methyl-7-(4,4,5,5-tetramethyl-1,3,2-dioxaborolan-2-yl)-4,5-dihydro[1,2,4]triazolo[4,3-a]quinoline To a vial containing the title compound from Example 53 Step 1 (0.100 g, 0.379 mmol), bis(pinacolato)diboron (0.115 g, 0.454 mmol), potassium acetate (0.111 g, 1.14 mmol), tris(dibenzylideneacetone)dipalladium (0) (0.035 g, 0.038 mmol) and tricyclohexylphosphine (0.021 g, 0.076 mmol) was added 1,4-dioxane (3.8 mL). The vial was flushed with nitrogen, sealed tightly and heated to 80° C. overnight. The reaction was poured into saturated aqueous sodium chloride solution and extracted with ethyl acetate. The combined organic extracts were washed with water, dried over sodium sulfate, filtered and concentrated. Purification by flash chromatography on silica gel (0-12% methanol in ethyl acetate) provided the title compound: LCMS m/z 311.98 [M+H]+; 1H NMR (500 MHz, CD3OD) δ (s, 1H), 8.50 (1H), 7.99 (s, 1H), 3.68 (s, 3H), 1.60 (s, 6H).

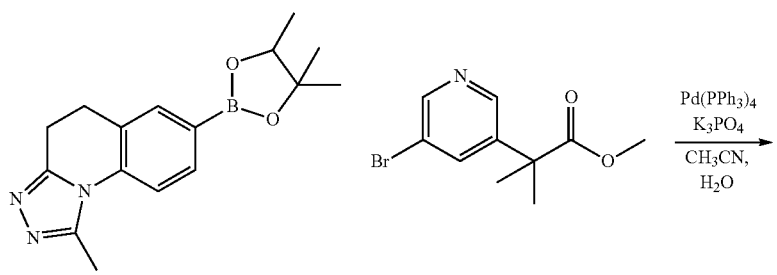

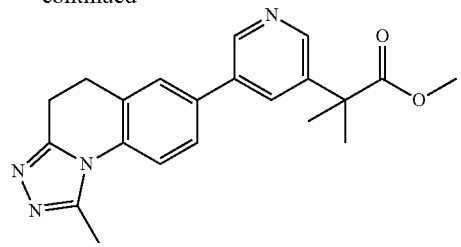

Step K. methyl 2-methyl-2-[5-(1-methyl-4,5-dihydro[1,2,4]triazolo[4,3-a]quinolin-7-yl)pyridin-3-yl]propanoate To a vial containing the title compound from Example 53 Step J (12.5 mg, 0.040 mmol), the title compound from Example 26 Step H (8.0 mg, 0.03 mmol) and tetrakis(triphenylphosphine)palladium (0) (7.2 mg, 6.2 µmol) was added acetonitrile (0.34 mL). The vial was flushed with nitrogen prior to the addition of potassium phosphate tribasic (19.7 mg, 0.093 mmol) in water (0.04 mL). The vial was capped tightly and heated to 100° C. overnight. The reaction was then poured into saturated aqueous sodium chloride solution and extracted with ethyl acetate. The combined organic extracts were washed with water, dried over sodium sulfate, filtered and concentrated under reduced pressure. The resulting residue was diluted with dimethylsulfoxide, passed through a syringe filter and purified by HPLC (C18 column, 10 to 100% acetonitrile/water, both 0.1% v/v trifluoroacetic acid) to provide the title compound: LCMS 363.11 [M+2+H]$^+$; $^1$H NMR (500 MHz, CDCl$_3$) δ 8.73 (s, 1H), 8.64 (s, 1H), 7.82 (m, 1H), 7.61-7.57 (m, 3H), 3.70 (s, 3H), 3.20-3.17 (m, 2H), 3.12-3.09 (m, 2H), 2.81 (s, 3H), 1.69 (s, 6H).

Step A. 2-methyl-2-[5-(1-methyl-4,5-dihydro[1,2,4]triazolo[4,3-a]quinolin-7-yl)pyridin-3-yl]propanoic acid To a vial containing the title compound from Example 53 Step J (30 mg, 0.123 mmol), the title compound from Example 53 Step G (46 mg, 0.15 mmol) and tetrakis(triphenylphosphine)palladium (0) (14.2 mg, 0.012 mmol) was added toluene (880 µL) and ethanol (180 µL). The vial was flushed thoroughly with nitrogen prior to addition of a solution of potassium phosphate tribasic (78 mg, 0.37 mmol) in water (180 µL) was added. The vial was then capped tightly and heated to 90° C. overnight. The reaction was quenched with the addition of water and then extracted with ethyl acetate. The combined organic extracts were washed with saturated aqueous sodium chloride solution, dried over sodium sulfate, filtered and concentrated to afford the title compound: LCMS m/z 349.0[M+H]$^+$.

Example 54

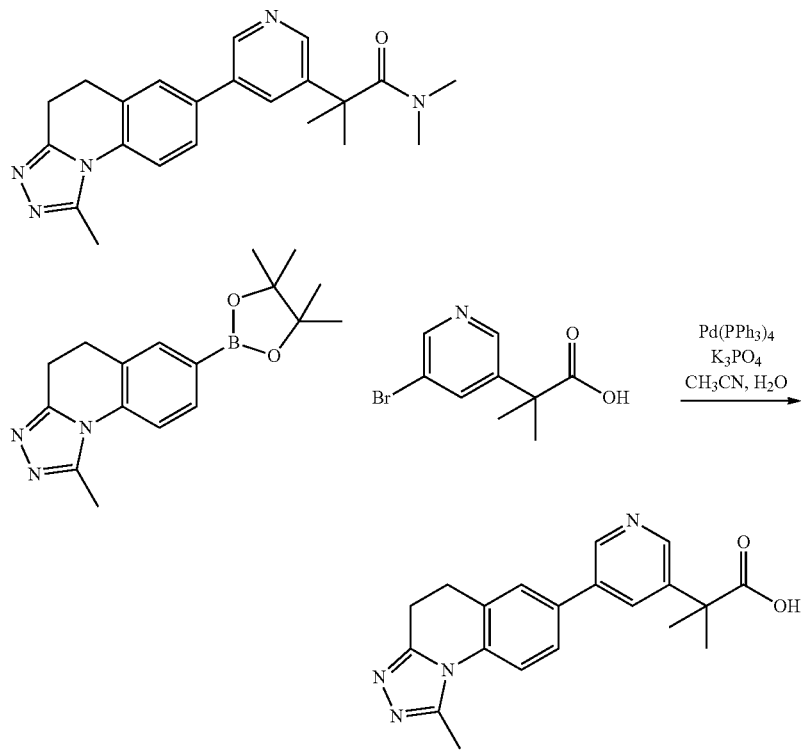

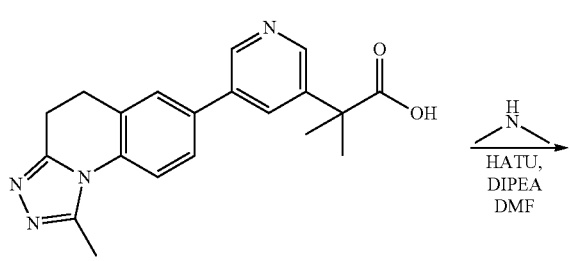

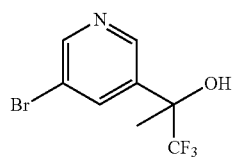

Step A.
2-(5-bromopyridin-3-yl)-1,1,1-trifluoropropan-2-ol

To a flask containing 3-acetyl-5-bromopyridine (2.27 g, 11.4 mmol) was added a solution of (trifluoromethyl)trimethylsilane in tetrahydrofuran (0.5 M, 40 mL, 20 mmol) at 0° C. A solution of tetrabutylammonium fluoride in tetrahydrofuran (1.0 M, 11.4 mL, 11.4 mmol) was then added, and the reaction stirred at room temperature until the reaction was complete. The reaction was then concentrated under reduced pressure, diluted with ethyl acetate, and washed with water and saturated aqueous sodium bicarbonate solution. The organic layer was separated, dried over sodium sulfate, filtered and concentrated to give a residue that was purified by flash chromatography on silica gel (10-50% ethyl acetate in hexanes) to provide the racemic title compound: LCMS m/z 269.85 [M+2+H]$^+$; $^1$H NMR (500 MHz, CD$_3$OD) δ 8.70 (s, 1H), 8.65 (1H), 8.13 (s, 1H), 1.81 (s, 3H). The racemic title compound was resolved by supercritical fluid chromatography on a chiral AD column, eluting with 10% ethanol:CO$_2$. Data for enantiomer A: LCMS m/z 271.85 [M+H]$^+$; $^1$H NMR (500 MHz, CDCl$_3$) 8.71 (s, 1H), 8.68 (d, J=2.0 Hz, 1H), 8.10 (s, 1H), 1.82 (s, 3H). Data for enantiomer B: LCMS m/z 271.83 [M+H]$^+$; $^1$H NMR (500 MHz, CDCl$_3$) 8.71 (s, 1H), 8.68 (s, 1H), 8.10 (s, 1H), 1.81 (s, 3H).

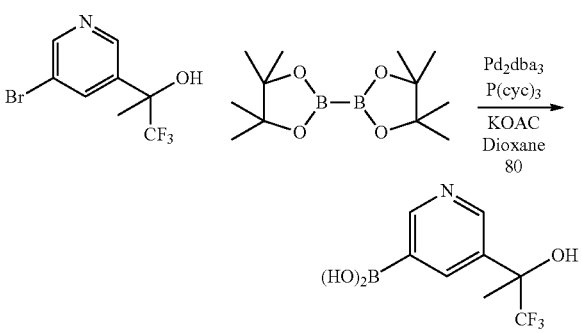

Step B. [5-(1,1,1-trifluoro-2-hydroxypropan-2-yl)pyridin-3-yl]boronic acid

A vial containing the title compound from Example 55 Step A [enantiomer B (0.647 g, 2.40 mmol)], bis(pinacolato)diboron (1.22 g, 4.79 mmol), tris(dibenzylideneacetone)dipalladium (0) (0.439 g, 0.479 mmol), tricyclohexylphosphine (0.269 g, 0.958 mmol) and potassium acetate (0.705 g, 7.19 mmol) in 1,4-dioxane (12 mL) was flushed with nitrogen, sealed tightly and heated to 80° C. overnight. The reaction was then passed through a syringe filter and concentrated under reduced pressure to provide the title compound: LCMS m/z 235.95 [M+H]$^+$.

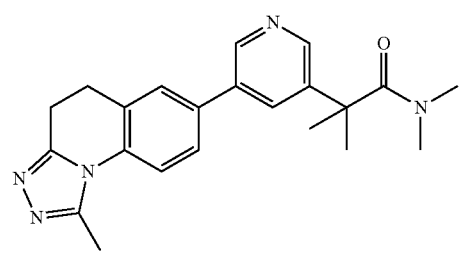

Step B. N,N,2-trimethyl-2-[5-(1-methyl-4,5-dihydro[1,2,4]triazolo[4,3-a]quinolin-7-yl)pyridin-3-yl]propanamide To a flask containing the title compound from Example 54 Step A (10 mg, 0.03 mmol) and O-(7-Azabenzotriazol-1-yl)-N,N,N',N'-tetramethyluronium hexafluorophosphate (13 mg, 0.034 mmol) in N,N-dimethylformamide (290 μL) was added a solution of dimethylamine in tetrahydrofuran (2 M, 17 μL, 0.034 mmol) followed by diisopropylethylamine (25 μL, 0.14 mmol). The reaction was stirred at room temperature overnight. The reaction was then acidified with trifluoroacetic acid, passed through a syringe filter and purified by HPLC (C18 column, 10 to 100% acetonitrile/water, both 0.1% v/v trifluoroacetic acid) to afford the title compound: LCMS m/z 376.06 [M+H]$^+$; $^1$H NMR (500 MHz, CDCl$_3$) 8.76 (s, 1H), 8.57 (s, 1H), 7.69 (s, 1H), 7.61-7.57 (m, 3H), 3.20-3.17 (m, 2H), 3.12-3.09 (m, 2H), 2.97 (br s, 3H), 2.81 (s, 3H), 2.59 (br s, 3H), 1.65 (s, 6H).

Example 55

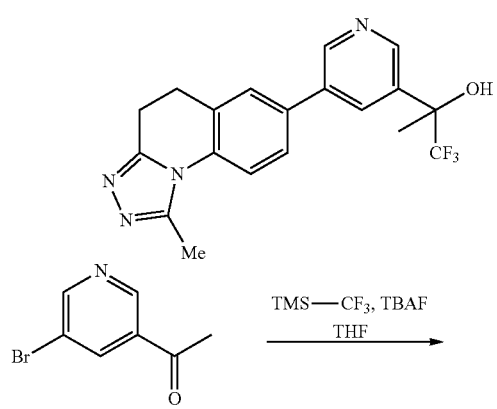

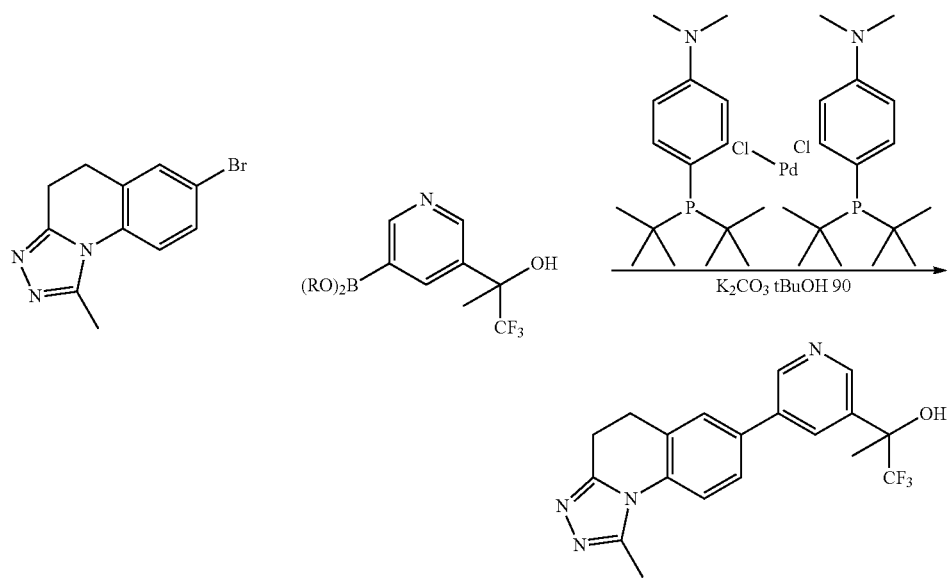

Step C. 1,1,1-trifluoro-2-[5-(1-methyl-4,5-dihydro-[1,2,4]triazolo[4,3-a]quinolin-7-yl)pyridin-3-yl]propan-2-ol To a vial containing the title compound from Example 53 Step 1 (0.58 g, 2.2 mmol), the title compound from Example 55 Step B (0.563 g, 2.34 mmol), bis(di-tert-butyl(4-dimethylaminophenyl)phosphine)dichloropalladium(II) (0.031 g, 0.044 mmol), and potassium carbonate (0.912 g, 6.60 mmol) was added tert-butanol (24 mL) and water (3.0 mL). The vial was flushed with nitrogen, sealed tightly and heated to 80° C. overnight. The reaction was then cooled to room temperature, concentrated under reduced pressure and purified by HPLC (C18 column, 10 to 100% acetonitrile/water, both 0.1% v/v trifluoroacetic acid). Fractions containing product were combined, aqueous 1 M hydrochloric acid solution was added, and the solution concentrated under reduced pressure to provide the title compound: LCMS m/z 375.02 [M+H]$^+$; $^1$H NMR (500 MHz, CD$_3$OD) δ 9.31 (s, 1H), 9.13 (1H), 9.08 (s, 1H), 8.09 (s, 1H), 8.03 (s, 2H), 3.34 (m, 4H), 3.06 (s, 3H), 1.96 (s, 3H).

The compounds in Table 4 were all prepared from either enantiomer A or enantiomer B of the title compound of Example 55 Step A using chemistry described in Example 55.

TABLE 4

| Example | Structure | IUPAC Name | LCMS |
|---|---|---|---|
| 56 | 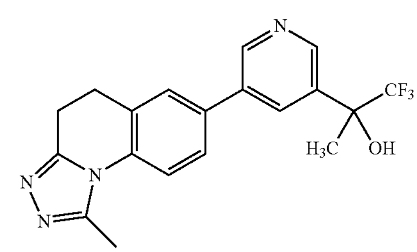 [SMILES: Cc1nnc2n1-c1ccc(-c3cncc(C(C)(O)C(F)(F)F)c3)cc1CC2] | 1,1,1-trifluoro-2-[5-(1-methyl-4,5-dihydro[1,2,4]triazolo[4,3-a]quinolin-7-yl)pyridin-3-yl]propan-2-ol | 375.02 |
| 57 | 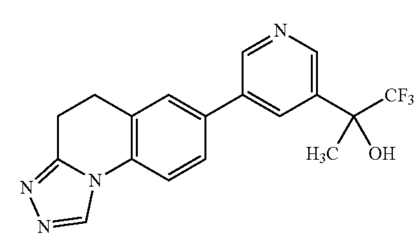 [SMILES: CC(O)(c1cncc(-c2ccc3c(c2)CCc2nncn2-3)c1)C(F)(F)F] | 2-[5-(4,5-dihydro[1,2,4]triazolo[4,3-a]quinolin-7-yl)pyridin-3-yl]-1,1,1-trifluoropropan-2-ol | 361.02 |

TABLE 4-continued

| Example | Structure | IUPAC Name | LCMS |
|---|---|---|---|
| 58 | 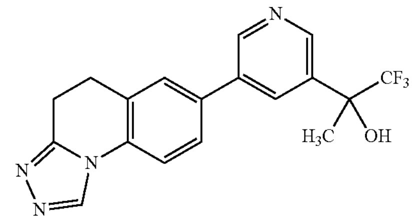 [SMILES: CC(O)(c1cncc(-c2ccc3c(c2)CCc2nncn2-3)c1)C(F)(F)F] | 2-[5-(4,5-dihydro[1,2,4]triazolo[4,3-a]quinolin-7-yl)pyridin-3-yl]-1,1,1-trifluoropropan-2-ol | 360.97 |
| 59 | 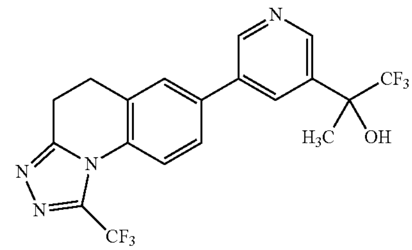 [SMILES: CC(O)(c1cncc(-c2ccc3c(c2)CCc2nnc(C(F)(F)F)n2-3)c1)C(F)(F)F] | 1,1,1-trifluoro-2-{5-[1-(trifluoromethyl)-4,5-dihydro[1,2,4]triazolo[4,3-a]quinolin-7-yl]pyridin-3-yl}propan-2-ol | 429.00 |
| 60 | 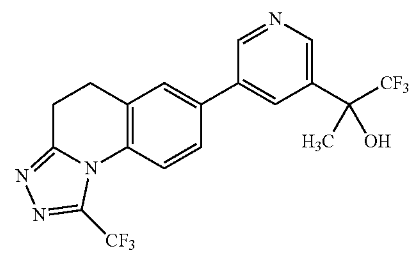 [SMILES: CC(O)(c1cncc(-c2ccc3c(c2)CCc2nnc(C(F)(F)F)n2-3)c1)C(F)(F)F] | 1,1,1-trifluoro-2-{5-[1-(trifluoromethyl)-4,5-dihydro[1,2,4]triazolo[4,3-a]quinolin-7-yl]pyridin-3-yl}propan-2-ol | 428.86 |

Example 61

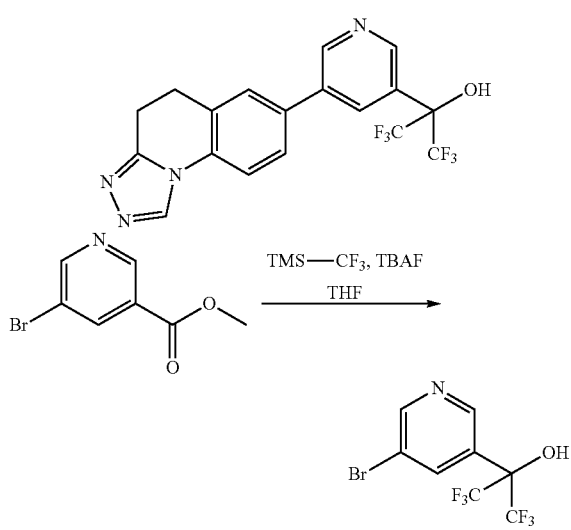

Step A. 2-(5-bromopyridin-3-yl)-1,1,1,3,3,3-hexafluoropropan-2-ol

To a cooled (0° C.) mixture of (trifluoromethyl)trimethylsilane in tetrahydrofuran (0.5 M, 2.31 mL, 1.16 mmol) and methyl 5-bromopyridine-3-carboxylate (0.10 g, 0.46 mmol) was added a solution of tetrabutylammonium fluoride in tetrahydrofuran (1.0 M, 0.463 mL, 0.463 mmol). The reaction was warmed to room temperature and stirred for 16 hours. It was then concentrated under reduced pressure, diluted with ethyl acetate and washed with water and saturated aqueous sodium chloride solution. The organic layer was separated, dried over sodium sulfate and purified by flash chromatography on silica gel (0-80% ethyl acetate in hexanes). The resulting material was further purified by HPLC (C18 column, 10 to 100% acetonitrile/water, both 0.1% v/v trifluoroacetic acid) to provide the title compound: LCMS m/z 325.86 [M+2+H]$^+$.

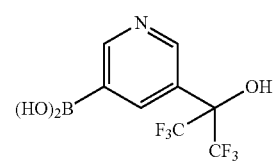

Step B. [5-(1,1,1,3,3,3-hexafluoro-2-hydroxypropan-2-yl)pyridin-3-yl]boronic acid A vial containing the title compound from Example 61 Step A (14 mg, 0.043 mmol), bis(pinacolato)diboron (21.9 mg, 0.086 mmol), tris(dibenzylideneacetone)dipalladium (0) (7.9 mg, 8.6 µmol), tricyclohexylphosphine (4.85 mg, 0.017 mmol) and potassium acetate (12.7 mg, 0.130 mmol) in 1,4-dioxane (216 µL) was flushed with nitrogen, sealed tightly and heated to 80° C. overnight. The reaction was then passed through a syringe filter and concentrated under reduced pressure to provide the title compound: LCMS m/z 290.13 [M+2+H]$^+$.

8.27 (s, 1H), 7.92 (d, J=8.34 Hz, 1H) 7.87 (d, J=1.71 Hz, 1H), 7.81 (dd, J=1.94, 8.34 Hz, 1H), 3.15 (s, 4H).

Example 62

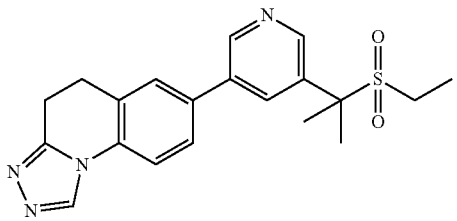

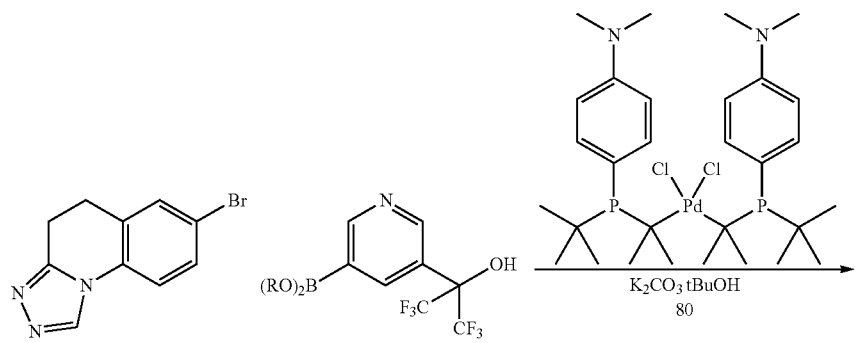

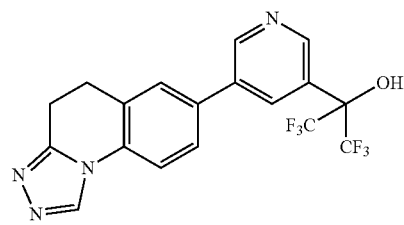

Step C. 2-[5-(4,5-dihydro[1,2,4]triazolo[4,3-a]quinolin-7-yl)pyridin-3-yl]-1,1,1,3,3,3-hexafluoropropan-2-ol A vial containing the title compound from Example 61 Step B (15 mg, 0.05 mmol), the title compound from Example 22 Step B (11.7 mg, 0.047 mmol), bis(di-tert-butyl(4-dimethylaminophenyl)phosphine)dichloropalladium(II) (3.68 mg, 5.19 µmol) and potassium carbonate (21.5 mg, 0.156 mmol) in tert-butanol (577 µL) and water (72 µL) was flushed with nitrogen, sealed tightly and heated to 80° C. overnight. The reaction solution was then cooled to room temperature and concentrated under reduced pressure. The resulting residue was diluted with acetonitrile and purified by HPLC (C18 column, 10 to 100% acetonitrile/water, both 0.1% v/v trifluoroacetic acid). Fractions containing product were combined, aqueous 1 M hydrochloric acid solution was added and the solution concentrated under reduced pressure to provide the title compound: LCMS m/z 414.79 [M+H]$^+$; $^1$H NMR (500 MHz, d6-DMSO) δ 9.38 (s, 1H), 9.11 (s, 1H), 8.85 (s, 1H),

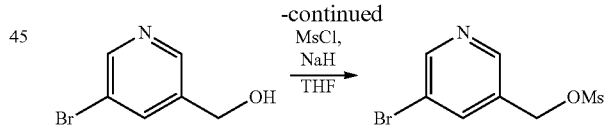

Step A. (5-bromopyridin-3-yl)methyl methanesulfonate

To a cooled (0° C.) suspension of sodium hydride (60% dispersion in mineral oil, 0.064 g, 1.60 mmol) in tetrahydrofuran (5 mL) was added a solution of (5-bromopyridin-3-yl) methanol (0.200 g, 1.06 mmol) in tetrahydrofuran (5 mL). After stirring for 1 hour, methanesulfonyl chloride (0.099 mL, 1.28 mmol) was added. The reaction was then warmed to room temperature and stirred until complete. The reaction was then poured into water and extracted with ethyl acetate. The organic extracts were combined, washed with water and saturated aqueous sodium chloride solution, dried, filtered, and concentrated under reduced pressure to provide the title compound: LCMS m/z 267.86 [M+2+H]$^+$.

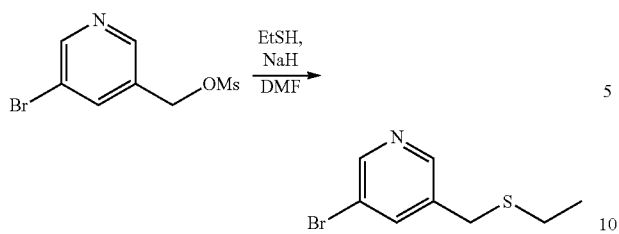

Step B. 3-bromo-5-[(ethylsulfanyl)methyl]pyridine

To a cooled (0° C.) solution of sodium hydride (60% dispersion in mineral oil, 0.094 g, 2.35 mmol) in N,N-dimethylformamide (9.4 mL) was added ethanethiol (0.140 mL, 1.88 mmol). The reaction was warmed to room temperature and stirred for 30 minutes. It was then cooled to 0° C., and a solution of the title compound from Example 62 Step A (0.250 g, 0.939 mmol) in N,N-dimethylformamide (1 mL) added. The resulting solution stirred at room temperature until the reaction was complete. The reaction was then quenched with water and extracted with ethyl acetate. The combined organic extracts were washed with water and saturated aqueous sodium chloride solution, dried, filtered and concentrated under reduced pressure. Purification by flash chromatography on silica gel (0-60% ethyl acetate in hexanes) provided the title compound: LCMS m/z 233.91 [M+2+H]$^+$; $^1$H NMR (500 MHz, CDCl$_3$) δ 8.50 (s, 1H), 8.39 (s, 1H), 7.79 (s, 1H), 3.62 (s, 2H), 2.39 (q, J=7.4, 2H), 1.19 (t, J=7.4, 3H).

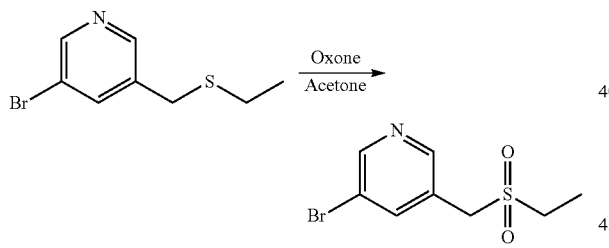

Step C. 3-bromo-5-[(ethylsulfonyl)methyl]pyridine

To a solution of the title compound from Example 62 Step B (96 mg, 0.41 mmol) in acetone (2.0 mL) was added OXONE® (763 mg, 1.24 mmol). The reaction was stirred at room temperature overnight, then filtered and concentrated under reduced pressure to provide the title compound: LCMS m/z 265.91 [M+2+H]$^+$; $^1$H NMR (500 MHz, CDCl$_3$) δ 8.72 (s, 1H), 8.53 (s, 1H), 8.00 (s, 1H), 4.19 (s, 2H), 2.96 (q, J=7.4, 2H), 1.43 (t, J=7.4, 3H).

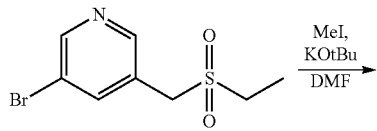

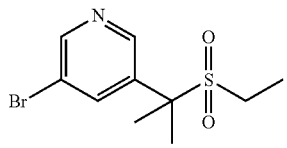

Step D. 3-bromo-5-[2-(ethylsulfonyl)propan-2-yl]pyridine

A solution of the title compound from Example 62 Step C (90 mg, 0.34 mmol) in N,N-dimethylformamide (1.5 mL) was cooled to −10° C. To this was added sodium tert-butoxide (33 mg, 0.34 mmol) followed by iodomethane (21 µL, 0.34 mmol). After stirring for 60 minutes, additional sodium tert-butoxide (33 mg, 0.34 mmol) and iodomethane (21 µL, 0.34 mmol) were added. The resulting solution stirred for 40 minutes before a additional sodium tert-butoxide (4.91 mg, 0.051 mmol) and iodomethane (3.20 µl, 0.051 mmol) were added. The reaction was then warmed to room temperature and stirred until complete. The reaction was quenched with aqueous acetic acid (2% by weight) and then extracted with ethyl acetate. The combined organic extracts were dried over sodium sulfate, filtered and concentrated under reduced pressure. Purification by flash chromatography on silica gel (30-100% ethyl acetate in hexanes) provided the title compound: LCMS m/z 293.89 [M+2+H]$^+$; $^1$H NMR (500 MHz, CDCl$_3$) δ 8.73 (s, 1H), 8.66 (s, 1H), 8.11 (s, 1H), 2.71 (q, J=7.4, 2H), 1.84 (s, 6H), 1.25 (t, J=7.4, 3H).

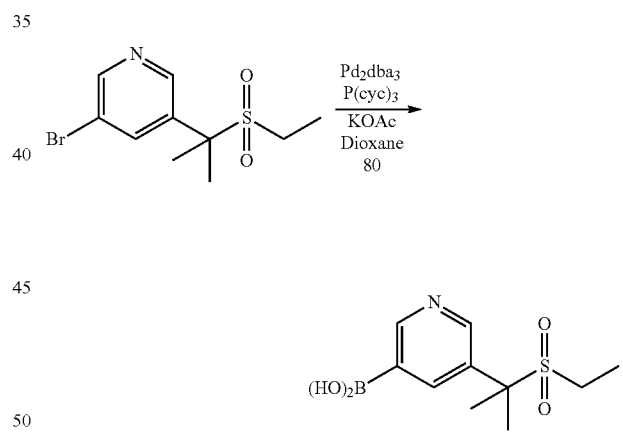

Step E. {5-[2-(ethylsulfonyl)propan-2-yl]pyridin-3-yl}boronic acid

A vial containing the title compound from Example 62 Step D (0.030 g, 0.103 mmol), bis(pinacolato)diboron (0.052 g, 0.205 mmol), tris(dibenzylideneacetone)dipalladium (0) (0.019 g, 0.021 mmol), tricyclohexylphosphine (0.012 g, 0.041 mmol) and potassium acetate (0.030 g, 0.308 mmol) in 1,4-dioxane (0.510 mL) was flushed with nitrogen, sealed tightly and heated to 80° C. overnight. The reaction was then passed through a syringe filter and concentrated under reduced pressure to provide the title compound: LCMS m/z 258.29 [M+H]$^+$.

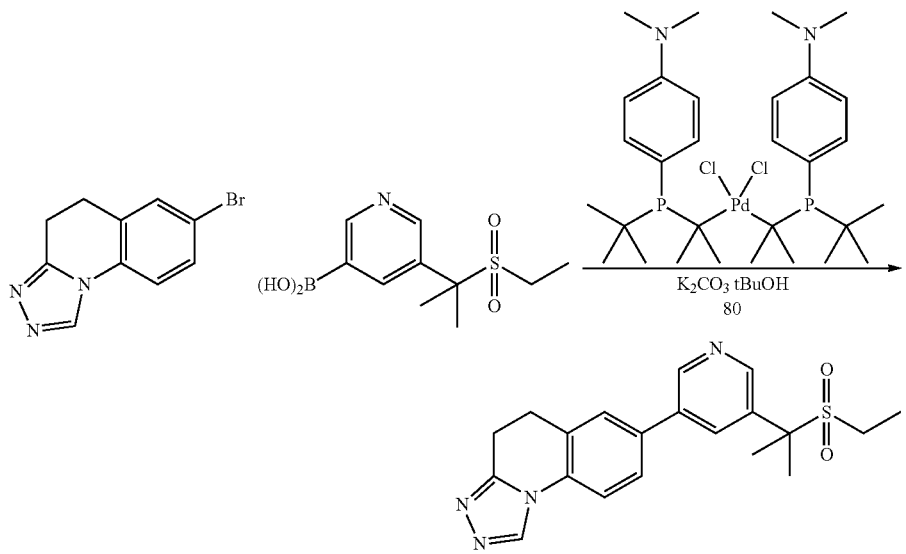

Step F. 7-{5-[2-(ethylsulfonyl)propan-2-yl]pyridin-3-yl}-4,5-dihydro[1,2,4]triazolo[4,3-a]quinoline To a vial containing the title compound from Example 22 Step B (0.020 g, 0.080 mmol), the title compound from Example 62 Step E (0.021 g, 0.080 mmol), bis(di-tert-butyl (4-dimethylaminophenyl)phosphine)dichloropalladium(II) (1.132 mg, 1.599 μmol), and potassium carbonate (0.033 g, 0.240 mmol) were added tert-butanol (0.90 mL) and water (0.10 mL). The vial was flushed with nitrogen, sealed tightly and heated to 80° C. overnight. The reaction solution was then cooled to room temperature and concentrated under reduced pressure. The resulting residue was diluted with acetonitrile and then purified by HPLC (C18 column, 10 to 100% acetonitrile/water, both 0.1% v/v trifluoroacetic acid). Fractions containing product were combined, aqueous 1 N hydrochloric acid solution was added and the solution concentrated to provide the title compound: LCMS m/z 382.99 [M+H]$^+$; $^1$H NMR (500 MHz, d6-DMSO) δ 9.42 (s, 1H), 8.97 (s, 1H), 8.83 (s, 1H), 8.29 (s, 1H), 7.93-7.91 (m, 2H), 7.85-7.83 (m, 1H), 3.18-3.13 (m, 4H), 2.96 (q, J=7.43 Hz, 2H), 1.87 (s, 6H), 1.07 (t, J=7.43, 3H).

Example 63

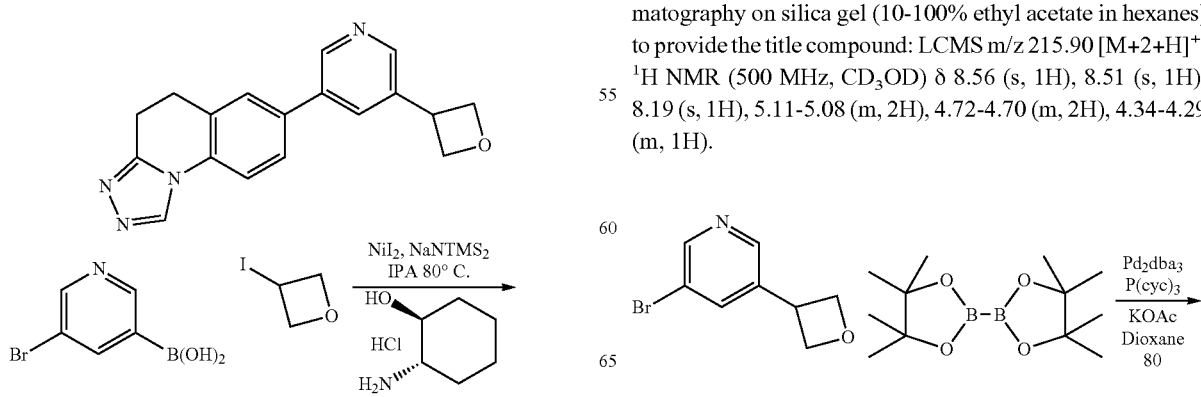

-continued

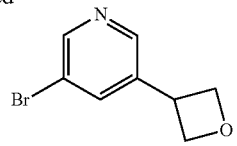

Step A. 3-bromo-5-(oxetan-3-yl)pyridine

To a vial were added (5-bromopyridin-3-yl)boronic acid (110 mg, 0.544 mmol), nickel iodide (5.10 mg, 0.016 mmol), trans-2-aminocyclohexanol hydrochloride (2.473 mg, 0.016 mmol), sodium bis(trimethylsilyl)amide (100 mg, 0.544 mmol) and 2-propanol (0.5 mL). The reaction was stirred under nitrogen for 10 minutes prior to addition of a solution of 3-iodooxetane (50 mg, 0.27 mmol) in 2-propanol (0.2 mL). The vial was sealed and heated at 80° C. overnight. The reaction was then filtered through celite with the aid of ethanol. The solution was concentrated and purified by flash chromatography on silica gel (10-100% ethyl acetate in hexanes) to provide the title compound: LCMS m/z 215.90 [M+2+H]$^+$; $^1$H NMR (500 MHz, CD$_3$OD) δ 8.56 (s, 1H), 8.51 (s, 1H), 8.19 (s, 1H), 5.11-5.08 (m, 2H), 4.72-4.70 (m, 2H), 4.34-4.29 (m, 1H).

101
-continued

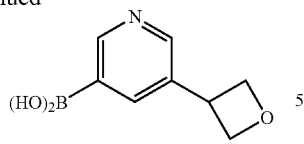

Step B. [5-(oxetan-3-yl)pyridin-3-yl]boronic acid

A vial containing the title compound from Example 63 Step A (45 mg, 0.21 mmol), bis(pinacolato)diboron (107 mg, 0.420 mmol), tris(dibenzylideneacetone)dipalladium (0) (38.5 mg, 0.042 mmol), tricyclohexylphosphine (23.6 mg, 0.084 mmol) and potassium acetate (61.9 mg, 0.631 mmol) in dioxane (1.0 mL) was flushed with nitrogen, sealed tightly and heated to 80° C. overnight. The reaction was then passed through a syringe filter and concentrated under reduced pressure to provide the title compound which was used without further purification.

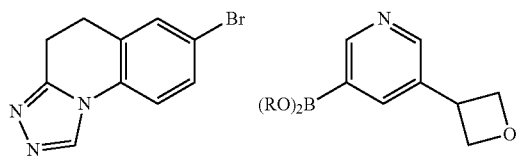
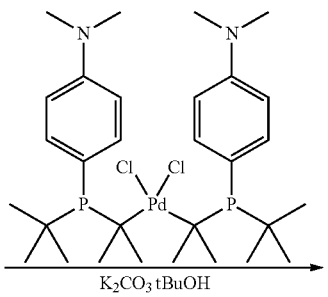

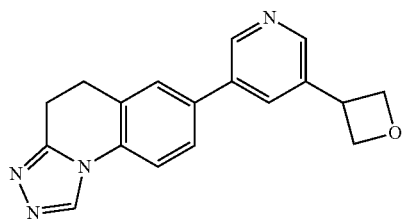

Step C. 7-[5-(oxetan-3-yl)pyridin-3-yl]-4,5-dihydro-[1,2,4]triazolo[4,3-a]quinoline To a vial containing the title compound from Example 22 Step B (0.020 g, 0.080 mmol), the title compound from Example 63 Step B (0.017 g, 0.096 mmol), bis(di-tert-butyl (4-dimethylaminophenyl)phosphine)dichloropalladium(II) (1.132 mg, 1.599 mop, and potassium carbonate (0.033 g, 0.240 mmol) were added tert-butanol (0.90 mL) and water (0.1 mL). The vial was flushed with nitrogen, sealed tightly and heated to 80° C. overnight. The reaction solution was then cooled to room temperature and concentrated under reduced pressure. The resulting residue was diluted with acetonitrile and purified by HPLC (C18 column, 10 to 100% acetonitrile/water, both 0.1% v/v trifluoroacetic acid) to provide the title compound: LCMS m/z 304.97 [M+H]+; 1H NMR (500 MHz, CD3OD) δ 9.22 (s, 1H), 8.79 (s, 1H), 8.59 (s, 1H), 8.29 (s, 1H), 7.88-7.80 (m, 3H), 5.20-5.17 (m, 2H), 4.85-4.84 (m, 2H), 4.48-4.42 (m 1H), 3.26 (s, 4H).

Example 64

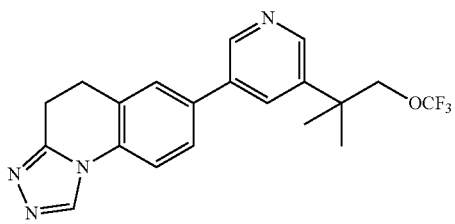

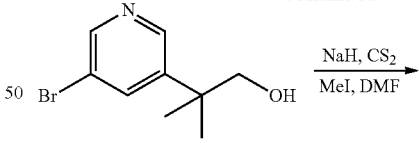

-continued

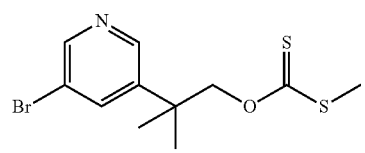

Step A.
O-[2-(5-bromo-3-pyridinyl)-2-methylpropyl]S-methyl carbonodithioate

To a cooled (0° C.) solution of the title compound from Example 53 Step E (100 mg, 0.435 mmol) in N,N-dimethylformamide (869 µl) was added sodium hydride (60% dispersion in mineral oil, 20.86 mg, 0.522 mmol). After stirring 1 hour at room temperature, carbon disulfide (52.4 µL, 0.869 mmol) was added. The resulting mixture was warmed to room temperature and stirred overnight. The reaction was then cooled to 0° C. and iodomethane (32.6 µL, 0.522 mmol) was added. The resulting solution was then warmed to room temperature where it stirred until the reaction was complete. The reaction solution was then concentrated under reduced pressure to afford the title compound: LCMS m/z 321.88 [M+2+H]$^+$; $^1$H NMR (500 MHz, CDCl$_3$) δ 8.58 (s, 1H), 8.56 (s, 1H), 7.82 (s, 1H), 4.59 (s, 2H), 2.49 (s, 3H), 1.46 (s, 6H).

reaction solution was then extracted with ethyl acetate. The organic extracts were combined, washed with saturated aqueous sodium chloride solution, dried, filtered and concentrated under reduced pressure. Purification by flash chromatography on silica gel (0-100% ethyl acetate in hexanes) provided the title compound: LCMS m/z 299.86 [M+2+H]$^+$, $^1$H NMR (500 MHz, CD$_3$OD) δ 8.58 (s, 1H), 8.53 (s, 1H), 8.08 (s, 1H), 4.11 (s, 2H), 1.42 (s, 6H).

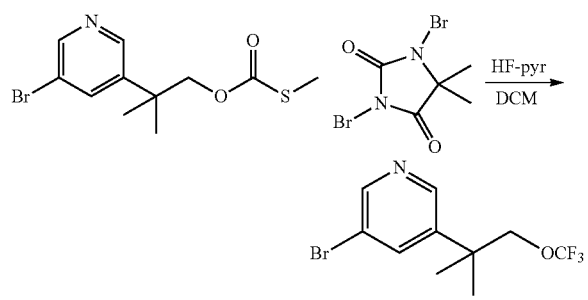

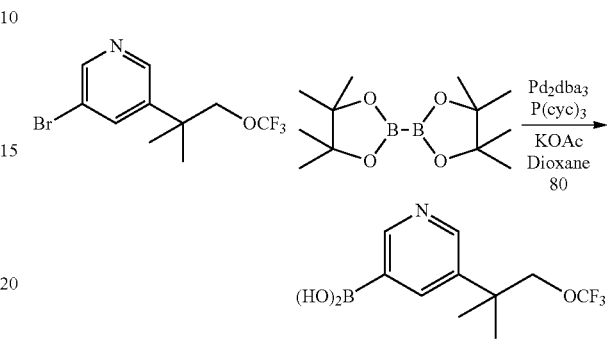

Step B. 3-bromo-5-[2-methyl-1-(trifluoromethoxy)-2-propanyl]pyridine

A small plastic bottle containing a solution of 1,3-dibromo-5,5-dimethylhydantoin (139 mg, 0.487 mmol) in dichloromethane (500 µL) was cooled to −78° C. HF-pyridine (200 µl, 0.156 mmol) was then added dropwise, and the resulting solution was stirred for 10 minutes. A solution of the title compound from Example 64 Step A (50 mg, 0.156 mmol) in dichloromethane (100 µL) was then added, and the reaction was allowed to warm to room temperature. After stirring overnight, the reaction was cooled to 0° C. and quenched by addition of aqueous 1 N sodium hydroxide solution. The Step C. {5-[2-methyl-1-(trifluoromethoxy)-2-propanyl]-3-pyridinyl}boronic acid A vial containing the title compound from Example 64 Step B (80 mg, 0.27 mmol), bis(pinacolato)diboron (136 mg, 0.537 mmol), tris(dibenzylideneacetone)dipalladium (0) (49.1 mg, 0.054 mmol), tricyclohexylphosphine (30.1 mg, 0.107 mmol) and potassium acetate (79 mg, 0.805 mmol) in 1,4-dioxane (1.3 mL) was flushed with nitrogen, sealed tightly and heated to 80° C. overnight. The reaction was then cooled to room temperature and passed through a syringe filter. The resulting solution was then concentrated under reduced pressure to afford the title compound which was used without further purification.

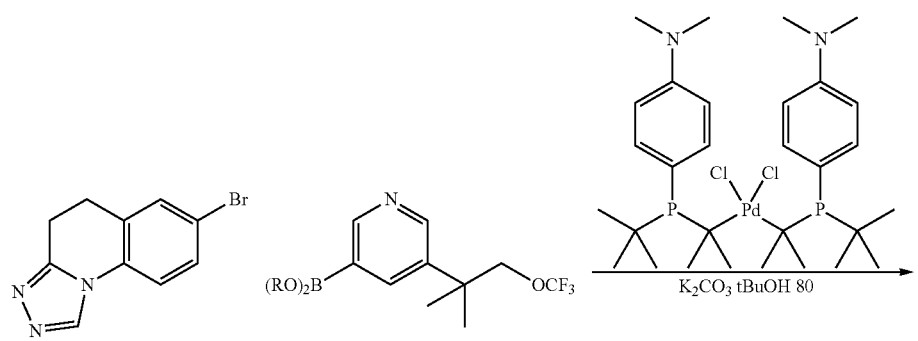

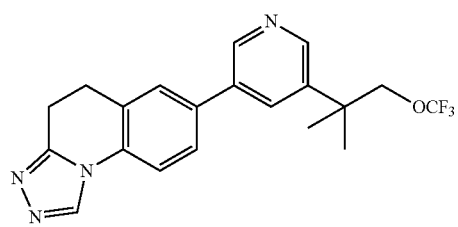

Step D. 7-{5-[2-methyl-1-(trifluoromethoxy)-2-propanyl]-3-pyridinyl}-4,5-dihydro[1,2,4]triazolo[4,3-a]quinoline To a vial containing the title compound from Example 22 Step B (50 mg, 0.200 mmol), the title compound from Example 64 Step C (63.1 mg, 0.240 mmol), bis(di-tert-butyl (4-dimethylaminophenyl)phosphine)dichloropalladium(II) (28.3 mg, 0.040 mmol) and potassium carbonate (83 mg, 0.600 mmol) were added tert-butanol (2.2 mL) and water (0.28 mL). The vial was capped tightly and heated to 80° C. overnight. The reaction was then cooled to room temperature and concentrated under reduced pressure. The resulting residue was diluted with acetonitrile and then purified by HPLC (C18 column, 10 to 100% acetonitrile/water, both 0.1% v/v trifluoroacetic acid) to provide the title compound: LCMS m/z 389.00 [M+H]$^+$; NMR (500 MHz, CD$_3$OD) δ 9.99 (s, 1H), 9.19 (s, 1H), 9.02 (s, 1H), 8.94 (s, 1H), 8.09-8.00 (m, 3H), 4.33 (s, 2H), 3.48-3.45 (m, 2H), 3.39-3.36 (m, 2H), 1.60 (s, 6H).

Example 65

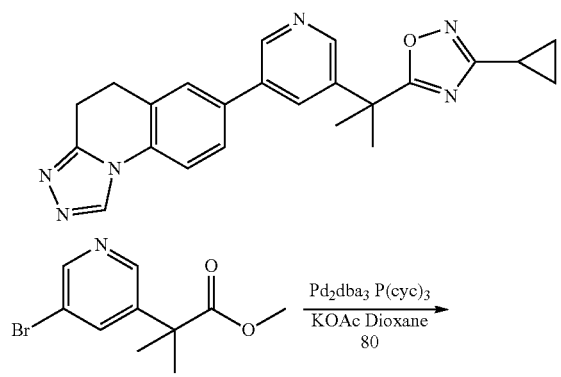

Step A. [5-(1-methoxy-2-methyl-1-oxopropan-2-yl)pyridin-3-yl]boronic acid

To a vial containing the title compound from Example 53 Step H (0.10 g, 0.39 mmol), bis(pinacolato)diboron (0.12 g, 0.47 mmol), tris(dibenzylideneacetone)dipalladium (0) (0.035 g, 0.039 mmol), tricyclohexylphosphine (0.022 g, 0.077 mmol) and potassium acetate (0.114 g, 1.16 mmol) was added 1,4-dioxane (3.9 mL). The reaction was heated to 80° C. for 16 hours. It was then cooled to room temperature, passed through a syringe filter, and concentrated under reduced pressure to afford the title compound: LCMS m/z 224.19 [M+H]$^+$.

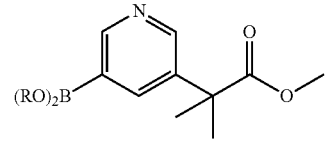

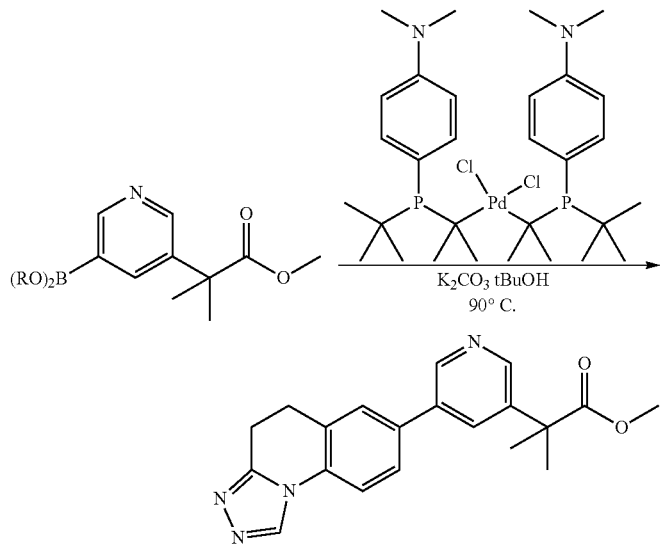

Step B. methyl 2-[5-(4,5-dihydro-[1,2,4]triazolo[4,3-a]quinolin-7-yl)pyridin-3-yl]-2-methylpropanoate To a vial containing the title compound from Example 22 Step B (105 mg, 0.420 mmol), the title compound from Example 65 Step A (112 mg, 0.504 mmol), bis(di-tert-butyl (4-dimethylaminophenyl)phosphine)dichloropalladium(II) (14.9 mg, 0.021 mmol) and potassium carbonate (174 mg, 1.26 mmol) were added tert-butanol (4.7 mL) and water (0.58 mL). The vial was capped tightly and heated to 90° C. overnight. The reaction was then concentrated under reduced pressure, diluted with acetonitrile and water, filtered, and purified by HPLC (C18 column, 10 to 100% acetonitrile/water, both 0.1% v/v trifluoroacetic acid) to provide title compound: LCMS m/z 348.99 [M+H]$^+$; $^1$H NMR (500 MHz, CD$_3$OD) δ 9.31 (s, 1H), 8.95 (s, 1H), 8.74 (s, 1H), 8.50 (s, 1H), 7.91-7.88 (m, 2H), 7.83-7.81 (m, 1H), 3.72 (s, 3H), 3.27-3.25 (m, 4H), 1.74 (s, 6H).

Step C. 7-{5-[2-(3-cyclopropyl-1,2,4-oxadiazol-5-yl)propan-2-yl]pyridin-3-yl}-4,5-dihydro[1,2,4]triazolo[4,3-a]quinoline A vial containing the title compound from Example 65 Step B (30 mg, 0.086 mmol), N'-hydroxycyclopropanecarboximidamide (17.2 mg, 0.172 mmol) and sodium ethoxide (17.6 mg, 0.258 mmol) in ethanol (0.80 mL) was sealed tightly and heated to 150° C. for 15 minutes in the microwave. The reaction was then concentrated under reduced pressure, diluted with acetonitrile and aqueous 0.1% trifluoroacetic acid solution, passed through a syringe filter, and purified by HPLC (C18 column, 10 to 100% acetonitrile/water, both 0.1% v/v trifluoroacetic acid). Fractions containing product were combined, aqueous 1 N HCl solution was added, and the solution concentrated under reduced pressure to provide the title compound: LCMS m/z 399.07 [M+H]$^+$; $^1$H NMR (500 MHz, CDCl$_3$ with a drop of CD$_3$OD) δ 8.83 (s, 1H), 8.61 (s, 1H), 7.92 (s, 1H), 7.67-7.62 (m, 1H), 7.56-7.54 (m, 1H), 7.50-7.47 (m, 2H), 3.13-3.07 (m, 4H), 1.96-1.91 (m, 1H), 1.79 (s, 6H), 0.96-0.89 (m, 4H).

The compounds in Table 5 were all prepared using chemistry described in Example 65.

TABLE 5

| Example | Structure | IUPAC Name | LCMS |
|---|---|---|---|
| 66 | | 7-{5-[2-(3-methyl-1,2,4-oxadiazol-5-yl)propan-2-yl]pyridin-3-yl}-4,5-dihydro[1,2,4]triazolo[4,3-a]quinoline | 373.01 |
| 67 | | 7-(5-{2-[3-(propan-2-yl)-1,2,4-oxadiazol-5-yl]propan-2-yl}pyridin-3-yl)-4,5-dihydro[1,2,4]triazolo[4,3-a]quinoline | 400.94 |
| 68 | | 7-(5-{2-[3-(trifluoromethyl)-1,2,4-oxadiazol-5-yl]propan-2-yl}pyridin-3-yl)-4,5-dihydro[1,2,4]triazolo[4,3-a]quinoline | 426.90 |
| 69 | | 7-{5-[2-(3-cyclopropyl-1,2,4-oxadiazol-5-yl)propan-2-yl]pyridin-3-yl}-4,5-dihydro[1,2,4]triazolo[4,3-a]quinoline | 434.99 |

Example 70

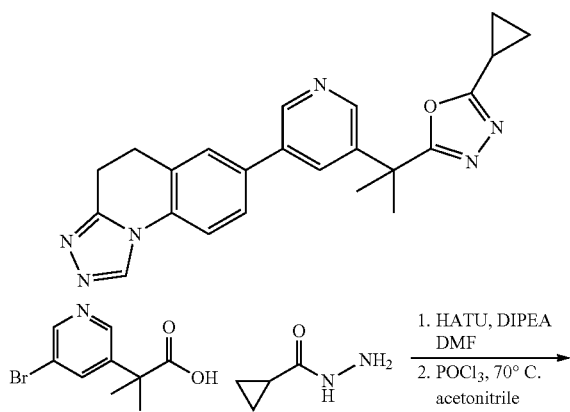

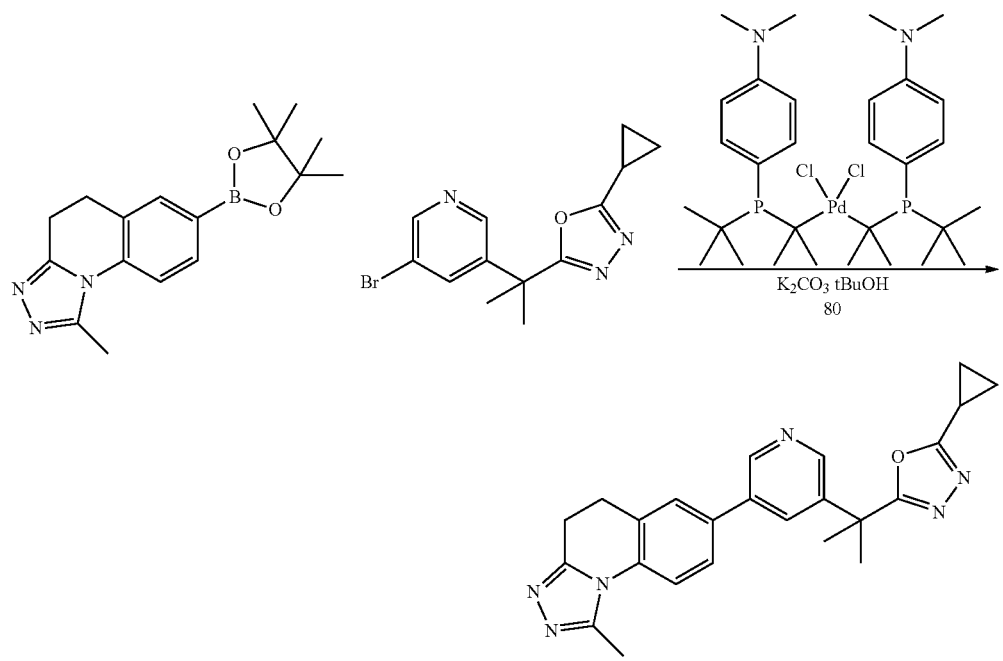

N,N',N'-tetramethyluronium hexafluorophosphate (93 mg, 0.25 mmol) were added N,N-dimethylformamide (2048 μl) and diisopropylethylamine (107 μl, 0.615 mmol). The reaction stirred at room temperature overnight, then poured into water and extracted with ethyl acetate. The organic extracts were combined, washed with water, dried over sodium sulfate, filtered and concentrated under reduced pressure. To a vial containing the resulting material were added acetonitrile (1.0 mL) and phosphorus oxychloride (46 μL, 0.50 mmol). The vial was capped tightly and heated to 70° C. overnight. The reaction was then cooled to room temperature, quenched with saturated aqueous sodium bicarbonate solution, stirred for 30 minutes, and then extracted with ethyl acetate. The organic extracts were combined, dried over sodium sulfate, filtered and concentrated under reduced pressure. Purification by flash chromatography on silica gel (20-80% ethyl acetate in hexanes, then 100% ethyl acetate) provided the title compound: LCMS m/z 307.82 [M+H]$^+$; $^1$H NMR (500 MHz, CDCl$_3$) δ 8.58 (s, 1H), 8.47 (s, 1H), 7.75 (s, 1H), 2.11-2.05 (m, 1H), 1.81 (s, 6H), 1.13-1.05 (m, 4H).

-continued

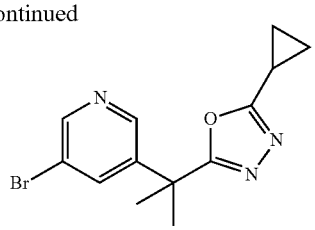

Step A. 3-bromo-5-[2-(5-cyclopropyl-1,3,4-oxadiazol-2-yl)-2-propanyl]pyridine To a vial containing the title compound from Example 53 Step G (50 mg, 0.21 mmol), cyclopropanecarbohydrazide (24.6 mg, 0.246 mmol) and O-(7-Azabenzotriazol-1-yl)-N,

Step B. 7-{5-[2-(5-cyclopropyl-1,3,4-oxadiazol-2-yl)-2-propanyl]-3-pyridinyl}-1-methyl-4,5-dihydro[1,2,4]triazolo[4,3-a]quinoline To a vial containing the title compound from Example 53 Step J (0.025 g, 0.080 mmol), the title compound from Example 70 Step A (0.025 g, 0.080 mmol), bis(di-tert-butyl(4-dimethylaminophenyl)phosphine)dichloropalladium(II) (1.1 mg, 1.6 μmol), and potassium carbonate (0.033 g, 0.241 mmol) were added tert-butanol (0.89 mL) and water (0.11 mL). The vial was flushed with nitrogen, sealed tightly and heated to 80° C. overnight. The reaction solution was then cooled to room temperature and concentrated under reduced pressure. The resulting material was diluted with acetonitrile and purified by HPLC (C18 column, 10 to 100% acetonitrile/water, both 0.1% v/v trifluoroacetic acid). Fractions containing product were combined, aqueous 1 N HCl solution was added, and the resulting solution concentrated under reduced pressure to afford the title compound: LCMS m/z 413.02 [M+H]+; 1H NMR (500 MHz, CD3OD) δ 8.90 (s, 1H), 8.64 (s, 1H), 8.30 (s, 1H), 7.90-7.81 (m, 3H), 3.22 (s, 4H), 2.90 (s, 3H), 2.20-2.14 (m, 1H), 1.92 (s, 6H), 1.18-1.16 (m, 2H), 1.07-1.04 (m, 2H).

Example 71

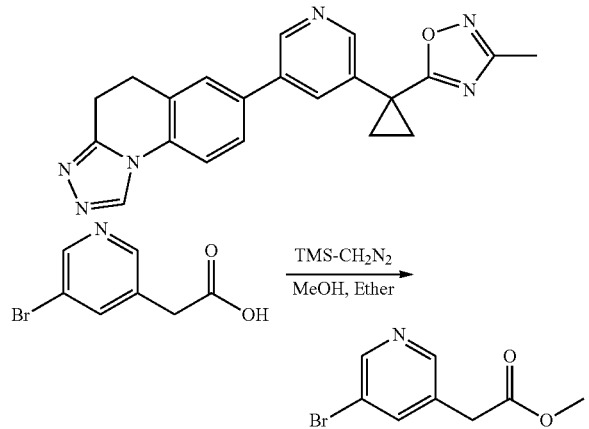

Step A. methyl(5-bromo-3-pyridinyl)acetate

To a cooled (0° C.) solution of (5-bromo-3-pyridinyl)acetic acid (1.00 g, 4.63 mmol) in diethyl ether (17 mL) and methanol (11 mL) was added a solution of (trimethylsilyl)diazomethane in diethyl ether (2.0 M, 4.6 ml, 9.3 mmol). The reaction was warmed to room temperature and then quenched by the dropwise addition of acetic acid. Once gas evolution ceased, the solution was concentrated under reduced pressure. The resulting material was diluted with ethyl acetate and washed with water and saturated aqueous sodium chloride solution. The organic layers were combined, dried over sodium sulfate, filtered and concentrated under reduced pressure. Purification by flash chromatography on silica gel (20-80% ethyl acetate in hexanes) provided the title compound: LCMS m/z 231.66 [M+2+H]+; 1H NMR (500 MHz, CD3OD) δ 7.01 (s, 1H), 6.88 (s, 1H), 6.45 (s, 1H), 2.21 (s, 2H), 2.17 (s, 3H).

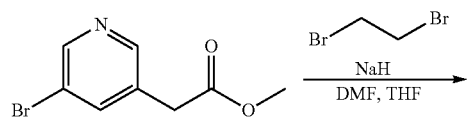

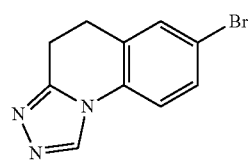

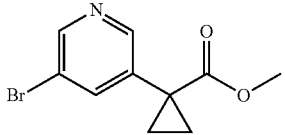

Step B. methyl 1-(5-bromo-3-pyridinyl)cyclopropanecarboxylate

To a solution of the title compound from Example 71 Step A (0.50 g, 2.17 mmol) in N,N-dimethylformamide (6.8 mL) and tetrahydrofuran (6.8 mL) was added sodium hydride (60% dispersion in mineral oil, 0.435 g, 10.9 mmol). After stirring for 15 minutes, 1,2-dibromoethane (0.56 ml, 6.5 mmol) was added. After stirring overnight, the reaction was poured into water and extracted with ethyl acetate. The combined organic extracts were washed with water and saturated aqueous sodium chloride solution, dried over sodium sulfate, filtered and concentrated. Purification by flash chromatography on silica gel (20-80% ethyl acetate in hexanes) provided the title compound: LCMS m/z 257.78 [M+2+H]+; 1H NMR (500 MHz, CD3OD) δ 8.53 (s, 1H), 8.49 (s, 1H), 8.02 (s, 1H), 3.63 (s, 3H), 1.64 (m, 2H), 1.29 (m, 2H).

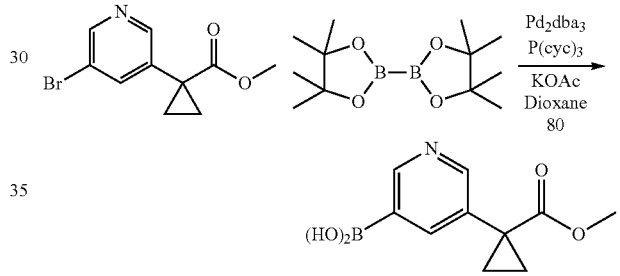

Step C. {5-[1-(methoxycarbonyl)cyclopropyl]-3-pyridinyl}boronic acid

To a vial containing the title compound from Example 71 Step B (0.150 g, 0.586 mmol), bis(pinacolato)diboron (0.178 g, 0.703 mmol), tris(dibenzylideneacetone)dipalladium (0) (0.054 g, 0.059 mmol), tricyclohexylphosphine (0.033 g, 0.117 mmol) and potassium acetate (0.17 g, 1.76 mmol) was added dioxane (5.9 mL). The reaction was heated to 80° C. for 16 hours. It was then cooled to room temperature, passed through a syringe filter and concentrated under reduced pressure to afford the title compound: LCMS m/z 221.63 [M+H]+.

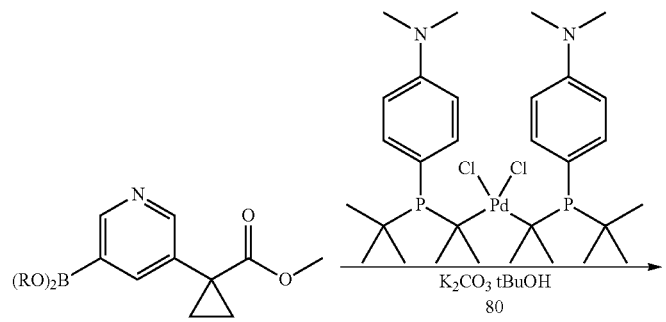

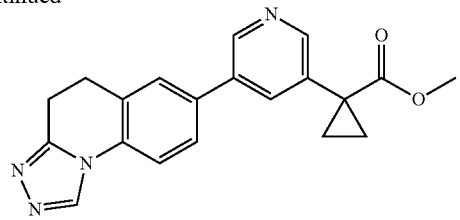

Step D. methyl 1-[5-(4,5-dihydro[1,2,4]triazolo[4,3-a]quinolin-7-yl)-3-pyridinyl]cyclopropanecarboxylate To a vial containing the title compound from Example 22 Step B (0.12 g, 0.48 mmol), the title compound from Example 71 Step C (0.13 g, 0.59 mmol), bis(di-tert-butyl(4-dimethylaminophenyl)phosphine)dichloropalladium(II) (6.8 mg, 9.6 µmol), and potassium carbonate (0.200 g, 1.44 mmol) were added tert-butanol (5.3 mL) and water (0.67 mL). The vial was flushed with nitrogen, sealed tightly and heated to 80° C. overnight. The reaction solution was then cooled to room temperature and concentrated under reduced pressure. The resulting material was diluted with acetonitrile and purified by HPLC (C18 column, 10 to 100% acetonitrile/water, both 0.1% v/v trifluoroacetic acid). Fractions containing product were combined, aqueous 1 N HCl solution was added, and the resulting solution concentrated under reduced pressure to provide the title compound: LCMS m/z 347.00 [M+H]$^+$; $^1$H NMR (500 MHz, CD$_3$OD) δ 10.1 (s, 1H), 9.21 (s, 1H), 9.02 (s, 1H), 8.99 (s, 1H), 8.12-8.03 (m, 3H), 3.70 (s, 3H), 3.51-3.48 (m, 2H), 3.41-3.38 (m, 2H), 1.85-1.82 (m, 2H), 1.59-1.56 (m, 2H).

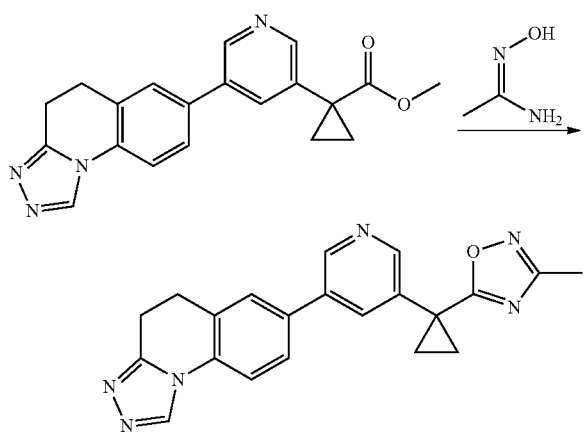

Step E. 7-{5-[1-(3-methyl-1,2,4-oxadiazol-5-yl)cyclopropyl]-3-pyridinyl}-4,5-dihydro[1,2,4]triazolo[4,3-a]quinoline To a vial containing the title compound from Example 71 Step D (75 mg, 0.217 mmol), acetamide oxime (32.1 mg, 0.433 mmol) and sodium ethoxide (73.7 mg, 1.083 mmol) was added ethanol (2.2 mL). The vial was capped tightly and heated to 150° C. for 15 minutes in the microwave. The reaction solution was then concentrated under reduced pressure. The resulting material was diluted with acetonitrile and then purified by HPLC (C18 column, 10 to 100% acetonitrile/water, both 0.1% v/v trifluoroacetic acid). Fractions containing product were combined, aqueous 1 N HCl solution was added, and the resulting solution concentrated to provide the title compound: LCMS m/z 370.97 [M+H]$^+$; $^1$H NMR (500 MHz, CD$_3$OD) δ 10.1 (s, 1H), 9.28 (s, 1H), 9.13 (s, 1H), 8.1-8.01 (m, 4H), 3.49-3.46 (m, 2H), 3.39-3.36 (m, 2H), 2.29 (s, 3H), 2.04-2.02 (m, 2H), 1.94-1.91 (m, 2H).

Example 72

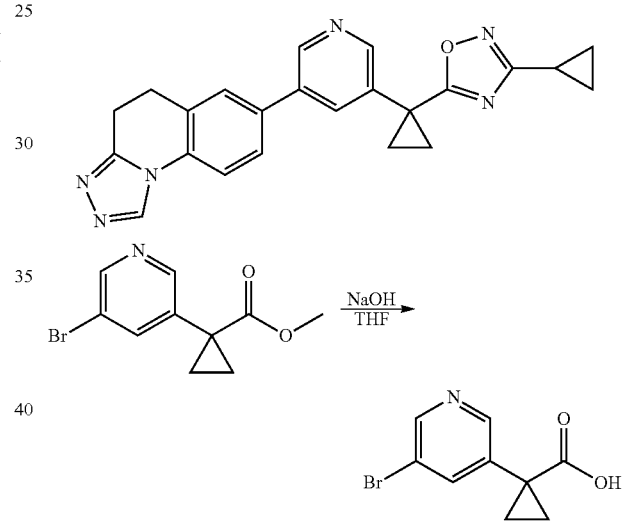

Step A. 1-(5-bromo-3-pyridinyl)cyclopropanecarboxylic acid

To a solution of the title compound from Example 71 Step B (100 mg, 0.390 mmol) in tetrahydrofuran (2.0 mL) was added aqueous 1 N sodium hydroxide solution (0.390 ml, 0.390 mmol). After stirring for several hours at room temperature, the reaction was concentrated under reduced pressure to provide the title compound: LCMS m/z 241.95 [M+H]$^+$; $^1$H NMR (500 MHz, CDCl$_3$) δ 8.58 (s, 1H), 8.53 (s, 1H), 7.86 (s, 1H), 1.76-1.74 (m, 2H), 1.29-1.27 (m, 2H).

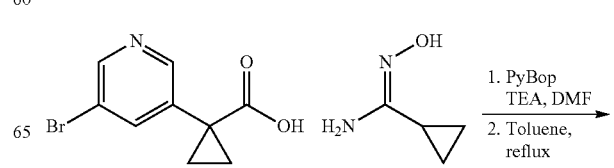

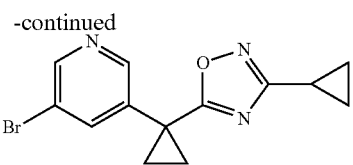

Step B. 3-bromo-5-[1-(3-cyclopropyl-1,2,4-oxadiazol-5-yl)cyclopropyl]pyridine To a solution of the title compound from Example 72 Step A (45 mg, 0.19 mmol), N'-hydroxycyclopropanecarboximidamide (22 mg, 0.22 mmol) and (benzotriazol-1-yloxy)tripyrrolidinophosphonium hexafluorophosphate (116 mg, 0.223 mmol) in N,N-dimethylformamide (0.93 mL) was added triethylamine (26 μl, 0.19 mmol). The reaction stirred at room temperature overnight. It was then diluted with water and extracted with ethyl acetate. The combined organic extracts were washed with saturated aqueous sodium chloride solution, dried over sodium sulfate, filtered and concentrated under reduced pressure. The resulting material was then diluted with toluene and heated to reflux overnight. Purification by flash chromatography on silica gel (10-100% ethyl acetate in hexanes) provided the title compound: LCMS m/z 307.85 [M+2+H]$^+$.

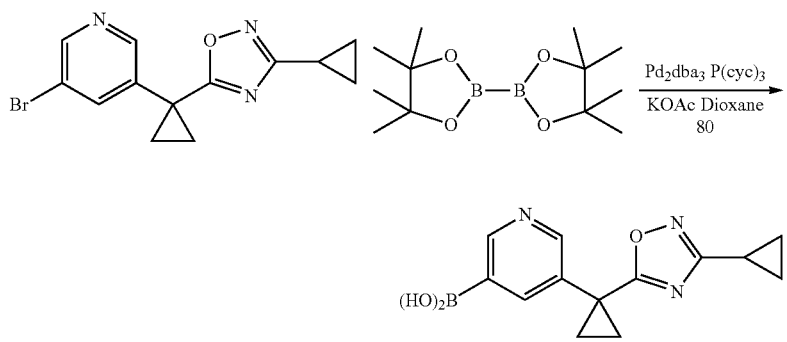

Step C. {5-[1-(3-cyclopropyl-1,2,4-oxadiazol-5-yl)cyclopropyl]-3-pyridinyl}boronic acid To a vial containing the title compound from Example 72 Step B (0.03 g, 0.10 mmol), bis(pinacolato)diboron (0.050 g, 0.20 mmol), tris(dibenzylideneacetone)dipalladium (0) (0.018 g, 0.020 mmol), tricyclohexylphosphine (11 mg, 0.039 mmol) and potassium acetate (0.029 g, 0.294 mmol) was added 1,4-dioxane (1.0 ml). The vial was capped tightly and heated to 80° C. overnight. The reaction was then concentrated under reduced pressure to provide the title compound: LCMS m/z 245.70 [M+H]$^+$.

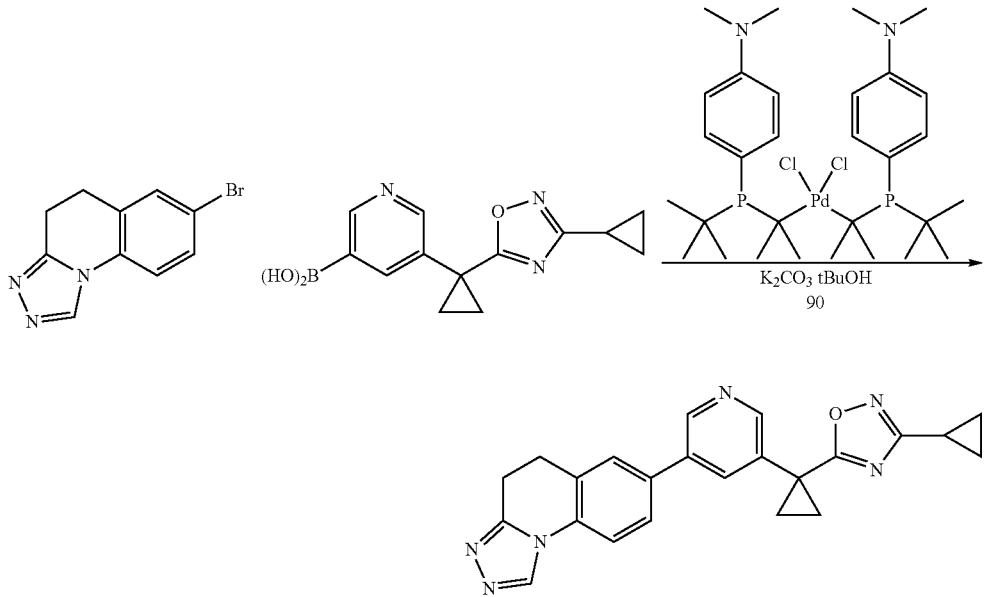

Step D. 7-{5-[1(3-cyclopropyl-1,2,4-oxadiazol-5-yl)cyclopropyl]-3-pyridinyl}-4,5-dihydro[1,2,4]triazolo[4,3-a]quinoline To a vial containing the title compound from Example 22 Step B (0.025 g, 0.100 mmol), the title compound from Example 72 Step C (0.027 g, 0.100 mmol), bis(di-tert-butyl(4-dimethylaminophenyl)phosphine)dichloropalladium(II) (1.4 mg, 2.0 μmol), and potassium carbonate (0.041 g, 0.300 mmol) were added tert-butanol (1.1 mL) and water (0.14 mL). The vial was flushed with nitrogen, sealed tightly and heated to 80° C. overnight. The reaction solution was then cooled to room temperature and concentrated under reduced pressure. The resulting material was diluted with acetonitrile and purified by HPLC (C18 column, 10 to 100% acetonitrile/water, both 0.1% v/v trifluoroacetic acid). Fractions containing product were combined, aqueous 1 N HCl solution was added, and the resulting solution concentrated under reduced pressure to provide the title compound: LCMS m/z 397.02 [M+H]$^+$; $^1$H NMR (500 MHz, CD$_3$OD) δ 9.37 (s, 1H), 9.01 (s, 1H), 8.85 (s, 1H), 8.60 (s, 1H), 7.92-7.86 (m, 3H), 3.27-3.24 (m, 4H), 2.02-1.99 (m, 1H), 1.92-1.90 (m, 2H), 1.78-1.76 (m, 2H), 1.04-1.00 (m, 2H), 0.91-0.89 (m, 2H).

Example 73

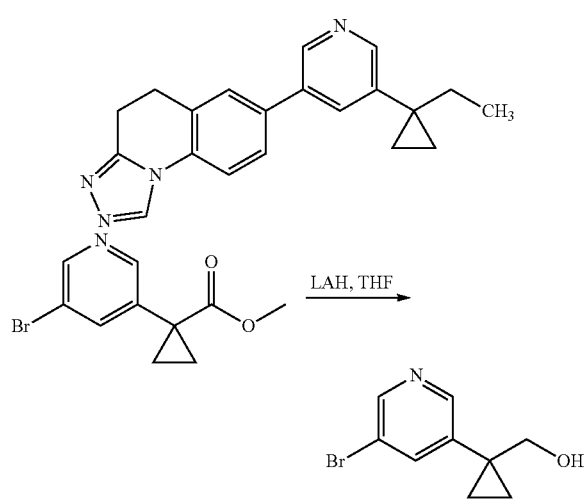

Step A. [1-(5-bromo-3-pyridinyl)cyclopropyl]methanol

To a cooled (0° C.) solution of the title compound from Example 71 Step B (200 mg, 0.78 mmol) in tetrahydrofuran (3.9 mL) at 0° C. was added a solution of diisobutyl aluminum hydride in hexanes (1.0 M, 1.56 mL, 1.56 mmol). The reaction was warmed to room temperature and stirred overnight. Water and magnesium sulfate were then added, and the resulting suspension was stirred for 30 minutes, then filtered and concentrated under reduced pressure. Purification by flash chromatography on silica gel (20-100% ethyl acetate in hexanes) provided the title compound: LCMS m/z 229.67 [M+2+H]$^+$; $^1$H NMR (500 MHz, CDCl$_3$) δ 8.50 (s, 2H), 7.83 (s, 1H), 3.69 (s, 2H), 0.96-0.90 (m, 4H).

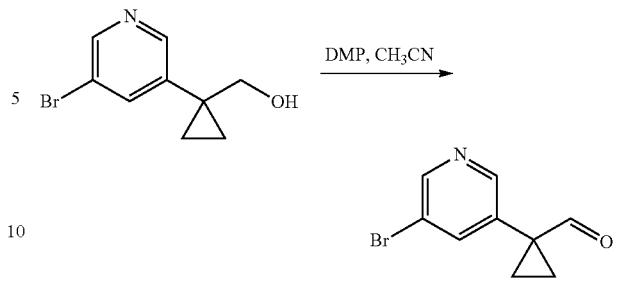

Step B. 1-(5-bromo-3-pyridinyl)cyclopropanecarbaldehyde

To a solution of the title compound from Example 73 Step A (114 mg, 0.500 mmol) in acetonitrile (2.5 mL) was added Dess-Martin Periodinane (254 mg, 0.600 mmol). The reaction stirred at room temperature until complete. It was then concentrated under reduced pressure, diluted with 2% methanol in dichloromethane, and passed through a syringe filter. Purification by flash chromatography on silica gel (20-100% ethyl acetate in hexanes) provided the title compound: LCMS m/z 227.86 [M+2+H]$^+$.

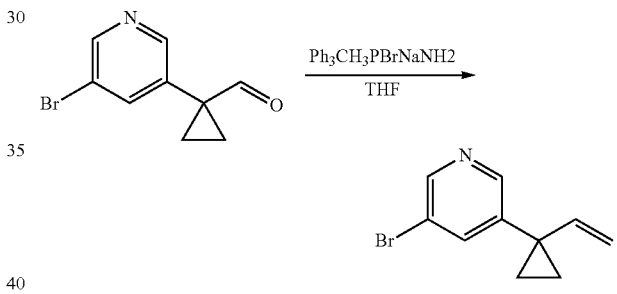

Step C. 3-bromo-5-(1-ethenylcyclopropyl)pyridine

To a solution of methyltriphenylphosphonium bromide-sodium amide complex (510 mg, 01.22 mmol) in tetrahydrofuran (2.0 mL) was added a solution of the title compound from Example 73 Step B (97 mg, 0.43 mmol) in tetrahydrofuran (1.0 mL) The reaction stirred at room temperature for 16 hours. It was then quenched with saturated ammonium chloride solution and extracted with ethyl acetate. The organic extracts were combined, washed with saturated aqueous sodium chloride solution, dried over sodium sulfate, filtered and concentrated under reduced pressure. Purification by flash chromatography on silica gel (0-100% ethyl acetate in hexanes) provided the title compound: LCMS m/z 225.77 [M+H]$^+$; $^1$H NMR (500 MHz, CD$_3$OD) δ 8.54 (s, 1H), 8.47 (s, 1H), 7.50 (s, 1H), 5.68 (dd, J=10.4, 17.1, 1 H), 4.98 (d, J=10.4, 1 H), 4.62 (d, J=17.1, 1 H), 1.12-1.05 (m, 4H).

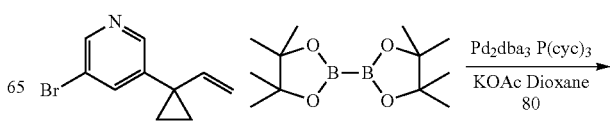

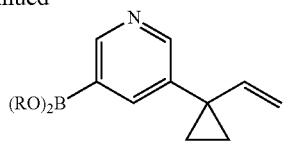

Step D.
[5-(1-ethenylcyclopropyl)-3-pyridinyl]boronic acid

A vial containing the title compound from Example 73 Step C (0.036 g, 0.161 mmol), bis(pinacolato)diboron (0.082 g, 0.321 mmol), tris(dibenzylideneacetone)-dipalladium (0) (0.029 g, 0.032 mmol), tricyclohexylphosphine (0.018 g, 0.064 mmol) and potassium acetate (0.047 g, 0.48 mmol) in dioxane (0.80 mL) was flushed with nitrogen, sealed tightly and heated to 80° C. overnight. The reaction was then passed through a syringe filter and concentrated under reduced pressure to provide the title compound: LCMS m/z 189.12 [M]$^+$.

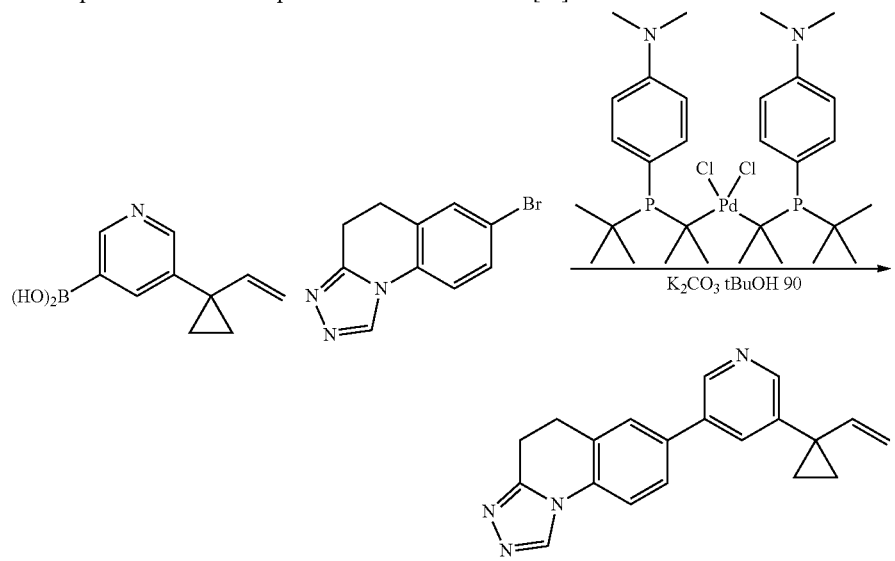

Step E. 7-[5-(1-ethenylcyclopropyl)-3-pyridinyl]-4,5-dihydro[1,2,4]triazolo[4,3-a]quinoline To a vial containing the title compound from Example 22 Step B (35 mg, 0.14 mmol), the title compound from Example 73 Step D (30 mg, 0.16 mmol), bis(di-tert-butyl(4-dimethylaminophenyl)phosphine)dichloropalladium(II) (2.0 mg, 2.8 μmol), and potassium carbonate 285 mg, 0.42 mmol) was added tert-butanol (1.6 mL) and water (0.19 mL). The vial was flushed with nitrogen, sealed tightly and heated to 80° C. overnight. The reaction solution was then cooled to room temperature and concentrated under reduced pressure to provide the title compound: LCMS m/z 315.05 [M+H]$^+$.

Step F. 7-[5-(1-ethylcyclopropyl)-3-pyridinyl]-4,5-dihydro[1,2,4]triazolo[4,3-a]quinoline To a flask containing rhodium (5% on alumina, 15 mg) in ethyl acetate (1.5 mL) was added a solution of the title compound from Example 76 Step E (48 mg, 0.15 mmol) in ethyl acetate (1.5 mL). The flask was flushed with nitrogen and then placed under a balloon of hydrogen. After stirring for one hour, the flask was flushed with nitrogen, and the reaction mixture passed through a syringe filter and concentrated under reduced pressure. The resulting material was diluted with acetonitrile and purified by HPLC (C18 column, 10 to 100% acetonitrile/water, both 0.1% v/v trifluoroacetic acid) to provide the title compound: LCMS m/z 317.07 [M+H]$^+$; $^1$H NMR (500 MHz, CD$_3$OD) δ 10.06 (s, 1H), 9.11 (s, 1H), 8.85 (s, 1H), 8.83 (s, 1H), 8.09-8.00 (m, 3H), 3.47-3.46 (m, 2H), 3.40-3.38 (m, 2H), 1.84 (q, J=7.3 Hz, 2H), 1.12-1.10 (m, 2H), 1.04-1.01 (m, 2H), 0.96 (t, J=7.3 Hz, 3H).

Example 74

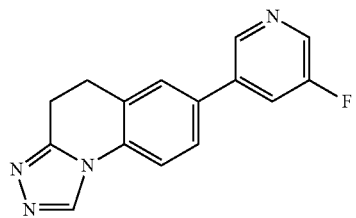

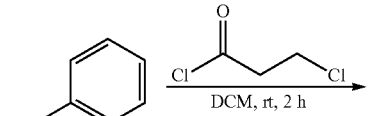

-continued

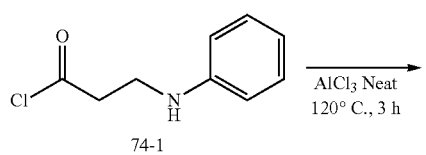

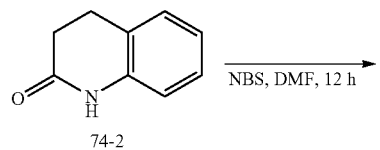

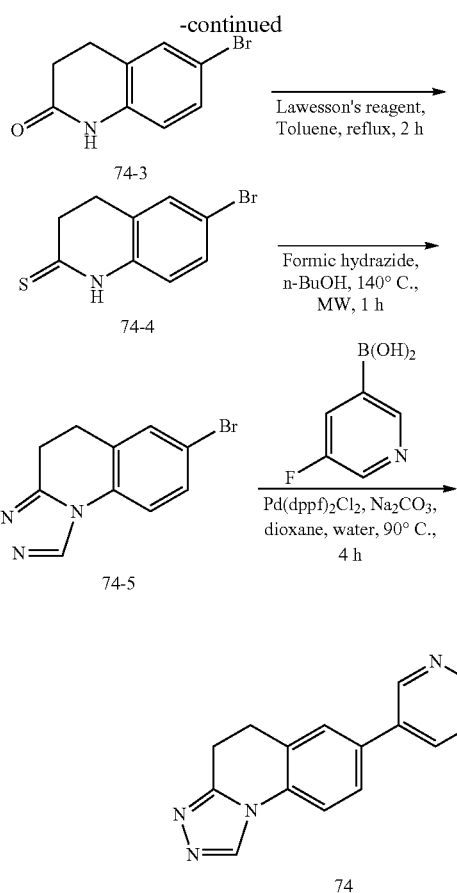

Step A. 3-chloro-N-phenylpropanamide

To a stirred solution of aniline (40 g, 0.429 mol) in dichloromethane (500 mL) cooled at 0° C., was added 3-chloropropanoyl chloride (49.1 mL, 0.515 mol) drop wise with constant stirring. Reaction mass was allowed to stir at room temperature for 2 h. The reaction mixture was diluted with water (500 mL) and extracted with dichloromethane (4×500 mL). The combined organic layer was washed with saturated sodium bicarbonate solution, saturated aqueous sodium chloride solution, dried over sodium sulphate and concentrated under vacuum to obtain the title compound. $^1$H NMR (400 MHz, DMSO-$d_6$) δ 10.01 (s, 1H), 7.58-7.56 (d, J=8 Hz, 2H), 7.30-7.26 (t, J=8 Hz, 2H), 7.05-7.01 (t, J=7.6 Hz, 1H), 3.88-3.85 (t, J=6.4 Hz, 2H), 2.82-2.81 (t, J=6.0 Hz, 2H). MS (M+1): 184.1.

Step B. 3,4-dihydroquinolin-2(1H)-one

To a stirred solution of AlCl$_3$ (116.2 g, 0.87 mol) was added 3-chloro-N-phenylpropanamide (74-1; 40 g, 0.22 mol). Reaction mass was heated at 120° C. for 3 h. The reaction mixture was cooled to room temperature and diluted with ice cold water (500 mL) and washed with 1N aqueous hydrochloric acid solution (500 mL) slowly under cooling condition and extracted with ethyl acetate (4×200 mL). The combined organic layer was washed with saturated aqueous sodium chloride solution, dried over sodium sulphate and concentrated under vacuum to afford the crude compound which was stirred with n-pentane (250 mL) for 0.5 h and filtered with n-pentane (50 mL) to obtain the title compound. $^1$H NMR (400 MHz, CDCl$_3$) δ 8.33 (bs, 1H), 7.26-7.15 (m, 2H), 7.00-6.97 (t, J=7.4 Hz, 1H), 6.79-6.77 (d, J=7.6 Hz, 1H), 2.99-2.95 (t, J=7.6 Hz, 2H), 2.66-2.63 (t, J=7.4 Hz, 2H). MS (M+1): 148.1.

Step C. 6-bromo-3,4-dihydroquinolin-2(1H)-one

To a stirred solution of 3,4-dihydroquinolin-2(1H)-one (74-2; 15.0 g, 0.11 mol) in N,N-dimethylformamide (150 mL) was added N-bromosuccinimide (18.4 g, 0.11 mol) portion wise at 0° C. Reaction mass was allowed to stir at room temperature for 12 h. The reaction mixture was concentrated and diluted with ice cold water (300 mL) with constant stirring and the solid residue was filtered and dried to obtain the title compound (1-3). $^1$H NMR (400 MHz, DMSO-$d_6$) δ 10.13 (s, 1H), 7.35 (s, 1H), 7.30-7.28 (d, J=8.4 Hz, 1H), 6.78-6.76 (d, J=8.0 Hz, 1H), 2.87-2.84 (t, J=7.2 Hz, 2H), 2.66-2.63 (t, J=7.4 Hz, 2H). MS (M+2): 228.0.

Step D. 6-bromo-3,4-dihydroquinoline-2(1H)-thione

To a stirred solution of 6-bromo-3,4-dihydroquinolin-2(1H)-one (74-3; 15.0 g, 0.066 mol) in toluene (150 mL) was added Lawesson's reagent (13.4 g, 0.033 mol). Reaction mass was refluxed at 100° C. for 3 h. The reaction mixture was concentrated and directly purified by silica gel column chromatography to obtain title compound. MS (M+2): 243.9.

Step E. 7-bromo-4,5-dihydro-[1,2,4]triazolo[4,3-a]quinoline

To a stirred solution of 6-bromo-3,4-dihydroquinoline-2(1H)-thione (74-4; 0.17 g, 0.0007 mol) in n-butanol (2 mL) was added formic hydrazide (0.105 g, 0.0017 mol) at room temperature. Reaction mass was allowed to stir at 140° C. for 1 h under microwave irradiation conditions. The reaction mixture was cooled to room temperature, diluted with water (10 mL) and extracted with ethyl acetate (2×10 mL). The combined organic layer was washed with saturated aqueous sodium chloride solution, dried over sodium sulphate and concentrated under vacuum to afford title compound. MS (M+3): 252.2.

Step F. 7-(5-fluoropyridin-3-yl)-4,5-dihydro-[1,2,4]triazolo[4,3-a]quinoline

To a stirred solution of 7-bromo-4,5-dihydro-[1,2,4]triazolo[4,3-a]quinoline (74-5; 0.146 g, 0.0005 mol) and (5-fluoropyridin-3-yl)boronic acid (0.122 g, 0.0008 mol) in the mixture of 1,4-dioxan (3 mL) and water (3 mL), was added sodium carbonate (0.184 g, 0.0015 mol). Reaction mass was purged with argon for 20 min. Then catalyst Pd(dppf)$_2$Cl$_2$ (0.023 g, 0.00002 mol) was added and allowed to stir at 90° C. for 4 h. The reaction mixture was filtered through CELITE and filter bed was thoroughly washed with ethyl acetate. The collected organic parts were concentrated under vacuum to afford the crude compound, which was purified by silica gel column chromatography to obtain title compound (74). $^1$H NMR (400 MHz, DMSO-$d_6$) δ 9.29 (s, 1H), 8.85 (s, 1H), 8.577-8.572 (d, J=2 Hz, 1H), 8.12-8.09 (d, J=12 Hz, 1H), 7.92-7.89 (m, 1H), 7.87-7.83 (m, 2H), 3.11 (s, 4H). MS (M+1): 267.1.

Example 75

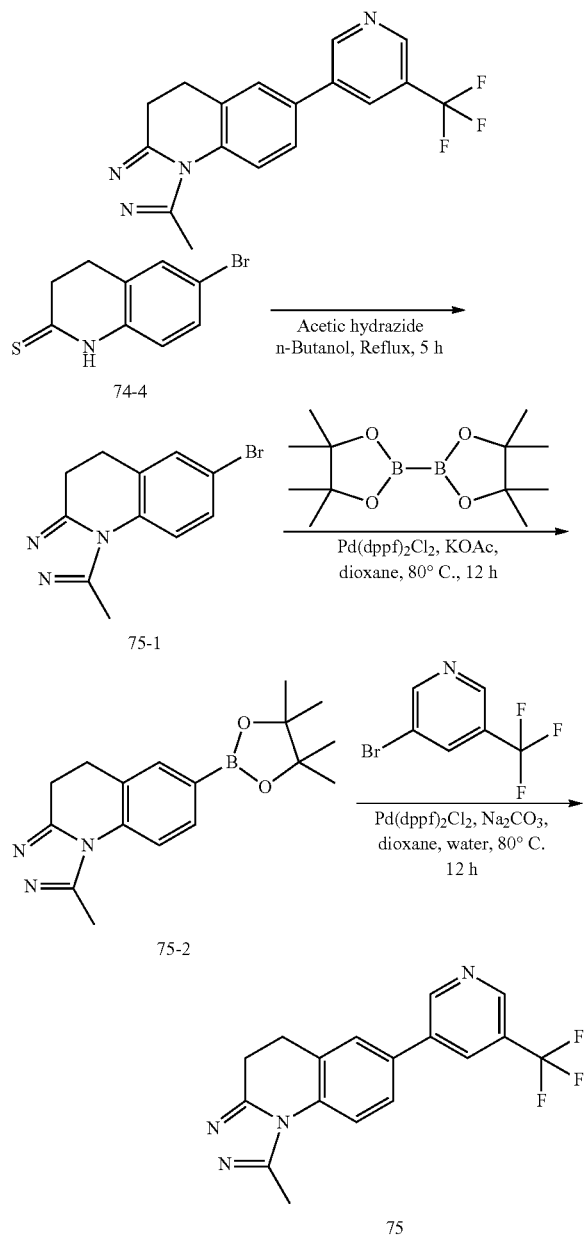

Step A. 7-bromo-1-methyl-4,5-dihydro-[1,2,4]triazolo[4,3-a]quinoline

To a stirred solution of 6-bromo-3,4-dihydroquinoline-2 (1H)-thione (74-4; 1.0 g, 0.004 mol) in n-butanol (20 mL) was added acetic hydrazide (1.19 g, 0.016 mol) at room temperature. Reaction mass was allowed to stir at 140° C. for 5 h. The reaction mixture was cooled to room temperature, diluted with water (50 mL) and extracted with ethyl acetate (3×25 mL). The combined organic layer was washed with saturated aqueous sodium chloride solution, dried over sodium sulphate and concentrated under vacuum to afford the crude compound. Crude compound was purified by silica gel column chromatography to obtain title compound. MS (M+2): 266.0.

Step B. 1-methyl-7-(4,4,5,5-tetramethyl-1,3,2-dioxaborolan-2-yl)-4,5-dihydro-[1,2,4]triazolo[4,3-a]quinoline To a stirred solution of 7-bromo-1-methyl-4,5-dihydro-[1,2,4]triazolo[4,3-a]quinoline (75-1; 1 g, 0.0037 mol) and 4,4,4',4',5,5,5',5'-octamethyl-2,2'-bi(1,3,2-dioxaborolane) (3.84 g, 0.015 mol) in 1,4-dioxan (20 mL) was added potassium acetate (1.1 g, 0.0113 mol). Reaction mass was purged with argon for the next 20 min. Catalyst Pd(dppf)$_2$Cl$_2$ (0.06 g, 0.00007 mol) was added and again purged with argon for 10 min and allowed to stirred at 80° C. for 12 h. The reaction mixture was filtered through CELITE bed and filter bed was thoroughly washed with ethyl acetate. The collected organic parts were concentrated under vacuum to afford the crude compound, which was purified by neutral alumina column chromatography to obtain title compound. MS (M+1): 312.2.

Step C. 1-methyl-7-(5-(trifluoromethyl)pyridin-3-yl)-4,5-dihydro-[1,2,4]triazolo[4,3-a]quinoline To a stirred solution of 1-methyl-7-(4,4,5,5-tetramethyl-1,3,2-dioxaborolan-2-yl)-4,5-dihydro-[1,2,4]triazolo[4,3-a]quinoline (75-2; 0.5 g, 0.00112 mol) and 3-bromo-5-(trifluoromethyl)pyridine (0.381 g, 0.00168 mol) in the mixture of 1,4-dioxan (10 mL) was added aqueous sodium carbonate (2M) (1.68 mL, 0.003376 mol). Reaction mass was purged with argon for 20 min. Then catalyst Pd(dppf)$_2$Cl$_2$ (0.0459 g, 0.003376 mol) was added and allowed to stir at 80° C. for 12 h. The reaction mixture was filtered through CELITE bed and filter bed was thoroughly washed with ethyl acetate. The collected organic parts were concentrated under vacuum to afford the crude compound, which was purified by silica gel column chromatography to obtain title compound. $^1$H NMR (400 MHz, DMSO-d$_6$) δ 9.25 (s, 1H), 8.97 (s, 1H), 8.51 (s, 1H), 8.02 (s, 1H), 7.91-7.89 (d, J 8.4 Hz, 1H), 7.78-7.76 (d, J=8 Hz, 1H), 3.04 (s, 4H), 2.70 (s, 3H). MS (M+1): 331.1.

The compounds in Table 6 were all prepared using the chemistry described in Example 75.

TABLE 6

| Example | Structure | IUPAC Name | LCMS |
|---|---|---|---|
| 76 | 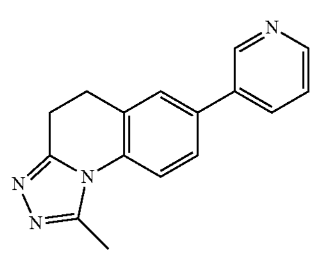 [SMILES: Cc1nnc2n1-c1ccc(-c3cccnc3)cc1CC2] | 1-methyl-7-(pyridin-3-yl)-4,5-dihydro-[1,2,4]triazolo[4,3-]quinoline | 263.3 |

TABLE 6-continued

| Example | Structure | IUPAC Name | LCMS |
|---|---|---|---|
| 77 | 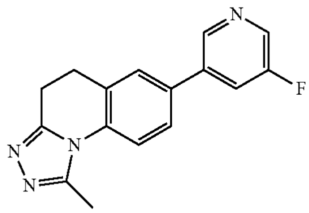 [SMILES: Cc1nnc2n1-c1ccc(-c3cncc(F)c3)cc1CC2] | 7-(5-fluoro-pyridin-3-yl)-1-methyl-4,5-dihydro-[1,2,4]triazolo[4,3-a]quinoline | 281.2 |
| 78 | 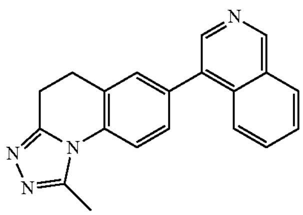 [SMILES: Cc1nnc2n1-c1ccc(-c3cncc4ccccc34)cc1CC2] | 7-(iso-quinolin-4-yl)-1-methyl-4,5-dihydro-[1,2,4]triazolo[4,3-a]quinoline | 313.3 |
| 79 | 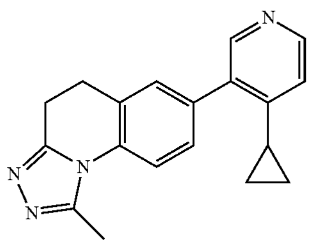 [SMILES: Cc1nnc2n1-c1ccc(-c3cnccc3C3CC3)cc1CC2] | 7-(4-cyclopropyl pyridin 3-yl)-1-methyl-4,5-dihydro-[1,2,4]triazolo[4,3-]quinoline | 303.3 |

Example 80

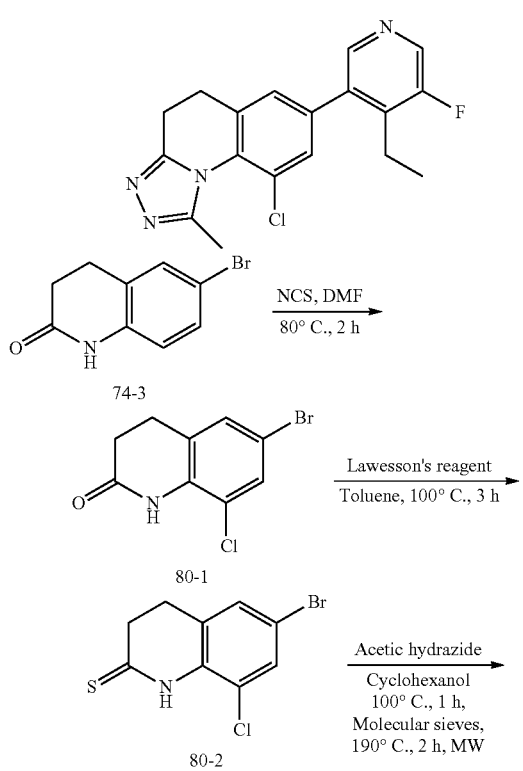

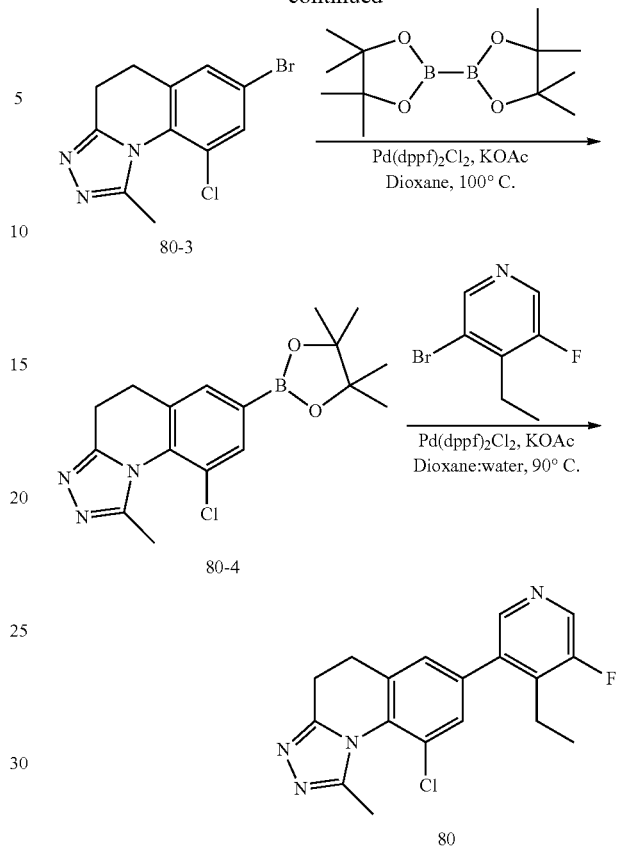

Step A.
6-bromo-8-chloro-3,4-dihydroquinolin-2(1H)-one

To a stirred solution of 6-bromo-3,4-dihydroquinolin-2 (1H)-one (74-3; 20 g, 0.088 mol) in N,N-dimethylformamide (200 mL) was added N-chlorosuccinimide portion wise (17.7 g, 0.132 mol) at 80° C. Reaction mass was allowed to stir at 80° C. for 2 h. The reaction mixture was cooled and diluted with ice cold water. The precipitated solid filtered and dried to obtain title compound. $^1$H NMR (400 MHz, DMSO-$d_6$) δ: 9.61 (bs, 1H), 7.52-7.51 (d, J=1.6 Hz, 1H), 7.41 (s, 1H), 2.93-2.90 (t, J=8 Hz, 2H). MS (M+1); 261.2.

Step B.
6-bromo-8-chloro-3,4-dihydroquinoline-2(1H)-thione

To a stirred solution of 6-bromo-8-chloro-3,4-dihydro-quinolin-2(1H)-one (80-1; 10 g, 0.038 mol) in toluene (130 mL) was added Lawesson's reagent (7.7 g, 0.019 mol). Reaction mass was refluxed at 100° C. for 3 h. The reaction mixture was concentrated and directly purified by silica gel column chromatography to obtain title compound. $^1$H NMR (400 MHz, DMSO-$d_6$) δ: 11.25 (s, 1H), 7.61-7.60 (d, J=2.4 Hz, 1H), 7.48 (s, 1H), 2.96-2.93 (m, 2H), 2.85-2.81 (m, 2H). MS (M+2): 277.

Step C. 7-bromo-9-chloro-1-methyl-4,5-dihydro-[1,2,4]triazolo[4,3-a]quinoline

To a solution of 6-bromo-8-chloro-3,4-dihydroquinoline-2(1H)-thione (80-2; 0.45 g, 0.0016 mol) in cyclohexanol (20 mL) was added acetic hydrazide (0.241 g, 0.0032 mol) and the reaction mixture was heated at 100° C. for 1 h under microwave irradiation conditions. Then 1.5 g of molecular sieves powder was added and the reaction mixture was again heated at 190° C. for 2 h under microwave conditions. The reaction mixture was filtered and the filtrate was evaporated. The crude was purified by silica gel column chromatography to obtain title compound. $^1$H NMR (400 MHz, DMSO-$d_6$) δ: 7.85 (s, 1H), 7.76 (s, 1H), 2.87 (bs, 4H), 2.50 (s, 3H). MS (M+1): 298.2.

Step D. 9-chloro-1-methyl-7-(4,4,5,5-tetramethyl-1,3,2-dioxaborolan-2-yl)-4,5-dihydro-[1,2,4]triazolo[4,3-a]quinoline To a stirred solution of 7-bromo-9-chloro-1-methyl-4,5-dihydro-[1,2,4]triazolo[4,3-a]quinoline (80-3; 0.62 g, 0.0020 mol) and 4,4,4',4',5,5,5',5'-octamethyl-2,2'-bi(1,3,2-dioxaborolane) (4.33 g, 0.017 mol) in 1,4-dioxan (60 mL) was added potassium acetate (0.408 g, 0.0041 mol). Reaction mass was purged with argon for the next 20 min. Catalyst Pd(dppf)$_2$Cl$_2$ (0.076 g, 0.00007 mol) was added and again purged with argon for 10 min and allowed to stirred at 80° C. for 18 h. The reaction mixture was filtered through CELITE bed and filter bed was thoroughly washed with ethyl acetate. The collected organic parts were concentrated under vacuum to afford the crude compound, which was purified by neutral alumina column chromatography to obtain title compound. MS (M+1): 346.4.

Step E. 9-chloro-7-(4-ethyl-5-fluoropyridin-3-yl)-1-methyl-4,5-dihydro[1,2,4]triazolo-[4,3-a]quinoline To a stirred solution of 9-chloro-1-methyl-7-(4,4,5,5-tetramethyl-1,3,2-dioxaborolan-2-yl)-4,5-dihydro-[1,2,4]triazolo[4,3-a]quinoline (80-4; 0.717 g, 0.0020 mol) and 3-bromo-4-ethyl-5-fluoropyridine (0.423 g, 0.0020 mol) in the mixture of 1,4-dioxan (5 mL) and water (5 mL) was added sodium carbonate (0.66 g, 0.0062 mol). Reaction mass was purged with argon for the next 20 min. Catalyst Pd(dppf)$_2$Cl$_2$.dichloromethane (0.084 g, 0.0001 mol) was added and again purged with argon for 10 min and allowed to stirred at 90° C. for 4 h. The reaction mixture was filtered through CELITE bed and filter bed was thoroughly washed with ethyl acetate. The collected organic parts was concentrated under vacuum to afford the crude compound, which was purified by silica gel column chromatography followed by preparative HPLC (analytical conditions; column: ZORBAX XDB (150 mm×4.6 mm×3.5 μm), mobile phase (A): water, Mobile phase (B): MeOH, flow rate: 1.0 mL/min, gradient T/% B:0/20,6/25,25/75,27/20,30/20) to obtain title compound. $^1$H NMR (400 MHz, DMSO-$d_6$) δ: 8.55 (s, 1H), 8.32 (s, 1H), 7.64 (s, 1H), 7.55 (s, 1H), 2.94 (bs, 4H), 2.65-2.59 (m, 2H), 2.56 (s, 3H), 1.09-1.05 (t, J=7.6 Hz, 3H). MS (M+1): 343.2.

The Compounds in Table 7 were all prepared using the chemistry described in Example 80.

TABLE 7

| Example | Structure | IUPAC Name | LCMS |
|---|---|---|---|
| 81 | 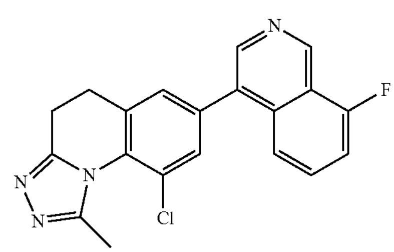 [SMILES: Cc1nnc2n1-c1c(Cl)cc(-c3cncc4c(F)cccc34)cc1CC2] | 9-chloro-7-(8-fluoro isoquinolin-4-yl)-1-methyl-4,5-dihydro-[1,2,4]triazolo[4,3-a]quinoline | 365.8 |
| 82 | 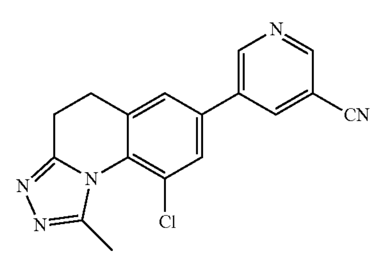 [SMILES: Cc1nnc2n1-c1c(Cl)cc(-c3cncc(C#N)c3)cc1CC2] | 5-(9-chloro-1-methyl-4,5-dihydro-[1,2,4]triazolo[4,3-a]quinolin-7-yl)nicotinonitrile | 322.7 |
| 83 | 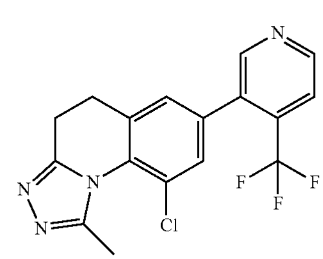 [SMILES: Cc1nnc2n1-c1c(Cl)cc(-c3cnccc3C(F)(F)F)cc1CC2] | 9-chloro-1-methyl-7-(4-(trifluoromethyl)pyridin-3-yl)-4,5-dihydro-[1,2,4]triazolo[4,3-a]quinoline | 365.7 |

TABLE 7-continued

| Example | Structure | IUPAC Name | LCMS |
|---|---|---|---|
| 84 | 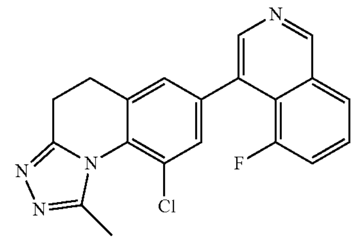 [SMILES: Cc1nnc2n1-c1c(Cl)cc(-c3cncc4cccc(F)c34)cc1CC2] | 9-chloro-7-(5-fluoro isoquinolin-4-yl)-1-methyl-4,5-dihydro-[1,2,4]triazolo[4,3-a]quinoline | 365.8 |
| 85 | 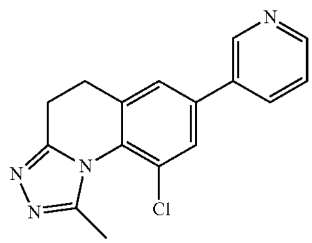 [SMILES: Cc1nnc2n1-c1c(Cl)cc(-c3cccnc3)cc1CC2] | 9-chloro-1-methyl-7-(pyridin-3-yl)-4,5-dihydro-[1,2,4]triazolo[4,3-a]quinoline | 297.7 |
| 86 | 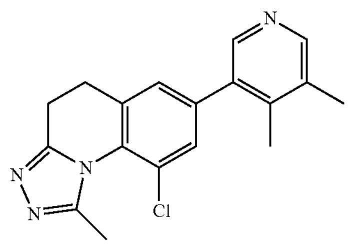 [SMILES: Cc1cncc(-c2cc(Cl)c3c(c2)CCc2nnc(C)n2-3)c1C] | 9-chloro-7-(4,5-dimethylpyridin-3-yl)-1-methyl-4,5-dihydro-[1,2,4]triazolo[4,3-a]quinoline | 325.8 |
| 87 | 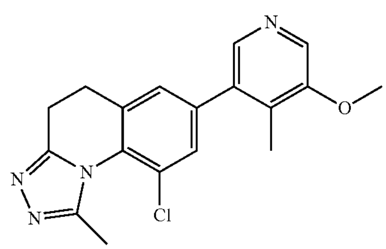 [SMILES: COc1cncc(-c2cc(Cl)c3c(c2)CCc2nnc(C)n2-3)c1C] | 9-chloro-7-(5-methoxy-4-methylpyridin-3-yl)-1-methyl-4,5-dihydro-[1,2,4]triazolo[4,3-a]quinoline | 341.8 |
| 88 | 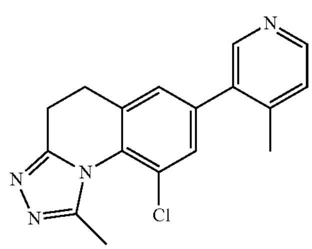 [SMILES: Cc1ccncc1-c1cc(Cl)c2c(c1)CCc1nnc(C)n1-2] | 9-chloro-1-methyl-7-(4-methylpyridin-3-yl)-4,5-dihydro-[1,2,4]triazolo[4,3-a]quinoline | 311.7 |
| 89 | 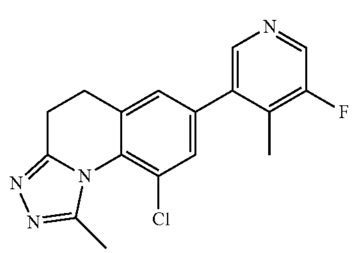 [SMILES: Cc1c(F)cncc1-c1cc(Cl)c2c(c1)CCc1nnc(C)n1-2] | 9-chloro-7-(5-fluoro-4-methylpyridin-3-yl)-1-methyl-4,5-dihydro-[1,2,4]triazolo[4,3-a]quinoline | 329.7 |

TABLE 7-continued

| Example | Structure | IUPAC Name | LCMS |
|---|---|---|---|
| 90 | 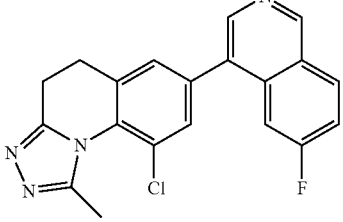 | 9-chloro-7-(6-fluoro isoquinolin-4-yl)-1-methyl-4,5-dihydro-[1,2,4]triazolo[4,3-a]quinoline | 365.8 |
| 91 | 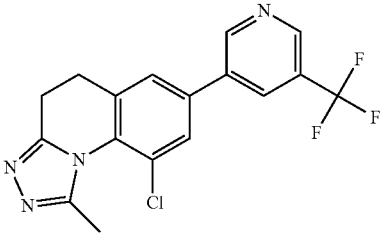 [SMILES: Cc1nnc2n1-c1c(Cl)cc(-c3cncc(C(F)(F)F)c3)cc1CC2] | 9-chloro-1-methyl-7-(5-(trifluoromethyl)pyridin-3-yl)-4,5-dihydro-[1,2,4]triazolo[4,3-a]quinoline | 365.7 |
| 92 | 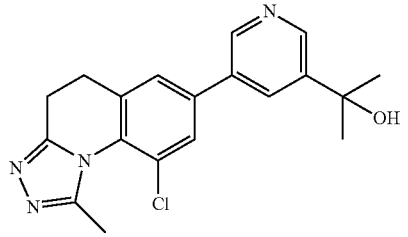 [SMILES: Cc1nnc2n1-c1c(Cl)cc(-c3cncc(C(C)(C)O)c3)cc1CC2] | 2-(5-(9-chloro-1-methyl-4,5-dihydro-[1,2,4]triazolo[4,3-a]quinolin-7-yl)pyridin-3-yl)propan-2-ol | 355.8 |
| 93 | 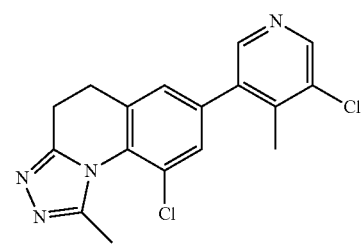 [SMILES: Cc1c(Cl)cncc1-c1cc(Cl)c2c(c1)CCc1nnc(C)n1-2] | 9-chloro-7-(5-chloro-4-methylpyridin-3-yl)-1-methyl-4,5-dihydro-[1,2,4]triazolo[4,3-a]quinoline | 346.2 |
| 94 | 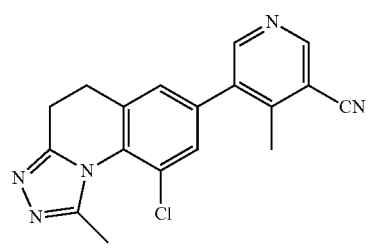 | 5-(9-chloro-1-methyl-4,5-dihydro-[1,2,4]triazolo[4,3-a]quinolin-7-yl)-4-methylnicotinonitrile | 336.7 |
| 95 | 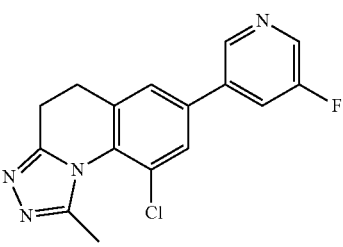 [SMILES: Cc1nnc2n1-c1c(Cl)cc(-c3cncc(F)c3)cc1CC2] | 9-chloro-7-(5-fluoropyridin-3-yl)-1-methyl-4,5-dihydro-[1,2,4]triazolo[4,3-a]quinoline | 315.7 |

TABLE 7-continued

| Example | Structure | IUPAC Name | LCMS |
|---|---|---|---|
| 96 | 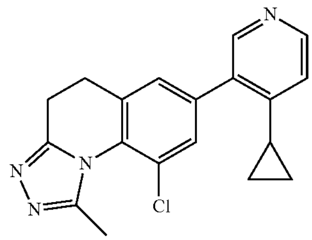 [SMILES: Cc1nnc2n1-c1c(Cl)cc(-c3cnccc3C3CC3)cc1CC2] | 9-chloro-7-(4-cyclopropyl pyridin-3-yl)-1-methyl-4,5-dihydro-[1,2,4]triazolo[4,3-a]quinoline | 337.8 |
| 97 | 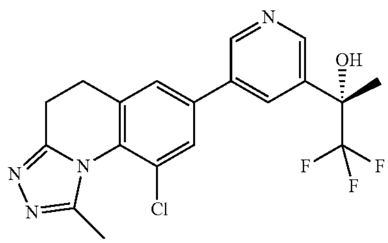 [SMILES: Cc1nnc2n1-c1c(Cl)cc(-c3cncc([C@](C)(O)C(F)(F)F)c3)cc1CC2] | (S)-2-(5-(9-chloro-1-methyl-4,5-dihydro-[1,2,4]triazolo[4,3-a]quinolin-7-yl)pyridin-3-yl)-1,1,1-trifluoropropan-2-ol | 409.8 |
| 98 | 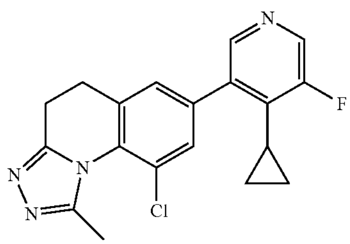 [SMILES: Cc1nnc2n1-c1c(Cl)cc(-c3cncc(F)c3C3CC3)cc1CC2] | 9-chloro-7-(4-cyclopropyl-5-fluoropyridin-3-yl)-1-methyl-4,5-dihydro-[1,2,4]triazolo[4,3-a]quinoline | 355.8 |
| 99 | 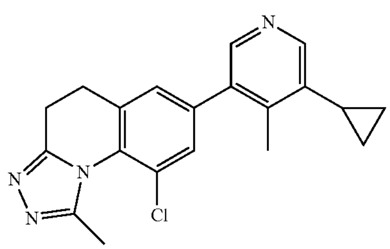 [SMILES: Cc1c(-c2cc(Cl)c3c(c2)CCc2nnc(C)n2-3)cncc1C1CC1] | 9-chloro-7-(5-cyclopropyl-4-methylpyridin-3-yl)-1-methyl-4,5-dihydro-[1,2,4]triazolo[4,3-a]quinoline | 351.8 |
| 100 | 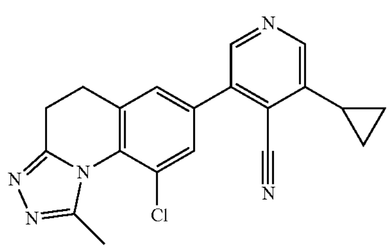 [SMILES: Cc1nnc2n1-c1c(Cl)cc(-c3cncc(C4CC4)c3C#N)cc1CC2] | 3-(9-chloro-1-methyl-4,5-dihydro-[1,2,4]triazolo[4,3-a]quinolin-7-yl)-5-cyclopropylisonicotinonitrile | 362.8 |
| 101 | 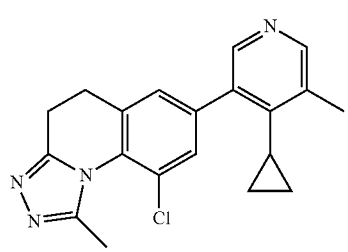 [SMILES: Cc1cncc(-c2cc(Cl)c3c(c2)CCc2nnc(C)n2-3)c1C1CC1] | 9-chloro-7-(4-cyclopropyl-5-methylpyridin-3-yl)-1-methyl-4,5-dihydro-[1,2,4]triazolo[4,3-a]quinoline | 351.8 |

TABLE 7-continued

| Example | Structure | IUPAC Name | LCMS |
|---|---|---|---|
| 102 | 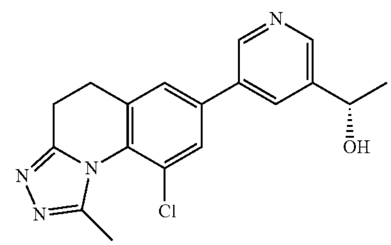 [SMILES: Cc1nnc2n1-c1c(Cl)cc(-c3cncc([C@H](C)O)c3)cc1CC2] | (S)-1-(5-(9-chloro-1-methyl-4,5-dihydro-[1,2,4]triazolo[4,3-a]quinolin-7-yl)pyridin-3-yl)ethanol | 341.8 |
| 103 | 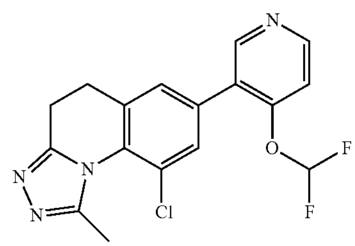 [SMILES: Cc1nnc2n1-c1c(Cl)cc(-c3cnccc3OC(F)F)cc1CC2] | 9-chloro-7-(4-(difluoro methoxy)pyridin-3-yl)-1-methyl-4,5-dihydro-[1,2,4]triazolo[4,3-a]quinoline | 363.7 |
| 104 | 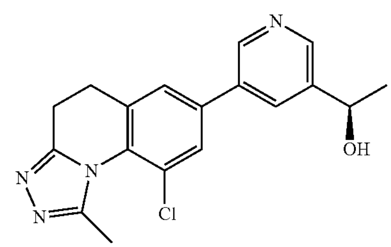 [SMILES: Cc1nnc2n1-c1c(Cl)cc(-c3cncc([C@@H](C)O)c3)cc1CC2] | (R)-1-(5-(9-chloro-1-methyl-4,5-dihydro-[1,2,4]triazolo[4,3-a]quinolin-7-yl)pyridin-3-yl)ethanol | 341.8 |
| 105 | 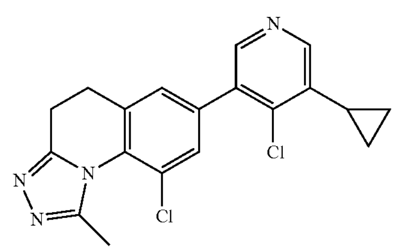 [SMILES: Cc1nnc2n1-c1c(Cl)cc(-c3cncc(C4CC4)c3Cl)cc1CC2] | 9-chloro-7-(4-chloro-5-cyclopropylpyridin-3-yl)-1-methyl-4,5-dihydro-[1,2,4]triazolo[4,3-a]quinoline | 372.2 |
| 106 | 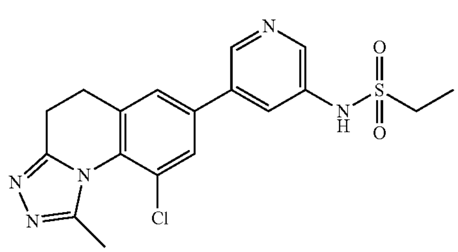 [SMILES: CCS(=O)(=O)Nc1cncc(-c2cc(Cl)c3c(c2)CCc2nnc(C)n2-3)c1] | N-(5-(9-chloro-1-methyl-4,5-dihydro-[1,2,4]triazolo[4,3-a]quinolin-7-yl)pyridin-3-yl)ethanesulfonamide | 404.8 |
| 107 | 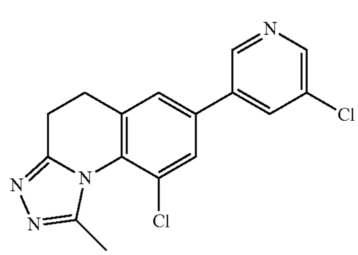 [SMILES: Cc1nnc2n1-c1c(Cl)cc(-c3cncc(Cl)c3)cc1CC2] | 9-chloro-7-(5-chloropyridin-3-yl)-1-methyl-4,5-dihydro-[1,2,4]triazolo[4,3-a]quinoline | 332.1 |

| Example | Structure | IUPAC Name | LCMS |
|---|---|---|---|
| 108 | 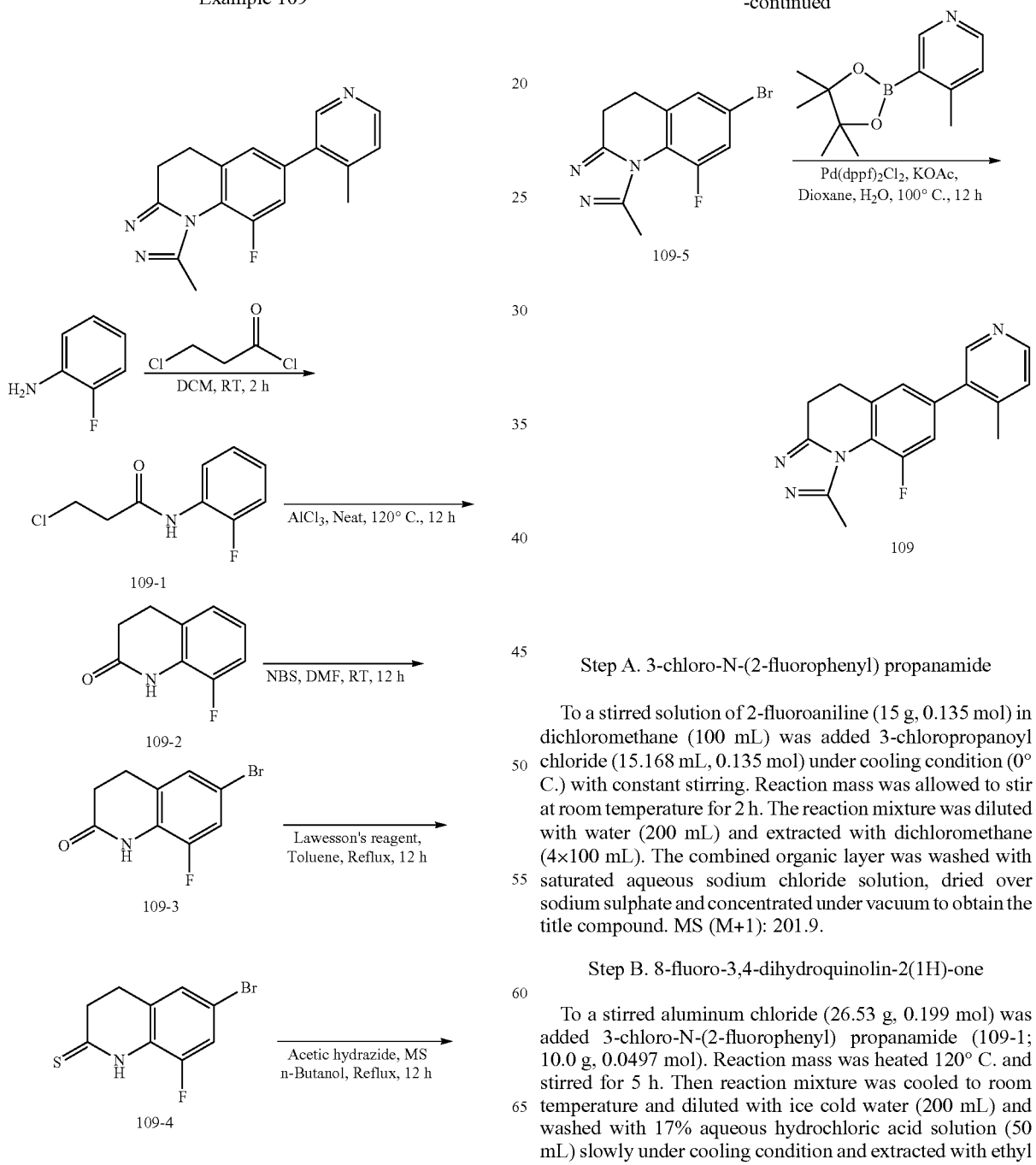 | N-(5-(9-chloro-1-methyl-4,5-dihydro-[1,2,4]triazolo[4,3-a]quinolin-7-yl)pyridin-3-yl)benzenesulfonamide | 452.9 |

Example 109

Step A. 3-chloro-N-(2-fluorophenyl) propanamide

To a stirred solution of 2-fluoroaniline (15 g, 0.135 mol) in dichloromethane (100 mL) was added 3-chloropropanoyl chloride (15.168 mL, 0.135 mol) under cooling condition (0° C.) with constant stirring. Reaction mass was allowed to stir at room temperature for 2 h. The reaction mixture was diluted with water (200 mL) and extracted with dichloromethane (4×100 mL). The combined organic layer was washed with saturated aqueous sodium chloride solution, dried over sodium sulphate and concentrated under vacuum to obtain the title compound. MS (M+1): 201.9.

Step B. 8-fluoro-3,4-dihydroquinolin-2(1H)-one

To a stirred aluminum chloride (26.53 g, 0.199 mol) was added 3-chloro-N-(2-fluorophenyl) propanamide (109-1; 10.0 g, 0.0497 mol). Reaction mass was heated 120° C. and stirred for 5 h. Then reaction mixture was cooled to room temperature and diluted with ice cold water (200 mL) and washed with 17% aqueous hydrochloric acid solution (50 mL) slowly under cooling condition and extracted with ethyl acetate (4×100 mL). The combined organic layer was washed with saturated aqueous sodium chloride solution, dried over sodium sulphate and concentrated under vacuum to afford the crude compound which was purified by silica gel column chromatography to obtain the title compound. MS (M+1): 166.1.

Step C.
6-bromo-8-fluoro-3,4-dihydroquinolin-2(1H)-one

To a stirred solution of 8-fluoro-3,4-dihydroquinolin-2 (1H)-one (109-2; 7 g, 0.0424 mol) in N,N-dimethylformamide (30 mL) was added N-bromosuccinimide (9.06 g, 0.050 mol) portion wise at 0° C. Reaction mixture was allowed to stir at room temperature for 12 h. The reaction mixture was concentrated and diluted with ice cold water (150 mL) with constant stirring and the solid residue was filtered and dried to obtain the title compound. MS (M+1): 245.1

Step D.
6-bromo-8-fluoro-3,4-dihydroquinoline-2(1H)-thione

To a stirred solution of 6-bromo-8-fluoro-3,4-dihydroquinolin-2(1H)-one (109-3; 8 g, 0.032 mol) in toluene (30 mL) was added Lawesson's reagent (13.26 g, 0.032 mol). Reaction mass was refluxed at 100° C. for 12 h. The reaction mixture was concentrated and directly purified by silica gel column chromatography to obtain title compound. MS (M+1): 262.0.

Step E. 7-bromo-9-fluoro-1-methyl-4,5-dihydro-[1,2, 4]triazolo[4,3-a]quinoline

To a stirred solution of 6-bromo-8-fluoro-3,4-dihydroquinoline-2(1H)-thione (109-4; 3.0 g, 0.011 mol) in n-butanol (25 mL) was added acetic hydrazide (4.81 g, 0.065 mol) and then followed by the addition of molecular sieves. Reaction mass was heated to 120° C. for 16 h. The reaction mixture was concentrated and directly purified by silica gel column chromatography to obtain title compound. MS (M+1): 284.2.

Step F. 9-fluoro-1-methyl-7-(4-methylpyridin-3-yl)-4,5-dihydro-[1,2,4]triazolo[4,3-a]quinoline To a stirred solution of 7-bromo-9-fluoro-1-methyl-4,5-dihydro-[1,2,4]triazolo[4,3-a]quinoline (109-5; 1.8 g, 0.0063 mol) and (4-methylpyridin-3-yl)boronic acid (1.73 g, 0.0127 mol) in the mixture of 1,4-dioxan (10 mL) and water (10 mL) was added potassium acetate (1.88 g, 0.0191 mol). Reaction mass was purged with argon for 20 min. Then catalyst Pd(dppf)$_2$Cl$_2$ (0.260 g, 0.000319 mol) was added and allowed to stir at 100° C. for 12 h. The reaction mixture was filtered through CELITE bed and filter bed was thoroughly washed with ethyl acetate. The collected organic parts was concentrated under vacuum to afford the crude compound, which was purified by silica gel column chromatography to obtain title compound. $^1$H NMR (400 MHz, DMSO-d$_6$) 8.46-8.44 (d, J=8 Hz, 1H), 8.422 (s, 1H), 7.52-7.48 (d, J=16 Hz, 1H), 7.423 (s, 1H), 7.36-7.35 (d, J=4 Hz, 1H), 2.99 (m, 4H), 2.52 (s, 3H), 2.31 (s, 3H). HPLC purity 98.68%, MS (M+1): 294.7.

Example 110

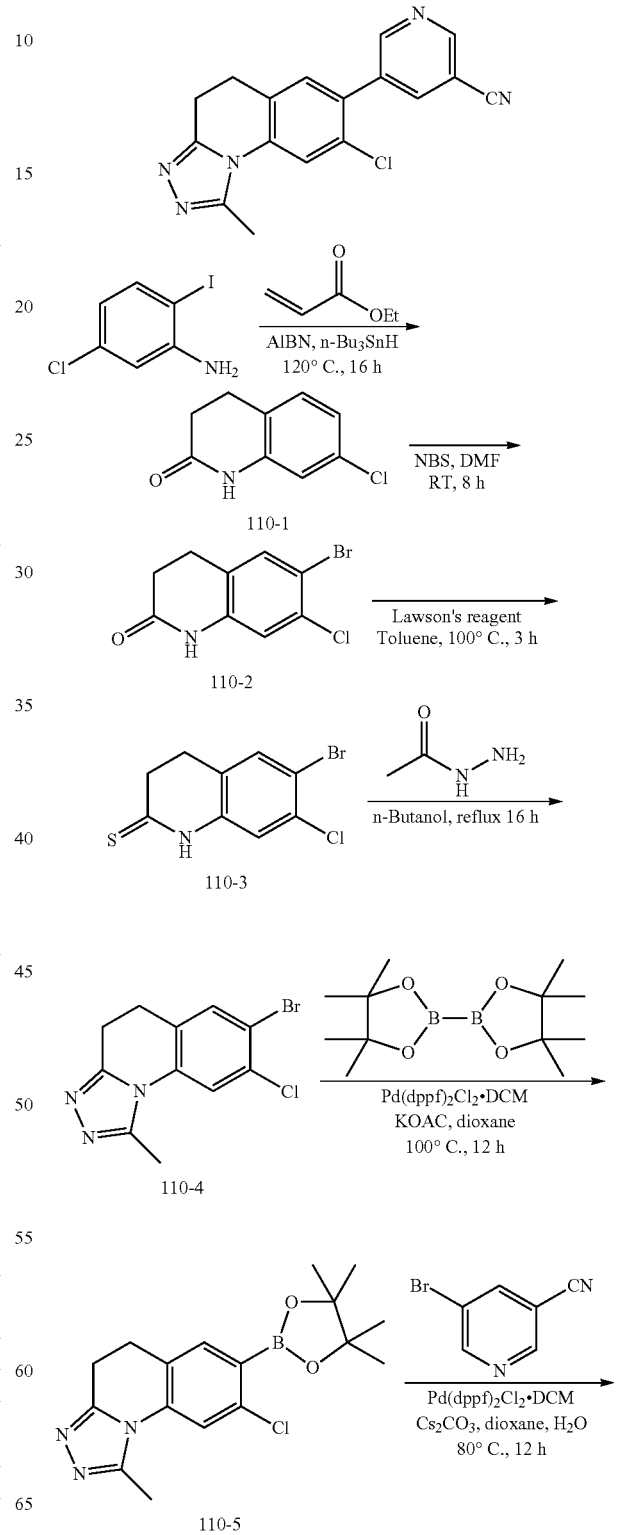

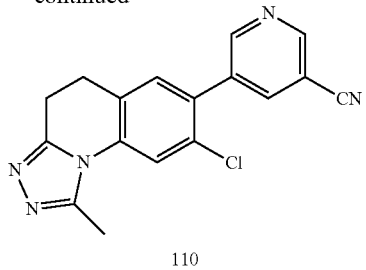

110

Step A. 7-chloro-3,4-dihydroquinolin-2(1H)-one

To a solution of 5-chloro-2-iodoaniline (14.0 g, 0.0552 mol) in dimethyl sulphoxide, ethyl acrylate (30.38 mL, 0.276 mol) and n-tributyltinhydride (22.3 mL, 0.0828 mol), AIBN (3.6 g, 0.022 mol) was added at room temperature. The reaction mixture was heated to 120° C. and stirred for 16 h. The reaction mixture was cooled to room temperature; the reaction mixture was diluted with water. The aqueous phase was extracted with ethyl acetate (3×500 mL), the combined organic layer was washed with cold water, saturated aqueous sodium chloride solution and dried over sodium sulphate, the solvent was evaporated under vacuum and the residue was purified with silica gel (60-120 mesh) silica gel column chromatography by 0-20% ethyl acetate in hexane to afford the title compound. $^1$H NMR (400 MHz, DMSO-d$_6$) δ 10.13 (s, 1H), 7.17-7.15 (d, J=7.6 Hz, 1H), 6.93-6.91 (d, J=8.0 Hz, 1H), 6.85 (s, 1H), 2.85-2.81 (t, J=7.2 Hz, 2H), 2.44-2.41 (t, J=8 Hz, 2H); MS (M+1): 181.9.

Step B. 6-bromo-7-chloro-3,4-dihydroquinolin-2(1H)-one

To solution of 7-chloro-3,4-dihydroquinolin-2(1H)-one (110-1; 2.92 g, 0.016 mol) in N,N-dimethylformamide (30 mL), was added N-bromosuccinimide (3.14 g, 0.0176 mol) portion-wise at room temperature. The resulting mixture was stirred at room temperature for 16 h. After 16 h, the reaction mixture was diluted with cold water, solid get precipitated, filtered the solid, washed the solid with water and dried under reduced pressure to afford the compound. $^1$H NMR (400 MHz, DMSO-d$_6$) δ 10.20 (s, 1H), 7.56 (s, 1H), 7.01 (s, 1H), 2.87-2.84 (t, J=7.2 Hz, 2H), 2.45-2.41 (t, J=7.6 Hz, 2H); MS (M+1): 259.9.

Step C. 6-bromo-7-chloro-3,4-dihydroquinoline-2(1H)-thione

To a stirred solution of 6-bromo-7-chloro-3,4-dihydroquinolin-2(1H)-one (110-2; 2.95 g, 0.0113 mol) in toluene (50 mL) was added Lawesson's reagent (2.2 g, 0.00566 mol). Reaction mass was refluxed at 100° C. for 3 h. The reaction mixture was concentrated under reduced pressure and the residue was purified by silica gel (60-120 mesh) column chromatography using 7% ethyl acetate in hexane to afford the title compound. $^1$H NMR (400 MHz, DMSO-d$_6$) δ 12.25 (s, 1H), 7.64 (s, 1H), 7.24 (s, 1H), 2.93-2.89 (t, J=6.8 Hz, 2H), 2.80-2.76 (t, J=8.0 Hz, 2H); MS (M+1): 275.8.

Step D. 7-bromo-8-chloro-1-methyl-4,5-dihydro-[1,2,4]triazolo[4,3-a]quinoline To a stirred solution of 6-bromo-7-chloro-3,4-dihydroquinoline-2(1H)-thione (110-3; 1.8 g, 0.0065 mol) in n-butanol (80 mL) was added acetic hydrazide (1.2 g, 0.0162 mol). Reaction mass was refluxed for 16 h. The reaction mixture was concentrated under reduced pressure and the residue was purified by silica gel (60-120 mesh) column chromatography using 0-5% methanol in dichloromethane to afford title compound. $^1$H NMR (400 MHz, DMSO-d$_6$) δ 7.91 (s, 1H), 7.81 (s, 1H), 2.96 (bs, 4H), 2.66 (s, 3H). MS (M+1): 296.0.

Step E. 7,8-dichloro-6-(4,4,5,5-tetramethyl-1,3,2-dioxaborolan-2-yl)-3,4-dihydroquinolin-2(1H)-one To a stirred solution of 7-bromo-8-chloro-1-methyl-4,5-dihydro-[1,2,4]triazolo[4,3-a]quinoline (110-4; 1.0 g, 0.00334 mol) in dioxin (20 mL) was added 4,4,4',4',5,5,5',5'-octamethyl-2,2'-bi(1,3,2-dioxaborolane) (6.7 g, 0.0267 mol), potassium acetate (0.65 g, 0.00669 mol). Reaction mass was purged with argon for the next 20 min. After purging, Pd(dppf)$_2$Cl$_2$.dichloromethane (0.13 g, 0.000016 mol) was added. The reaction mixture was heated to 100° C. and stirred for 8 h. The reaction mixture was cooled to room temperature, filtered the reaction mixture through celite bed and celite bed was thoroughly washed with ethyl acetate. The filtrate was concentrated under vacuum. The residue was dissolved in ethyl acetate, the organic layer was washed with water, saturated aqueous sodium chloride solution, dried over sodium sulphate, concentrated under vacuum to obtain crude compound 7,8-dichloro-6-(4,4,5,5-tetramethyl-1,3,2-dioxaborolan-2-yl)-3,4-dihydroquinolin-2(1H)-one as brown semi solid (the crude product taken for next step without further purification). MS (M+1): 346.2.

Step F. 5-(8-chloro-1-methyl-4,5-dihydro-[1,2,4]triazolo[4,3-a]quinolin-7-yl)nicotinonitrile To a stirred solution of 7,8-dichloro-6-(4,4,5,5-tetramethyl-1,3,2-dioxaborolan-2-yl)-3,4-dihydroquinolin-2(1H)-one (110-5; 0.2 g, 0.000578 mol) and 5-bromonicotinonitrile (0.83 g, 0.000578 mol) in the mixture of 1,4-dioxan (10 mL) and water (5 mL) was added cesium carbonate (0.37 g, 0.00115 mol). Reaction mass was purged with argon for 20 min. After 20 min, Pd(dppf)$_2$Cl$_2$.dichloromethane (0.023 g, 0.0000289 mol) was added. The reaction mixture was heated to 100° C. and stirred for 6 h. The reaction mixture was cooled to room temperature, filtered through CELITE bed and the bed was thoroughly washed with ethyl acetate. The filtrate was concentrated under vacuum. The residue was dissolved with dichloromethane, the organic layer was washed with water, saturated aqueous sodium chloride solution, dried over sodium sulphate, concentrated under vacuum, which was purified by silica gel (60-120 mesh) column chromatography using 5% methanol in dichloromethane. Again it was purified by preparative HPLC (analytical conditions; column: Xbridge C18(250 mm×4.6 mm×5 μm), mobile phase (A): water, Mobile phase (B): acetonitrile, flow rate: 1.0 mL/min, gradient T/% B:0/95,8/50,25/50,27/95,30/95) to obtain title compound. $^1$H NMR (400 MHz, DMSO-d$_6$) δ 9.09 (s, 1H), 8.977-8.972 (d, J=2 Hz, 1H), 8.50 (s, 1H), 7.86 (s, 1H), 7.72 (s, 1H), 3.01 (bs, 4H), 2.71 (s, 3H). MS (M+1): 322.2

The compounds in Table 8 were prepared using the chemistry detailed in Example 110.

TABLE 8

| Example | Structure | IUPAC Name | LCMS |
|---|---|---|---|
| 111 | 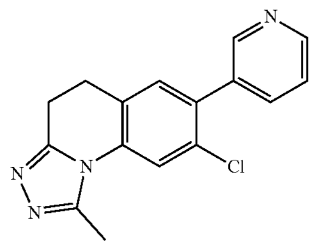 [SMILES: Cc1nnc2n1-c1cc(Cl)c(-c3cccnc3)cc1CC2] | 8-chloro-1-methyl-7-(pyridin-3-yl)-4,5-dihydro-[1,2,4]triazolo[4,3-a]quinoline | 297.7 |
| 112 | 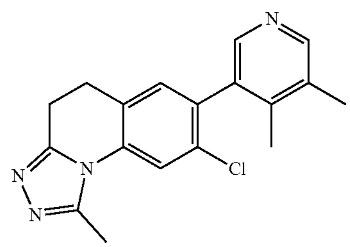 [SMILES: Cc1cncc(-c2cc3c(cc2Cl)-n2c(C)nnc2CC3)c1C] | 8-chloro-7-(4,5-dimethyl-pyridin-3-yl)-1-methyl-4,5-dihydro-[1,2,4]triazolo[4,3-a]quinoline | 325.8 |
| 113 | 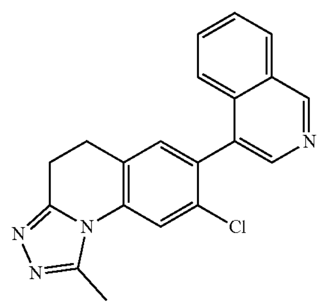 [SMILES: Cc1nnc2n1-c1cc(Cl)c(-c3cncc4ccccc34)cc1CC2] | 8-chloro-7-(isoquinolin-4-yl)-1-methyl-4,5-dihydro-[1,2,4]triazolo[4,3-a]quinoline | 347.8 |
| 114 | 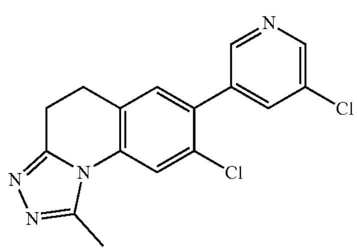 [SMILES: Cc1nnc2n1-c1cc(Cl)c(-c3cncc(Cl)c3)cc1CC2] | 8-chloro-7-(5-chloro-pyridin-3-yl)-1-methyl-4,5-dihydro-[1,2,4]triazolo[4,3-a]quinoline | 332.1 |
| 115 | 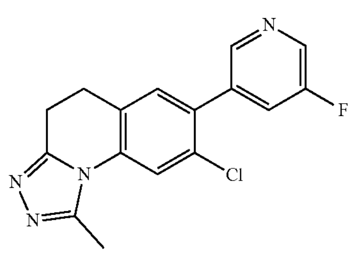 [SMILES: Cc1nnc2n1-c1cc(Cl)c(-c3cncc(F)c3)cc1CC2] | 8-chloro-7-(5-fluoro-pyridin-3-yl)-1-methyl-4,5-dihydro-[1,2,4]triazolo[4,3-a]quinoline | 315.7 |
| 116 | 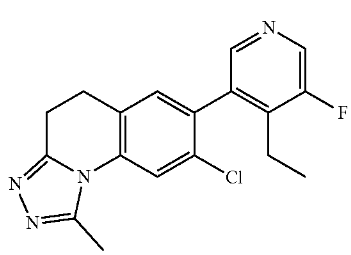 [SMILES: CCc1c(F)cncc1-c1cc2c(cc1Cl)-n1c(C)nnc1CC2] | 8-chloro-7-(4-ethyl-5-fluoropyridin-3-yl)-1-methyl-4,5-dihydro-[1,2,4]triazolo[4,3-a]quinoline | 343.7 |

TABLE 8-continued

| Example | Structure | IUPAC Name | LCMS |
|---|---|---|---|
| 117 | 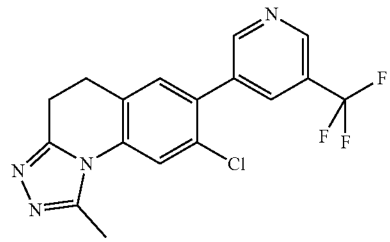 [SMILES: Cc1nnc2n1-c1cc(Cl)c(-c3cncc(C(F)(F)F)c3)cc1CC2] | 8-chloro-1-methyl-7-(5-(trifluoromethyl)pyridin-3-yl)-4,5-dihydro-[1,2,4]triazolo[4,3-a]quinoline | 365.7 |
| 118 | 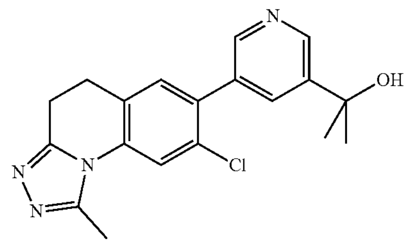 [SMILES: Cc1nnc2n1-c1cc(Cl)c(-c3cncc(C(C)(C)O)c3)cc1CC2] | 2-(5-(8-chloro-1-methyl-4,5-dihydro-[1,2,4]triazolo[4,3-a]quinolin-7-yl)pyridin-3-yl)propan-2-ol | 355.8 |
| 119 | 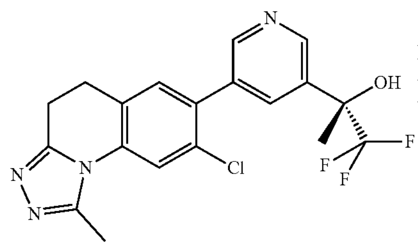 | (S)-2-(5-(8-chloro-1-methyl-4,5-dihydro-[1,2,4]triazolo[4,3-a]quionolin-7-yl)pyridin-3-yl)-1,1,1-trifluoropropan-2-ol | 409.8 |
| 120 | 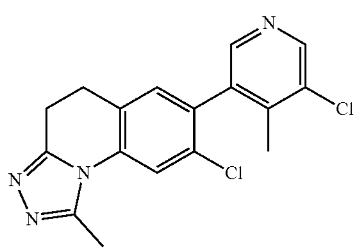 [SMILES: Cc1c(Cl)cncc1-c1cc2c(cc1Cl)-n1c(C)nnc1CC2] | 8-chloro-7-(5-chloro-4-methylpyridin-3-yl)-1-methyl-4,5-dihydro-[1,2,4]triazolo[4,3-a]quinoline | 346.2 |
| 121 | 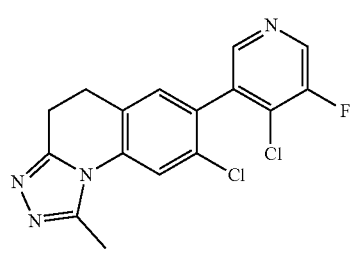 [SMILES: Cc1nnc2n1-c1cc(Cl)c(-c3cncc(F)c3Cl)cc1CC2] | 8-chloro-7-(4-chloro-5-fluoropyridin-3-yl)-1-methyl-4,5-dihydro-[1,2,4]triazolo[4,3-a]quinoline | 350.1 |

Example 122

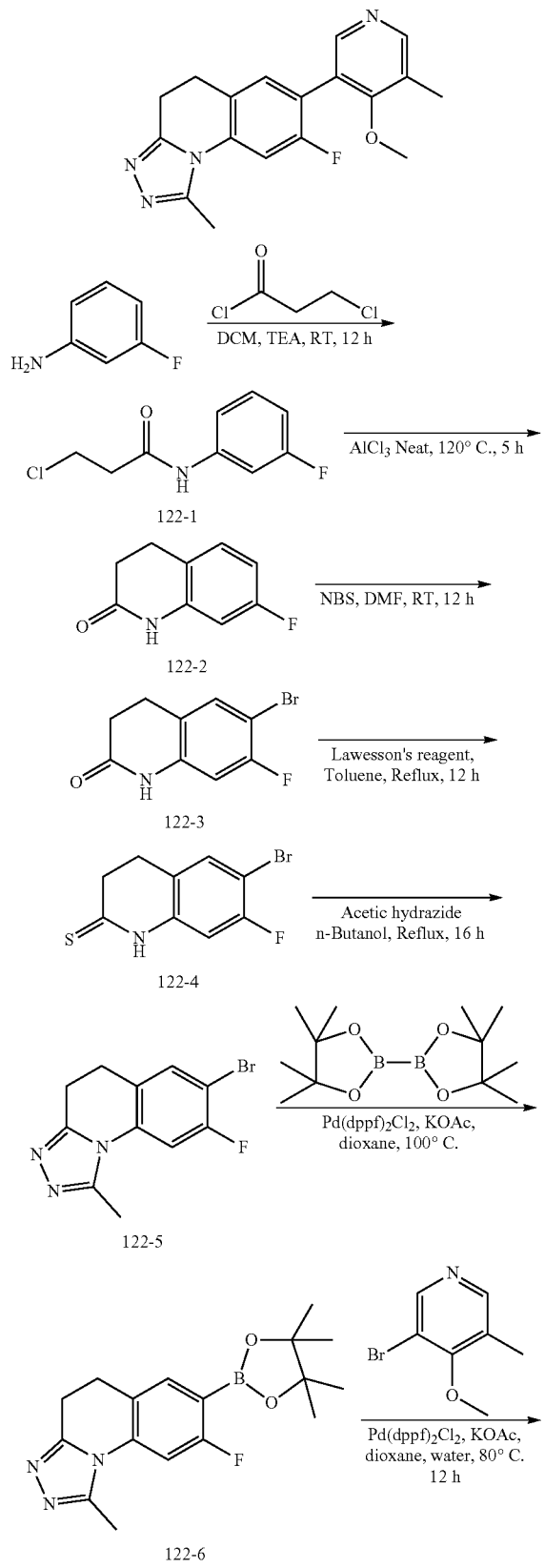

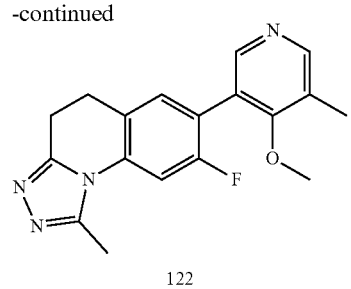

Step A. 3-chloro-N-(3-fluorophenyl) propanamide

To a stirred solution of 3-fluoroaniline (20 g, 0.180 mol) in dichloromethane (100 mL) was added triethylamine (21.816 g, 0.216 mol) and 3-chloropropanoyl chloride (17.18 mL, 0.180 mol) under cooling condition (0° C.) with constant stirring. Reaction mass was allowed to stir at room temperature for 12 h. The reaction mixture was diluted with water (300 mL) and extracted with dichloromethane (4×100 mL). The combined organic layer was washed with saturated aqueous sodium chloride solution, dried over sodium sulphate and concentrated under vacuum to obtain the title compound. $^1$H NMR (400 MHz, CDCl$_3$) δ 7.51-7.48 (d, J=10.4 Hz, 1H), 7.42 (bs, 1H), 7.29-7.24 (dd, J=14.8 Hz, 8.0 Hz, 1H), 7.15-7.13 (d, J=8.0 Hz, 1H), 6.84-6.81 (t, J=6.8 Hz, 1H), 3.89-3.86 (t, J=6.4 Hz, 2H), 2.83-2.80 (t, J=6.4 Hz, 2H). MS (M+1): 201.9.

Step B. 7-fluoro-3,4-dihydroquinolin-2(1H)-one

To a stirred aluminum chloride (66.33 g, 0.497 mol) was added 3-chloro-N-(3-fluorophenyl) propanamide (122-1; 25.0 g, 0.124 mol). Reaction mass was heated at 120° C. for 5 h. Then reaction mixture was cooled to room temperature and diluted with ice cold water (400 mL) and washed with 17% aqueous hydrochloric acid solution (150 mL) slowly under cooling condition and extracted with ethyl acetate (4×200 mL). The combined organic layer was washed with saturated aqueous sodium chloride solution, dried over sodium sulphate and concentrated under vacuum to afford the crude compound which was purified by silica gel column chromatography to obtain the title compound (6-2). MS (M+1):165.9.

Step C.
6-bromo-7-fluoro-3,4-dihydroquinolin-2(1H)-one

To a stirred solution of 7-fluoro-3,4-dihydroquinolin-2 (1H)-one (122-2; 15 g, 0.090 mol) in N,N-dimethylformamide (50 mL) was added N-bromosuccinimide (19.22 g, 0.108 mol) portion wise at 0° C. Reaction mixture was allowed to stir at room temperature for 12 h. The reaction mixture was concentrated and diluted with ice cold water (150 mL) with constant stirring and the solid residue was filtered and dried to obtain the title compound. $^1$H NMR (400 MHz, CDCl$_3$) δ 8.0 (bs, 1H), 7.34-7.32 (d, J=7.2 Hz, 1H), 6.59-6.57 (d, J=8.8 Hz, 1H), 2.95-2.91 (t, J=7.6 Hz, 2H), 2.65-2.61 (t, J=–7.6 Hz, 2H). MS (M+1): 245.9.

Step D.
6-bromo-7-fluoro-3,4-dihydroquinoline-2(1H)-thione

To a stirred solution of 6-bromo-7-fluoro-3,4-dihydroquinolin-2(1H)-one (122-3; 13 g, 0.02 mol) in toluene (50 mL) was added Lawesson's reagent (21.54 g, 0.0532 mol). Reaction mass was refluxed at 100° C. for 12 h. The reaction mixture was concentrated and directly purified by silica gel column chromatography to obtain title compound. MS (M+1): 261.88.

Step F. 7-bromo-8-fluoro-1-methyl-4,5-dihydro-[1,2,4]triazolo[4,3-a]quinoline

To a stirred solution of 6-bromo-7-fluoro-3,4-dihydroquinoline-2(1H)-thione (122-4; 7.0 g, 0.026 mol) in n-butanol (30 mL) was added acetic hydrazide (4.81 g, 0.065 mol). Reaction mass was warmed at 120° C. for 16 h. The reaction mixture was concentrated and directly purified by silica gel column chromatography to obtain title compound. $^1$H NMR (400 MHz, DMSO-d$_6$) δ 7.88-7.86 (d, J=7.6 Hz, 1H), 7.70-7.67 (d, J=10 Hz, 1H), 3.0-2.94 (m, 4H), 2.67 (s, 3H). MS (M+1): 284.2.

Step G. 8-fluoro-1-methyl-7-(4,4,5,5-tetramethyl-1,3,2-dioxaborolan-2-yl)-4,5-dihydro-[1,2,4]triazolo[4,3-a]quinoline To a stirred solution of 7-bromo-8-fluoro-1-methyl-4,5-dihydro-[1,2,4]triazolo[4,3-a]quinoline (122-5; 5.0 g, 0.0177 mol) and 4,4,4',4',5,5,5',5'-octamethyl-2,2'-bi(1,3,2-dioxaborolane) (18.65 g, 0.070 mol) in 1,4-dioxan (50 mL) was added potassium acetate (4.33 g, 0.044 mol). Reaction mass was purged with argon for 20 min. Then catalyst Pd(dppf)$_2$Cl$_2$ (0.29 g, 0.00003 mol) was added and allowed to stir at 100° C. for 12 h. The reaction mixture was filtered through CELITE bed and filter bed was thoroughly washed with ethyl acetate. The collected organic part was concentrated under vacuum to afford the crude compound, which was then purified by neutral alumina column chromatography using neutral alumina to obtain title compound. Crude LCMS; MS (M+1): 330.0.

Step H. 8-fluoro-7-(4-methoxy-5-methylpyridin-3-yl)-1-methyl-4,5-dihydro-[1,2,4]triazolo[4,3-a]quinoline To a stirred solution of 8-fluoro-1-methyl-7-(4,4,5,5-tetramethyl-1,3,2-dioxaborolan-2-yl)-4,5-dihydro-[1,2,4]triazolo[4,3-a]quinoline (122-6; 0.247 g, 0.00375 mol) and 3-Bromo-4-methoxy-5-methyl-pyridine (0.909 g, 0.0045 mol) in the mixture of 1,4-dioxan (10 mL) and water (10 mL) was added Potassium acetate (1.109 g, 0.0112 mol). Reaction mass was purged with argon for 20 min. Then catalyst Pd(dppf)$_2$Cl$_2$ (0.153 g, 0.000187 mol) was added and allowed to stir at 80° C. for 12 h. The reaction mixture was filtered through CELITE bed and filter bed was thoroughly washed with ethyl acetate. The collected organic parts were concentrated under vacuum to afford the crude compound, which was purified by silica gel column chromatography to obtain title compound. $^1$H NMR (400 MHz, DMSO-d$_6$) δ 8.42 (s, 1H), 8.27 (s, 1H), 7.65-7.62 (d, J=12 Hz, 1H), 7.57-7.55 (d, J=8 Hz, 1H), 3.54 (s, 3H), 3.03-2.97 (m, 4H), 2.71 (s, 3H), 2.28 (s, 3H). LCMS (M+1): 325.1.

The compounds described in Table 9 were prepared using the chemistry described in Example 122.

TABLE 9

| Example | Structure | IUPAC Name | LCMS |
|---|---|---|---|
| 123 | 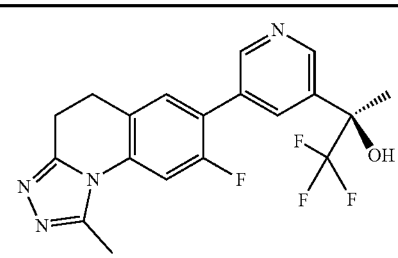 | (R)-1,1,1-trifluoro-2-(5-(8-fluoro-1-methyl-4,5-dihydro-[1,2,4]triazolo[4,3-a]quinolin-7-yl)pyridin-3-yl)propan-2-ol | 393.3 |
| 124 | 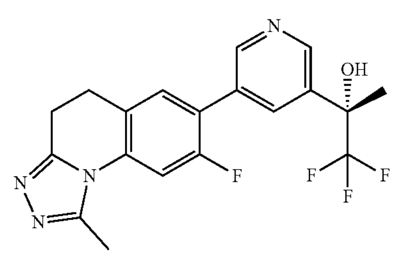 [SMILES: Cc1nnc2n1-c1cc(F)c(-c3cncc([C@](C)(O)C(F)(F)F)c3)cc1CC2] | (S)-1,1,1-trifluoro-2-(5-(8-fluoro-1-methyl-4,5-dihydro-[1,2,4]triazolo[4,3-a]quinolin-7-yl)pyridin-3-yl)propan-2-ol | 393.3 |
| 125 | 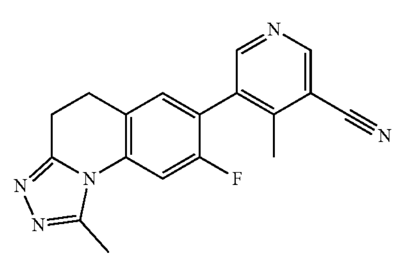 [SMILES: Cc1c(C#N)cncc1-c1cc2c(cc1F)-n1c(C)nnc1CC2] | 5-(8-fluoro-1-methyl-4,5-dihydro-[1,2,4]triazolo[4,3-a]quinolin-7-yl)-4-methylnicotinonitrile | 320.3 |

TABLE 9-continued

| Example | Structure | IUPAC Name | LCMS |
|---|---|---|---|
| 126 | 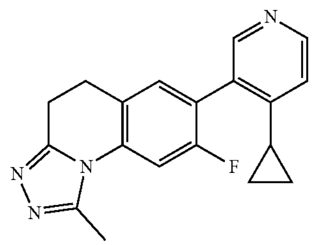 [SMILES: Cc1nnc2n1-c1cc(F)c(-c3cnccc3C3CC3)cc1CC2] | 7-(4-cyclopropylpyridin-3-yl)-8-fluoro-1-methyl-4,5-dihydro-[1,2,4]triazolo[4,3-a]quinoline | 321.3 |
| 127 | 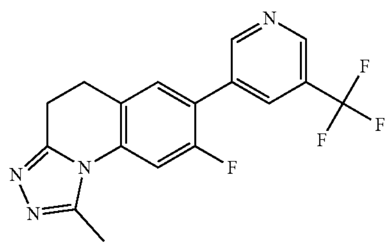 [SMILES: Cc1nnc2n1-c1cc(F)c(-c3cncc(C(F)(F)F)c3)cc1CC2] | 8-fluoro-1-methyl-7-(5-(trifluoromethyl)pyridin-3-yl)-4,5-dihydro-[1,2,4]triazolo[4,3-a]quinoline | 349.2 |
| 128 | 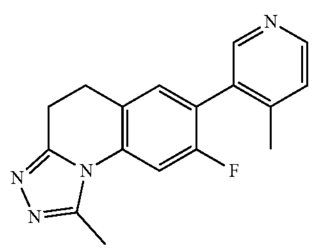 [SMILES: Cc1ccncc1-c1cc2c(cc1F)-n1c(C)nnc1CC2] | 8-fluoro-1-methyl-7-(4-methylpyridin-3-yl)-4,5-dihydro-[1,2,4]triazolo[4,3-a]quinoline | 296.3 |
| 129 | 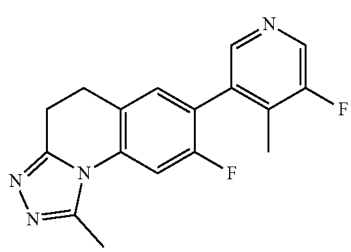 [SMILES: Cc1c(F)cncc1-c1cc2c(cc1F)-n1c(C)nnc1CC2] | 8-fluoro-7-(5-fluoro-4-methylpyridin-3-yl)-1-methyl-4,5-dihydro-[1,2,4]triazolo[4,3-a]quinoline | 314.3 |
| 130 | 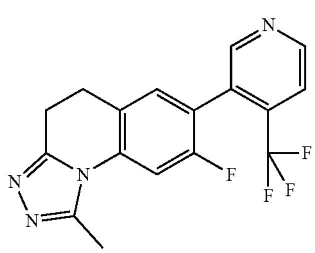 [SMILES: Cc1nnc2n1-c1cc(F)c(-c3cnccc3C(F)(F)F)cc1CC2] | 8-fluoro-1-methyl-7-(4-(trifluoromethyl)pyridin-3-yl)-4,5-dihydro-[1,2,4]triazolo[4,3-a]quinoline | 349.2 |
| 131 | 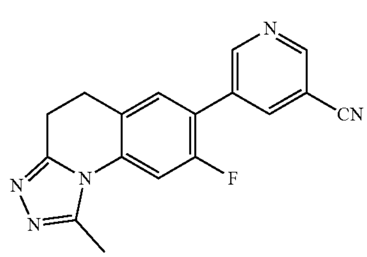 [SMILES: Cc1nnc2n1-c1cc(F)c(-c3cncc(C#N)c3)cc1CC2] | 5-(8-fluoro-1-methyl-4,5-dihydro-[1,2,4]triazolo[4,3-a]quinolin-7-yl)nicotinonitrile | 306.3 |

TABLE 9-continued

| Example | Structure | IUPAC Name | LCMS |
|---|---|---|---|
| 132 | 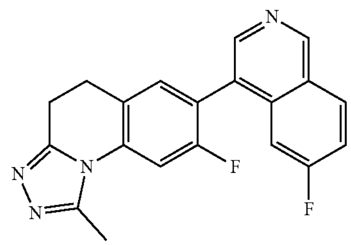 [SMILES: Cc1nnc2n1-c1cc(F)c(-c3cncc4ccc(F)cc34)cc1CC2] | 8-fluoro-7-(6-fluoro-isoquinolin-4-yl)-1-methyl-4,5-dihydro-[1,2,4]triazolo[4,3-a]quinoline | 349.3 |
| 133 | 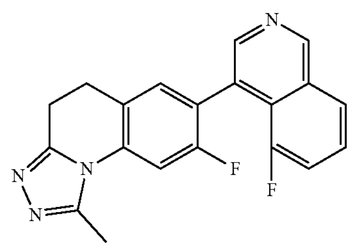 [SMILES: Cc1nnc2n1-c1cc(F)c(-c3cncc4cccc(F)c34)cc1CC2] | 8-fluoro-7-(5-fluoro-isoquinolin-4-yl)-1-methyl-4,5-dihydro-[1,2,4]triazolo[4,3-a]quinoline | 349.3 |
| 134 | 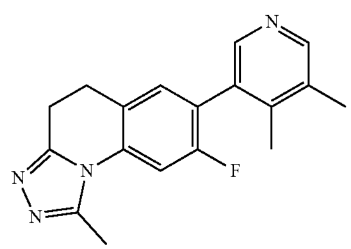 [SMILES: Cc1cncc(-c2cc3c(cc2F)-n2c(C)nnc2CC3)c1C] | 7-(4,5-dimethylpyridin-3-yl)-8-fluoro-1-methyl-4,5-dihydro-[1,2,4]triazolo[4,3-a]quinoline | 309.3 |
| 135 | 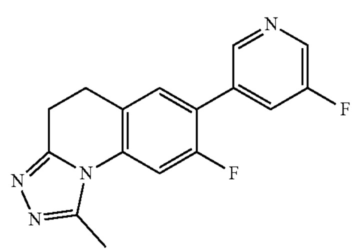 [SMILES: Cc1nnc2n1-c1cc(F)c(-c3cncc(F)c3)cc1CC2] | 8-fluoro-7-(5-fluoro-pyridin-3-yl)-1-methyl-4,5-dihydro-[1,2,4]triazolo[4,3-a]quinoline | 299.2 |
| 136 | 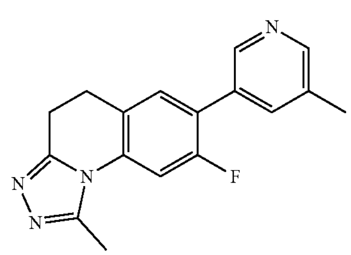 [SMILES: Cc1cncc(-c2cc3c(cc2F)-n2c(C)nnc2CC3)c1] | 8-fluoro-1-methyl-7-(5-methylpyridin-4-yl)-4,5-dihydro-[1,2,4]triazolo[4,3-a]quinoline | 295.3 |
| 137 | 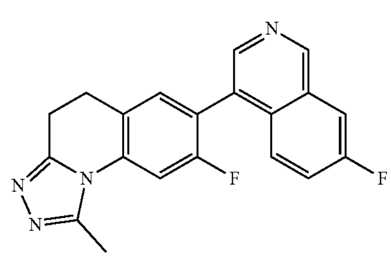 [SMILES: Cc1nnc2n1-c1cc(F)c(-c3cncc4cc(F)ccc34)cc1CC2] | 8-fluoro-7-(7-fluoro-isoquinolin-4-yl)-1-methyl-4,5-dihydro-[1,2,4]triazolo[4,3-a]quinoline | 349.3 |

TABLE 9-continued

| Example | Structure | IUPAC Name | LCMS |
|---|---|---|---|
| 138 | 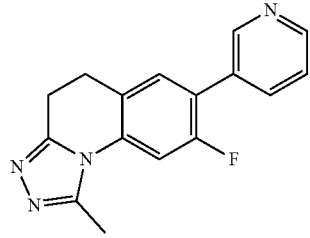 [SMILES: Cc1nnc2n1-c1cc(F)c(-c3cccnc3)cc1CC2] | 8-fluoro-1-methyl-7-(pyridin-3-yl)-4,5-dihydro-[1,2,4]triazolo[4,3-a]quinoline | 281.2 |
| 139 | 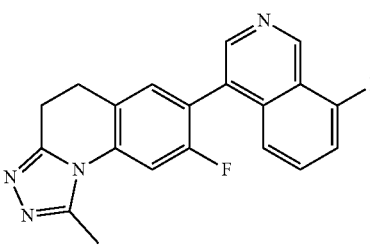 | 8-fluoro-7-(8-fluoroisoquinolin-4-yl)-1-methyl-4,5-dihydro-[1,2,4]triazolo[4,3-a]quinoline | 349.3 |
| 140 | 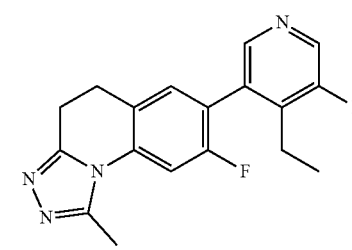 | 7-(4-ethyl-5-fluoropyridin-3-yl)-8-fluoro-1-methyl-4,5-dihydro-[1,2,4]triazolo[4,3-a]quinoline | 327.3 |
| 141 | 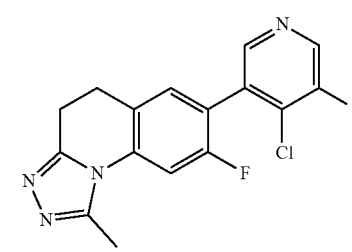 | 7-(4-chloro-5-fluoropyridin-3-yl)-8-fluoro-1-methyl-4,5-dihydro-[1,2,4]triazolo[4,3-a]quinoline | 333.7 |
| 142 | 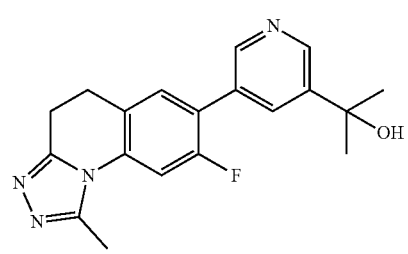 [SMILES: Cc1nnc2n1-c1cc(F)c(-c3cncc(C(C)(C)O)c3)cc1CC2] | 2-(5-(8-fluoro-1-methyl-4,5-dihydro-[1,2,4]triazolo[4,3-a]quinolin-7-yl)pyridin-3-yl)propan-2-ol | 339.3 |

Example 143

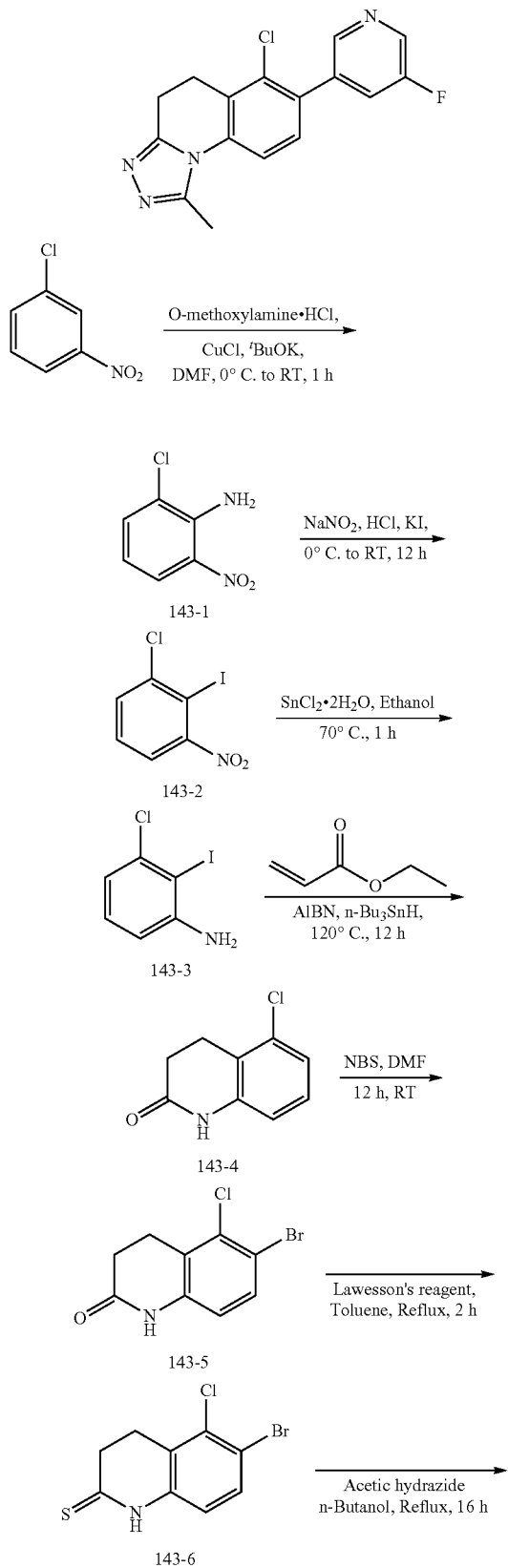

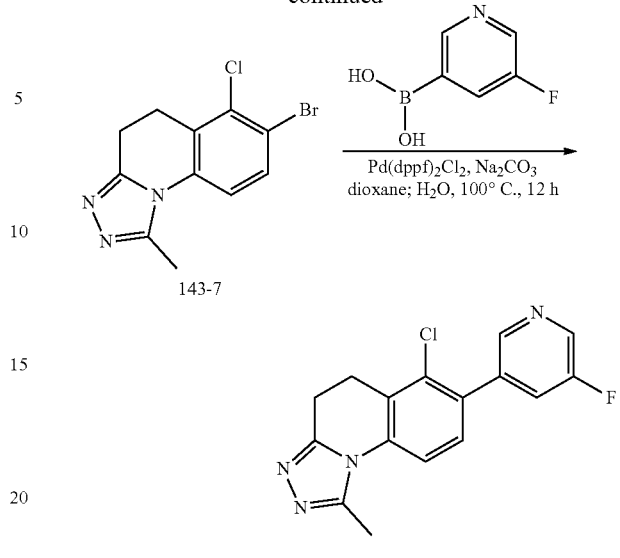

Step A. 2-chloro-6-nitroaniline 1-chloro-3-nitrobenzene (3.1 g, 0.0197 mol) and o-methoxylamine hydrochloride (2.02 g, 0.0236 mol) were dissolved in N,N-dimethylformamide (15 mL). The solution was added drop wise in 15 min to a suspension of cuprous chloride and potassium tert-butoxide (11.07 g, 0.965 mol) in N,N-dimethylformamide (15 mL) cooled in a 15° C. bath. The cold bath was removed; the mixture was allowed to come to RT and stirred for 1 h. The reaction was quenched with aqueous ammonium chloride solution and extracted with ethyl acetate (4×100 mL). The combined organic layer was washed with saturated aqueous sodium chloride solution, dried over sodium sulphate, concentrated under vacuum and purified by silica gel column chromatography to obtain the title compound. $^1$H NMR (400 MHz, CDCl$_3$) δ 8.020-7.994 (dd, J=8.8 Hz, 10.4 Hz, 1H), 7.696-7.674 (dd, J=7.2 Hz, 8.8 Hz, 1H), 7.229 (bs, 1H), 6.705-6.664 (t, J=8.4 Hz, 1H).

Step B. 1-chloro-2-iodo-3-nitrobenzene 2-chloro-6-nitroaniline (143-1; 1.0 g, 0.0058 mol) was dissolved in hydrochloric acid (10 mL) and cooled in an ice bath. Then a solution of sodium nitrite (0.68 g, 0.0098 mol) in water (10 mL) was added very slowly with stirring. After 15 min the reaction mixture was filtered through glass wool in to a solution of potassium iodide (4.1 g, 0.024 mol) in water (10 mL). The resulting orange mixture was stirred at room temperature overnight. Then it was extracted with ethyl acetate and washed with 10% aqueous sodium hydroxide solution (50 mL) solution. Organic layer was washed with saturated aqueous sodium chloride solution and concentrated under vacuum to obtain the title compound. $^1$H NMR (400 MHz, CDCl$_3$) δ 7.854-7.835 (d, J=7.6 Hz, 1H), 7.788-7.768 (d, J=8 Hz, 1H), 7.624-7.584 (t, J=7.6 Hz, 1H).

Step C. 3-chloro-2-iodoaniline

To a stirred solution of 1-chloro-2-iodo-3-nitrobenzene (143-2; 1.4 g, 0.00490 mol) in ethanol (20 mL) was added stannous chloride dihydrate (5.5 g, 0.0245 mol) portion wise at 0° C. Reaction mixture was allowed to stir at 70° C. for 30 min. The reaction mixture was concentrated and diluted with ice cold water (150 mL) and P$^H$ was made slightly basic by addition of saturated aqueous sodium carbonate solution before being extracted with ethyl acetate (4×100 mL). The combined organic layer was washed with saturated aqueous sodium chloride solution, dried over sodium sulphate and concentrated under vacuum to obtain the title compound. $^1$H NMR (400 MHz, CDCl$_3$) δ 7.048-7.008 (t, 8 Hz, 1H), 6.713-6.693 (dd, J=8, 8.8 Hz, 1H), 6.655-6.632 (dd, J=8.4, 9.2 Hz, 1H), 5.5 (bs, 2H).

Step D. 5-chloro-3,4-dihydroquinolin-2(1H)-one

To a stirred solution of 3-chloro-2-iodoaniline (143-3; 1.1 g, 0.0043 mol), AIBN (0.282 g, 0.0017 mol), tributyl tinhydride (1.8 g, 0.0064 mol) in dimethyl sulphoxide (10 mL) was added ethylacrylate (1.7 g, 0.173 mol) portion wise at 0° C. Reaction mixture was allowed to stir at 120° C. for 12 h. The reaction mixture was diluted with ice cold water (150 mL) and extracted with ethyl acetate (4×100 mL). The combined organic layer was washed with saturated aqueous sodium chloride solution, dried over sodium sulphate and concentrated under vacuum to obtain the title compound. $^1$H NMR (400 MHz, CDCl$_3$) δ 7.159-7.119 (t, J=7.6 Hz, 1H), 7.021-7.002 (d, J=7.6 Hz, 1H), 6.819-6.800 (d, J=7.6 Hz, 1H), 2.941-2.651 (t, J=8 Hz, 4H). MS (M+1): 181.8.

Step E.
6-bromo-5-chloro-3,4-dihydroquinolin-2(1H)-one

To a stirred solution of 5-chloro-3,4-dihydroquinolin-2(1H)-one (143-4; 0.4 g, 0.022 mol) in N,N-dimethylformamide (10 mL) was added N-bromosuccinimide (0.47 g, 0.0026 mol) portion wise at 0° C. Reaction mixture was allowed to stir at room temperature for 12 h. The reaction mixture was concentrated and diluted with ice cold water (100 mL) with constant stirring and the solid residue was filtered and dried to obtain the title compound. MS (M+1): 259.9.

Step F.
6-bromo-5-chloro-3,4-dihydroquinoline-2(1H)-thione

To a stirred solution of 6-bromo-5-chloro-3,4-dihydroquinolin-2(1H)-one (143-5; 1.2 g, 0.0046 mol) in toluene (20 mL) was added Lawesson's reagent (1.8 g, 0.0046 mol). Reaction mass was refluxed at 100° C. for 12 h. The reaction mixture was concentrated and directly purified by silica gel column chromatography to obtain title compound 6-bromo-5-chloro-3,4-dihydroquinoline-2(1H)-thione. MS (M+1): 277.8.

Step G. 7-bromo-6-chloro-1-methyl-4,5-dihydro-[1,2,4]triazolo[4,3-a]quinoline

To a stirred solution of 6-bromo-5-chloro-3,4-dihydroquinoline-2(1H)-thione (143-6; 0.3 g, 0.0012 mol) in n-butanol (10 mL) was added acetic hydrazide (0.2 g, 0.00213 mol). Reaction mass was heated at 120° C. for 16 h. The reaction mixture was concentrated and directly purified by silica gel column chromatography to obtain title compound. MS (M+1): 298.0.

Step H. 6-chloro-7-(5-fluoropyridin-3-yl)-1-methyl-4,5-dihydro-[1,2,4]triazolo[4,3-a]quinoline To a stirred solution of 7-bromo-6-chloro-1-methyl-4,5-dihydro-[1,2,4]triazolo[4,3-a]quinoline (143-7; 0.20 g, 0.0006 mol) and (5-fluoropyridin-3-yl)boronic acid (0.93 g, 0.0006 mol) in the mixture of 1,4-dioxan (10 mL) and water (10 mL) was added sodium carbonate (0.127 g, 0.0012 mol). Reaction mass was purged with argon for 20 min. Then catalyst Pd(dppf)$_2$Cl$_2$ (0.048 g, 0.00006 mol) was added and allowed to stir at 80° C. for 12 h. The reaction mixture was filtered through CELITE bed and filter bed was thoroughly washed with ethyl acetate. The collected organic part was concentrated under vacuum to afford the crude compound, which was purified by silica gel column chromatography to obtain title compound. $^1$H NMR (400 MHz, DMSO-d$_6$) δ 8.659-8.652 (d, J=2.8 Hz, 1H), 8.514 (s, 1H), 7.908-7.884 (d, J=9.6 Hz, 1H), 7.789-7.768 (d, J=8.4 Hz, 1H), 7.566-7.504 (d, J 8.4 Hz, 1H), 3.186-3.152 (m, 2H), 3.084-3.035 (m, 2H), 2.695 (s, 3H). MS (M+1): 315.1.

The compound in Table 10 was prepared using the chemistry described in Example 143.

TABLE 10

| Example | Structure | IUPAC Name | LCMS |
|---|---|---|---|
| 144 | 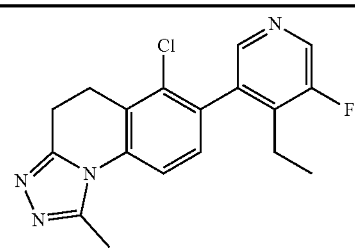 | 6-chloro-7-(4-ethyl-5-fluoropyridin-3-yl)-1-methyl-4,5-dihydro-[1,2,4]triazolo[4,3-a]quinoline | 343.7 |

Example 145

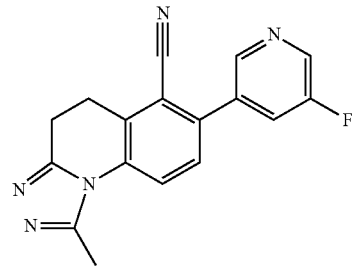

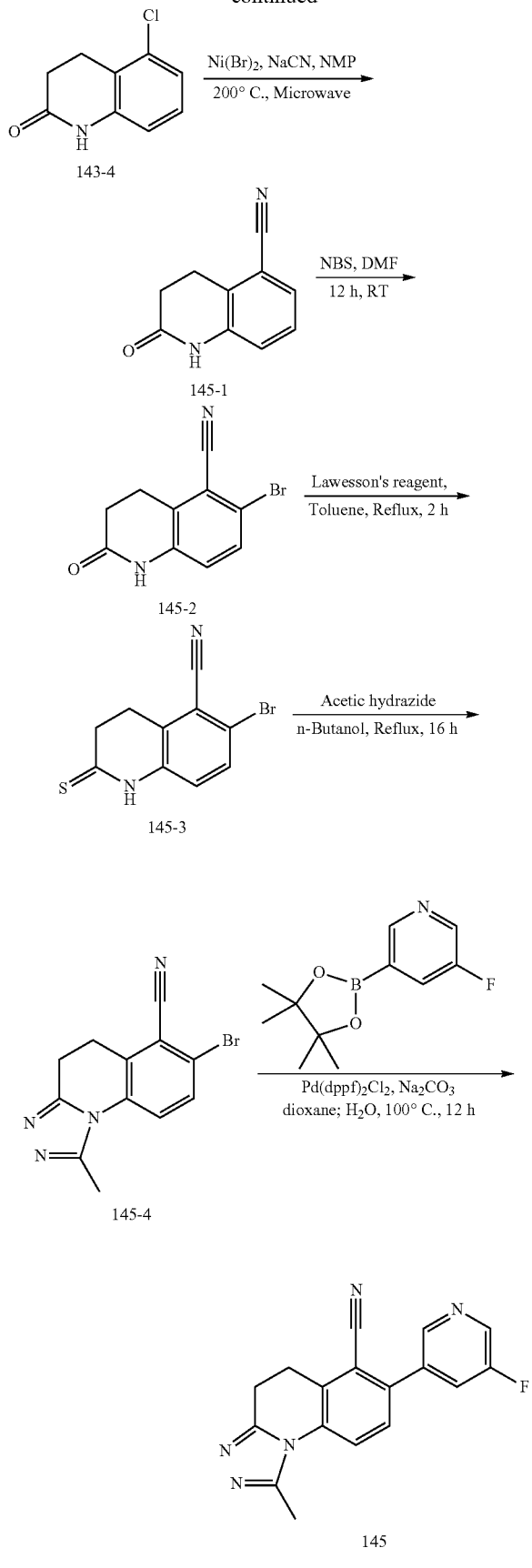

Step A.
2-oxo-1,2,3,4-tetrahydroquinoline-5-carbonitrile

To a stirred solution of 5-chloro-3,4-dihydroquinolin-2 (1H)-one (143-4; 1.8 g, 0.0099 mol) and nickel bromide (2.15 g, 0.0099 mol) in N-methyl-2-pyrrolidone (10 mL) was added sodium cyanide (0.97 g, 0.0198 mol) portion wise at room temperature. Reaction mixture was heated at 200° C. for 10 min under microwave irradiation. The reaction mixture was diluted with water (50 mL) and extracted with ethyl acetate (2×100 mL). The combined organic layer was washed with saturated aqueous sodium chloride solution, dried over sodium sulphate and concentrated under vacuum to obtain the title compound. MS (M−1): 171.2.

Step B. 6-bromo-2-oxo-1,2,3,4-tetrahydroquinoline-5-carbonitrile

To a stirred solution of 2-oxo-1,2,3,4-tetrahydroquinoline-5-carbonitrile (145-1; 1.5 g, 0.0087 mol) in N,N-dimethylformamide (10 mL) was added N-bromosuccinimide (1.8 g, 0.01046 mol) portion wise at 0° C. Reaction mixture was allowed to stir at room temperature for 12 h. It was concentrated and diluted with ice cold water (100 mL) with constant stirring; the solid residue obtained was filtered and dried to obtain the title compound. MS (M+1): 251.2.

Step C. 6-bromo-2-thioxo-1,2,3,4-tetrahydroquinoline-5-carbonitrile

To a stirred solution of 6-bromo-2-oxo-1,2,3,4-tetrahydroquinoline-5-carbonitrile (145-2; 1.3 g, 0.0052 mol) in toluene (20 mL) was added Lawesson's reagent (2.1 g, 0.0052 mol). Reaction mass was refluxed at 100° C. for 12 h. The reaction mixture was concentrated and directly purified by silica gel column chromatography to obtain title compound. $^1$H NMR (400 MHz, CDCl$_3$) δ $^1$H NMR (400 MHz, DMSO-d$_6$) δ 7.612-7.561 (m, 1H), 6.980-6.959 (t, J=8.4 Hz, 1H), 3.779-3.769 (d, J=4 Hz, 4H).

Step D. 7-bromo-1-methyl-4,5-dihydro-[1,2,4]triazolo[4,3-a]quinoline-6-carbonitrile To a stirred solution of 6-bromo-2-thioxo-1,2,3,4-tetrahydroquinoline-5-carbonitrile (145-3; 0.5 g, 0.00188 mol) in n-butanol (10 mL) was added acetic hydrazide (0.35 g, 0.0047 mol). Reaction mass was heated at 120° C. for 16 h. The reaction mixture was concentrated and directly purified by silica gel column chromatography to obtain title compound. (MS (M+1): 289.

Step F. 7-(5-fluoropyridin-3-yl)-1-methyl-4,5-dihydro-[1,2,4]triazolo[4,3-a]quinoline-6-carbonitrile To a stirred solution of 7-bromo-1-methyl-4,5-dihydro-[1,2,4]triazolo[4,3-a]quinoline-6-carbonitrile (145-4; 0.20 g, 0.0006 mol) and (5-fluoropyridin-3-yl)boronic acid (0.97 g, 0.0006 mol) in the mixture of 1,4-dioxan (10 mL) and water (10 mL) was added sodium carbonate (0.190 g, 0.0018). Reaction mass was purged with argon for 20 min. Then catalyst Pd(dppf)$_2$Cl$_2$ (0.048 g, 0.00006 mol) was added and allowed to stir at 80° C. for 12 h. The reaction mixture was filtered through celite bed and filter bed was thoroughly washed with ethyl acetate. The collected organic part was concentrated under vacuum to afford the crude compound, which was purified by silica gel column chromatography to obtain title compound. $^1$H NMR (400 MHz, DMSO-d$_6$) δ

8.739-8.732 (d, J=2.8 Hz, 1H), 8.685 (s, 1H), 8.095-8.066 (d, J=11.6 Hz, 2H), 7.782-7.742 (d, J 8 Hz, 1H), 3.282-3.240 (t, J=8.8 Hz, 2H), 3.143-3.109 (t, J=7.6 Hz, 2H), 2.702 (s, 3H). MS (M+1): 306.1

Example 146

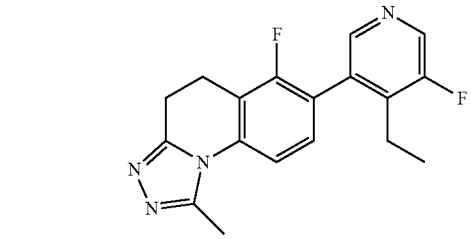 [SMILES: CCc1c(F)cncc1-c1ccc2c(c1Cl)CCc1nnc(C)n1-2]

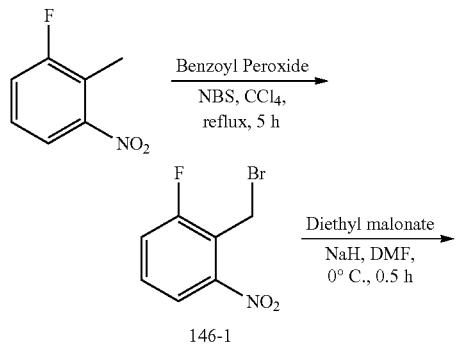

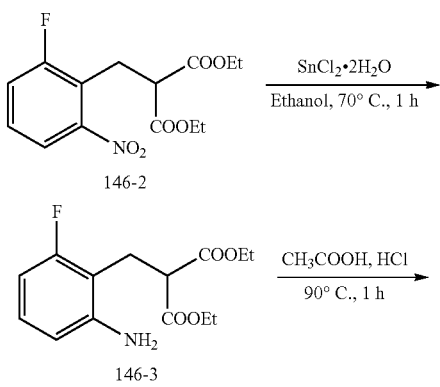

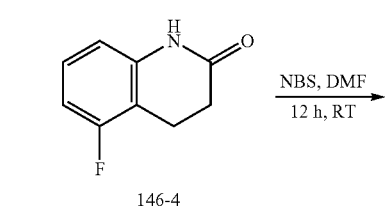

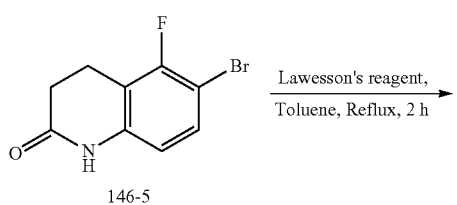

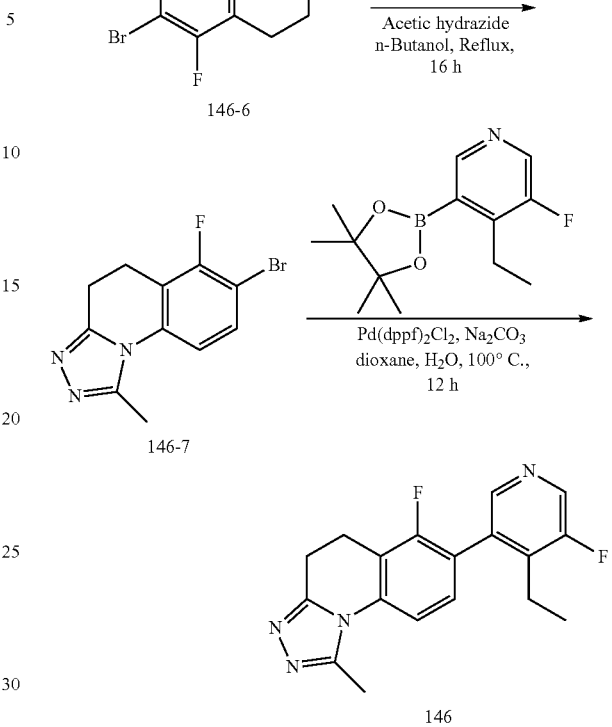

Step A. 2-(bromomethyl)-1-fluoro-3-nitrobenzene

To a stirred solution of 1-fluoro-2-methyl-3-nitrobenzene (1.0 g, 0.00645 mol) in carbon tetrachloride (50 mL) were added N-bromosuccinimide (1.25 g, 0.00709 mol) and benzoylperoxide (0.3 g, 0.00129 mol) at room temperature with constant stirring. Reaction mass was refluxed for 5 h. The reaction mixture was cooled to room temperature and filtered through CELITE bed and the bed was washed thoroughly with carbon tetrachloride. The filtrate was concentrated under vacuum to obtain the title compound. $^1$H NMR (400 MHz, DMSO) δ 7.93-7.91 (d, J=8 Hz, 1H), 7.723-7.653 (m, 2H), 4.77 (s, 2H).

Step B. diethyl 2-(2-fluoro-6-nitrobenzyl)malonate

Sodium hydride (0.3 g, 0.0127 mol) was suspended in N,N-dimethylformamide at 0° C. and diethylmalonate (1.96 g, 0.0117 mol) was added slowly portion wise. The resulting suspension was stirred at 0° C. for 10 min. A solution of 2-(bromomethyl)-1-fluoro-3-nitrobenzene (146-1; 2.3 g, 0.00982 mol) in N,N-dimethylformamide (20 mL) was added drop wise. The reaction mixture was stirred for 45 min at 0° C., then diluted with saturated ammonium chloride solution and extracted with ethyl acetate (4×50 mL). The combined organic layer was washed with saturated aqueous sodium chloride solution, dried over sodium sulphate and concentrated under vacuum to afford the crude compound which was purified by silica gel column chromatography to obtain the title compound. NMR (400 MHz, DMSO) δ 7.85-7.83 (d, J=8 Hz, 1H), 7.65-7.54 (m, 2H), 4.09-4.03 (m, 4H), 3.71-3.67 (t, J 7.6 Hz, 1H), 3.38-3.36 (d, J=7.6 Hz, 2H), 1.123-1.074 (m, 6H). MS (M+1): 314.1.

Step C. diethyl 2-(2-amino-6-fluorobenzyl)malonate

To a stirred solution of diethyl 2-(2-fluoro-6-nitrobenzyl) malonate (146-2; 2.5 g, 0.0079 mol) in ethanol (30 mL) was added $SnCl_2.2H_2O$ (8.9 g, 0.0395 mol) with constant stirring. The reaction mixture was heated at 70° C. for 0.5 h to 1 h. The reaction mixture was cooled to room temperature and then filtered through CELITE bed. The filtrate was basified with saturated $Na_2HCO_3$ solution and extracted with ethyl acetate (3×50 mL). The combined organic layer was washed with saturated aqueous sodium chloride solution, dried over sodium sulphate and concentrated under vacuum to afford the title compound. MS (M+1): 284.1.

Step D. 5-fluoro-3,4-dihydroquinolin-2(1H)-one

To a stirred solution of diethyl 2-(2-amino-6-fluorobenzyl) malonate (146-3; 2.0 g, 0.00706 mol)) in acetic acid (20 mL) was added hydrochloric acid (20 mL). The reaction mixture was heated at 90° C. for 1 h. The reaction mixture was cooled to room temperature and then poured into ice cold water. It was extracted with ethyl acetate (3×40 mL). The combined organic layer was washed with 10% aqueous sodium hydroxide solution, saturated aqueous sodium chloride solution, dried over sodium sulphate and concentrated under vacuum to afford the title compound. $^1$H NMR (400 MHz, DMSO) δ 10.219 (s, 1H), 7.164-7.108 (q, J=7.6 Hz, 1H), 6.769-6.725 (t, J=8.4 Hz, 1H), 6.684-6.664 (d, J=8.0 Hz, 1H), 2.871-2.832 (t, J=7.6 Hz, 2H), 2.472-2.434 (t, J=8.0 Hz, 2H). MS (M+1): 166.1.

Step F. 6-bromo-5-fluoro-3,4-dihydroquinolin-2(1H)-one

To a stirred solution of 5-fluoro-3,4-dihydroquinolin-2 (1H)-one (146-4; 0.45 g, 0.00272 mol) in N,N-dimethylformamide (10 mL) was added N-bromosuccinamide (0.53 g, 0.0029 mol). Reaction mass was allowed to stir for overnight. Ice cold water was added to reaction mass. The solid separated was filtered and dried thoroughly to obtain the title compound. MS (M+1): 246.0.

Step G. 6-bromo-5-fluoro-3,4-dihydroquinoline-2(1H)-thione

To a stirred solution of 6-bromo-5-fluoro-3,4-dihydroquinolin-2(1H)-one (146-5; 0.45 g, 0.00184 mol) in toluene (10 mL) was added Lawesson's reagent (0.745 g, 1.00184 mol). Reaction mass heated at 120° C. and maintained for 2 h. The reaction mixture was cooled, quenched with sodium bicarbonate solution and extracted with ethyl acetate (3×30 mL). The combined organic layer was washed with saturated aqueous sodium chloride solution, dried over sodium sulphate and concentrated under vacuum to afford the title compound. $^1$H NMR (400 MHz, DMSO) δ 12.364 (s, 1H), 7.543-7.503 (t, J=8.0 Hz, 1H), 6.895-6.874 (d, J=0.1-8.4 Hz, 1H) 2.968-2.930 (t, J=7.2 Hz, 2H), 2.843-2.805 J 8.0 Hz, 2H): MS (M 1): 260.1.

Step H. 7-bromo-6-fluoro-1-methyl-4,5-dihydro-[1, 2,4]triazolo[4,3-a]quinoline To a stirred solution 6-bromo-5-fluoro-3,4-dihydroquinoline-2(1H)-thione (146-6; 0.25 g, 0.00096 mol) in n-butanol (10 mL) was added acetic hydrazide (0.177 g, 0.0024 mol). Reaction mass was heated at 120° C. and maintained for overnight. The reaction mixture was cooled, diluted with water (50 mL) and extracted with ethyl acetate (3×30 mL). The combined organic layer was washed with saturated aqueous sodium chloride solution, dried over sodium sulphate and concentrated under vacuum to afford the title compound. $^1$H NMR (400 MHz, DMSO) δ 7.755-7.714 (t, J=8.4 Hz, 1H), 7.487-7.462 (dd, J=1.2 Hz, 1H), 3.034-3.008 (d, J=10.4 Hz, 4H), 2.640 (s, 3H) MS (M+1): 284.0.

Step G. 7-(4-ethyl-5-fluoropyridin-3-yl)-6-fluoro-1-methyl-4,5-dihydro-[1,2,4]-triazolo[4,3-a]quinoline To a stirred solution of 7-bromo-6-fluoro-1-methyl-4,5-dihydro-[1,2,4]triazolo[4,3-a]quinoline (146-7; 0.2 g, 0.00704 mol) and 4-ethyl-3-fluoro-5-(4,4,5,5-tetramethyl-1,3,2-dioxaborolan-2-yl)pyridine (0.21 g, 0.0084 mol) in the mixture of 1,4-dioxan (5 mL) and water (5 mL) was added sodium carbonate (0.186 g, 0.0176 mol). Reaction mass was purged with argon for the next 20 min. Catalyst $Pd(dppf)_2Cl_2$.dichloromethane (0.28 g, 0.00352 mol) was added and again purged with argon for 10 min and allowed to stir at 100° C. for 12 h. The reaction mixture was filtered through CELITE bed and filter bed was thoroughly washed with ethyl acetate. The collected organic parts was concentrated under vacuum to afford the crude compound, which was purified by silica gel column chromatography followed by preparative HPLC (analytical conditions: column: ZORBAX XDB (150 mm×4.6 mm×3.5 µm), mobile phase (A): water, mobile phase (B): methanol, flow rate: 1.0 mL/min, gradient T/% B:0/20,8/70,25/70,27/20,30/20) to obtain title compound. $^1$H NMR (400 MHz, CDCl3-d$_6$) δ 8.451 (s, 1H), 8.238 (s, 1H), 7.427-7.406 (d, J=8.4 Hz, 1H), 7.297-7.278 (d, J=7.6 Hz, 1H), 3.219-3.184 (t, J=6.4 Hz, 2H), 3.132-3.097 (t, J=7.6 Hz, 2H), 2.812 (s, 3H), 2.604-2.586 (d, J=7.2 Hz, 2H), 1.130-1.093 (t, J=7.6 Hz, 3H). MS (M+1): 327.1.

Example 147

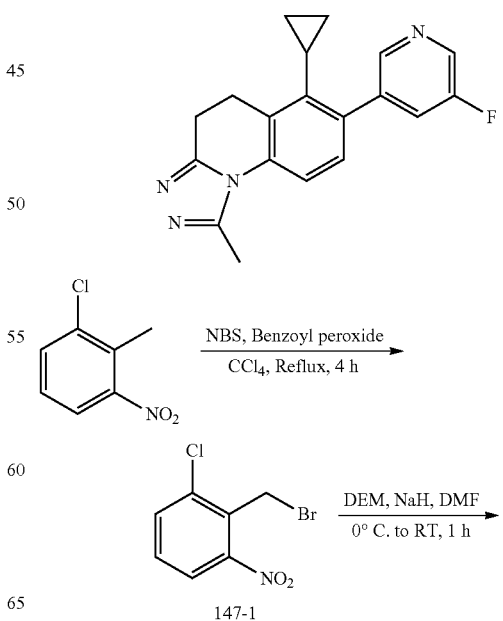

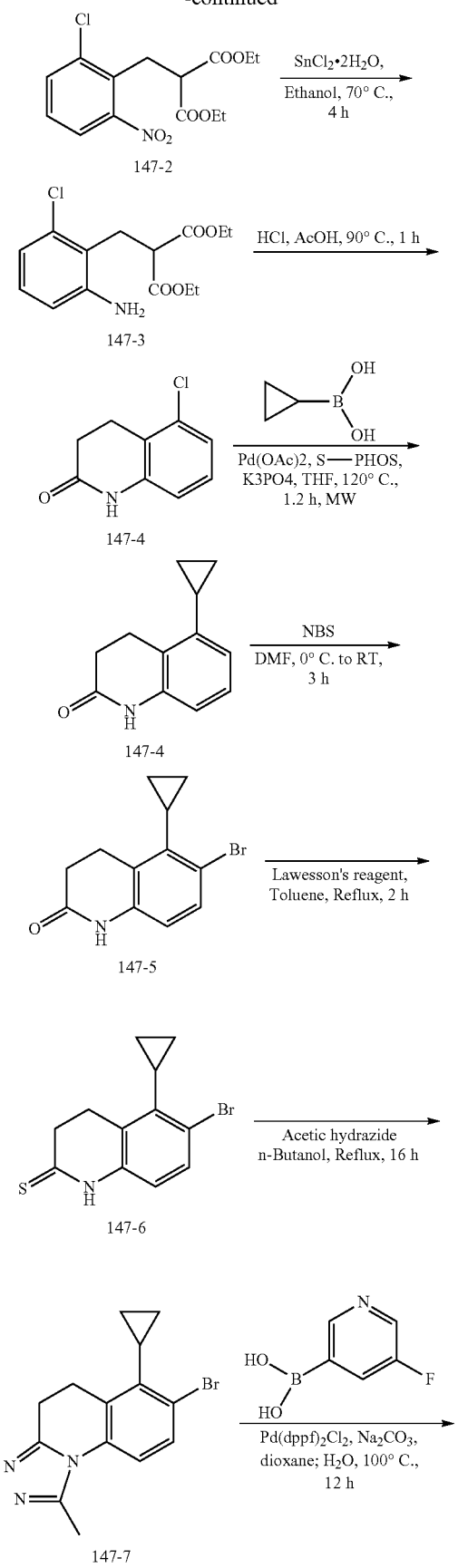

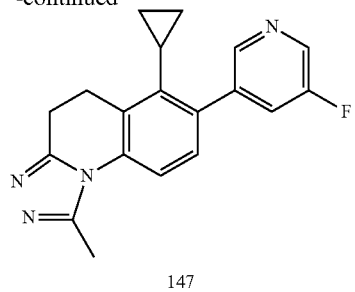

147

Step A. 2-(bromomethyl)-1-chloro-3-nitrobenzene

To a stirred solution of 1-chloro-2-methyl-3-nitrobenzene (10 g, 0.0584 mol) in $CCl_4$ (100 mL) was added N-bromosuccinimide (12.4 g, 0.0701 mol), benzoyl peroxide (2.8 g, 0.0116 mol) portion wise at 0° C. Reaction mixture was stirred at reflux for 4 h. The mixture was filtered, concentrated and dried to obtain the title compound. $^1$H NMR (400 MHz, $CDCl_3$) δ 8.042-7.986 (m, 1H), 7.925-7.905 (d, J=8 Hz, 1H), 7.658-7.617 (t, J=8.4 Hz, 1H), 4.784 (s, 2H).

Step B. diethyl 2-(2-chloro-6-nitrobenzyl)-malonate

Sodium hydride (1.8 g, 0.077 mol) was suspended in N,N-dimethylformamide (150 mL) at 0° C. Diethyl malonate (9.9 g, 0.0623 mol) was added in three portions and the resulting suspension was stirred at 0° C. for 10 min. A solution of 2-(bromomethyl)-1-chloro-3-nitrobenzene (147-1; 13 g, 0.0519 mol) in N,N-dimethylformamide (150 mL) was added drop wise. The reaction mixture was stirred for 45 min at 0° C., then diluted with saturated ammonium chloride and extracted with ethyl acetate (2×250 mL). The combined organics were dried over anhydrous sodium sulphate and concentrated to obtain the title compound. $^1$H NMR (400 MHz, $CDCl_3$) δ 7.762-7.741 (d, J=8.4 Hz, 1H), 7.635-7.616 (d, J=7.6 Hz, 1H), 7.365-7.324 (t, J=8.4 Hz, 1H), 4.195-4.142 (q, J=7.2 Hz, 4H), 3.817-3.779 (t, J=7.6 Hz, 1H), 3.675-3.656 (d, J=7.6 Hz, 2H), 1.236-1.201 (t, J=7.2 Hz, 6H).

Step C. diethyl 2-(2-amino-6-chlorobenzyl)malonate

To a stirred solution of diethyl 2-(2-chloro-6-nitrobenzyl)-malonate (147-2; 13.5 g, 0.0410 mol) in ethanol (200 mL) was added stannous chloride dihydrate (50 g, 0.225 mol) portion wise at 0° C. Reaction mixture was allowed to stir at 70° C. for 30 min. The reaction mixture was concentrated and diluted with ice cold water (1500 mL) and pH was made slightly basic by addition of saturated aqueous sodium carbonate solution before being extracted with ethyl acetate (2×1000 mL). The combined organic layer was washed with saturated aqueous sodium chloride solution, dried over sodium sulphate and concentrated under vacuum to obtain the title compound. MS (M+1): 300.1.

Step D. 5-chloro-3,4-dihydroquinolin-2(1H)-one

To a stirred solution of diethyl 2-(2-amino-6-chlorobenzyl)malonate (147-3; 8 g, 0.026 mol) in acetic acid (80 mL) was added hydrochloric acid (80 mL), and the mixture was stirred at 90° C. for 1 h. The reaction mixture was poured into water and extracted with ethyl acetate (2×250 mL). The combined organic layer was washed with saturated aqueous sodium chloride solution, dried over sodium sulphate and concentrated under vacuum to obtain the title compound. MS (M+1): 182.1.

Step E.
5-cyclopropyl-3,4-dihydroquinolin-2(1H)-one

To a stirred solution of 5-chloro-3,4-dihydroquinolin-2 (1H)-one (147-4; 1 g, 0.0055 mol) and cyclopropylboronic acid (0.95 g, 0.0110 mol) in tetrahydrofuran (30 mL) was added potassium phosphate (3.4 g, 0.0165 mol) and S-Phos (0.45 g, 0.0011 mol). Reaction mass was purged with argon for 20 min. Then catalyst palladium acetate (0.123 g, 0.00055 mol) was added and allowed to stir at 120° C. for 12 h. The reaction mixture was filtered through CELITE bed and filter bed was thoroughly washed with ethyl acetate. The collected organic part was concentrated under vacuum to afford the crude compound, which was purified by silica gel column chromatography to obtain title compound. MS (M+1): 188.1.

Step F. 6-bromo-5-cyclopropyl-3,4-dihydroquinolin-2(1H)-one

To a stirred solution of 5-cyclopropyl-3,4-dihydroquinolin-2(1H)-one (147-5; 0.5 g, 0.00267 mol) in N,N-dimethylformamide (10 mL) was added N-bromosuccinimide (0.47 g, 0.0026 mol) portion wise at 0° C. Reaction mixture was allowed to stir at room temperature for 4 h. The reaction mixture was concentrated and diluted with ice cold water (100 mL) with constant stirring, the solid residue obtained was filtered and dried to obtain the title compound. MS (M+1): 266.1.

Step C. 6-bromo-5-cyclopropyl-3,4-dihydroquinoline-2(1H)-thione

To a stirred solution of 6-bromo-5-cyclopropyl-3,4-dihydroquinolin-2(1H)-one (147-6; 0.8 g, 0.0030 mol) in toluene (10 mL) was added Lawesson's reagent (1.2 g, 0.003 mol). Reaction mass was refluxed at 100° C. for 12 h. The reaction mixture was concentrated and directly purified by silica gel column chromatography to obtain title compound. MS (M+1): 284.0.

Step H. 7-bromo-6-cyclopropyl-1-methyl-4,5-dihydro-[1,2,4]triazolo[4,3-a]quinoline To a stirred solution of 6-bromo-5-cyclopropyl-3,4-dihydroquinoline-2(1H)-thione (147-7; 0.6 g, 0.00212 mol) in n-butanol (10 mL) was added acetic hydrazide (0.3 g, 0.005 mol). Reaction mass was warmed at 120° C. for 16 h. The reaction mixture was concentrated and directly purified by silica gel column chromatography to obtain title compound. MS (M+1): 305.1.

Step I. 6-cyclopropyl-7-(5-fluoropyridin-3-yl)-1-methyl-4,5-dihydro-[1,2,4]triazolo[4,3-a]quinoline To a stirred solution of 7-bromo-6-cyclopropyl-1-methyl-4,5-dihydro-[1,2,4]triazolo[4,3-a]quinoline (147-8; 0.250 g, 0.00082 mol) and (5-fluoropyridin-3-yl)boronic acid (0.126 g, 0.009 mol) in the mixture of 1,4-dioxane (10 mL) and water (10 mL) was added sodium carbonate (0.260 g, 0.00246 mol). Reaction mass was purged with argon for 20 min. Then catalyst Pd(dppf)$_2$Cl$_2$ (0.066 g, 0.000082 mol) was added and allowed to stir at 80° C. for 12 h. The reaction mixture was filtered through CELITE bed and filter bed was thoroughly washed with ethyl acetate. The collected organic layer was concentrated under vacuum to afford the crude compound, which was purified by silica gel column chromatography to obtain title compound. $^1$H NMR (400 MHz, DMSO-d$_6$) δ 8.587-8.580 (d, J=2.8 Hz, 1H), 8.548 (s, 1H), 7.881-7.856 (d, J=10 Hz, 1H), 7.679-7.658 (d, J=8.4 Hz, 1H), 7.401-7.380 (d, J 8.4 Hz, 1H), 3.237-3.203 (t, J=6.8 Hz, 2H), 3.050-3.016 (t, J=7.2 Hz, 2H), 2.671 (s, 3H), 2.175 (s, 1H), 0.759-0739 (d, J 8 Hz, 2H), 0.034-0.022 (d, J=4.8 Hz, 2H), MS (M+1): 321.2.

The compounds in Table 11 were prepared using the chemistry described in Example 147

TABLE 11

| Example | Structure | IUPAC Name | LCMS |
|---|---|---|---|
| 148 | 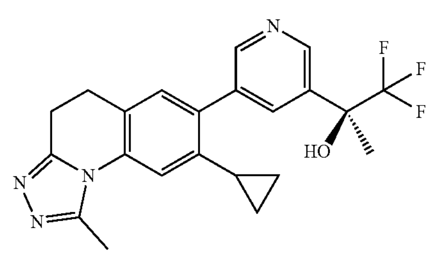 [SMILES: Cc1nnc2n1-c1cc(C3CC3)c(-c3cncc([C@](C)(O)C(F)(F)F)c3)cc1CC2] | S)-2-(5-(8-cyclopropyl-1-methyl-4,5-dihydro-[1,2,4]triazolo[4,3-a]quinolin-7-yl)pyridin-3-yl)-1,1,1-trifluoropropan-2-ol | 415.1 |
| 149 | 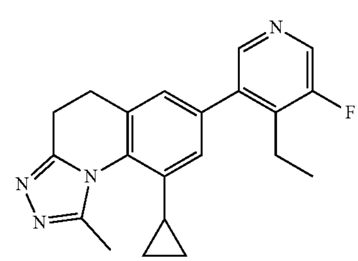 [SMILES: CCc1c(F)cncc1-c1cc2c(c(C3CC3)c1)-n1c(C)nnc1CC2] | 9-cyclopropyl-7-(4-ethyl-5-fluoropyridin-3-yl)-1-methyl-4,5-dihydro-[1,2,4]triazolo[4,3-a]quinoline | 349.2 |

Example 150

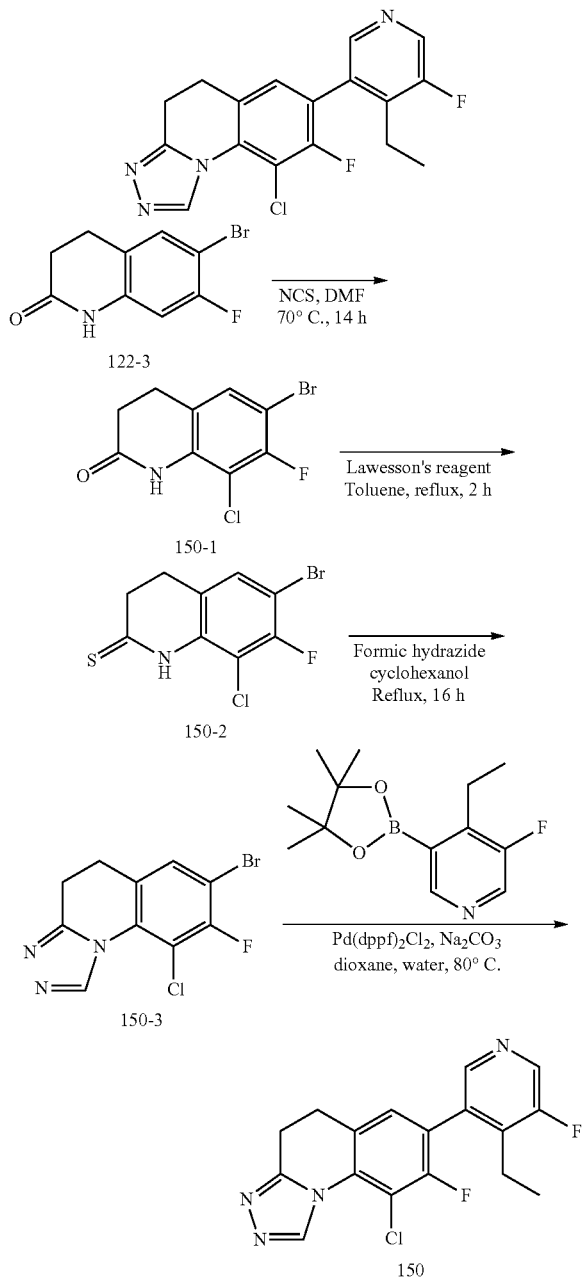

Step A.
6-bromo-8-chloro-3,4-dihydroquinolin-2(1H)-one

To a stirred solution of 6-bromo-7-fluoro-3,4-dihydroquinolin-2(1H)-one (122-3; 3 g, 0.0012 mol) in N,N-dimethylformamide (30 mL) was added N-chlorosuccinimide in N,N-dimethylformamide (3 mL) (1.4 g, 0.0105 mol) at 70° C. drop wise over a period of 2 h. Reaction mass was allowed to stir at 70° C. for 14 h. The reaction mixture was cooled and diluted with ice cold water. The precipitated solid was filtered and dried to obtain title compound. MS (M−1): 278.12.

Step B. 6-bromo-8-chloro-7-fluoro-3,4-dihydroquinoline-2(1H)-thione

To a stirred solution of 6-bromo-8-chloro-3,4-dihydroquinolin-2(1H)-one (150-1; 3.1 g, 0.0118 mol) in toluene (50 mL) was added Lawesson's reagent (2.4 g, 0.0059 mol). Reaction mass was refluxed at 100° C. for 3 h. The reaction mixture was concentrated and directly purified by silica gel column chromatography to obtain title compound. $^1$H NMR (400 MHz, DMSO-d$_6$) δ 11.36 (s, 1H), 7.63 (s, 1H), 7.54 (s, 1H), 2.96-2.93 (m, 2H), 2.85-2.81 (m, 2H). MS (M−1): 278.1.

Step C. 7-bromo-9-chloro-8-fluoro-4,5-dihydropyrrolo[1,2-a]quinoline

To a stirred solution of 6-bromo-8-chloro-3,4-dihydroquinoline-2(1H)-thione (150-2; 0.2 g, 0.06802 mol) in n-butanol (5 mL) was added formic hydrazide in n-butanol (2 mL) (0.102 g, 0.017 mol) at 80° C. drop wise over a period of 1 h. Reaction mass was allowed to stir at 80° C. for 8 h. The reaction mixture was concentrated and directly purified by silica gel column chromatography to obtain title compound. MS (M+1): 302.1.

Step D. 9-chloro-7-(4-ethyl-5-fluoropyridin-3-yl)-8-fluoro-4,5-dihydro-[1,2,4]triazolo[4,3-a]quinoline To a stirred solution of 7-bromo-9-chloro-8-fluoro-4,5-dihydropyrrolo[1,2-a]quinoline (150-3; 0.183 g, 0.000609 mol) and 4-ethyl-3-fluoro-5-(4,4,5,5-tetramethyl-[1,3,2]dioxaborolan-2-yl)-pyridine (0.203 g, 0.00121 mol) in the mixture of 1,4-dioxan (5 mL) and water (5 mL) was added sodium carbonate (0.192 g, 0.00181 mol). Reaction mass was purged with argon for 20 min. Catalyst Pd(dppf)$_2$Cl$_2$ (0.024 g, 0.000002 mol) was added and again purged with argon for 10 min and allowed to stir at 80° C. for 8 h. The reaction mixture was filtered through CELITE bed and filter bed was thoroughly washed with ethyl acetate. The collected organic layer was concentrated under vacuum to afford the crude compound, which was purified by silica gel column chromatography to obtain title compound. $^1$H NMR (400 MHz, DMSO-d$_6$) δ 9.44 (s, 1H), 8.609 (s, 1H), 8.320 (s, 1H), 7.59-7.7.58 (s, J=4 Hz, 1H), 3.11-3.03 (m, 4H), 2.51-2.48 (q, J=12 Hz, 2H), 1.04-1.02 (t, J=8 Hz, 3H). MS (M+1): 347.1.

Example 151

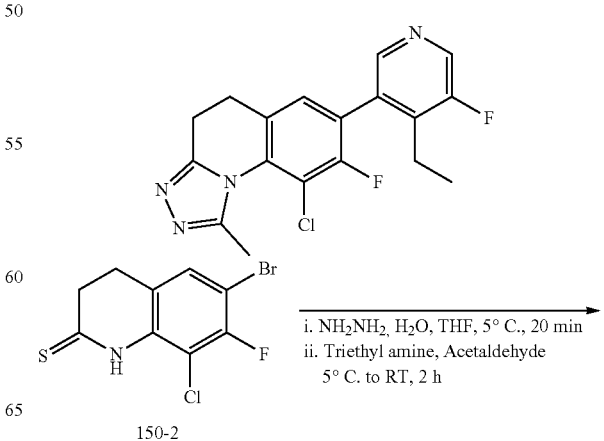

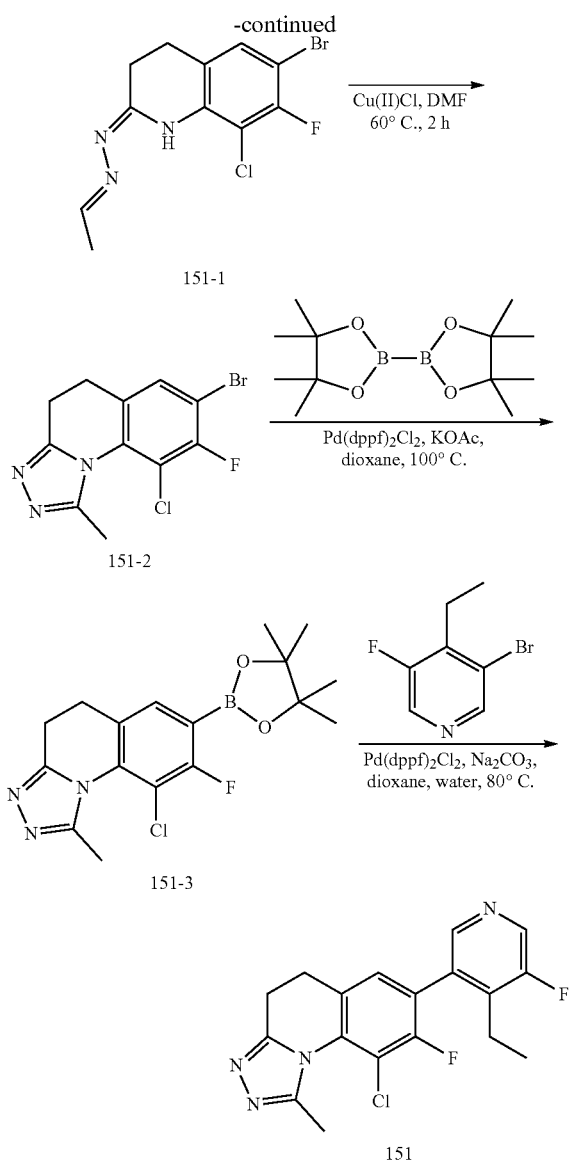

Step A. Compound 151-1

To a stirred solution of 6-bromo-8-chloro-7-fluoro-3,4-dihydroquinoline-2(1H)-thione (150-2; 0.5 g, 0.00169 mol), in dry tetrahydrofuran was added hydrazine hydrate (0.16 mL, 0.00509 mol), at 5° C., the resulting mixture was stirred for 30 min at 5° C. After completion of starting material by TLC, was added triethyl amine and acetaldehyde at 5° C. The reaction mixture was slowly warmed to room temperature and stirred for 1 h. The reaction mixture was diluted with ethyl acetate, washed with saturated aqueous solution of sodium bicarbonate, dried over sodium sulphate, filtered and concentrated to afford crude compound, which was purified with silica gel (60-120) column chromatography by 5% methanol in dichloromethane to afford compound 151-1. $^1$H NMR (400 MHz, DMSO-$d_6$) δ: 8.76 (s, 1H), 7.81-7.80 (d, J=5.2 Hz, 1H), 7.53-7.51 (d, J=7.6 Hz, 1H), 2.89-2.85 (t, J=7.2 Hz, 2H), 2.61-2.58 (t, J=7.6 Hz, 2H), 1.99-1.98 (d, J=5.2, 3H).

Step B. 7-bromo-9-chloro-8-fluoro-1-methyl-4,5-dihydro-[1,2,4]triazolo[4,3-a]quinoline To a stirred solution compound 151-1 (0.5 g), in N,N-dimethylformamide was added copper (II) chloride (0.68 g). The resulting solution was heated to 60° C. and stirred for 3 h. The reaction mixture was allowed to cool to room temperature, diluted with ethyl acetate (10 mL) and aqueous ammonia (10 mL). The organic layer was separated, aqueous layer extracted with ethyl acetate (50 mL×3), the combined organic layer were washed with brine, dried over sodium sulphate, filtered and concentrated. The crude was purified by silica gel (60-120) column chromatography by 5% methanol in dichloromethane to afford the title compound. MS (M+1): 316.

Step C. 9-chloro-8-fluoro-1-methyl-7-(4,4,5,5-tetramethyl-1,3,2-dioxaborolan-2-yl)-4,5-dihydro-[1,2,4]triazolo[4,3-a]quinoline To a stirred solution of 7-bromo-9-chloro-8-fluoro-1-methyl-4,5-dihydro-[1,2,4]triazolo[4,3-a]quinoline (151-2; 0.43 g, 0.00135 mol) in dioxane (20 ml) was added 4,4,4',4',5,5,5',5'-octamethyl-2,2'-bi(1,3,2-dioxaborolane) (2.75 g, 0.0108 mol), potassium acetate (0.26 g, 0.00271 mol). The reaction mass was purged with argon for 20 min. Then Pd(dppf)$_2$Cl$_2$.DCM (0.055 g, 0.000067 mol) was added. The reaction mixture was heated to 100° C. and stirred for 8 h. The reaction mixture was allowed to cool to room temperature, filtered the reaction mixture through CELITE bed and CELITE bed was thoroughly washed with ethyl acetate. The filtrate was concentrated under vacuum. The residue was dissolved with ethyl acetate, the organic layer was washed with water, brine solution, dried over Na$_2$SO$_4$, concentrated under vacuum to obtain crude title compound. MS (M+1): 282.1.

Step D. 9-chloro-7-(4-ethyl-5-fluoropyridin-3-yl)-8-fluoro-1-methyl-4,5-dihydro-[1,2,4]triazolo[4,3-a]quinoline To a stirred solution of 9-chloro-8-fluoro-1-methyl-7-(4,4,5,5-tetramethyl-1,3,2-dioxaborolan-2-yl)-4,5-dihydro-[1,2,4]triazolo[4,3-a]quinoline (151-3; 0.4 g, 0.0011 mol) and 3-bromo-4-ethyl-5-fluoropyridine (0.22 g, 0.0011 mol) in the mixture of 1,4-dioxan (15 ml) and water (5 ml) was added cesium carbonate (0.71 g, 0.0022 mol). Reaction mass was purged with argon for 20 min. Then Pd(dppf)$_2$Cl$_2$ (0.04 g, 0.000055 mol) was added. The reaction mixture was heated 95° C. and stirred at 95° C. for 6 h. The reaction mixture was allowed to cool to room temperature, the reaction mixture was filtered through celite bed and filter bed was thoroughly washed with ethyl acetate. The filtrate was concentrated under vacuum. The residue was dissolved in dichloromethane, washed with water, brine solution, dried over sodium sulphate, concentrated to afford the crude compound, which was purified by silica gel (60-120) column chromatography and preparative HPLC (analytical conditions: column: XTERRA C18(250 mm×4.6 mm×5 μm), mobile phase (A): 0.01% ammonia in water, mobile phase (B): acetonitrile, flow rate: 1.0 mL/min, Time/% B: 0/20,8/50,25/50,26/20,30/20) to obtain title compound (76). $^1$H NMR (400 MHz, DMSO-$d_6$) δ: 8.61 (s, 1H), 8.33 (s, 1H), 7.62-7.60 (d, J=7.2 Hz, 1H), 2.91 (bs, 4H), 2.58 (s, 3H) 2.57-2.54 (m, 2H), 1.06-1.02 (t, J=7.6 Hz, 3H). MS (M+1): 361.1.

The compound in Table 12 was prepared using the chemistry described in Example 151.

TABLE 12

| Example | Structure | IUPAC Name | LCMS |
|---|---|---|---|
| 152 | 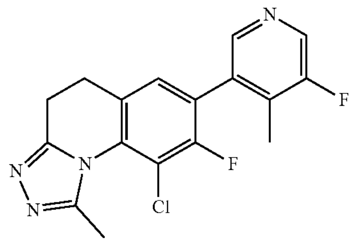 [SMILES: Cc1c(F)cncc1-c1cc2c(c(Cl)c1F)-n1c(C)nnc1CC2] | 9-chloro-8-fluoro-7-(5-fluoro-4-methylpyridin-3-yl)-1-methyl-4,5-dihydro-[1,2,4]triazolo[4,3-a]quinoline | 347.05 |

The compounds in Table 13 were prepared using chemistry described in Example 80.

TABLE 13

| Example | Structure | IUPAC Name | LCMS |
|---|---|---|---|
| 153 | 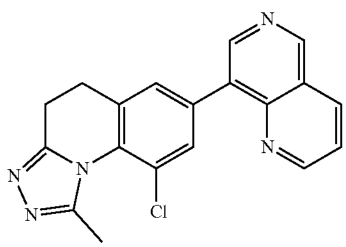 [SMILES: Cc1nnc2n1-c1c(Cl)cc(-c3cncc4cccnc34)cc1CC2] | 9-chloro-1-methyl-7(1,6-naphthyridin-8-yl)-4,5-dihydro-[1,2,4]triazolo[4,3-a]quinoline | 347.82 |
| 154 | 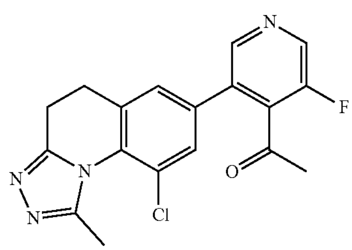 [SMILES: CC(=O)c1c(F)cncc1-c1cc(Cl)c2c(c1)CCc1nnc(C)n1-2] | 1-(3-(9-chloro-1-methyl-4,5-dihydro-[1,2,4]triazolo[4,3-a]quinolin-7-yl)-5-fluoropyridin-4-yl)ethanone | 356.72 |
| 155 | 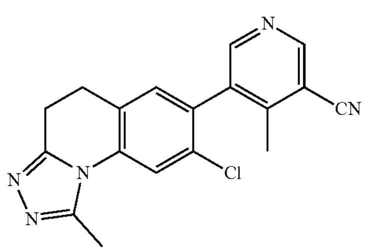 [SMILES: Cc1c(C#N)cncc1-c1cc2c(cc1Cl)-n1c(C)nnc1CC2] | 5-(8-chloro-1-methyl-4,5-dihydro-[1,2,4]triazolo[4,3-a]quinolin-7-yl)-4-methylnicotinonitrile | 336.71 |
| 156 | 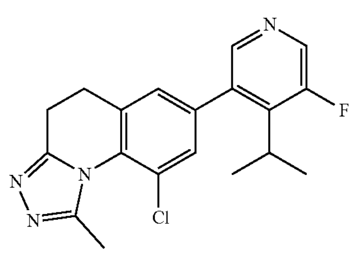 [SMILES: Cc1nnc2n1-c1c(Cl)cc(-c3cncc(F)c3C(C)C)cc1CC2] | 9-chloro-7-(5-fluoro-4-isopropylpyridin-3-yl)-1-methyl-4,5-dihydro-[1,2,4]triazolo[4,3-a]quinoline | 356.89 |

Example 157

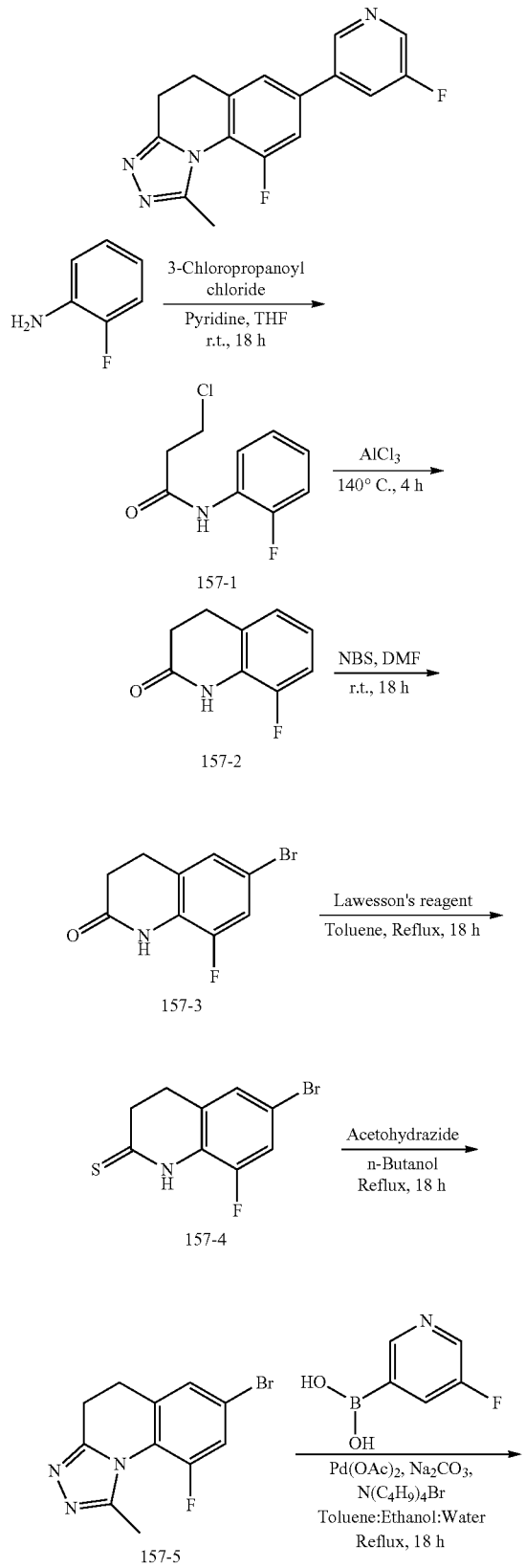

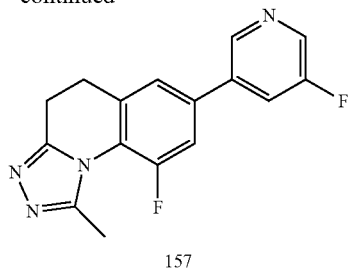

157

Step A. 3-chloro-N-(2-fluorophenyl)propanamide

A solution of 2-fluoroaniline (20.00 g, 180.0 mmol) in tetrahydrofurane (100 mL) and pyridine (22 mL) was stirred for 15 min, and then 3-chloropropionyl chloride (25.14 g, 198 mmol) in tetrahydrofurane (50 ml) was added at 0° C. The mixture was stirred for 18 h at room temperature under inert atmosphere. After completion of the reaction, the mixture was diluted with water. The aqueous layer was separated and extracted with diethylether. The collected organic parts were washed with water and brine, then dried over $Na_2SO_4$, filtered and concentrated under vacuum to afford the title compound (white solid). This intermediate was used directly in the next step without further purification and characterization.

Step B. 8-fluoro-3,4-dihydroquinolin-2(1H)-one

A mixture of 3-chloro-N-(2-fluorophenyl)propanamide (157-1, 17.2 g, 85.30 mmol) and aluminium trichloride (56.9 g, 427.0 mmol) was heated at 140° C. for 4 h under inert atmosphere. After cooling down to 0° C., ice cold water (350 mL) was added slowly. The resulting precipitate filtered, washed with water and hexane. The crude compound was purified by flash chromatography on silica gel to obtain title compound (B); yield: 7.00 g (50%); white solid. This intermediate was used directly in the next step without characterization.

Step C.
6-bromo-8-fluoro-3,4-dihydroquinolin-2(1H)-one

To a stirred solution of 8-fluoro-3,4-dihydroquinolin-2 (1H)-one (157-2; 8.30 g, 50.10 mmol) in N,N-dimethylformamide (250 mL) was added N-bromosuccinimide (9.80 g, 55.10 mmol) in N,N-dimethylformamide (120 mL) at 0° C. Reaction mixture was allowed to stir at room temperature for 18 h, then cooled and diluted with ice cold water (500 mL). The resulting precipitated was filtered and dried to obtain title compound (white solid). $^1$H NMR (DMSO-$D_6$, 500 MHz) δ=10.20 (s, 1H), 7.37 (dd, J=2.0 Hz, $J_{HF}$=10.0 Hz, 1H), 7.26 (s, 1H), 2.93 (t, J=7.0 Hz, 2H), 2.47 (t, J=7.5 Hz, 2H).

Step D.
6-bromo-8-fluoro-3,4-dihydroquinoline-2(1H)-thione

To a suspension of 6-bromo-8-fluoro-3,4-dihydroquinolin-2(1H)-one (157-3, 2.00 g, 8.19 mmol) in toluene (50 mL) was added Lawesson's reagent (1.66 g, 4.10 mmol). After reflux for 2 h, toluene was distilled off to yield the crude product, which was then purified by flash chromatography on silica gel to obtain title compound (yellow solid). $^1$H NMR (DMSO-D$_6$, 500 MHz) δ=12.14 (s, 1H), 7.46 (dd, J=2.0 Hz, J$_{HF}$=10.0 Hz, 1H), 7.34 (s, 1H), 2.94 (d, J=8.0 Hz, 2H), 2.84 (d, J=8.0 Hz, 2H).

Step E. 7-Bromo-9-fluoro-4,5-dihydro-1-methyl-[1,2,4]triazolo[4,3-a]quinoline A suspension of 6-bromo-8-fluoro-3,4-dihydroquinoline-2(1H)-thione (157-4, 1.71 g, 6.57 mmol) and acetohydrazide (0.58 g, 7.89 mmol) in n-butanol (7 mL) was refluxed for 18 h under inert atmosphere. After cooling down to ambient temperature, ethyl acetate (10 mL) and water (10 mL) were added. Then the organic phase was separated, and the water phase was extracted with ethyl acetate (5×10 mL). The combined organic phases were washed with brine, dried over Na$_2$SO$_4$, and evaporated under reduced pressure. The crude compound was purified by flash chromatography on silica gel to obtain title compound (white solid). $^1$H NMR (DMSO-D$_6$, 500 MHz) δ=7.79 (dd, J=2.0 Hz, J$_{HF}$=11.0 Hz, 1H), 7.63 (s, 1H), 2.95 (br s, 4H), 2.46 (d, J$_{HF}$=8.5 Hz, 3H).

Step F. 9-fluoro-7-(5-fluoro-pyridin-3-yl)-1-methyl-4,5-dihydro-[1,2,4]triazolo[4,3-a]quinoline 7-Bromo-9-fluoro-4,5-dihydro-1-methyl-[1,2,4]triazolo[4,3-a]quinoline (157-5, 0.25 g, 0.89 mmol) was dissolved in toluene (6.3 mL), and an aqueous 2.0 M sodium carbonate solution (2.8 mL), an ethanolic solution (2.8 mL) of 5-fluoropyridin-3-yl-3-boronic acid (0.19 g, 1.33 mmol) and tetrabutylammonium bromide (0.29 g, 0.89 mmol) were added. The mixture was deoxygenated under reduced pressure and flushed with nitrogen. After having repeated this cycle several times catalyst Pd(OAc)$_2$ (0.01 g, 5 mol %) was added and the resulting suspension was heated under reflux for 18 h. After cooling, ethyl acetate (10 mL) and water (10 mL) were added and the organic layer was separated. The water phase was extracted with ethyl acetate (2×10 mL). The combined organic phases were washed with brine, dried over Na$_2$SO$_4$, filtered over a short plug of CELITE and evaporated under reduced pressure. The crude compound was purified by flash chromatography on silica gel to obtain title compound (white solid); $^1$H NMR (CDCl$_3$, 500 MHz) δ 8.67 (t, J=1.5 Hz, 1H), 8.52 (d, J=2.7 Hz, 1H), 7.59 (ddd, J=2.0, 2.6 Hz, J$_{HF}$=9.2 Hz, 1H), 7.39 (dd, J=1.9 Hz, J$_{HF}$=14.6 Hz, 1H), 7.41 (d, J=1.7 Hz, 1H), 3.13 (t, J=7.5 Hz, 2H), 3.04 (t, J=7.5 Hz, 2H), 2.65 (d, J$_{HF}$=8.3 Hz, 3H); MS (ESI): m/z=299 [M+H]$^+$.

The compounds in Table 14 were prepared using chemistry described in Example 157.

TABLE 14

| Example | Structure | IUPAC Name | LCMS |
|---|---|---|---|
| 158 | 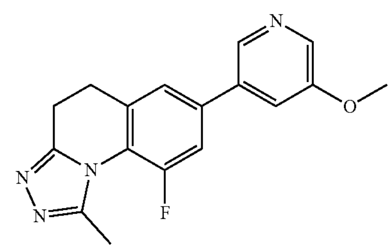 [SMILES: COc1cncc(-c2cc(F)c3c(c2)CCc2nnc(C)n2-3)c1] | 9-fluoro-7-(5-methoxy-pyridin-3-yl)-1-methyl-4,5-dihydro-[1,2,4]triazolo[4,3-a]quinoline | 311.16 |
| 159 | 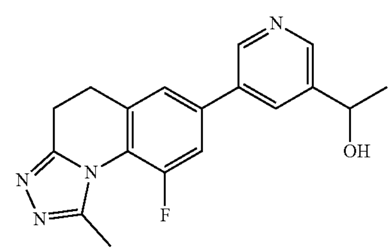 [SMILES: Cc1nnc2n1-c1c(F)cc(-c3cncc(C(C)O)c3)cc1CC2] | 1-[5-(9-fluoro-1-methyl-4,5-dihydro-[1,2,4]triazolo[4,3-a]quinolin-7-yl)-pyridin-3-yl]-ethanol | 325.36 |
| 160 | 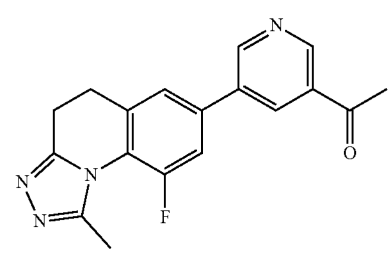 [SMILES: CC(=O)c1cncc(-c2cc(F)c3c(c2)CCc2nnc(C)n2-3)c1] | 1-[5-(9-fluoro-1-methyl-4,5-dihydro-[1,2,4]triazolo[4,3-a]quinolin-7-yl)-pyridin-3-yl]-ethanone | 322.99 |

TABLE 14-continued

| Example | Structure | IUPAC Name | LCMS |
|---|---|---|---|
| 161 | 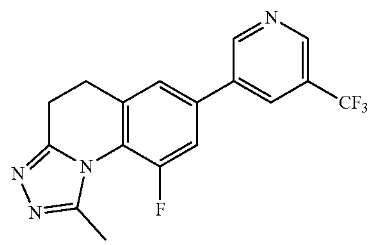 [SMILES: Cc1nnc2n1-c1c(F)cc(-c3cncc(C(F)(F)F)c3)cc1CC2] | 9-fluoro-1-methyl-7-(5-trifluoromethyl-pyridin-3-yl)-4,5-dihydro-[1,2,4]triazolo[4,3-a]quinoline | 349.01 |
| 162 | 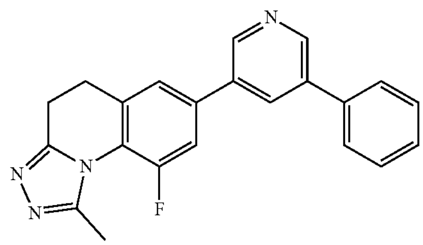 [SMILES: Cc1nnc2n1-c1c(F)cc(-c3cncc(-c4ccccc4)c3)cc1CC2] | 9-fluoro-1-methyl-7-(5-phenyl-pyridin-3-yl)-4,5-dihydro-[1,2,4]triazolo[4,3-a]quinoline | 357.05 |
| 163 | 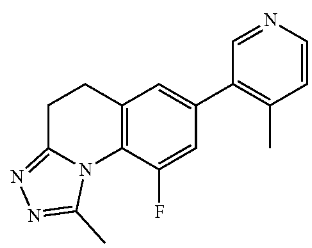 [SMILES: Cc1ccncc1-c1cc(F)c2c(c1)CCc1nnc(C)n1-2] | 9-fluoro-1-methyl-7-(4-methyl-pyridin-3-yl)-4,5-dihydro-[1,2,4]triazolo[4,3-a]quinoline | 295.07 |
| 164 | 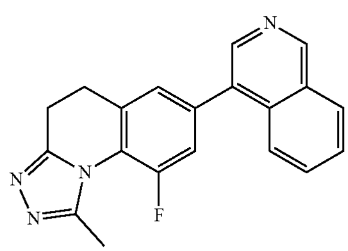 [SMILES: Cc1nnc2n1-c1c(F)cc(-c3cncc4ccccc34)cc1CC2] | 9-fluoro-7-isoquinolin-4-yl-1-methyl-4,5-dihydro-[1,2,4]triazolo[4,3-a]quinoline | 331.05 |
| 165 | 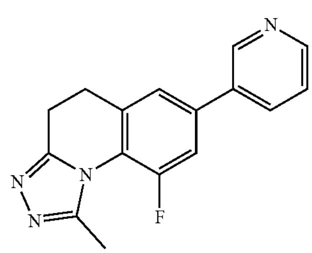 [SMILES: Cc1nnc2n1-c1c(F)cc(-c3cccnc3)cc1CC2] | 9-fluoro-1-methyl-7-pyridin-3-yl-4,5-dihydro-[1,2,4]triazolo[4,3-a]quinoline | 281.02 |
| 166 | 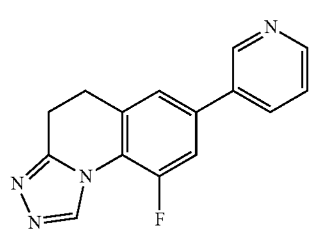 [SMILES: Fc1cc(-c2cccnc2)cc2c1-n1cnnc1CC2] | 9-fluoro-7-pyridin-3-yl-4,5-dihydro-[1,2,4]triazolo[4,3-a]quinoline | 267.37 |

TABLE 14-continued

| Example | Structure | IUPAC Name | LCMS |
|---|---|---|---|
| 167 | 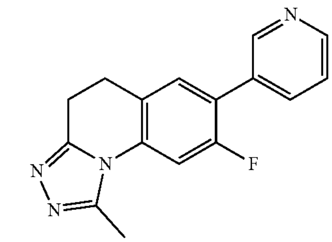 [SMILES: Cc1nnc2n1-c1cc(F)c(-c3cccnc3)cc1CC2] | 8-fluoro-1-methyl-7-pyridin-3-yl-4,5-dihydro-[1,2,4]triazolo[4,3-a]quinoline | 281.57 |
| 168 | 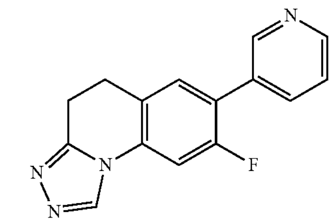 [SMILES: Fc1cc2c(cc1-c1cccnc1)CCc1nncn1-2] | 8-fluoro-7-pyridin-3-yl-4,5-dihydro-[1,2,4]triazolo[4,3-a]quinoline | 267.39 |
| 169 | 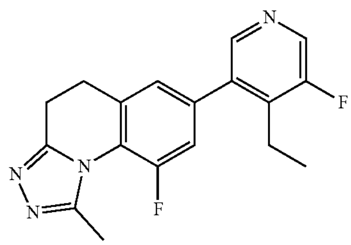 [SMILES: CCc1c(F)cncc1-c1cc(F)c2c(c1)CCc1nnc(C)n1-2] | 7-(4-ethyl-5-fluoropyridin-3-yl)-9-fluoro-1-methyl-4,5-dihydro-[1,2,4]triazolo[4,3-a]quinoline | 326.92 |
| 170 | 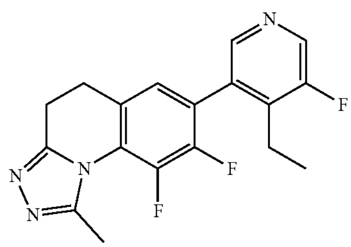 [SMILES: CCc1c(F)cncc1-c1cc2c(c(F)c1F)-n1c(C)nnc1CC2] | 7-(4-ethyl-5-fluoropyridin-3-yl)-8,9-difluoro-1-methyl-4,5-dihydro-[1,2,4]triazolo[4,3-a]quinoline | 344.85 |

Assay Description and Results

Methods for V79-Human-CYP11B2 and V79-Human-CYP11B1 Assays:

V79 cell lines stably expressing the either the human CYP11B2 or the human CYP11B1 enzyme were generated using a standard transfection protocol. V79 cells were transfected with plasmids pTriEx3-Hygro-hCyp11B2 or pTriEx3-Hygro-hCyp11B1 using Lipofectamine2000 reagent. V79 cells that stably express the human CYP11B2 or human CYP11B1 enzyme were selected for and maintained in DMEM supplemented with 10% FBS and 400 µg/mL hygromycin for ~2 weeks. Single cell clones were generated by infinite dilution in DMEM supplemented with 10% FBS and 400 µg/mL hygromycin until single colonies were obtained. Clones V79-hCYP11B2-CLE9 and V79-hCYP11B1-8C7, were determined to produce the most aldosterone and cortisol, respectively, and were selected for inhibitor screening. For testing of inhibitors, cells were harvested at 80% confluency with 0.5% Trypsan-EDTA, washed once in PBS, and reconstituted in DMEM+0.1% BSA media at a cell concentration of 400,000 cells/mL. 25 µl of cells were added to a 384 well tissue culture treated plate and mixed with 0.25 µl of inhibitor or DMSO (1% final DMSO concentration) for 1 hour at 37° C., 5% $CO_2$. After pre-incubation with inhibitor, the reaction was initiated by adding 5 µl of substrate (final concentration of 125 nM 11-deoxycorticosterone for the CYP11B2 assay or 250 nM 11-deoxycortisol for the CYP11B1 assay). The reaction was carried out for 3 hours at 37° C., 5% $CO_2$ and was stopped by harvesting the supernatants. The amount of product in the supernatant (aldosterone for CYP11B2 assay and cortisol for the CYP11B1 assay) was measured using HTRF-based assay kit (Aldosterone HTRF-CisBio#64ALDPEB, Cortisol HTRF-CisBio #631DC002-CORT). $IC_{50}$'s for the inhibitor were determined by plotting the amount of product formed against the concentration of inhibitor using sigmoidal dose-response curve (variable slope) fit in GraphPad.

The compounds of Examples 1-75, 148 and 149 were tested in the V79-Human-CYP11B2 cell assay and found to have $IC_{50}$'s for inhibition of human CYP11B2 of less than 10000 nM. A sub-group of compounds had $IC_{50}$'s less than or equal to 250 nM, and a further sub-group of compounds had $IC_{50}$'s less than or equal to 50 nM.

The compounds of Examples 1-75, 148 and 149 were also tested in the V79-Human-CYP11B1 cell assay. A sub-group of compounds were at least 10-fold more selective for inhibition of CYP11B2 as compared to CYP11B1, and a further sub-group of compounds were at least 30-fold more selective for inhibition of CYP11B2. Representative examples of data collected for compounds of the present invention are shown in Table 15 below

TABLE 15

| Example | Structure | IUPAC Name | V79 Human CYP11B2 IC₅₀ (nM) | V79 Human CYP11B1 IC₅₀ (nM) |
|---|---|---|---|---|
| 46 | 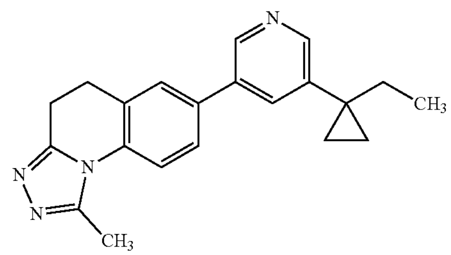 [SMILES: CCC1(c2cncc(-c3ccc4c(c3)CCc3nnc(C)n3-4)c2)CC1] | 7-[5-(1-ethylcyclopropyl)pyridin-3-yl]-4,5-dihydro [1,2,4]triazolo[4,3-a]quinoline | 1.2 | 54 |
| 37 | 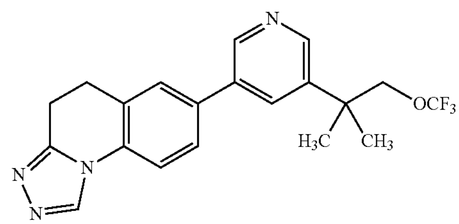 [SMILES: CC(C)(COC(F)(F)F)c1cncc(-c2ccc3c(c2)CCc2nncn2-3)c1] | 7-{5-[2-methyl-1-(trifluoromethoxy)propan-2-yl]pyridin-3-yl}-4,5-dihydro[1,2,4]triazolo[4,3-a]quinoline | 4 | 69 |
| 15 | 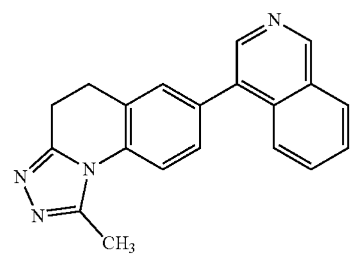 [SMILES: Cc1nnc2n1-c1ccc(-c3cncc4ccccc34)cc1CC2] | 7-(isoquinolin-4-yl)-1-methyl-4,5-dihydro[1,2,4]triazolo[4,3-a]quinoline | 5 | 407 |
| 22 | 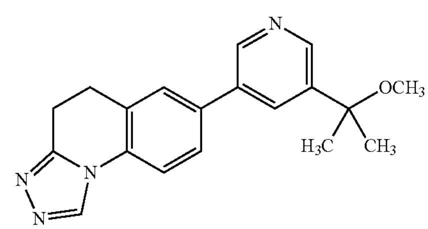 [SMILES: COC(C)(C)c1cncc(-c2ccc3c(c2)CCc2nncn2-3)c1] | 7-[5-(2-methoxypropan-2-yl)pyridin-3-yl]-4,5-dihydro[1,2,4]triazolo[4,3-a]quinoline | 5 | 108 |
| Step D, p 76 | 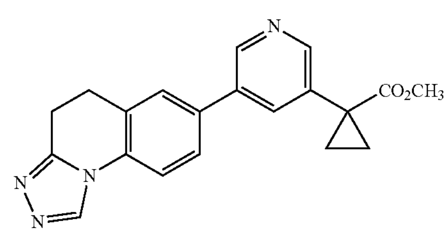 [SMILES: COC(=O)C1(c2cncc(-c3ccc4c(c3)CCc3nncn3-4)c2)CC1] | methyl 1-[5-(4,5-dihydro[1,2,4]triazolo[4,3-a]quinolin-7-yl)pyridin-3-yl]cyclopropanecarboxylate | 17 | 157 |
| 17 | 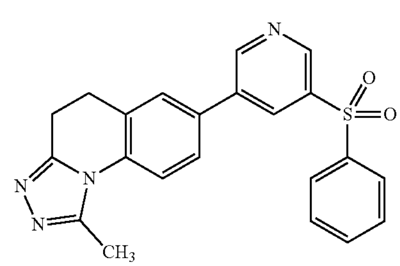 [SMILES: Cc1nnc2n1-c1ccc(-c3cncc(S(=O)(=O)c4ccccc4)c3)cc1CC2] | 1-methyl-7-[5-(phenylsulfonyl)pyridin-3-yl]-4,5-ihydro[1,2,4]triazolo[4,3-a]quinoline | 40 | 1501 |

TABLE 15-continued

| Example | Structure | IUPAC Name | V79 Human CYP11B2 IC$_{50}$ (nM) | V79 Human CYP11B1 IC$_{50}$ (nM) |
|---|---|---|---|---|
| 38 | 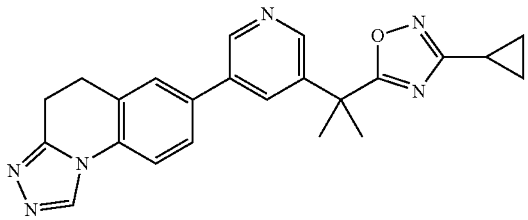 [SMILES: CC(C)(c1cncc(-c2ccc3c(c2)CCc2nncn2-3)c1)c1nc(C2CC2)no1] | 7-{5-[2-(3-cyclopropyl-1,2,4-oxadiazol-5-yl)propan-2-yl]pyridin-3-yl}-4,5-ihydro[1,2,4]triazolo[4,3-a]quinoline | 45 | 527 |
| 16 | 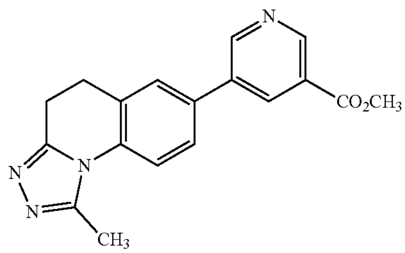 [SMILES: COC(=O)c1cncc(-c2ccc3c(c2)CCc2nnc(C)n2-3)c1] | methyl 5-(1-methyl-4,5-dihydro[1,2,4]triazolo[4,3-a]quinolin-7-yl)pyridine-3-carboxylate | 58 | 2198 |

The compounds 74-147, 150 and 151 were assayed were assayed with a modified protocol from the one described above and found to have IC$_{50}$'s for inhibition of human CYP11B2 of less than 10000 nM. For the CYP11B2 assay, cells were reconstituted in DMEM+0.1% BSA media at a cell concentration of 600,000 cells/mL and for the CYP11B1 assay cells were reconstituted in DMEM+0.1% BSA media at a cell concentration of 280,000 cells/mL. 25 µl of cells were added to a 384 well tissue culture treated plate and mixed with 0.30 µl of inhibitor or DMSO (1% final DMSO concentration) for 1 hour at 37° C., 5% CO$_2$.

Representative examples of data collected for some of compounds of the present invention using this modified procedure are shown in Table 16 below.

TABLE 16

| Example | Structure | IUPAC Name | V79 Human CYP11B2 IC$_{50}$ (nM) | V79 Human CYP11B1 IC$_{50}$ (nM) |
|---|---|---|---|---|
| 83 | 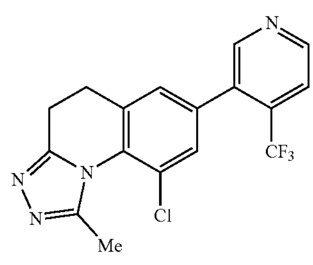 [SMILES: Cc1nnc2n1-c1c(Cl)cc(-c3cnccc3C(F)(F)F)cc1CC2] | 9-chloro-1-methyl-7-(4-(trifluoromethyl)pyridin-3-yl)-4,5-dihydro-[1,2,4]triazolo[4,3-a]quinoline | 22 | >30,000 |
| 113 | 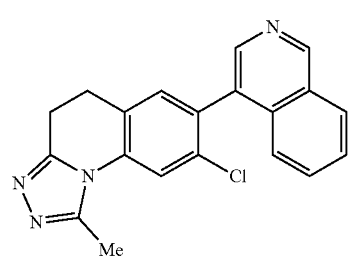 [SMILES: Cc1nnc2n1-c1cc(Cl)c(-c3cncc4ccccc34)cc1CC2] | 8-chloro-7-isoquinolin-4-yl)-1-methyl-4,5-dihydro-[1,2,4]triazolo[4,3-a]quinoline | 17 | >10,000 |

TABLE 16-continued

| Example | Structure | IUPAC Name | V79 Human CYP11B2 IC$_{50}$ (nM) | V79 Human CYP11B1 IC$_{50}$ (nM) |
|---|---|---|---|---|
| 80 | 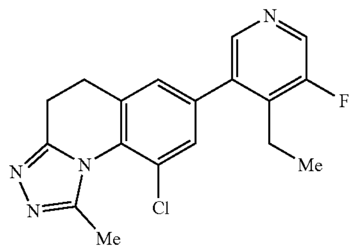 [SMILES: CCc1c(F)cncc1-c1cc(Cl)c2c(c1)CCc1nnc(C)n1-2] | 9-chloro-7-(4-ethyl-5-fluoropyridin-3-yl)-1-methyl-4,5-dihydro-[1,2,4]triazolo[4,3-a]quinoline | 7 | 3,140 |
| 122 | 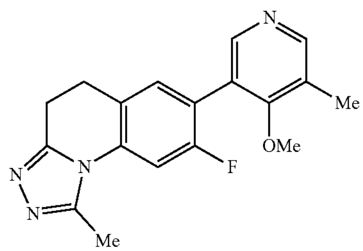 [SMILES: COc1c(C)cncc1-c1cc2c(cc1F)-n1c(C)nnc1CC2] | 8-fluoro-7-(4-methoxy-5-methylpyridin-3-yl)-1-methyl-4,5-dihydro[1,2,4]triazolo[4,3-a]quinoline | 32 | >10,000 |
| 96 | 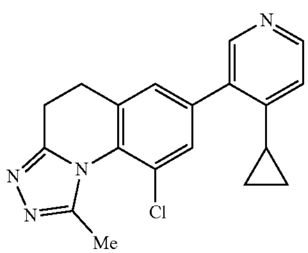 [SMILES: Cc1nnc2n1-c1c(Cl)cc(-c3cnccc3C3CC3)cc1CC2] | 9-chloro-7-(4-cyclopropylpyridin-3-yl)-1-methyl-4,5-dihydro-[1,2,4]triazolo[4,3-a]quinoline | 48 | 6,930 |
| 93 | 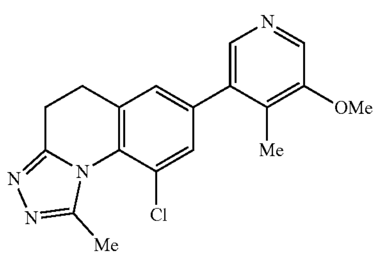 [SMILES: COc1cncc(-c2cc(Cl)c3c(c2)CCc2nnc(C)n2-3)c1C] | 9-chloro-7-(5-chloro-4-methylpyridin-3-yl)-1-methyl-4,5-dihydro-[1,2,4]triazolo[4,3-a]quinoline | 6 | 765 |

Compounds of the Examples 157-170 were assayed for V79-Human-CYP11B2 and V79-Human-CYP11B1 by modifying the protocol described in *J. Steroid Biochem. Mol. Biol.* 81; 173-179 (2002). V79MZh11B1 and V79MZh11B2 cells (8×10$^5$ cells/well) were grown on 24-well culture plates until confluence. Before testing, the DMEM culture medium was removed and 450 µl of fresh DMEM containing the inhibitor was added to each well. After a preincubation step of 60 min at 37° C., the reaction was started by the addition of 50 µl of DMEM in which the substrate deoxycorticosterone (containing 0.15 µCi of [1,2-3H]-deoxycorticosterone in ethanol, final test concentration 100 nM) was dissolved. Incubation times were 25 min for V79MZh11B1 and 50 min for V79MZh11B2 cells at 37° C., respectively. The enzyme reactions were stopped by extracting the supernatant with ethyl acetate. Samples were centrifuged (10.000 g, 5 min) and the solvent was pipetted into fresh cups. After evaporation of the solvent, the steroids were redissolved in 40 µl of methanol (50:50, v/v) and analyzed by HPLC. Detection and quantification of the steroids were performed using a radioflow detector. To first estimate the different IC$_{50}$ values, five different concentrations ranging from 1 to 10,000 nM were measured. For the following IC$_{50}$ determination, three different concentrations (repeat-determinations) were measured for each IC$_{50}$ value of each inhibitor in which the second concentration led to an inhibition of approximately 40 to 60%. The inhibitor concentrations were all in the linear range of the dose-response-curves, so that the coefficients of correlation were at least 0.95 for each determination. The final IC$_{50}$ value was estimated as the average of three or four independent IC$_{50}$ values and a selectivity factor corresponding to the ratio between the IC$_{50}$ values of CYP11B1 and CYP11B2 was calculated for each substance.

Representative examples of data collected for some of compounds of the present invention using this modified procedure are shown in Table 17 below.

TABLE 17

| Example | Structure | IUPAC Name | V79 Human CYP11B2 IC$_{50}$ (nM) | V79 Human CYP11B1 IC$_{50}$ (nM) |
| --- | --- | --- | --- | --- |
| 157 | 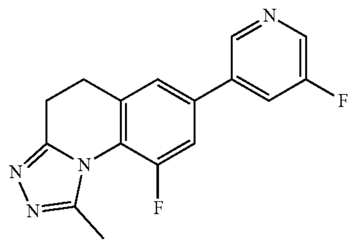 [SMILES: Cc1nnc2n1-c1c(F)cc(-c3cncc(F)c3)cc1CC2] | 9-fluoro-7-(5-fluoro-pyridin-3-yl)-1-methyl-4,5-dihydro-[1,2,4]triazolo[4,3-a]quinoline | 89.7 | 29540 |
| 158 | 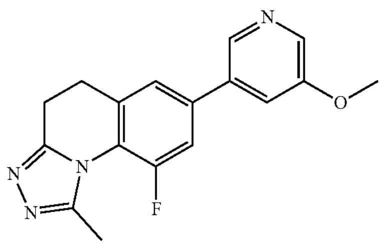 [SMILES: COc1cncc(-c2cc(F)c3c(c2)CCc2nnc(C)n2-3)c1] | 9-fluoro-7-(5-methoxy-pyridin-3-yl)-1-methyl-4,5-dihydro-[1,2,4]triazolo[4,3-a]quinoline | 20.3 | 1810 |
| 159 | 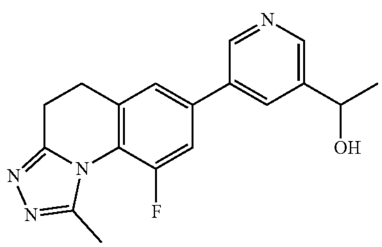 [SMILES: Cc1nnc2n1-c1c(F)cc(-c3cncc(C(C)O)c3)cc1CC2] | 1-[5-(9-fluoro-1-methyl-4,5-dihydro-[1,2,4]triazolo[4,3-a]quinolin-7-yl)-pyridin-3-yl]-ethanol | 28.3 | 3910 |
| 160 | 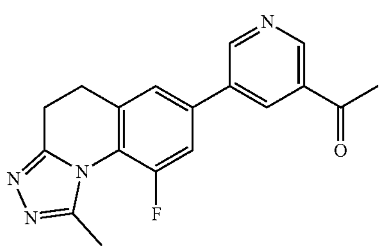 [SMILES: CC(=O)c1cncc(-c2cc(F)c3c(c2)CCc2nnc(C)n2-3)c1] | 1-[5-(9-fluoro-1-methyl-4,5-dihydro-[1,2,4]triazolo[4,3-a]quinolin-7-yl)-pyridin-3-yl]-ethanone | 87.6 | 6970 |
| 161 | 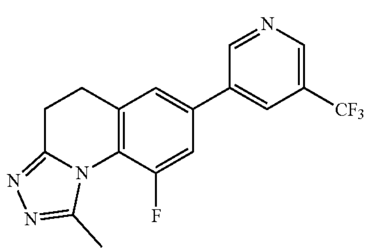 [SMILES: Cc1nnc2n1-c1c(F)cc(-c3cncc(C(F)(F)F)c3)cc1CC2] | 9-fluoro-1-methyl-7-(5-trifluoromethyl-pyridin-3-yl)-4,5-dihydro-[1,2,4]triazolo[4,3-a]quinoline | 57.2 | 3570 |
| 162 | 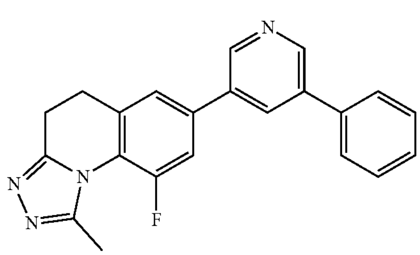 [SMILES: Cc1nnc2n1-c1c(F)cc(-c3cncc(-c4ccccc4)c3)cc1CC2] | 9-fluoro-1-methyl-7-(5-phenyl-pyridin-3-yl)-4,5-dihydro-[1,2,4]triazolo[4,3-a]quinoline | 7.1 | 428 |

TABLE 17-continued

| Example | Structure | IUPAC Name | V79 Human CYP11B2 IC$_{50}$ (nM) | V79 Human CYP11B1 IC$_{50}$ (nM) |
|---|---|---|---|---|
| 163 | 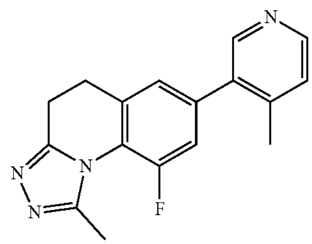 [SMILES: Cc1ccncc1-c1cc(F)c2c(c1)CCc1nnc(C)n1-2] | 9-fluoro-1-methyl-7-(4-methyl-pyridin-3-yl)-4,5-dihydro-[1,2,4]triazolo[4,3-a]quinoline | 4.2 | 1770 |
| 164 | 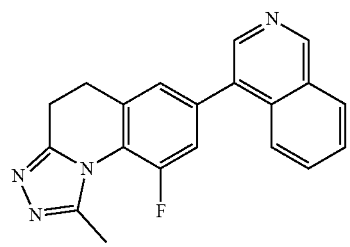 [SMILES: Cc1nnc2n1-c1c(F)cc(-c3cncc4ccccc34)cc1CC2] | 9-fluoro-7-isoquinolin-4-yl-1-methyl-4,5-dihydro-[1,2,4]triazolo[4,3-a]quinoline | 2.2 | 110 |
| 165 | 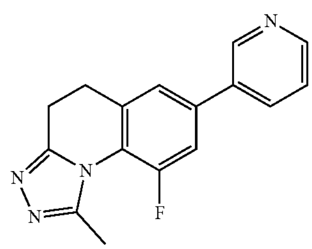 [SMILES: Cc1nnc2n1-c1c(F)cc(-c3cccnc3)cc1CC2] | 9-fluoro-1-methyl-7-pyridin-3-yl-4,5-dihydro-[1,2,4]triazolo[4,3-a]quinoline | 62.5 | 16990 |
| 166 | 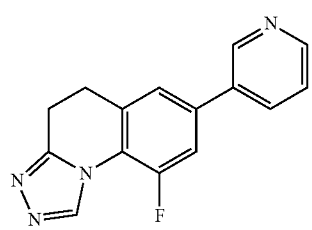 [SMILES: Fc1cc(-c2cccnc2)cc2c1-n1cnnc1CC2] | 9-fluoro-7-pyridin-3-yl-4,5-dihydro-[1,2,4]triazolo[4,3-a]quinoline | 172.2 | 16100 |
| 167 | 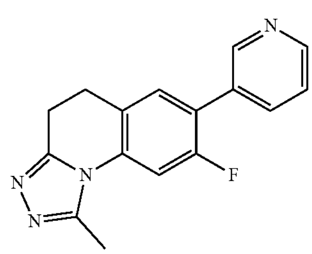 [SMILES: Cc1nnc2n1-c1cc(F)c(-c3cccnc3)cc1CC2] | 8-fluoro-1-methyl-7-pyridin-3-yl-4,5-dihydro-[1,2,4]triazolo[4,3-a]quinoline | 131.4 | 12620 |
| 168 | 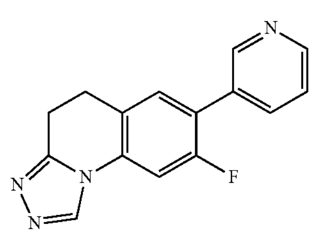 [SMILES: Fc1cc2c(cc1-c1cccnc1)CCc1nncn1-2] | 8-fluoro-7-pyridin-3-yl-4,5-dihydro-[1,2,4]triazolo[4,3-a]quinoline | 244.0 | 7900 |

TABLE 17-continued

| Example | Structure | IUPAC Name | V79 Human CYP11B2 IC$_{50}$ (nM) | V79 Human CYP11B1 IC$_{50}$ (nM) |
|---|---|---|---|---|
| 169 | 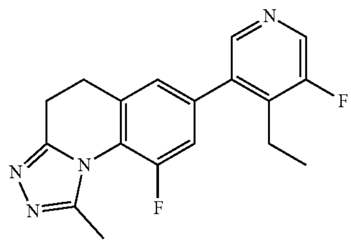 [SMILES: CCc1c(F)cncc1-c1cc(F)c2c(c1)CCc1nnc(C)n1-2] | 7-(4-ethyl-5-fluoropyridin-3-yl)-9-fluoro-1-methyl-4,5-dihydro-[1,2,4]triazolo[4,3-a]quinoline | 11 | 3071 |
| 170 | 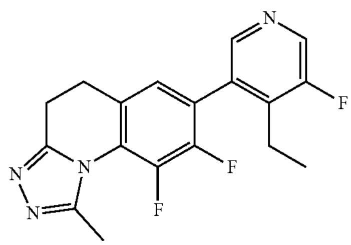 [SMILES: CCc1c(F)cncc1-c1cc2c(c(F)c1F)-n1c(C)nnc1CC2] | 7-(4-ethyl-5-fluoropyridin-3-yl)-8,9-difluoro-1-methyl-4,5-dihydro-[1,2,4]triazolo[4,3-a]quinoline | 41 | 17296 |

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

We claim:
1. A compound of the formula I

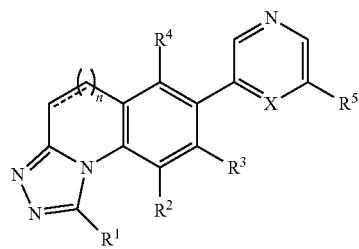

or a pharmaceutically acceptable salt thereof
wherein:
X is N or C(R$^6$);
R$^1$ is H; alkyl optionally independently substituted one or more times by halogen, —OR$^7$, NR$^8$R$^9$, —CN, —N(R$^{11}$)C(O)R$^7$, —C(O)N(R$^8$)(R$^9$), —C(O)OR$^7$, or —S(O)$_m$—R$^7$; cycloalkyl optionally independently substituted one or more times by halogen, alkyl, haloalkyl, —OR$^7$, —NR$^8$R$^9$, —CN, —N(R$^{11}$)C(O)R$^7$, —C(O)N(R$^8$)(R$^9$), —C(O)OR$^7$ or —S(O)$_m$—R$^7$; aryl optionally independently substituted one or more times by halogen, alkyl, haloalkyl, cycloalkyl, —OR$^7$, —CN, —NR$^8$R$^9$ —N(R$^{11}$)C(O)R$^7$, —C(O)N(R$^8$)(R$^9$), —C(O)OR$^7$, or —S(O)$_m$—R$^7$; or heteroaryl optionally independently substituted one or more times by halogen, alkyl, haloalkyl, cycloalkyl, —OR$^7$, —CN, —NR$^8$R$^9$, —N(R$^{11}$)C(O)R$^7$, —C(O)N(R$^8$)(R$^9$), —C(O)OR$^7$ or —S(O)$_m$—R$^7$;

R$^2$ is H; halogen; —CN; alkyl optionally independently substituted one or more times by halogen; or cycloalkyl optionally independently substituted once or twice by alkyl or halogen;

R$^3$ is H; halogen; —CN; alkyl optionally independently substituted one or more times by halogen; or cycloalkyl optionally substituted once or twice by alkyl or halogen;

R$^4$ is H; halogen; —CN; alkyl optionally independently substituted one or more times by halogen; or cycloalkyl optionally independently substituted once or twice by alkyl or halogen;

R$^5$ is H; halogen; —CN; —OR$^7$; —NR$^8$R$^9$; —N(R$^{11}$)C(O)R$^7$; —C(O)R$^7$; —C(O)N(R$^8$)(R$^9$); —C(O)OR$^7$; —N(R$^{11}$)S(O)$_2$R$^7$; —S(O)$_2$N(R$^8$)(R$^9$); —S(O)$_m$—R$^7$; alkyl optionally independently substituted one or more times by halogen, —OR$^7$, —NR$^8$R$^9$, —CN, —N(R$^{11}$)C(O)R$^7$, —C(O)N(R$^8$)(R$^9$), —C(O)OR$^7$ or —S(O)$_m$—R$^7$; cycloalkyl optionally independently substituted one or more times by halogen, alkyl, haloalkyl, aryl (optionally substituted once or twice by halogen, alkyl, haloalkyl, cycloalkyl or aryl), heteroaryl (optionally substituted one or twice by halogen, alkyl, haloalkyl, cycloalkyl or aryl), —OR$^7$, —NR$^8$R$^9$, —CN, —N(R$^{11}$) C(O)R$^7$, —C(O)N(R$^8$)(R$^9$), —C(O)OR$^7$ or —S(O)$_m$—R$^7$; aryl optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —CN, —NR$^8$R$^9$ —N(R$^{11}$)C(O)R$^7$, —C(O)N(R$^8$)(R$^9$), —C(O)OR$^7$ or —S(O)$_m$—R$^7$; aralkyl wherein the aryl ring is optionally independently substituted one or more times by halogen, alkyl, haloalkyl, cycloalkyl, aryl (optionally substituted one or twice by halogen, alkyl, or haloalkyl), heteroaryl (optionally substituted once or twice by halogen, alkyl, or haloalkyl), —$OR^7$, —CN, —$NR^8R^9$ —$N(R^{11})C(O)R^7$, —$C(O)N(R^8)(R^9)$, —$C(O)OR^7$ or —$S(O)_m$—$R^7$ and the alkyl chain is straight or branched and optionally substituted one or more times by halogen or —$OR^7$; heterocycloalkyl optionally independently substituted one or more times by halogen, alkyl, haloalkyl, —$OR^7$, —CN, —$NR^8R^9$ —$N(R^{11})C(O)R^7$, —$C(O)N(R^8)(R^9)$, —$C(O)OR^7$ or —$S(O)_m$—$R^7$; heteroaryl optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$, —$N(R^{11})C(O)R^7$, —$C(O)N(R^8)(R^9)$, —$C(O)OR^7$ or —$S(O)_m$—$R^7$; or heteroaralkyl wherein the heteroaryl ring is optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$ —$N(R^{11})C(O)R^7$, —$C(O)N(R^8)(R^9)$, —$C(O)OR^7$ or —$S(O)_m$—$R^7$ and the alkyl chain is straight or branched and optionally substituted one or more times by halogen or —$OR^7$;

$R^6$ is H; halogen; —CN; —$OR^7$; —$NR^8R^9$; —$N(R^{11})C(O)R^7$; —$C(O)N(R^8)(R^9)$; —$C(O)R^7$; —$C(O)OR^7$; —$N(R^{11})S(O)_2R^7$; —$S(O)_2N(R^8)(R^9)$; —$S(O)_m$—$R^7$; alkyl optionally independently substituted one or more times by halogen, —$OR^7$, —$NR^8R^9$, —CN, —$N(R^{11})C(O)R^7$, —$C(O)N(R^8)(R^9)$, —$C(O)OR^7$ or —$S(O)_m$—$R^7$; cycloalkyl optionally independently substituted one or more times by halogen, alkyl, haloalkyl, aryl (optionally substituted once or twice by halogen, alkyl, haloalkyl, cycloalkyl or aryl), heteroaryl (optionally substituted once or twice by halogen, alkyl, haloalkyl, cycloalkyl or aryl), —$OR^7$, —$NR^8R^9$, —CN, —$N(R^{11})C(O)R^7$, —$C(O)N(R^8)(R^9)$, —$C(O)OR^8$ or —$S(O)_m$—$R^8$; aryl optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$ —$N(R^{11})C(O)(R^7)$, —$C(O)N(R^8)(R^9)$, —$C(O)OR^7$ or —$S(O)_m$—$R^7$; aralkyl wherein the aryl ring is optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$—$N(R^{11})C(O)R^7$,—$C(O)N(R^8)(R^9)$,—$C(O)OR^7$ or —$S(O)_m$—$R^7$ and the alkyl chain is straight or branched and optionally substituted one or more times by halogen or —$OR^7$; heterocycloalkyl optionally independently substituted one or more times by halogen, alkyl, haloalkyl, cycloalkyl, —$OR^7$, —CN, —$NR^8R^9$ —$N(R^{11})C(O)R^7$, —$C(O)N(R^8)(R^9)$, —$C(O)OR^7$ or —$S(O)_m$—$R^7$; heteroaryl optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$, —$N(R^{11})C(O)R^7$, —$C(O)N(R^8)(R^9)$, —$C(O)OR^7$ or —$S(O)_m$—$R^7$; heteroaralkyl wherein the heteroaryl ring is optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —$OR^7$, —CN, —$NR^8R^9$ —$N(R^{11})C(O)R^7$, —$C(O)N(R^8)(R^9)$, —$C(O)OR^7$ or —$S(O)_m$—$R^7$ and the alkyl chain is straight or branched and optionally substituted one or more times by halogen or —$OR^7$;

or $R^5$ and $R^6$ are joined together to form a 5-7 membered carbocyclic or heterocyclic ring that is fused to the pyridyl ring to which $R^5$ and $R^6$ are attached, wherein the ring formed by $R^5$ and $R^6$ is optionally independently substituted by 1 to 3 $R^{10}$;

$R^7$ is independently selected from the group consisting of H; alkyl optionally independently substituted one or more times by halogen, —$OR^{11}$, —$NR^8R^9$, —CN, —$N(R^{11})C(O)R^{11}$, —$C(O)N(R^8)(R^9)$, —$C(O)OR^{11}$ or —$S(O)_m$—$R^{11}$, aryl (optionally substituted once or twice by halogen, alkyl, or haloalkyl), heteroaryl (optionally substituted once or twice by halogen, alkyl, or haloalkyl); cycloalkyl optionally independently substituted one or more times by halogen, alkyl, haloalkyl, —$OR^{11}$, —$NR^8R^9$, —CN, —$N(R^{11})C(O)R^{11}$, —$C(O)N(R^8)(R^9)$, —$C(O)OR^{11}$ or —$S(O)_m$—$R^{11}$, aryl optionally independently substituted one or more times by halogen, alkyl, haloalkyl, cycloalkyl, —OH, —$OR^{11}$, —$NR^8R^9$, —CN, —$N(R^{11})C(O)R^{11}$, —$C(O)N(R^8)(R^9)$, —$C(O)OR^{11}$ or —$S(O)_m$—$R^{11}$; or heteroaryl optionally independently substituted one or more times by halogen, alkyl, haloalkyl, cycloalkyl, —$OR^{11}$, —$NR^8R^9$, —CN, —$N(R^9)C(O)R^{11}$, —$C(O)N(R^8)(R^9)$, —$C(O)OR^{11}$ or —$S(O)_m$—$R^{11}$;

$R^8$ is independently H or alkyl;

$R^9$ is independently H or alkyl;

$R^{10}$ is independently H; halogen; —CN; —$OR^7$; —$NR^8R^9$; —$N(R^{11})C(O)R^7$; —$C(O)N(R^7)(R^8)$; —$C(O)N(R^8)(R^9)$; —$C(O)OR^7$; —$S(O)_m$—$R^7$; alkyl optionally independently substituted one or more times by halogen, —$OR^7$, —$NR^8R^9$, —CN, —$N(R^{11})C(O)R^7$, —$C(O)N(R^8)(R^9)$, —$C(O)OR^7$ or —$S(O)_m$—$R^7$; cycloalkyl optionally independently substituted one or more times by halogen, alkyl, haloalkyl, —$OR^1$, —$NR^8R^9$, —CN, —$N(R^{11})C(O)R^7$, —$C(O)N(R^8)(R^9)$, —$C(O)OR^8$ or —$S(O)_m$—$R^8$; aryl optionally independently substituted one or more times by halogen, alkyl, haloalkyl, cycloalkyl, —$OR^7$, —CN, —$NR^8R^9$ —$N(R^{11})C(O)(R^7)$, —$C(O)N(R^7)(R^8)$, —$C(O)OR^7$ or —$S(O)_m$—$R^7$; heterocycloalkyl optionally independently substituted one or more times by halogen, alkyl, haloalkyl, —$OR^7$, —CN, —$NR^8R^9$ —$N(R^{11})C(O)R^7$, —$C(O)N(R^8)(R^9)$, —$C(O)OR^7$ or —$S(O)_m$—$R^7$; or heteroaryl optionally independently substituted one or more times by halogen, alkyl, haloalkyl, cycloalkyl, —$OR^7$, —CN, —$NR^8R^9$, —$N(R^{11})C(O)R^7$, —$C(O)N(R^8)(R^9)$, —$C(O)OR^7$ or —$S(O)_m$—$R^7$;

$R^{11}$ is independently H or alkyl;

---- is an optional double bond;

n is 1 or 2; and m is 0, 1 or 2.

2. The compound as defined in claim 1 or a pharmaceutically acceptable salt thereof which has the structural formula

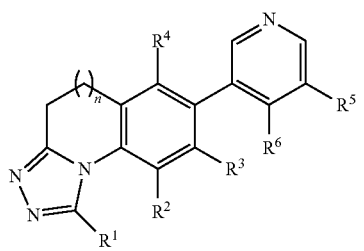

wherein:
- R$^1$ is H; alkyl optionally independently substituted one or more times by halogen, —OR$^7$, NR$^8$R$^9$, —CN, —N(R$^{11}$)C(O)R$^7$, —C(O)N(R$^8$)(R$^9$), —C(O)OR$^7$, or —S(O)$_m$—R$^7$; cycloalkyl optionally independently substituted one or more times by halogen, alkyl, haloalkyl, —OR$^7$, —NR$^8$R$^9$, —CN, —N(R$^{11}$)C(O)R$^7$, —C(O)N(R$^8$)(R$^9$), —C(O)OR$^7$ or —S(O)$_m$—R$^7$; aryl optionally independently substituted one or more times by halogen, alkyl, haloalkyl, cycloalkyl, —OR$^7$, —CN, —NR$^8$R$^9$ —N(R$^{11}$)C(O)R$^7$, —C(O)N(R$^8$)(R$^9$), —C(O)OR$^7$, or —S(O)$_m$—R$^7$; or heteroaryl optionally independently substituted one or more times by halogen, alkyl, haloalkyl, cycloalkyl, —OR$^7$, —CN, —NR$^8$R$^9$, —N(R$^{11}$)C(O)R$^7$, —C(O)N(R$^8$)(R$^9$), —C(O)OR$^7$ or —S(O)$_m$—R$^7$;
- R$^2$ is H; halogen; —CN; alkyl optionally independently substituted one or more times by halogen; or cyclopropyl optionally independently substituted once or twice by alkyl or halogen;
- R$^3$ is H; halogen; —CN; alkyl optionally independently substituted one or more times by halogen; or cyclopropyl optionally independently substituted once or twice by alkyl or halogen;
- R$^4$ is H; halogen; —CN; alkyl optionally independently substituted one or more times by halogen; or cycloalkyl optionally independently substituted once or twice by alkyl or halogen;
- R$^5$ is H; halogen; —CN; —OR$^7$; —NR$^8$R$^9$; —N(R$^{11}$)C(O)R$^7$; —C(O)R$^7$; —C(O)N(R$^8$)(R$^9$); —C(O)OR$^7$; —S(O)$_m$—R$^7$; alkyl optionally independently substituted one or more times by halogen, —OR$^7$, —NR$^8$R$^9$, —CN, —N(R$^{11}$)C(O)R$^7$, —C(O)N(R$^8$)(R$^9$), —C(O)OR$^7$ or —S(O)$_m$—R$^7$; cycloalkyl optionally independently substituted one or more times by halogen, alkyl, haloalkyl, aryl (optionally substituted one or twice by halogen, alkyl, haloalkyl, cycloalkyl or aryl), heteroaryl (optionally substituted once or twice by halogen, alkyl, haloalkyl, cycloalkyl or aryl), —OR$^7$, —NR$^8$R$^9$, —CN, —N(R$^{11}$)C(O)R$^7$, —C(O)N(R$^8$)(R$^9$), —C(O)OR$^7$ or —S(O)$_m$—R$^7$; aryl optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —OR$^7$, —CN, —NR$^8$R$^9$ —N(R$^{11}$)C(O)R$^7$, —C(O)N(R$^8$)(R$^9$), —C(O)OR$^7$ or —S(O)$_m$—R$^7$; aralkyl wherein the aryl ring is optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —OR$^7$, —CN, —NR$^8$R$^9$ —N(R$^{11}$)C(O)R$^7$, —C(O)N(R$^8$)(R$^9$), —C(O)OR$^7$ or —S(O)$_m$—R$^7$ and the alkyl chain is straight or branched and optionally substituted one or more times by halogen or —OR$^7$; heterocycloalkyl optionally independently substituted one or more times by halogen, alkyl, haloalkyl, —OR$^7$, —CN, —NR$^8$R$^9$ —N(R$^{11}$)C(O)R$^7$, —C(O)N(R$^8$)(R$^9$), —C(O)OR$^7$ or —S(O)$_m$—R$^7$; heteroaryl optionally independently substituted one or more times by halogen, alkyl, haloalkyl, cycloalkyl, aryl (optionally substituted once or twice by halogen, alkyl, or haloalkyl); heteroaryl (optionally substituted once or twice by halogen, alkyl, or haloalkyl), —OR$^7$, —CN, —NR$^8$R$^9$, —N(R$^{11}$)C(O)R$^7$, —C(O)N(R$^8$)(R$^9$), —C(O)OR$^7$ or —S(O)$_m$—R$^7$; or heteroaralkyl wherein the heteroaryl ring is optionally substituted one or more times independently by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —OR$^7$, —CN, —NR$^8$R$^9$ —N(R$^{11}$)C(O)R$^7$, —C(O)N(R$^8$)(R$^9$), —C(O)OR$^7$ or —S(O)$_m$—R$^7$ and the alkyl chain is straight or branched and optionally substituted one or more times by halogen or —OR$^7$;
- R$^6$ is H; halogen; —CN; —OR$^7$; —NR$^8$R$^9$; —N(R$^{11}$)C(O)R$^7$, —C(O)N(R$^8$)(R$^9$), —C(O)OR$^7$, —C(O)OR$^7$; —S(O)$_m$—R$^7$; alkyl optionally independently substituted one or more times by halogen, —OR$^7$, —NR$^8$R$^9$, —CN, —N(R$^{11}$)C(O)R$^7$, —C(O)N(R$^8$)(R$^9$), —C(O)OR$^7$ or —S(O)$_m$—R$^7$; cycloalkyl optionally independently substituted one or more times by independently halogen, alkyl, haloalkyl, aryl (optionally substituted once or twice by halogen, alkyl, haloalkyl, cycloalkyl or aryl), heteroaryl (optionally substituted once or twice by halogen, alkyl, haloalkyl, cycloalkyl or aryl), —OR$^7$, —NR$^8$R$^9$, —CN, —N(R$^{11}$)C(O)R$^7$, —C(O)N(R$^8$)(R$^9$), —C(O)OR$^8$ or —S(O)$_m$—R$^8$; aryl optionally independently substituted one or more times independently by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —OR$^7$, —CN, —NR$^8$R$^9$ —N(R$^{11}$)C(O)(R$^{11}$), —C(O)N(R$^8$)(R$^9$), —C(O)OR$^7$ or —S(O)$_m$—R$^7$; aralkyl wherein the aryl ring is optionally independently substituted one or more times independently by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —OR$^7$, —CN, —NR$^8$R$^9$ —N(R$^{11}$)C(O)R$^7$, —C(O)N(R$^8$)(R$^9$), —C(O)OR$^7$ or —S(O)$_m$—R$^7$ and the alkyl chain is straight or branched and is optionally substituted once or more times by halogen or —OR$^7$); heterocycloalkyl optionally independently substituted one or more times by halogen, alkyl, haloalkyl, cycloalkyl, —OR$^7$, —CN, —NR$^8$R$^9$ —N(R$^{11}$)C(O)R$^7$, —C(O)N(R$^8$)(R$^9$), —C(O)OR$^7$ or —S(O)$_m$—R$^7$; heteroaryl optionally independently substituted once or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —OR$^7$, —CN, —NR$^8$R$^9$, —N(R$^{11}$)C(O)R$^7$, —C(O)N(R$^8$)(R$^9$), —C(O)OR$^7$ or —S(O)$_m$—R$^7$; or heteroaralkyl wherein the heteroaryl ring is optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —OR$^7$, —CN, —NR$^8$R$^9$ —N(R$^{11}$)C(O)R$^7$, —C(O)N(R$^8$)(R$^9$), —C(O)OR$^7$ or —S(O)$_m$—R$^7$ and the alkyl chain is straight or branched and is optionally substituted one or more times by halogen or —OR$^7$;

or $R^5$ and $R^6$ are joined together to form a 5-7 membered carbocyclic or heterocyclic ring that is fused to the pyridyl ring to which $R^5$ and $R^6$ are attached, wherein the ring formed by $R^5$ and $R^6$ is optionally independently substituted by 1 to 3 $R^{10}$;

$R^7$ is independently selected from the group consisting of H; alkyl optionally independently substituted one or more times by halogen, —$OR^{11}$, —$NR^8R^9$, —CN, —$N(R^{11})C(O)R^{11}$, —$C(O)N(R^8)(R^9)$, —$C(O)OR^{11}$, —$S(O)_m$—$R^{11}$, aryl (optionally substituted once or twice by halogen, alkyl, or haloalkyl); heteroaryl (optionally substituted once or twice by halogen, alkyl, or haloalkyl); cycloalkyl optionally independently substituted one or more times by halogen, alkyl, haloalkyl, —$OR^{11}$, —$NR^8R^9$, —CN, —$N(R^{11})C(O)R^{11}$, —$C(O)N(R^8)(R^9)$, —$C(O)OR^{11}$ or —$S(O)_m$—$R^{11}$; aryl optionally independently substituted one or more times by halogen, alkyl, haloalkyl, cycloalkyl, —OH, —$OR^{11}$, —$NR^8R^9$, —CN, —$N(R^{11})C(O)R^{11}$, —$C(O)N(R^8)(R^9)$, —$C(O)OR^{11}$ or —$S(O)_m$—$R^{11}$; or heteroaryl optionally independently substituted one or more times by halogen, alkyl, haloalkyl, cycloalkyl, —$OR^{11}$, —$NR^8R^9$, —CN, —$N(R^9)C(O)R^{11}$, —$C(O)N(R^8)(R^9)$, —$C(O)OR^{11}$ or —$S(O)_m$—$R^{11}$;

$R^8$ is independently H or alkyl;
$R^9$ is independently H or alkyl;
$R^{10}$ is independently H; halogen; —CN; —$OR^7$; —$NR^8R^9$; —$N(R^{11})C(O)R^7$; —$C(O)N(R^7)(R^8)$; —$C(O)N(R^8)(R^9)$; —$C(O)OR^7$; —$S(O)_m$—$R^7$; alkyl optionally independently substituted one or more times by halogen, —$OR^7$, —$NR^8R^9$, —CN, —$N(R^{11})C(O)R^7$, —$C(O)N(R^8)(R^9)$, —$C(O)OR^7$ or —$S(O)_m$—$R^7$; cycloalkyl optionally independently substituted one or more times by halogen, alkyl, haloalkyl, —$OR^7$, —$NR^8R^9$, —CN, —$N(R^{11})C(O)R^7$, —$C(O)N(R^8)(R^9)$, —$C(O)OR^8$ or —$S(O)_m$—$R^8$; aryl optionally independently substituted one or more times by halogen, alkyl, haloalkyl, cycloalkyl, —$OR^7$, —CN, —$NR^8R^9$ —$N(R^{11})C(O)(R^7)$, —$C(O)N(R^7)(R^8)$, —$C(O)OR^7$ or —$S(O)_m$—$R^7$; heterocycloalkyl optionally independently substituted one or more times by halogen, alkyl, haloalkyl, —$OR^7$, —CN, —$NR^8R^9$ —$N(R^{11})C(O)R^7$, —$C(O)N(R^8)(R^9)$, —$C(O)OR^7$ or —$S(O)_m$—$R^7$; or heteroaryl optionally independently substituted one or more times by halogen, alkyl, haloalkyl, cycloalkyl, —$OR^7$, —CN, —$NR^8R^9$, —$N(R^{11})C(O)R^7$, —$C(O)N(R^8)(R^9)$, —$C(O)OR^7$ or —$S(O)_m$—$R^7$; and $R^{11}$ is independently H or alkyl;
n is 1 or 2;
m is 0, 1 or 2.

3. The compound as defined in claim 1 or a pharmaceutically acceptable salt thereof which has the structural formula

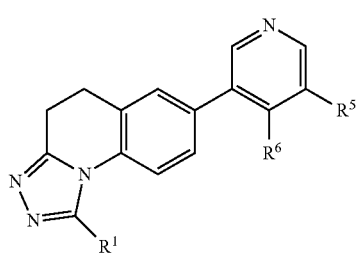

II wherein
$R^1$ is H, alkyl, haloalkyl, cycloalkyl, phenyl, halo-substituted phenyl, alkyl-substituted phenyl, heteroaryl, alkyl-substituted heteroaryl, cyclopropyl-substituted heteroaryl, where heteroaryl is selected from the group consisting of pyridyl, pyrazinyl, furanyl, thienyl, pyrimidinyl, pyridone, isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl or 7-azaindolyl.

4. The compound as defined in claim 3 or a pharmaceutically acceptable salt thereof wherein;
$R^5$ is H, —$C(O)OR^7$, —$S(O)_2R^7$, or oxetanyl and $R^7$ is independently $C_1$-$C_4$-alkyl or phenyl; and
$R^6$ is H.

5. The compound as defined in claim 3 or a pharmaceutically acceptable salt thereof wherein:
$R^5$ is H, halogen, alkyl, haloalkyl, $N(R^{11})SO_2R^7$ or —$C(O)R^7$, where $R^7$ is independently $C_1$-$C_4$-alkyl or phenyl; and
$R^6$ is H, alkyl or cycloalkyl.

6. The compound as defined in claim 3 or a pharmaceutically acceptable salt thereof, wherein
$R^5$ is a group of the formulae:

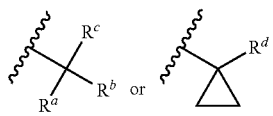

where:
$R^a$ is —$C_1$-$C_4$-alkyl optionally substituted with 1 to 3 —F;
$R^b$ is halogen, —OH, or —$C_1$-$C_4$-alkyl optionally substituted with 1 to 3 —F;
$R^c$ is halogen, —OH, —$C_1$-$C_4$-alkyl substituted with 1 to 3 —F or —O—$C_1$-$C_4$-alkyl substituted with 1 to 3 —F, —O—$C_1$-$C_4$-alkyl optionally substituted with 1 to 3 —F, —C(O)O—$C_1$-$C_4$-alkyl, —$S(O)_2$—$C_1$-$C_4$-alkyl, —C(O)N($C_1$-$C_4$-alkyl)($C_1$-$C_4$-alkyl), cyclopropyl or heteroaryl, which is optionally substituted by $C_1$-$C_4$alkyl, phenyl, $C_1$-$C_4$-alkyl substituted with 1 to 3 —F or cyclopropyl, and the heteroaryl ring is triazole or oxadiazole; and
$R^d$ is —$C_1$-$C_4$-alkyl, —C(O)O—$C_1$-$C_4$-alkyl, —$S(O)_2$—$C_1$-$C_4$-alkyl, or heteroaryl, which is optionally substituted by $C_1$-$C_4$alkyl, phenyl, $C_1$-$C_4$-alkyl substituted with 1 to 3 —F or cyclopropyl, and the heteroaryl ring is triazole or oxadiazole; and
$R^6$ is H or alkyl.

7. The compound as defined in claim 2 or a pharmaceutically acceptable salt thereof which has the structural formula

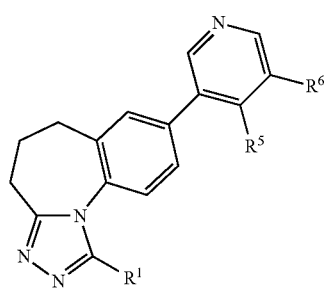

V wherein
R¹ is H, alkyl, haloalkyl, cycloalkyl, phenyl, halo-substituted phenyl, alkyl-substituted-substituted phenyl, heteroaryl, alkyl-substituted heteroaryl, cyclopropyl-substituted heteroaryl, where heteroaryl is selected from the group consisting of pyridyl, pyrazinyl, furanyl, thienyl, pyrimidinyl, pyridone, isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl, or 7-azaindolyl; and R⁶ is H.

8. The compound as defined in claim 2 or a pharmaceutically acceptable salt thereof which has the structural formula

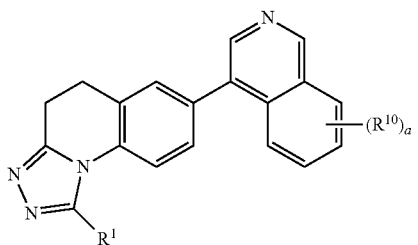

III wherein R¹ is H, alkyl, haloalkyl, cycloalkyl, phenyl, halo-substituted phenyl, alkyl-substituted-substituted phenyl, heteroaryl, alkyl-substituted heteroaryl, cyclopropyl-substituted heteroaryl, where heteroaryl is selected from the group consisting of pyridyl, pyrazinyl, furanyl, thienyl, pyrimidinyl, pyridone, isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl, or 7-azaindolyl R¹⁰ is independently alkyl or halo;
and a is 0, 1 or 2.

9. A compound of formula VI

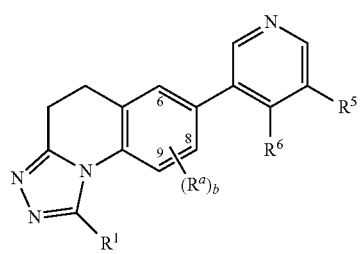

VI or a pharmaceutically acceptable salt thereof
wherein
R¹ is independently H or alkyl;
R⁵ is H; halogen; —CN; —OR⁷, —NR⁸R⁹; —N(R¹¹)C(O)R⁷; —C(O)R⁷; —C(O)N(R⁸)(R⁹); —C(O)OR⁷; —N(R¹¹)S(O)₂R⁷; —S(O)₂N(R⁸)(R⁹); —S(O)ₘ—R⁷; alkyl optionally independently substituted one or more times by halogen, —OR⁷, —NR⁸R⁹, —CN, —N(R¹¹)C(O)R⁷; —C(O)N(R⁸)(R⁹), —C(O)OR⁷ or —S(O)ₘ—R⁷; cycloalkyl optionally independently substituted one or more times by halogen, alkyl, haloalkyl, aryl (optionally substituted once or twice by halogen, alkyl, haloalkyl, cycloalkyl or aryl), heteroaryl (optionally substituted one or twice by halogen, alkyl, haloalkyl, cycloalkyl or aryl), —OR⁷; —NR⁸R⁹, —CN, —N(R¹¹)C(O)R⁷; —C(O)N(R⁸)(R⁹), —C(O)OR⁷ or —S(O)ₘ—R⁷; aryl optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —OR⁷, —CN, —NR⁸R⁹ —N(R¹¹)C(O)R⁷, —C(O)N(R⁸)(R⁹), —C(O)OR⁷ or —S(O)ₘ—R⁷; aralkyl wherein the aryl ring is optionally independently substituted one or more times by halogen, alkyl, haloalkyl, cycloalkyl, aryl (optionally substituted one or twice by halogen, alkyl, or haloalkyl), heteroaryl (optionally substituted once or twice by halogen, alkyl, or haloalkyl), —OR⁷, —CN, —NR⁸R⁹ —N(R¹¹)C(O)R⁷, —C(O)N(R⁸)(R⁹), —C(O)OR⁷ or —S(O)ₘ—R⁷ and the alkyl chain is straight or branched and optionally substituted one or more times by halogen or —OR⁷; heterocycloalkyl optionally independently substituted one or more times by halogen, alkyl, haloalkyl, —OR⁷, —CN, —NR⁸R⁹ —N(R¹¹)C(O)R⁷, —C(O)N(R⁸)(R⁹), —C(O)OR⁷ or —S(O)ₘ—R⁷, heteroaryl optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —OR⁷, —CN, —NR⁸R⁹, —N(R¹¹)C(O)R⁷, —C(O)N(R⁸)(R⁹), —C(O)OR⁷ or —S(O)ₘ—R⁷; or heteroaralkyl wherein the heteroaryl ring is optionally independently substituted one or more times by halogen, alkyl, haloalkyl, cycloalkyl, aryl (optionally substituted once or twice by halogen, alkyl, or haloalkyl), heteroaryl (optionally substituted once or twice by halogen, alkyl, or haloalkyl), —OR⁷, —CN, —NR⁸R⁹ —N(R¹¹)C(O)R⁷, —C(O)N(R⁸)(R⁹), —C(O)OR⁷ or —S(O)ₘ—R⁷ and the alkyl chain is straight or branched and optionally substituted one or more times by halogen or —OR⁷;

or R⁵ and R⁶ are joined together to form a 5-7 membered carbocyclic or heterocyclic ring that is fused to the pyridyl ring to which R⁵ and R⁶ are attached, wherein the ring formed by R⁵ and R⁶ is optionally independently substituted by 1 to 3 R¹⁰;

R⁷ is independently selected from the group consisting of H; alkyl optionally independently substituted one or more times by halogen, —OR¹¹, —NR⁸R⁹, —CN, —N(R¹¹)C(O)R¹¹, —C(O)N(R⁸)(R⁹), —C(O)OR¹¹ or —S(O)ₘ—R¹¹, aryl (optionally substituted once or twice by halogen, alkyl, or haloalkyl), heteroaryl (optionally substituted once or twice by halogen, alkyl, or haloalkyl); cycloalkyl optionally independently substituted one or more times by halogen, alkyl, haloalkyl, —OR¹¹, —NR⁸R⁹, —CN, —N(R¹¹)C(O)R¹¹, —C(O)N(R⁸)(R⁹), —C(O)OR¹¹ or —S(O)ₘ—R¹¹, aryl optionally independently substituted one or more times by halogen, alkyl, haloalkyl, cycloalkyl, —OH, —OR¹¹, —NR⁸R⁹, —CN, —N(R¹¹)C(O)R⁷, —C(O)N(R⁸)(R⁹), —C(O)OR¹¹ or —S(O)ₘ—R¹¹; or heteroaryl optionally independently substituted one or more times by halogen, alkyl, haloalkyl, cycloalkyl, —OR$^{11}$, —NR$^8$R$^9$, —CN, —N(R$^9$)C(O)R$^{11}$, —C(O)N(R$^8$)(R$^9$), —C(O)OR$^{11}$ or —S(O)$_m$—R$^{11}$;

R$^8$ is independently H or alkyl;

R$^9$ is independently H or alkyl;

R$^{10}$ is independently H; halogen; —CN; —OR$^7$; —NR$^8$R$^9$; —N(R$^{11}$)C(O)R$^7$; —C(O)N(R$^7$)(R$^8$); —C(O)N(R$^8$)(R$^9$); —C(O)OR$^7$; —S(O)$_m$—R$^7$; alkyl optionally independently substituted one or more times by halogen, —OR$^7$, —NR$^8$R$^9$, —CN, —N(R$^{11}$)C(O)R$^7$, —C(O)N(R$^8$)(R$^9$); —C(O)OR$^7$ or —S(O)$_m$R$^7$; cycloalkyl optionally independently substituted one or more times by halogen, alkyl, haloalkyl, —OR$^7$, —NR$^8$R$^9$, —CN, —N(R$^{11}$)C(O)R$^7$, —C(O)N(R$^8$)(R$^9$), —C(O)OR$^8$ or —S(O)$_m$—R$^8$; aryl optionally independently substituted one or more times by halogen, alkyl, haloalkyl, cycloalkyl, —OR$^7$, —CN, —NR$^8$R$^9$ —N(R$^{11}$)C(O)(R$^7$), —C(O)N(R$^7$)(R$^8$), —C(O)OR$^7$ or —S(O)$_m$—R$^7$; heterocycloalkyl optionally independently substituted one or more times by halogen, alkyl, haloalkyl, —OR$^7$, —CN, —NR$^8$R$^9$ —N(R$^{11}$)C(O)R$^7$, —C(O)N(R$^8$)(R$^9$); —C(O)OR$^7$ or —S(O)$_m$—R$^7$; or heteroaryl optionally independently substituted one or more times by halogen, alkyl, haloalkyl, cycloalkyl, —OR$^7$, —CN, —NR$^8$R$^9$, —N(R$^{11}$)C(O)R$^7$, —C(O)N(R$^8$)(R$^9$); —C(O)OR$^7$ or —S(O)$_m$—R$^7$;

R$^{11}$ is independently H or alkyl;

m is 0, 1 or 2;

R$^{a'}$ is at the 6-, 8-, and/or 9-positions and is independently halogen, CN, alkyl or cycloalkyl; and b is 1, 2 or 3.

10. The compound as defined in claim 9 or a pharmaceutically acceptable salt thereof wherein R$^5$ is hydrogen, halogen, —CN, alkyl, haloalkyl, cycloalkyl, hydroxy-substituted alkyl, hydroxy substituted-haloalkyl, alkoxy, haloalkoxy, phenyl, —C(O)R$^7$ or —N(H)SO$_2$R$^7$, where R$^7$ is alkyl or phenyl; and R$^6$ is hydrogen, —CN, alkyl, haloalkyl, cycloalkyl, cyano, hydroxy-substituted alkyl, alkoxy, haloalkoxy or —C(O)R$^7$, where R$^7$ is alkyl or phenyl.

11. The compound as defined in claim 9 or a pharmaceutically acceptable salt thereof wherein R$^5$ is a group of the formulae:

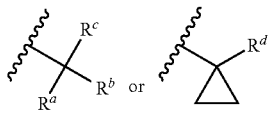

where:

R$^a$ is —C$_1$-C$_4$-alkyl optionally substituted with 1 to 3 —F;

R$^b$ is halogen, —OH, or —C$_1$-C$_4$-alkyl optionally substituted with 1 to 3 —F;

R$^c$ is halogen, —OH, —C$_1$-C$_4$-alkyl substituted with 1 to 3 —F or —O—C$_1$-C$_4$-alkyl substituted with 1 to 3 —F, —O—C$_1$-C$_4$-alkyl optionally substituted with 1 to 3 —F, —C(O)O—C$_1$-C$_4$-alkyl, —S(O)$_2$—C$_1$-C$_4$-alkyl, —C(O)N(C$_1$-C$_4$-alkyl)(C$_1$-C$_4$-alkyl), cyclopropyl or heteroaryl, which is optionally substituted by C$_1$-C$_4$alkyl, phenyl, C$_1$-C$_4$-alkyl substituted with 1 to 3 —F or cyclopropyl, and the heteroaryl ring is triazole or oxadiazole; and R$^d$ is —C$_1$-C$_4$-alkyl, —C(O)O—C$_1$-C$_4$-alkyl, —S(O)$_2$—C$_1$-C$_4$-alkyl, or heteroaryl, which is optionally substituted by C$_1$-C$_4$alkyl, phenyl, C$_1$-C$_4$-alkyl substituted with 1 to 3 —F or cyclopropyl, and the heteroaryl ring is triazole or oxadiazole, and R$^6$ is H or alkyl.

12. A compound of formula VII

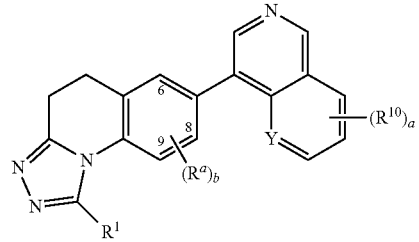

or a pharmaceutically acceptable salt thereof
wherein
R$^1$ is independently H or alkyl;
R$^{a'}$ is at the 6-, 8-, and/or 9-positions and is independently halogen, CN, alkyl or cycloalkyl,
R$^{10}$ is alkyl or halo,
Y is N or CH;
a is 0 or 1 and
b is 1, 2 or 3.

13. The compound as defined in claim 9 that has the formula:

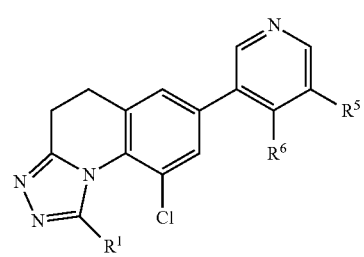

or a pharmaceutically acceptable salt thereof.

14. The compound as defined in claim 9 that has the formula:

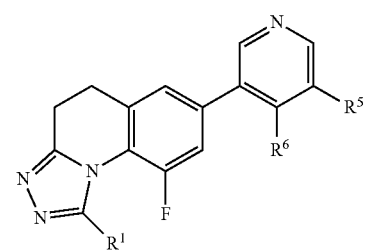

or a pharmaceutically acceptable salt thereof.

15. The compound selected from the group consisting of
7-[5-(1-ethylcyclopropyl)pyridin-3-yl]-1-methyl-4,5-dihydro[1,2,4]triazolo[4,3-a]quinoline;
7-[5-[2-methyl-1-(trifluoromethoxy)propan-2-yl]pyridin-3-yl]-4,5-dihydro[1,2,4]triazolo[4,3-a]quinoline;
7-(isoquinolin-4-yl)-1-methyl-4,5-dihydro[1,2,4]triazolo[4,3-a]quinoline;

7-[5-(2-methoxypropan-2-yl)pyridin-3-yl]-4,5-dihydro[1,2,4]triazolo[4,3-a]quinoline;
methyl 1-[5-(4,5-dihydro[1,2,4]triazolo[4,3-a]quinolin-7-yl)pyridin-3-yl]cyclopropanecarboxylate;
1-methyl-7-[5-(phenylsulfonyl)pyridin-3-yl]-4,5-dihydro[1,2,4]triazolo[4,3-a]quinoline;
7-{5-[2-(3-cyclopropyl-1,2,4-oxadiazol-5-yl)propan-2-yl]pyridin-3-yl}-4,5-dihydro[1,2,4]triazolo[4,3-a]quinoline;
methyl 5-(1-methyl-4,5-dihydro[1,2,4]triazolo[4,3-a]quinolin-7-yl)pyridine-3-carboxylate;
or a pharmaceutically acceptable salt thereof.

16. The compound selected from the group consisting of
9-chloro-1-methyl-7-(4-(trifluoromethyl)pyridin-3-yl)-4,5-dihydro-[1,2,4]triazolo[4,3-a]quinoline;
8-chloro-7-(isoquinolin-4-yl)-1-methyl-4,5-dihydro-[1,2,4]triazolo[4,3-a]quinoline;
9-chloro-7-(4-ethyl-5-fluoropyridin-3-yl)-1-methyl-4,5-dihydro-[1,2,4]triazolo[4,3-a]quinoline;
8-fluoro-7-(4-methoxy-5-methylpyridin-3-yl)-1-methyl-4,5-dihydro-[1,2,4]triazolo[4,3-a]quinoline;
9-chloro-7-(4-cyclopropylpyridin-3-yl)-1-methyl-4,5-dihydro-[1,2,4]triazolo[4,3-a]quinoline;
9-chloro-7-(5-chloro-4-methylpyridin-3-yl)-1-methyl-4,5-dihydro-[1,2,4]triazolo[4,3-a]quinoline;
9-chloro-7-(4-ethyl-5-fluoropyridin-3-yl)-8-fluoro-1-methyl-4,5-dihydro-[1,2,4]triazolo[4,3-a]quinoline;
9-chloro-8-fluoro-7-(5-fluoro-4-methylpyridin-3-yl)-1-methyl-4,5-dihydro-[1,2,4]triazolo[4,3-a]quinoline;
1-(3-(9-chloro-1-methyl-4,5-dihydro-[1,2,4]triazolo[4,3-a]quinolin-7-yl)-5-fluoropyridin-4-yl]ethanone;
9-chloro-7-(5-fluoro-4-isopropylpyridin-3-yl)-1-methyl-4,5-dihydro-[1,2,4]triazolo[4,3-a]quinoline
or a pharmaceutically acceptable salt thereof.

17. The compound selected from the group consisting of:
9-fluoro-7-(5-fluoro-pyridin-3-yl)-1-methyl-4,5-dihydro-[1,2,4]triazolo[4,3-a]quinoline;
9-fluoro-7-(5-methoxy-pyridin-3-yl)-1-methyl-4,5-dihydro-[1,2,4]triazolo[4,3-a]quinoline;
1-[5-(9-fluoro-1-methyl-4,5-dihydro-[1,2,4]triazolo[4,3-a]quinolin-7-yl)-pyridin-3-yl]-ethanol;
1-[5-(9-fluoro-1-methyl-4,5-dihydro-[1,2,4]triazolo[4,3-a]quinolin-7-yl)-pyridin-3-yl]-ethanone;
9-fluoro-1-methyl-7-(5-trifluoromethyl-pyridin-3-yl)-4,5-dihydro-[1,2,4]triazolo[4,3-a]quinoline;
9-fluoro-1-methyl-7-(5-phenyl-pyridin-3-yl)-4,5-dihydro-[1,2,4]triazolo[4,3-a]quinoline;
9-fluoro-1-methyl-7-(4-methyl-pyridin-3-yl)-4,5-dihydro-[1,2,4]triazolo[4,3-a]quinoline;
9-fluoro-7-isoquinolin-4-yl-1-methyl-4,5-dihydro-[1,2,4]triazolo[4,3-a]quinoline;
9-fluoro-1-methyl-7-pyridin-3-yl-4,5-dihydro-[1,2,4]triazolo[4,3-a]quinoline;
9-fluoro-7-pyridin-3-yl-4,5-dihydro-[1,2,4]triazolo[4,3-a]quinoline;
8-fluoro-1-methyl-7-pyridin-3-yl-4,5-dihydro-[1,2,4]triazolo[4,3-a]quinoline
8-fluoro-7-pyridin-3-yl-4,5-dihydro-[1,2,4]triazolo[4,3-a]quinoline
or a pharmaceutically acceptable salt thereof.

18. The compound selected from the group consisting of:
7-(4-ethyl-5-fluoropyridin-3-yl)-9-fluoro-1-methyl-4,5-dihydro-[1,2,4]triazolo[4,3-a]quinoline;
7-(4-ethyl-5-fluoropyridin-3-yl)-8,9-difluoro-1-methyl-4,5-dihydro-[1,2,4]triazolo[4,3-a]quinoline;
or a pharmaceutically acceptable salt thereof.

19. A pharmaceutical composition comprising a therapeutically effective amount of at least one compound of Formula I as defined in claim 1 or a pharmaceutically acceptable salt thereof and a pharmaceutically acceptable carrier.

20. A pharmaceutical composition comprising a therapeutically effective amount of at least one compound of Formula I as defined in claim 1 or a pharmaceutically acceptable salt thereof, a therapeutically effective amount of at least one additional therapeutic agent and a pharmaceutically acceptable carrier.

* * * * *